United States Patent
Seifermann

(10) Patent No.: US 11,661,412 B2
(45) Date of Patent: May 30, 2023

(54) ORGANIC MOLECULES FOR USE IN ORGANIC OPTOELECTRONIC DEVICES

(71) Applicant: SAMSUNG DISPLAY CO., LTD., Yongin-si (KR)

(72) Inventor: Stefan Seifermann, Buhl (DE)

(73) Assignee: Samsung Display Co., Ltd., Yongin-si (KR)

( * ) Notice: Subject to any disclaimer, the term of this patent is extended or adjusted under 35 U.S.C. 154(b) by 506 days.

(21) Appl. No.: 16/621,108

(22) PCT Filed: Jun. 25, 2018

(86) PCT No.: PCT/EP2018/066887
§ 371 (c)(1),
(2) Date: Dec. 10, 2019

(87) PCT Pub. No.: WO2019/002175
PCT Pub. Date: Jan. 3, 2019

(65) Prior Publication Data
US 2020/0123131 A1    Apr. 23, 2020

(30) Foreign Application Priority Data
Jun. 28, 2017   (DE) .................. 102017114345.9

(51) Int. Cl.
*C07D 403/10*      (2006.01)
*C07D 403/14*      (2006.01)
(Continued)

(52) U.S. Cl.
CPC ......... *C07D 403/10* (2013.01); *C07D 403/14* (2013.01); *C09K 11/06* (2013.01);
(Continued)

(58) Field of Classification Search
CPC .. C07D 403/10; C07D 403/14; C07D 519/00; C07D 401/14; C09K 11/06;
(Continued)

(56) References Cited

U.S. PATENT DOCUMENTS

2017/0244049 A1* 8/2017 Aspuru-Guzik ..... C07D 209/88

FOREIGN PATENT DOCUMENTS

| EP | 3287450 A1 | 2/2018 |
| WO | 2015175678 A1 | 11/2015 |

(Continued)

OTHER PUBLICATIONS

Ming-Shiang Lin "Incorporation of a CN group into mCP: a new bipolar host material for highly efficient blue and white electrophosphorescent devices" J. Mater. Chem., 2012, 22, 16114 (Year: 2012).*

*Primary Examiner* — Michael Y Sun
(74) *Attorney, Agent, or Firm* — Lewis Roca Rothgerber Christie LLP

(57) ABSTRACT

An organic molecule is disclosed comprising:
a first chemical unit having a structure according, to Formula I (Continued)

and

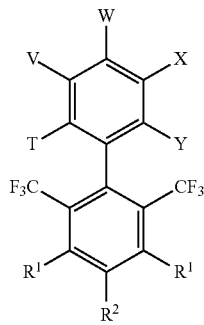

Formula I two second chemical units, which in each case are the same or different in each occurrence, having a structure according to Formula II,

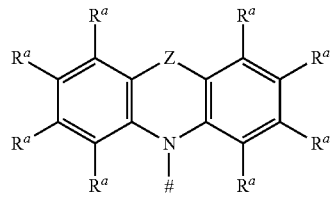

Formula II wherein, in each case, the first chemical unit is connected to the two second chemical units via a single bond.

20 Claims, 1 Drawing Sheet

(51) Int. Cl.
    *C09K 11/06*     (2006.01)
    *H01L 51/00*     (2006.01)
    *H01L 51/50*     (2006.01)

(52) U.S. Cl.
    CPC .. *H01L 51/0072* (2013.01); *C09K 2211/1018* (2013.01); *H01L 51/5012* (2013.01)

(58) Field of Classification Search
    CPC ........ C09K 2211/1018; H01L 51/0072; H01L 51/5012; H01L 51/0508; H01L 51/42; H01L 51/0067; Y02E 10/549; H05B 33/14
    See application file for complete search history.

(56) References Cited

FOREIGN PATENT DOCUMENTS

WO         2017011531 A2     1/2017
WO   PCT/EP2018/066887     8/2018

\* cited by examiner

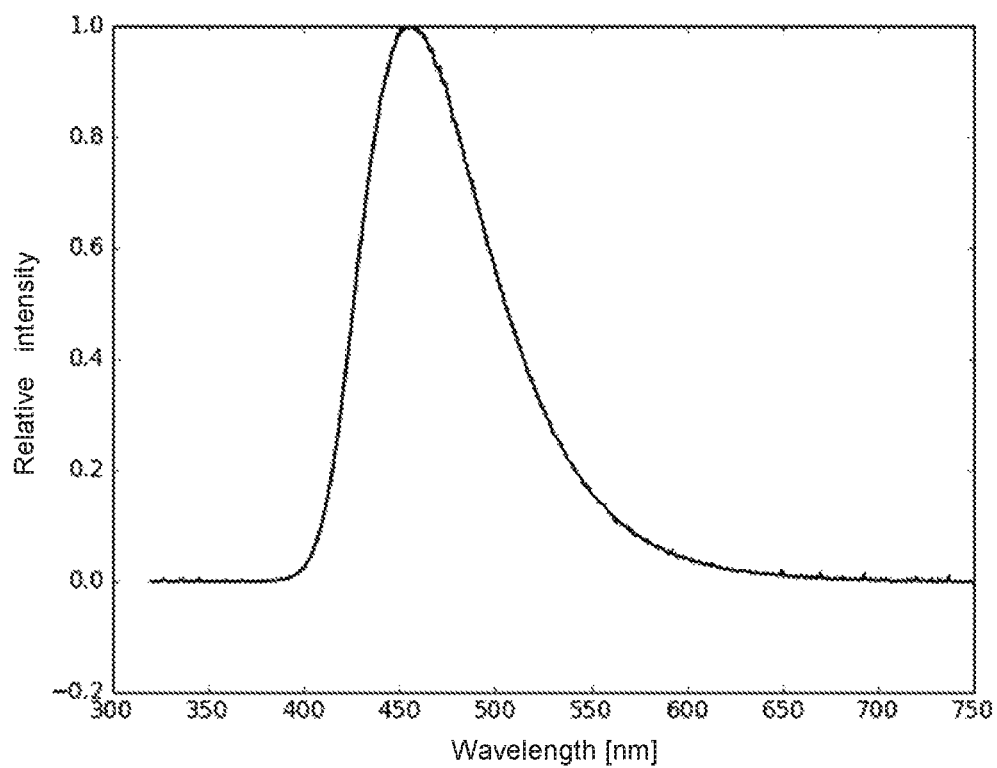

ORGANIC MOLECULES FOR USE IN ORGANIC OPTOELECTRONIC DEVICES

CROSS-REFERENCE TO RELATED APPLICATIONS

This application claims priority under 35 U.S.C. § 371 to International Application No. PCT/EP2018/066887, filed Jun. 25, 2018, which claims priority to German Patent Application No. 10 2017 114 345.9 filed Jun. 28, 2017, the disclosures of which are incorporated by reference herein in their entireties.

FIELD OF INVENTION

The invention relates to purely organic molecules and the use thereof in organic light-emitting diodes (OLEDs) and in other optoelectronic devices.

BRIEF DESCRIPTION OF THE DRAWINGS

Exemplary embodiments of the present invention will be described below in more detail, with reference to the accompanying drawings, of which:

FIG. 1 shows the emission spectrum of Example 1 (10% in PMMA).

DETAILED DESCRIPTION OF EXEMPLARY EMBODIMENTS OF THE INVENTION

Exemplary embodiments of the invention will now be discussed in further detail. This invention may, however, be embodied in many different forms and should not be construed as limited to the embodiments set forth herein.

The underlying object of the present invention was to provide molecules which are suitable for use in optoelectronic devices.

This task is solved by the novel class of organic molecules described here.

The organic molecules according to the invention are purely organic molecules; i.e. they do not have any metal ions, and thus differ from the metal complex compounds known for use in optoelectronic devices.

The organic molecules according to the invention are characterized by emissions in the blue, sky blue, or green spectral range. The photoluminescence quantum yields of the organic molecules according to the invention are, in particular, 20% and more. The molecules according to the invention in particular exhibit thermally activated delayed fluorescence (TADF). The use of the molecules according to the invention in an optoelectronic device, for example an organic light-emitting diode (OLED), results in higher efficiencies of the device.

The corresponding OLEDs have a higher stability than OLEDs having known emitter materials and comparable color.

The blue spectral range here is understood to be the visible range from >420 nm to 480 nm. The sky blue spectral range here is understood to be the range from >480 nm and 500 nm. The green spectral range here is understood to be the range from >500 nm and 560 nm. The emission maximum lies within the respective range.

The organic molecules include a first chemical unit comprising or consisting of a structure according to Formula I:

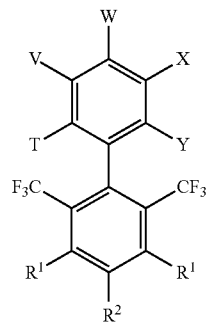

Formula I and two second chemical units D, which are respectively the same or different in each occurrence, comprising or consisting of a structure according to Formula II,

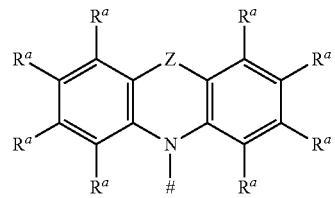

Formula II

The first chemical unit is thereby respectively connected to the two second chemical units D via a single bond.

T is the point of attachment of the single bond between the first chemical unit and a second chemical unit or is H.

V is the point of attachment of the single bond between the first chemical unit and a second chemical unit or is H.

W is the point of attachment of the single bond between the first chemical unit and a second chemical unit or is selected from the group consisting of H, CN and $CF_3$.

X is the point of attachment of the single bond between the first chemical unit and a second chemical unit or is selected from the group consisting of H, CN and $CF_3$.

Y is the point of attachment of the single bond between the first chemical unit and a second chemical unit or is selected from the group consisting of H, CN and $CF_3$;

\# identifies the point of attachment of the single bond between a second chemical unit and the first chemical unit.

Z is the same or different in each occurrence, is a direct bond or is selected from the group consisting of $CR^3R^4$, $C=CR^3R^4$, $C=O$, $C=NR^3$, $NR^3$, O, $SiR^3R^4$, S, S(O) and $S(O)_2$.

$R^1$ is the same or different in each occurrence and is selected from the group consisting of:

H. deuterium;

a linear alkyl group having 1 to 5 C atoms, a linear alkenyl or alkynyl group having 2 to 8 C atoms, a branched or cyclic alkyl, alkenyl or alkynyl group having 3 to 10 C atoms, wherein one or more H atoms in the aforementioned groups can be replaced by deuterium; and an aromatic ring system having 6 to 15 aromatic ring atoms, which can in each case be substituted with one or more radicals $R^6$.

$R^2$ is the same or different in each occurrence and is selected from the group consisting of:

H, deuterium;

a linear alkyl group having 1 to 5 C atoms, a linear alkenyl or alkynyl group having 2 to 8 C atoms, a branched or cyclic alkyl, alkenyl or alkynyl group having 3 to 10 C atoms, wherein one or more H atoms in the aforementioned groups can be replaced by deuterium;

an aromatic ring system having 6 to 15 aromatic ring atoms, which can in each case be substituted with one or more radicals $R^6$.

$R^1$, $R^3$ and $R^4$ is the same or different in each occurrence and is selected from the group consisting of:

H, deuterium, $N(R^5)_2$, OH, $Si(R^5)_3$, $B(OR^5)_2$, $OSO_2R^5$, $CF_3$, CN, F, Br, I;

a linear alkyl, alkoxy or thioalkoxy group having 1 to 40 C atoms, which can in each case be substituted with one or more radicals $R^5$, wherein one or more non-adjacent $CH_2$ groups can be replaced by $R^5C=CR^5$, $C\equiv C$, $Si(R^5)_2$, $Ge(R^5)_2$, $Sn(R^5)_2$, $C=O$, $C=S$, $C=Se$, $C=NR^5$, $P(=O)(R^5)$, SO, $SO_2$, $NR^5$, O, S or $CONR^5$ and wherein one or more H atoms can be replaced by deuterium, CN, $CF_3$ or $NO_2$;

a linear alkenyl or alkynyl group having 2 to 40 C atoms, which can in each case be substituted with one or more radicals $R^5$, wherein one or more non-adjacent $CH_2$ groups can be replaced by $R^5C=CR^5$, $C=C$, $Si(R^5)_2$, $Ge(R^5)_2$, $Sn(R^5)_2$, $C=O$, $C=S$, $C=Se$, $C=NR^5$, $P(=O)(R^5)$, SO, $SO_2$. $NR^5$, O, S or $CONR^5$ and wherein one or more H atoms can be replaced by deuterium, CN, $CF_3$ or $NO_2$;

a branched or cyclic alkyl, alkenyl, alkynyl, alkoxy or thioalkoxy group having 3 to 40 C atoms, which can in each case be substituted with one or more radicals $R^5$, wherein one or more non-adjacent $CH_2$ groups can be replaced by $R^5C=CR^5$, $C=C$, $Si(R^5)_2$, $Ge(R^5)_2$, $Sn(R^5)_2$, $C=O$, $C=S$, $C=Se$, $C=NR^5$, $P(=O)(R^5)$, SO, $SO_2$, $NR^5$, O, S or $CONR^5$ and wherein one or more H atoms can be replaced by deuterium, CN, $CF_3$ or $NO_2$;

an aromatic ring system having 6 to 60 aromatic ring atoms, which can in each case be substituted with one or more radicals $R^5$;

a heteroaromatic ring system having 5 to 60 aromatic ring atoms, which can in each case be substituted with one or more radicals $R^5$;

an aryloxy or heteroaryloxy group having 5 to 60 aromatic ring atoms, which can in each case be substituted with one or more radicals $R^5$; and a diarylamino group, diheteroarylamino group or aryiheteroarylamino group having 10 to 40 aromatic ring atoms, which can in each case be substituted with one or more radicals $R^5$.

$R^5$ is the same or different in each occurrence and is selected from the group consisting of:

H, deuterium, $N(R^6)_2$, OH, $Si(R^6)_3$, $B(OR^6)_2$, $OSO_2R^6$, $CF_3$, CN, F, Br, I;

a linear alkyl, alkoxy or thioalkoxy group having 1 to 40 C atoms, which can in each case be substituted with one or more radicals $R^6$, wherein one or more non-adjacent $CH_2$ groups can be replaced by $R^6C=CR^6$, $C=C$, $Si(R^6)_2$, $Ge(R^6)_2$, $Sn(R^6)_2$, $C=O$, $C=S$, $C=Se$, $C=NR^6$, $P(=O)(R^6)$, SO, $SO_2$, $NR^6$, O, S or $CONR^6$ and wherein one or more H atoms can be replaced by deuterium, CN, $CF_3$ or $NO_2$;

a linear alkenyl or alkynyl group having 2 to 40 C atoms, which can in each case be substituted with one or more radicals $R^6$, wherein one or more non-adjacent $CH_2$ groups can be replaced by $R^6C=CR^6$, $C=C$, $Si(R^6)_2$, $Ge(R^6)_2$, $Sn(R^6)_2$, $C=O$, $C=S$, $C=Se$, $C=NR^6$, $P(=O)(R^6)$, SO, $SO_2$, $NR^6$, O, S or $CONR^6$ and wherein one or more H atoms can be replaced by deuterium, CN, $CF_3$ or $NO_2$;

a branched or cyclic alkyl, alkenyl, alkynyl, alkoxy or thioalkoxy group having 3 to 40 C atoms, which can in each case be substituted with one or more radicals $R^6$, wherein one or more non-adjacent $CH_2$ groups can be replaced by $R^6C=CR^6$, $C=C$, $Si(R^6)_2$, $Ge(R^6)_2$, $Sn(R^6)_2$, $C=O$, $C=S$, $C=Se$, $C=NR^6$, $P(=O)(R^6)$, SO, $SO_2$, $NR^6$, O, S or $CONR^6$ and wherein one or more H atoms can be replaced by deuterium, CN, $CF_3$ or $NO_2$;

an aromatic ring system having 6 to 60 aromatic ring atoms, which can in each case be substituted with one or more radicals $R^6$;

a heteroaromatic ring system having 5 to 60 aromatic ring atoms, which can in each case be substituted with one or more radicals $R^6$;

an aryloxy or heteroaryloxy group having 5 to 60 aromatic ring atoms, which can in each case be substituted with one or more radicals $R^8$; and a diarylamino group, diheteroarylamino group or arylheteroarylamino group having 10 to 40 aromatic ring atoms, which can in each case be substituted with one or more radicals $R^6$.

$R^6$ is the same or different in each occurrence and is selected from the group consisting of:

H, deuterium, OH, $CF_3$, CN, F;

a linear alkyl, alkoxy or thioalkoxy group having 1 to 5 C atoms, wherein one or more H atoms can be replaced by deuterium, CN, $CF_3$ or $NO_2$;

a linear alkenyl or alkynyl group having 2 to 5 C atoms, wherein one or more H atoms can be replaced by deuterium, CN, $CF_3$ or $NO_2$;

a branched or cyclic alkyl, alkenyl, alkynyl, alkoxy or thioalkoxy group having 3 to 5 C atoms, wherein one or more H atoms can be replaced by deuterium, CN, $CF_3$ or $NO_2$;

an aromatic ring system having 6 to 60 aromatic ring atoms;

a heteroaromatic ring system having 5 to 60 aromatic ring atoms;

an aryloxy or heteroaryloxy group having 5 to 60 aromatic ring atoms; and a diarylamino group, diheteroarylamino group or arylheteroarylamino group having 10 to 40 aromatic ring atoms.

Each of the radicals $R^a$, $R^3$, $R^4$ or $R^5$ can also form a mono- or polycyclic, aliphatic, aromatic and/or benzoannelated ring system with one or more further radicals $R^a$, $R^3$, $R^4$ or $R^5$.

Exactly one radical selected from the group consisting of W, X and Y is CN or $CF_3$ and exactly two radicals selected from the group consisting of T, V, W, X and Y are a point of attachment of a single bond between the first chemical unit as per Formula I and a second chemical unit D.

In one embodiment, $R^1$ is selected from the group consisting of H, methyl or phenyl.

In one embodiment, $R^2$ is selected from the group consisting of H, methyl or phenyl.

In one embodiment, $R^1$ is H.

In one embodiment, $R^2$ is H.

In one embodiment, W is CN.

In one embodiment, W is $CF_3$.

In a further embodiment of the organic molecules, the second chemical unit D is the same or different in each occurrence and comprises a structure of Formula IIa or consists of a structure of Formula IIa:

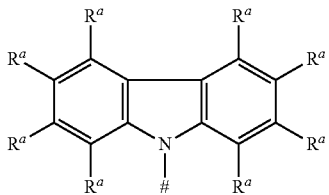

Formula IIa wherein the definitions stated for Formula I and II apply for # and $R^1$.

In a further embodiment of the organic molecules according to the invention, $R^a$ is the same or different in each occurrence and is selected from the group consisting of:
- H, deuterium;
- $N(R^5)_2$, OH, $Si(R^5)_3$, $B(OR^5)_2$, $OSO_2R^5$, CF, CN, F, Br, I;
- a linear alkyl, alkoxy or thioalkoxy group having 1 to 40 C atoms, wherein one or more non-adjacent $CH_2$ groups can be replaced by $R^5C=CR^5$, C≡C, $Si(R^5)_2$, $Ge(R^5)_2$, $Sn(R^5)_2$, C=O, C=S, C=Se, C=$NR^5$, P(=O)($R^5$), SO, $SO_2$, $NR^5$, O, S or $CONR^5$ and wherein one or more H atoms can be replaced by deuterium, CN. $CF_3$ or $NO_2$;
- a linear alkenyl or alkynyl group having 2 to 40 C atoms, wherein one or more non-adjacent $CH_2$ groups can be replaced by $R^5C=CR^5$, C≡C, $Si(R^5)_2$, $Ge(R^5)_2$, $Sn(R^5)_2$, C=O, C=S, C=Se, C=$NR^5$, P(=O)($R^5$), SO, $SO_2$, $NR^5$, O, S or $CONR^5$ and wherein one or more H atoms can be replaced by deuterium, CN, $CF_3$ or $NO_2$;
- a branched or cyclic alkyl, alkenyl, alkynyl, alkoxy or thioalkoxy group having 3 to 40 C atoms, which can in each case be substituted with one or more radicals $R^5$, wherein one or more non-adjacent $CH_2$ groups can be replaced by $R^5C=CR^5$, C≡C, $Si(R^5)_2$, $Ge(R^5)_2$, $Sn(R^5)_2$, C=O, C=S, C=Se, C=$NR^5$, P(=O)($R^5$), SO, $SO_2$, $NR^5$, O, S or $CONR^5$ and wherein one or more H atoms can be replaced by deuterium, CN, $CF_3$ or $NO_2$;
- an aromatic ring system having 6 to 60 aromatic ring atoms, which can in each case be substituted with one or more radicals $R^5$;
- a heteroaromatic ring system having 5 to 60 aromatic ring atoms, which can in each case be substituted with one or more radicals $R^5$;
- an aryloxy or heteroaryloxy group having 5 to 60 aromatic ring atoms, which can in each case be substituted with one or more radicals $R^5$; and
- a diarylamino group, diheteroarylamino group or arylheteroarylamino group having 10 to 40 aromatic ring atoms, which can in each case be substituted with one or more radicals $R^5$;

and for $R^5$ the above definition applies.

In a further embodiment of the organic molecules according to the invention, $R^a$ is the same or different in each occurrence and is selected from the group consisting of H, Me, $^iPr$, $^tBu$, CN, $CF_3$;
Ph, which can in each case be substituted with one or more radicals selected independently of one another from Me, $^iPr$, $^tBu$, CN, $CF_3$ or Ph, pyridinyl, which can in each case be substituted with one or more radicals selected independently of one another from Me, $^iPr$, $^tBu$, CN, $CF_3$ or Ph, pyrimidinyl, which can in each case be substituted with one or more radicals selected independently of one another from Me, Pr, $^tBu$, CN, $CF_3$ or Ph and triazinyl, which can in each case be substituted with one or more radicals selected independently of one another from Me, $^iPr$, $^tBu$, CN, $CF_3$ or Ph.

In a further embodiment of the organic molecules according to the invention, $R^a$ is the same or different in each occurrence and is selected from the group consisting of
H, me, $^tBu$;
Ph, which can in each case be substituted with one or more radicals selected independently of one another from Me, $^iPr$, $^tBu$, CN, $CF_3$ or Ph,
triazinyl, which can in each case be substituted with one or more radicals selected independently of one another from Me, Pr, $^tBu$, CN, $CF_3$ or Ph.

In a further embodiment of the organic molecules according to the invention, $R^a$ is the same in each occurrence and is H.

In a further embodiment of the organic molecules according to the invention, the second chemical unit D is the same or different in each occurrence and comprises a structure of Formula IIb, Formula IIb-2, Formula IIb-3 or Formula IIb-4 or consists thereof:

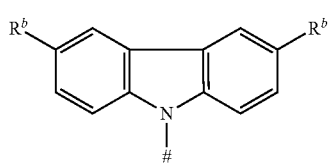

Formula IIb

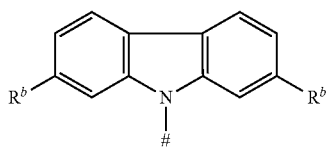

Formula IIb-2

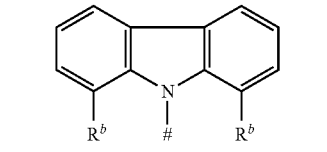

Formula IIb-3

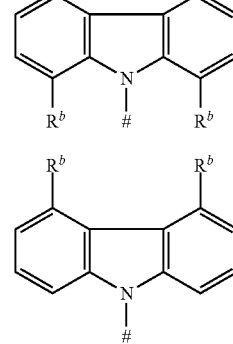

Formula IIb-4 wherein
$R^b$ is the same or different in each occurrence and is selected from the group consisting of:
$N(R^5)_2$, OH, $Si(R^5)_3$, $B(OR^5)_2$, $OSO_2R^5$, $CF_3$, CN, F, Br, I;
a linear alkyl, alkoxy or thioalkoxy group having 1 to 40 C atoms, wherein one or more non-adjacent $CH_2$ groups can be replaced by $R^5C=CR^5$, C=C, $Si(R^5)_2$, $Ge(R^5)_2$, $Sn(R^5)_2$, C=O, C=S, C=Se, C=$NR^5$, P(=O)(R$^5$), SO, SO$_2$, NR$^5$, O, S or CONR$^5$ and wherein one or more H atoms can be replaced by deuterium, CN, CF$_3$ or NO$_2$;

a linear alkenyl or alkynyl group having 2 to 40 C atoms, wherein one or more non-adjacent CH$_2$ groups can be replaced by R$^5$C=CR$^5$, C≡C, Si(R$^5$)$_2$, Ge(R$^5$)$_2$, Sn(R$^5$)$_2$, C=O, C=S, C=Se, C=NR$^5$, P(=O)(R$^5$), SO, SO$_2$, NR$^5$, O, S or CONR$^5$ and wherein one or more H atoms can be replaced by deuterium, CN, CF$_3$ or NO$_2$;

a branched or cyclic alkyl, alkenyl, alkynyl, alkoxy or thioalkoxy group having 3 to 40 C atoms, which can in each case be substituted with one or more radicals R$^5$, wherein one or more non-adjacent CH$_2$ groups can be replaced by R$^5$C=CR$^5$, C≡C, Si(R$^5$)$_2$, Ge(R$^5$)$_2$, Sn(R$^5$)$_2$, C=O, C=S, C=Se, C=NR$^5$, P(=O)(R$^5$), SO, SO$_2$, NR$^5$, O, S or CONR$^5$ and wherein one or more H atoms can be replaced by deuterium, CN, CF$_3$ or NO$_2$;

an aromatic ring system having 6 to 60 aromatic ring atoms, which can in each case be substituted with one or more radicals R$^5$;

a heteroaromatic ring system having 5 to 60 aromatic ring atoms, which can in each case be substituted with one or more radicals R$^5$;

an aryloxy or heteroaryloxy group having 5 to 60 aromatic ring atoms, which can in each case be substituted with one or more radicals R$^5$; and a diarylamino group, diheteroarylamino group or arylheteroarylamino group having 10 to 40 aromatic ring atoms, which can in each case be substituted with one or more radicals R$^5$;

Otherwise, the above-mentioned definitions apply.

In a further embodiment of the organic molecules according to the invention, the second chemical unit D is respectively the same or different in each occurrence and comprises a structure of Formula IIc, Formula IIc-2, Formula IIc-3 or Formula IIc-4 or consists thereof:

Formula IIc

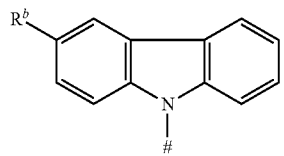

Formula IIc-2

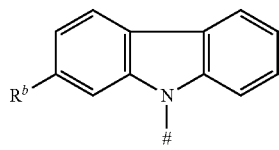

Formula IIc-3

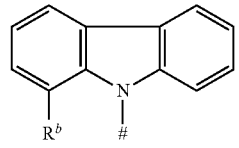

Formula IIc-4

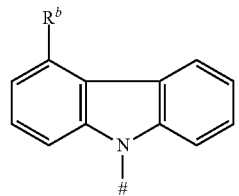

wherein the abovementioned definitions apply.

In a further embodiment of the organic molecules according to the invention, R$^b$ is the same or different in each occurrence and is selected from the group consisting of:

Me, $^i$Pr, $^t$Bu, CN, CF$_3$

Ph, which can in each case be substituted with one or more radicals selected independently of one another from Me, $^i$Pr, $^t$Bu, CN, CF$_3$ or Ph, pyridinyl, which can in each case be substituted with one or more radicals selected independently of one another from Me, $^i$Pr, $^t$Bu, CN, CF$_3$ or Ph, pyrimidinyl, which can in each case be substituted with one or more radicals selected independently of one another from Me, $^i$Pr, $^t$Bu, CN, CF$_3$ or Ph, triazinyl, which can in each case be substituted with one or more radicals selected independently of one another from Me, $^i$Pr, $^t$Bu, CN, CF$_3$ or Ph, carbazolyl which can in each case be substituted with one or more radicals selected independently of one another from Me, $^i$Pr, $^t$Bu, CN, CF$_3$ or Ph, and N(Ph)$_2$.

In a further embodiment of the organic molecules according to the invention, R$^b$ is the same or different in each occurrence and is selected from the group consisting of Me, $^i$Pr, $^t$Bu, CN, CF$_3$ Ph, which can in each case be substituted with one or more radicals selected independently of one another from Me, $^i$Pr, $^t$Bu, CN, CF$_3$ or Ph, pyridinyl, which can in each case be substituted with one or more radicals selected independently of one another from Me, Pr, $^t$Bu, CN, CF$_3$ or Ph, pyrimidinyl, which can in each case be substituted with one or more radicals selected independently of one another from Me, $^i$Pr, $^t$Bu, CN, CF$_3$ or Ph and triazinyl, which can in each case be substituted with one or more radicals selected independently of one another from Me, Pr, $^t$Bu, CN, CF$_3$ or Ph.

In a further embodiment of the organic molecules according to the invention, R$^b$ is the same or different in each occurrence and is selected from the group consisting of Me, $^t$Bu, Ph, which can in each case be substituted with one or more radicals selected independently of one another from Me, $^i$Pr, $^t$Bu, CN, CF$_3$ or Ph, and triazinyl, which can in each case be substituted with one or more radicals selected independently of one another from Me, $^i$Pr, $^t$Bu, CN, CF$_3$ or Ph.

Examples of the second chemical unit D are shown below:

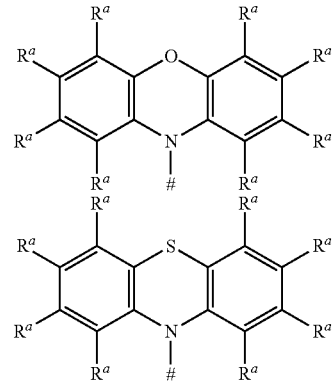

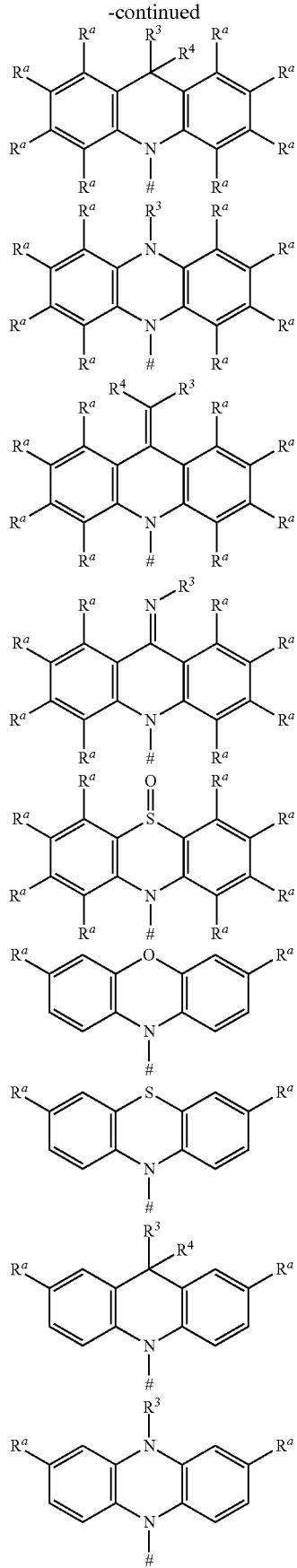
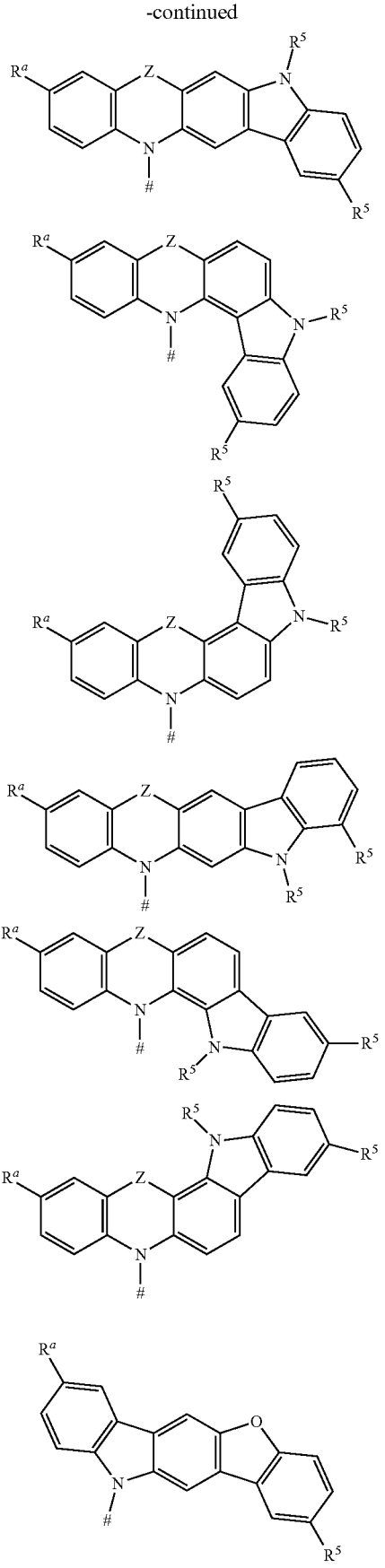

-continued

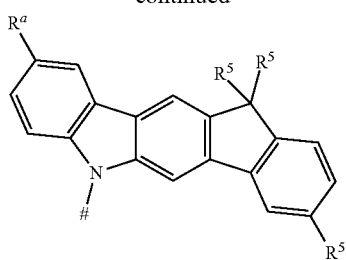
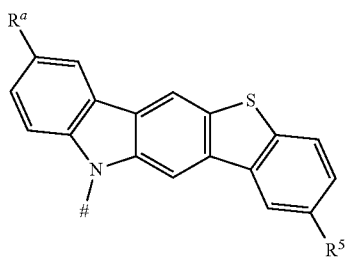
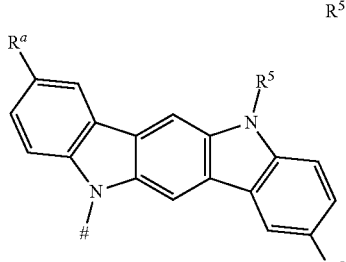
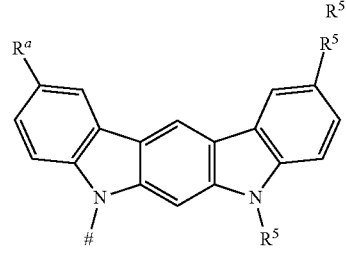
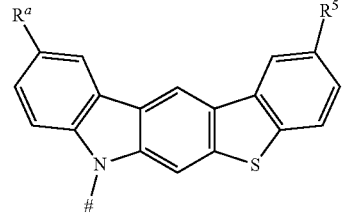
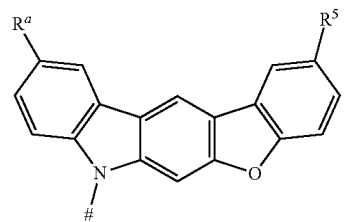
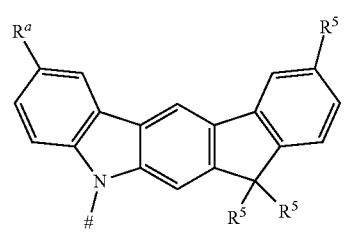

-continued

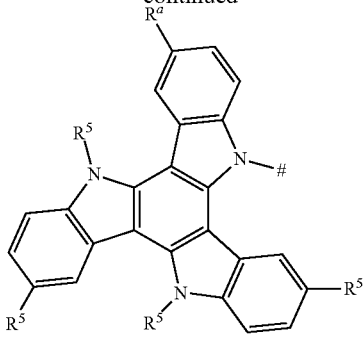

wherein the abovementioned definitions apply for #, Z, $R^1$, $R^3$, $R^4$ and $R^5$. In one embodiment, the radical $R^5$ is the same or different in each occurrence and is selected from the group consisting of H, methyl, ethyl, phenyl and mesityl. In one embodiment, the radical $R^1$ is the same or different in each occurrence and is selected from the group consisting of H, methyl (Me), i-propyl ($CH(CH_3)_2$) ($^i$Pr), t-butyl ($^t$Bu), phenyl (Ph), CN, $CF_3$ and diphenylamine ($NPh_2$).

In one embodiment, the organic molecules according to the invention comprise a structure of Formula III-1 or Formula III-2 or consist thereof:

Formula III-1

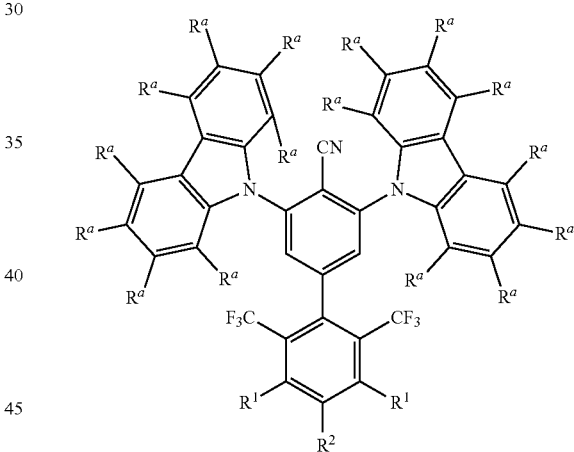

Formula III-2

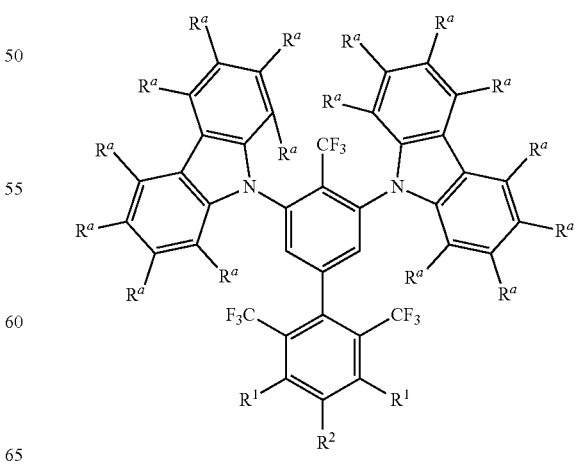

wherein the abovementioned definitions apply.

In a further embodiment, the organic molecules according to the invention have a structure of Formula IIIa-1 or Formula IIIa-2:

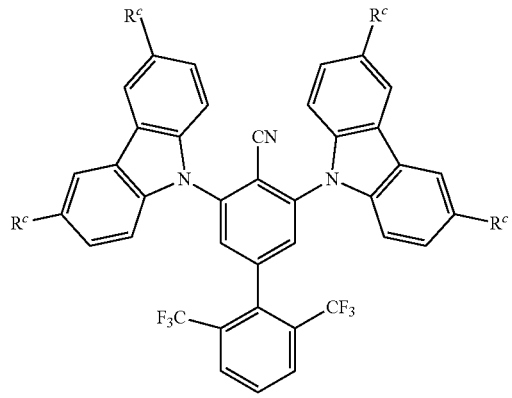

Formula IIIa-1

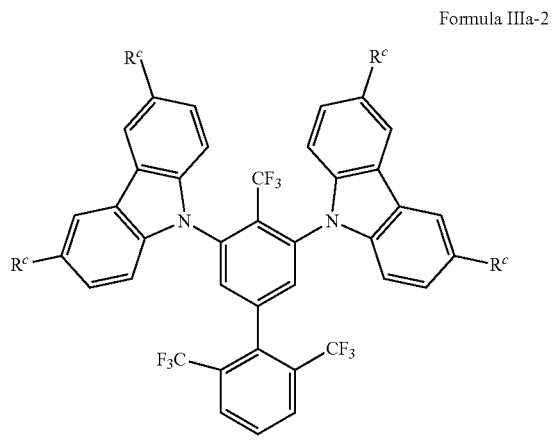

Formula IIIa-2 wherein in each occurrence $R^c$ is independently selected from the group consisting of Me, $^i$Pr, $^t$Bu, CN, CF$_3$, Ph, which can in each case be substituted with one or more radicals selected from Me, $^i$Pr, $^t$Bu, CN, CF$_3$ or Ph, pyridinyl, which can in each case be substituted with one or more radicals selected from Me, $^i$Pr, $^t$Bu, CN, CF$_3$ or Ph, pyrimidinyl, which can in each case be substituted with one or more radicals selected from Me, $^i$Pr, $^t$Bu, CN, CF$_3$ or Ph, carbazolyl, which can in each case be substituted with one or more radicals selected from Me, $^i$Pr, $^t$Bu, CN. CF$_3$ or Ph, triazinyl, which can in each case be substituted with one or more radicals selected from Me, $^i$Pr, $^t$Bu, CN, CF$_3$ or Ph. and N(Ph)$_2$.

In a further embodiment, the organic molecules according to the invention comprise a structure of Formula IIIb-1 or Formula IIIb-2 or consist thereof:

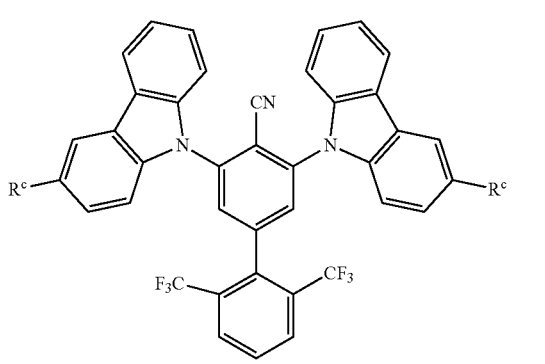

Formula IIIb-1

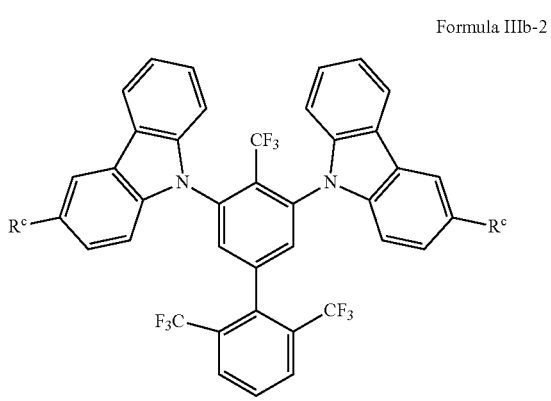

Formula IIIb-2 wherein the abovementioned definitions apply.

In a further embodiment, the organic molecules according to the invention comprise a structure of Formula IIIc-1 or Formula IIIc-2 or consist thereof:

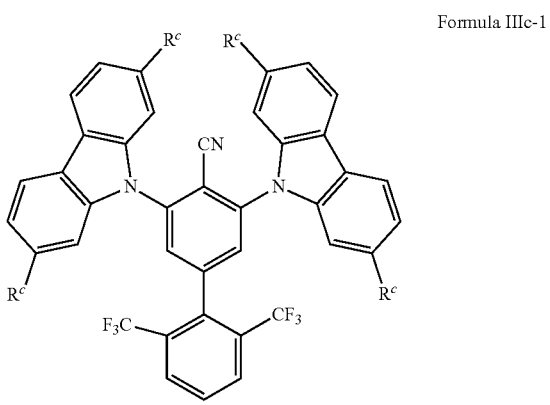

Formula IIIc-1

15

-continued

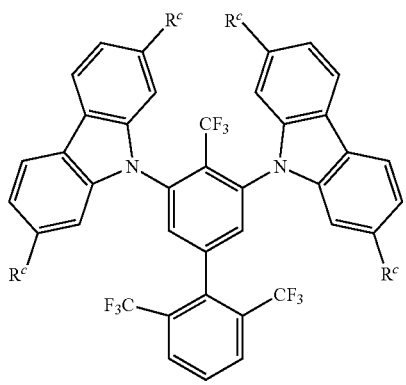

Formula IIIc-2 wherein the abovementioned definitions apply.

In a further embodiment, the organic molecules according to the invention comprise a structure of Formula IIId-1 or Formula IIId-2 or consist thereof:

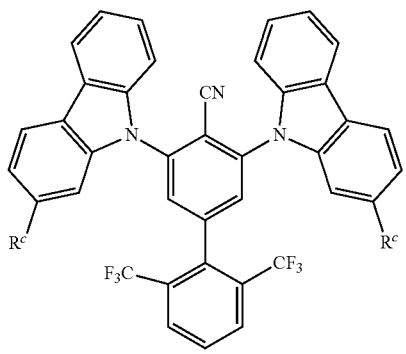

Formula IIId-1

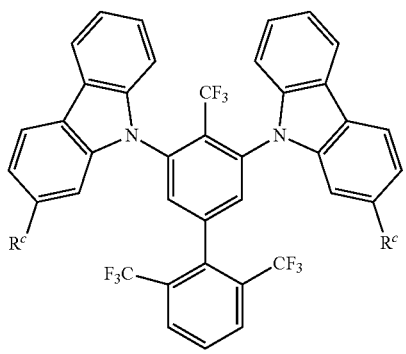

Formula IIId-2 wherein the abovementioned definitions apply.

16

In one embodiment, the organic molecules according to the invention comprise a structure of Formula IV-1 or Formula IV-2 or consist thereof:

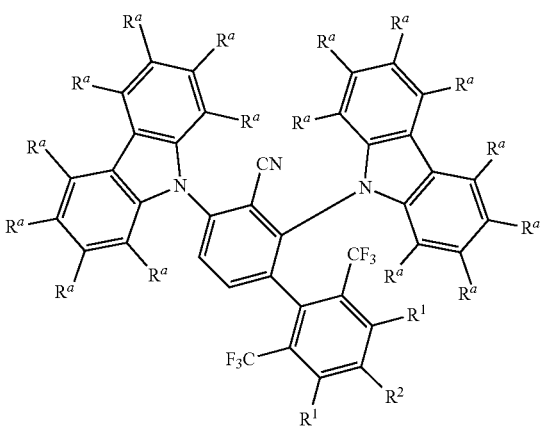

Formula IV-1

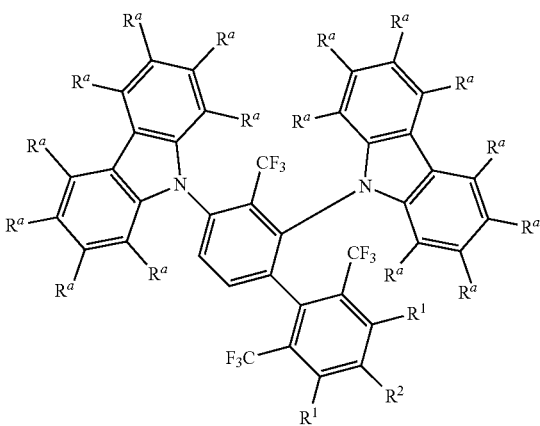

Formula IV-2 wherein the abovementioned definitions apply.

In a further embodiment, the organic molecules according to the invention comprise a structure of Formula IVa-1 or Formula IVa-2 or consist thereof:

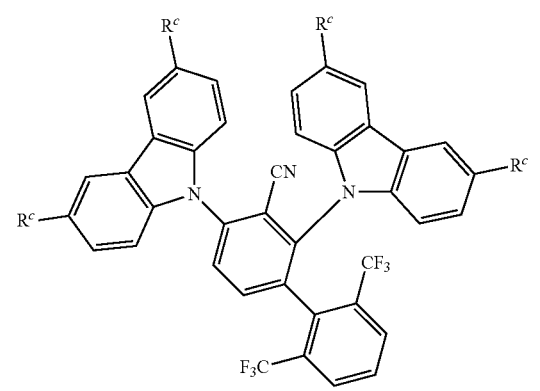

Formula IVa-1

-continued

Formula IVa-2

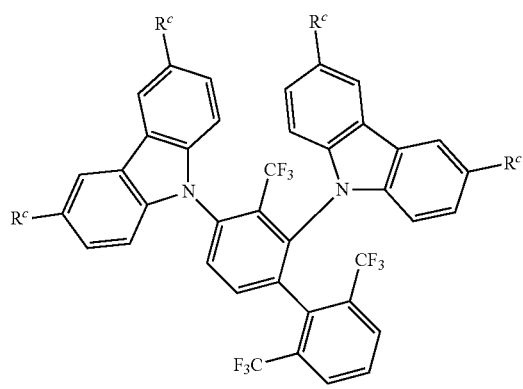

wherein the abovementioned definitions apply.

In a further embodiment, the organic molecules according to the invention comprise a structure of Formula IVb-1 or Formula IVb-2 or consist thereof:

Formula IVb-1

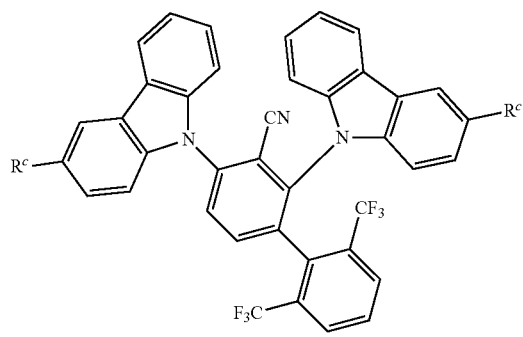

Formula IVb-2

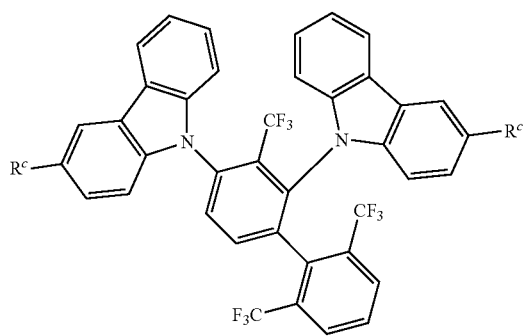

wherein the abovementioned definitions apply.

In a further embodiment, the organic molecules according to the invention comprise a structure of Formula IVc-1 or Formula IVc-2 or consist thereof:

Formula IVc-1

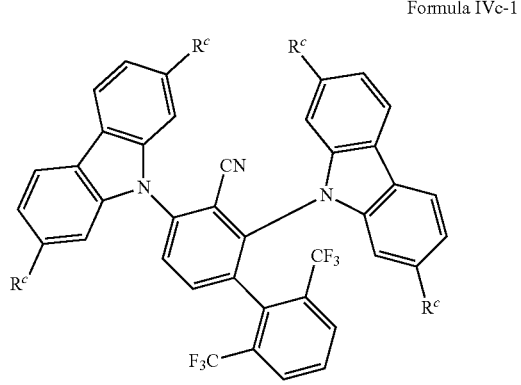

Formula IVc-2

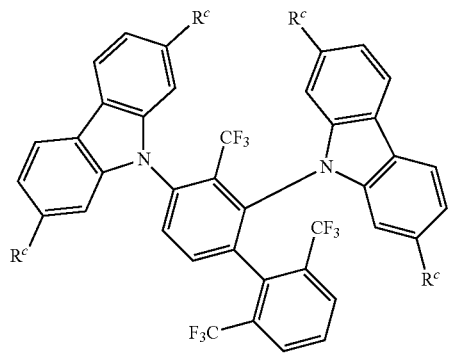

wherein the abovementioned definitions apply.

In a further embodiment, the organic molecules according to the invention comprise a structure of Formula IVd-1 or Formula IVd-2 or consist thereof:

Formula IVd-1

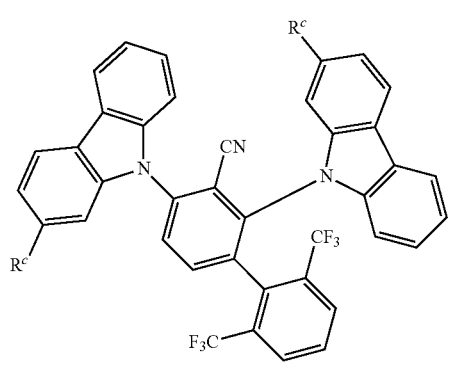

-continued

Formula IVd-2

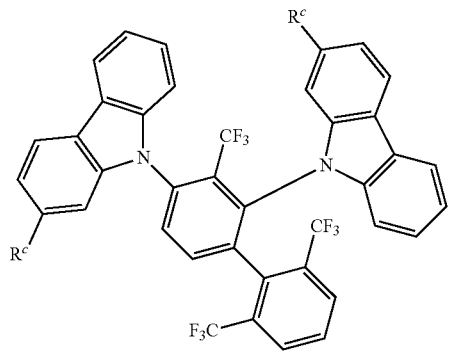

wherein the abovementioned definitions apply.

In one embodiment, the organic molecules according to the invention comprise a structure of Formula V-1 or Formula V-2 or consist thereof:

Formula V-1

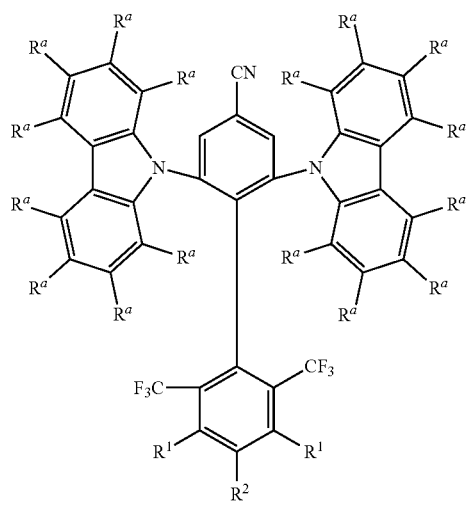

Formula V-2

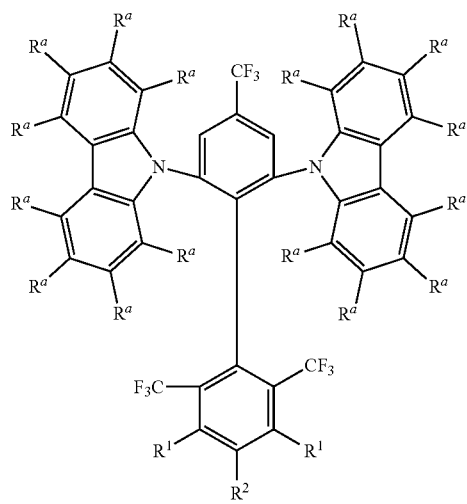

wherein the abovementioned definitions apply.

In a further embodiment, the organic molecules according to the invention comprise a structure of Formula Va-1 or Formula Va-2 or consist thereof:

Formula Va-1

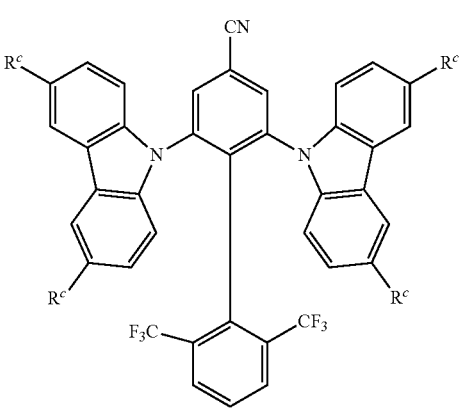

Formula Va-2

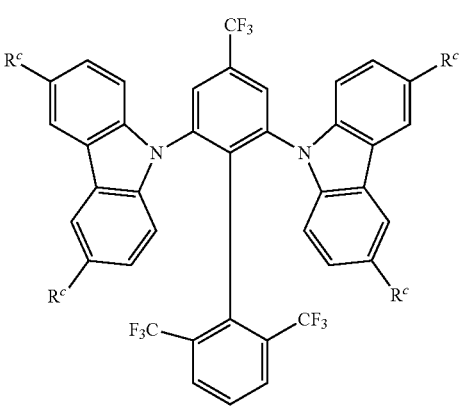

wherein the abovementioned definitions apply.

In a further embodiment, the organic molecules according to the invention comprise a structure of Formula Vb-1 or Formula Vb-2 or consist thereof:

Formula Vb-1

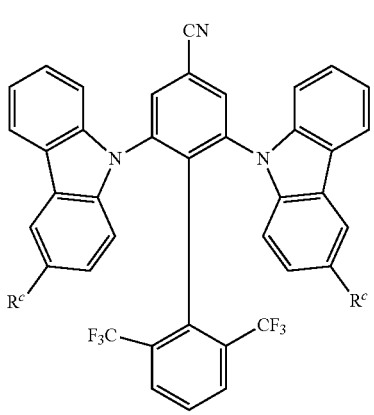

-continued

Formula Vb-2

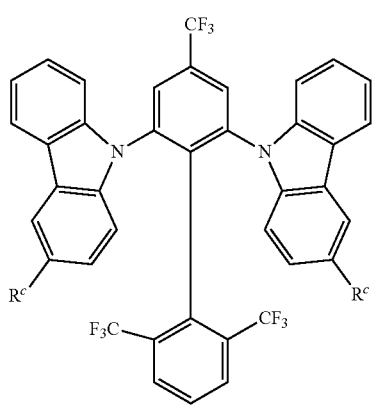

wherein the abovementioned definitions apply.

In a further embodiment, the organic molecules according to the invention comprise a structure of Formula Vc-1 or Formula Vc-2 or consist thereof:

Formula Vc-1

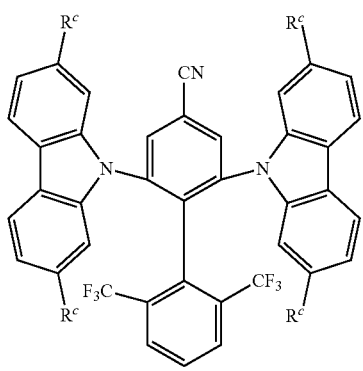

Formula Vc-2 wherein the abovementioned definitions apply.

In a further embodiment, the organic molecules according to the invention comprise a structure of Formula Vd-1 or Formula Vd-2 or consist thereof:

Formula Vd-1

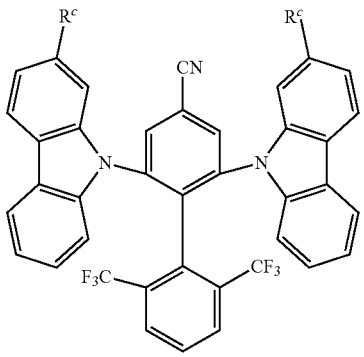

Formula Vd-2

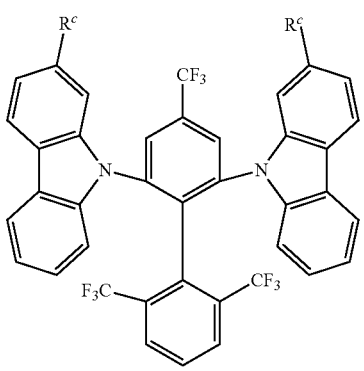

wherein the abovementioned definitions apply.

In one embodiment, the organic molecules according to the invention comprise a structure of Formula VI-1 or Formula VI-2 or consist thereof:

Formula VI-1

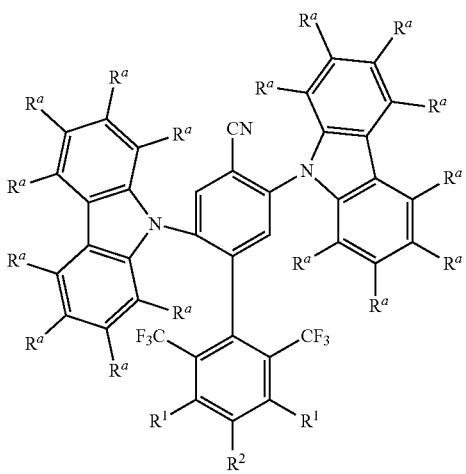

Formula VI-2

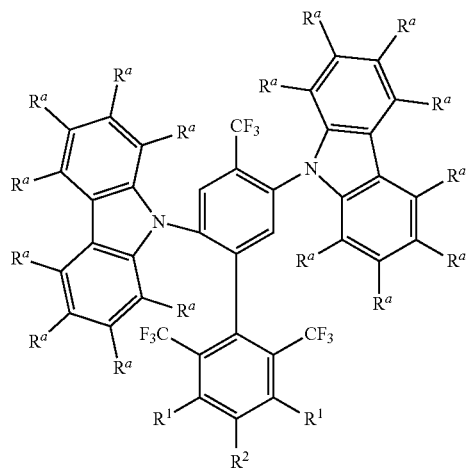

wherein the abovementioned definitions apply.

Formula VIa-2

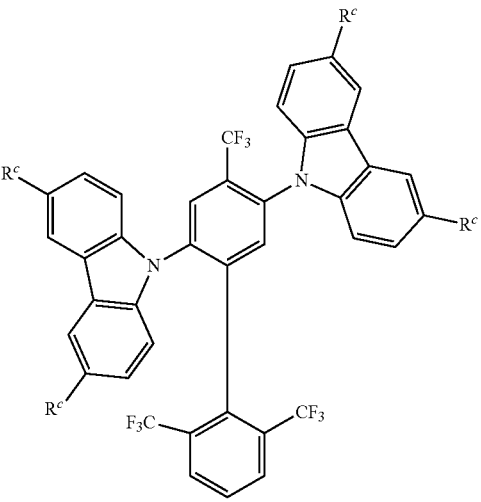

wherein the abovementioned definitions apply.

In a further embodiment, the organic molecules according to the invention comprise a structure of Formula Via-1 or of Formula Via-2 or consist thereof:

Formula VIa-1

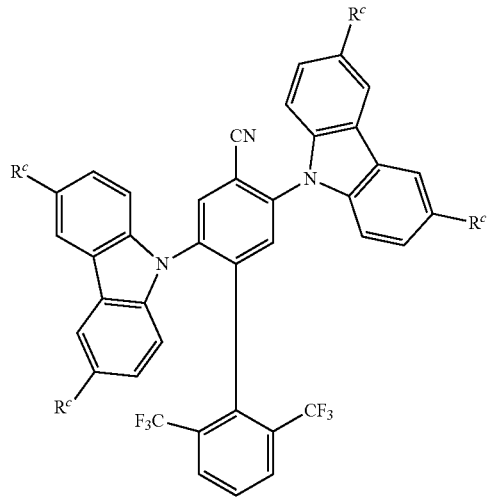

In a further embodiment, the organic molecules according to the invention comprise a structure of Formula VIb-1 or Formula VIb-2 or consist thereof:

Formula VIb-1

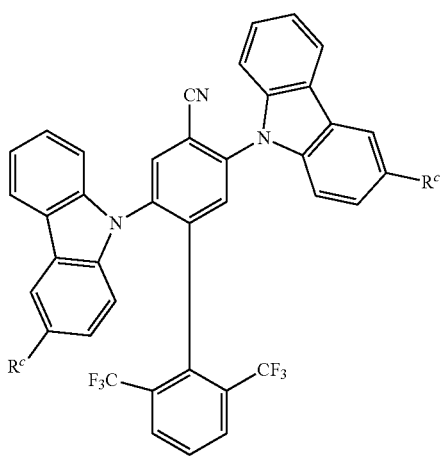

Formula VIb-2

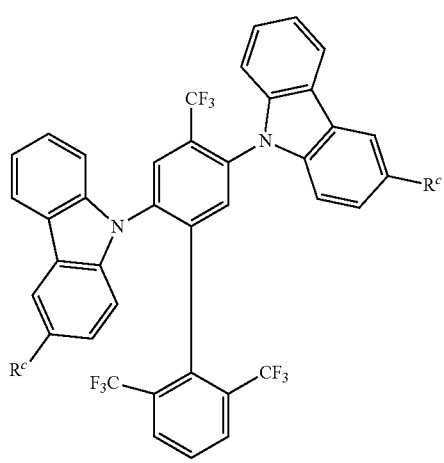

wherein the abovementioned definitions apply.

In a further embodiment, the organic molecules according to the invention comprise a structure of Formula VIc-1 or Formula VIc-2 or consist thereof:

Formula VIc-1

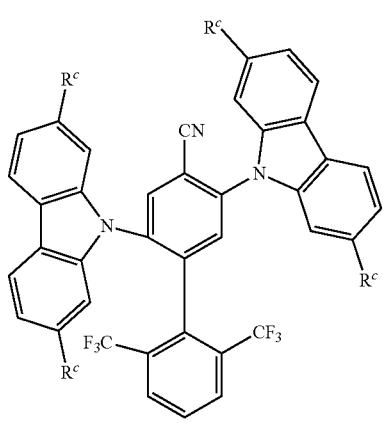

Formula VIc-2

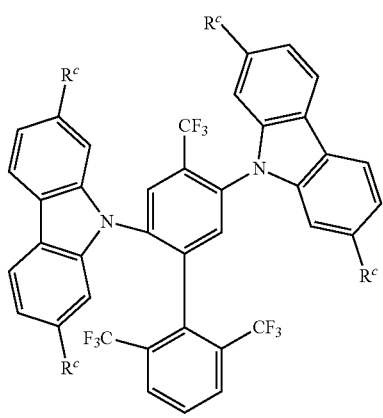

wherein the abovementioned definitions apply.

In a further embodiment, the organic molecules according to the invention comprise a structure of Formula VId-1 or Formula VId-2 or consist thereof:

Formula VId-1

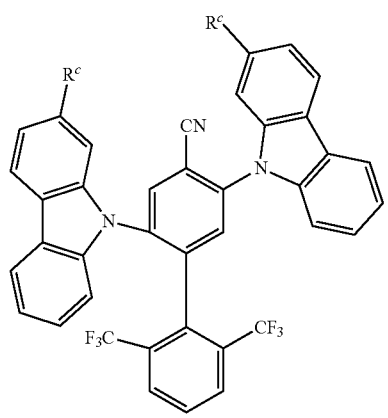

Formula VId-2

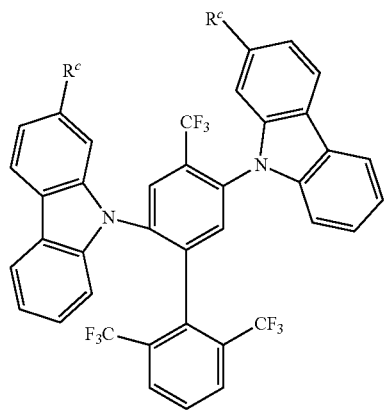

wherein the abovementioned definitions apply.

In one embodiment, the organic molecules according to the invention comprise a structure of Formula VII-1 or Formula VII-2 or consist thereof:

Formula VII-1

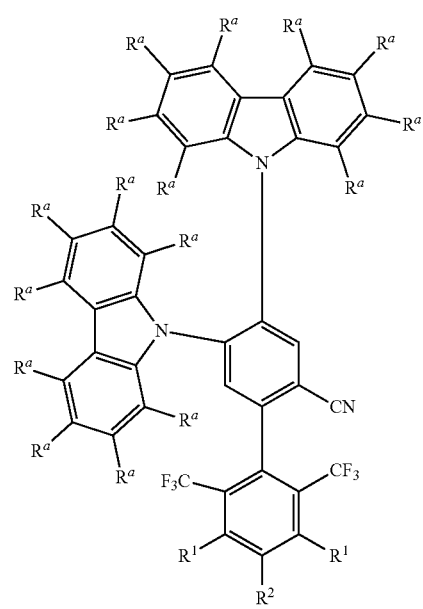

-continued

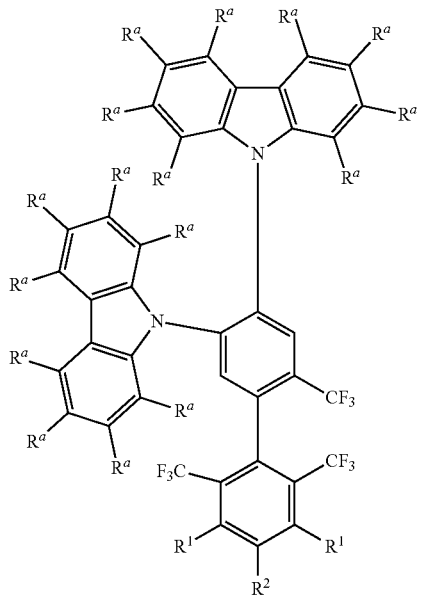

Formula VII-2 wherein the abovementioned definitions apply.

In a further embodiment, the organic molecules according to the invention comprise a structure of Formula VIIa-1 or Formula VIIa-2 or consist thereof:

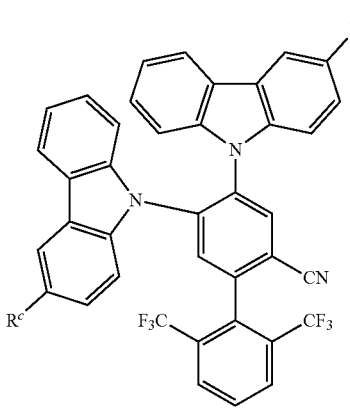

Formula VIIa-1

Formula VIIa-2 wherein the abovementioned definitions apply.

In a further embodiment, the organic molecules according to the invention comprise a structure of Formula VIIb-1 or Formula VIIb-2 or consist thereof:

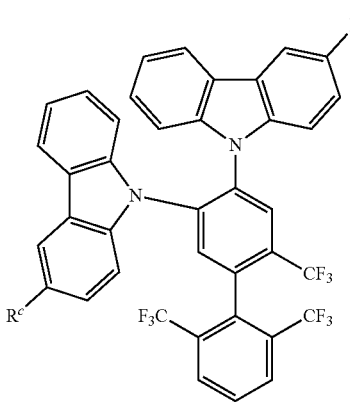

Formula VIIb-1

Formula VIIb-2 wherein the abovementioned definitions apply.

In a further embodiment, the organic molecules according to the invention comprise a structure of Formula VIIc-1 or Formula VIIc-2 or consist thereof:

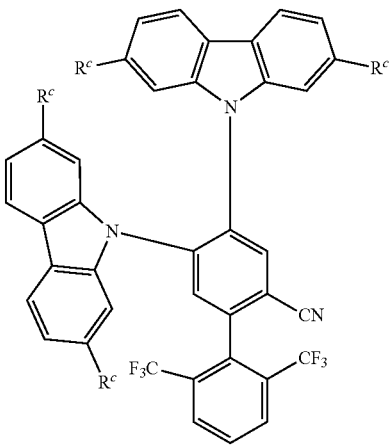

Formula VIIc-1

Formula VIIc-2

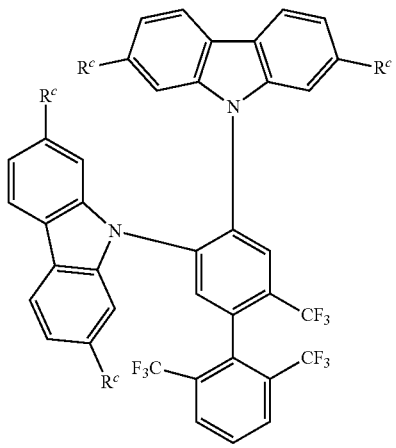

wherein the abovementioned definitions apply.

In a further embodiment, the organic molecules according to the invention comprise a structure of Formula VIId-1 or Formula VIId-2 or consist thereof:

Formula VIId-1

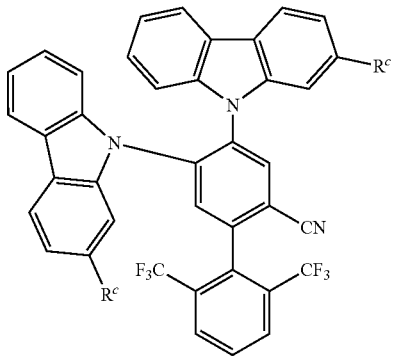

Formula VIId-2

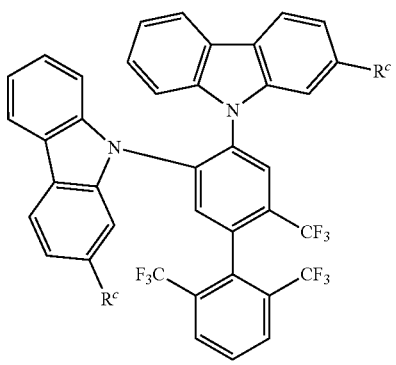

wherein the abovementioned definitions apply.

In one embodiment, the organic molecules according to the invention comprise a structure of Formula VIII-1 or Formula VIII-2 or consist thereof:

Formula VIII-1

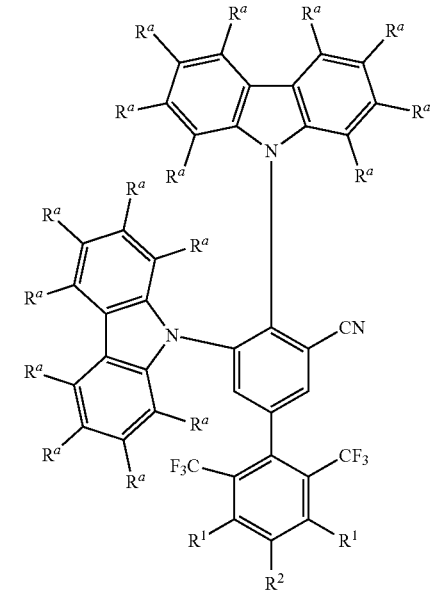

Formula VIII-2

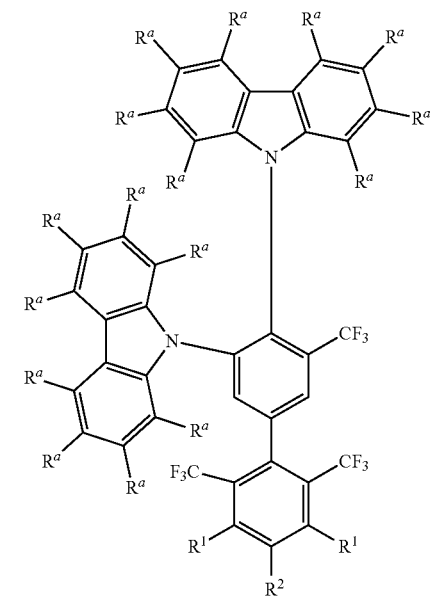

wherein the abovementioned definitions apply.

In one embodiment, the organic molecules according to the invention comprise a structure of Formula VIIIa-1 or Formula VIIIa-2 or consist thereof:

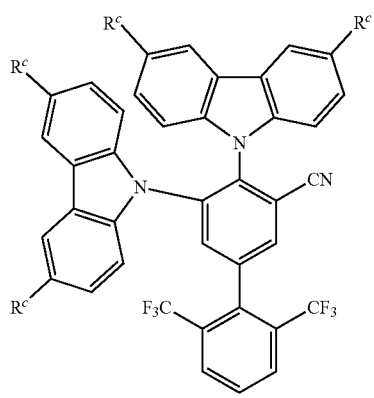

Formula VIIIa-1

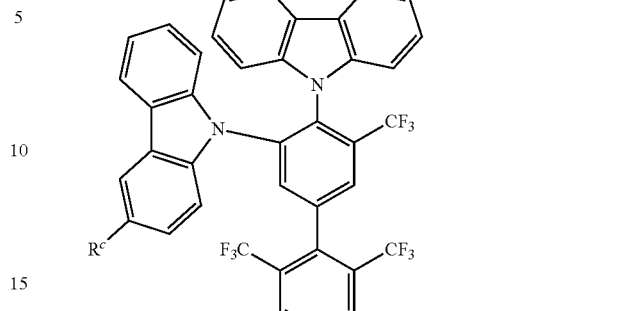

Formula VIIIb-2 wherein the abovementioned definitions apply.

In one embodiment, the organic molecules according to the invention comprise a structure of Formula VIIIc-1 or Formula VIIIc-2 or consist thereof:

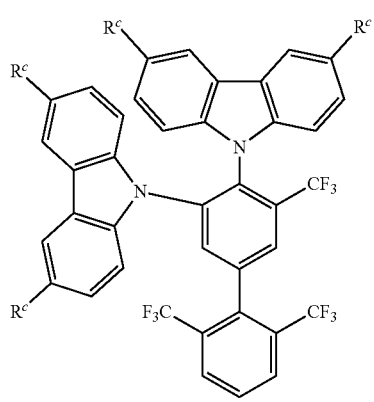

Formula VIIIa-2

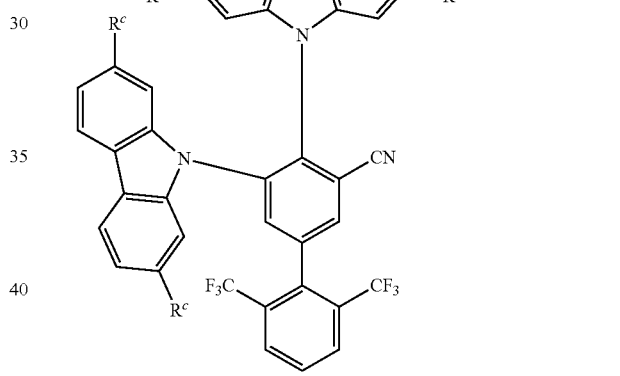

Formula VIIIc-1 wherein the abovementioned definitions apply.

In one embodiment, the organic molecules according to the invention comprise a structure of Formula VIIIb-1 or Formula VIIIb-2 or consist thereof:

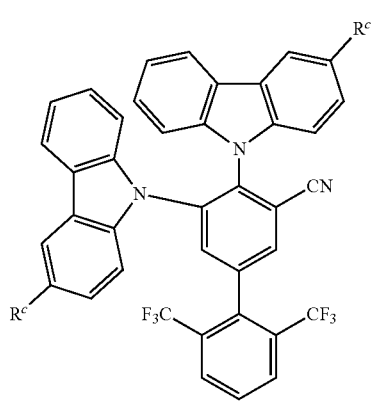

Formula VIIIb-1

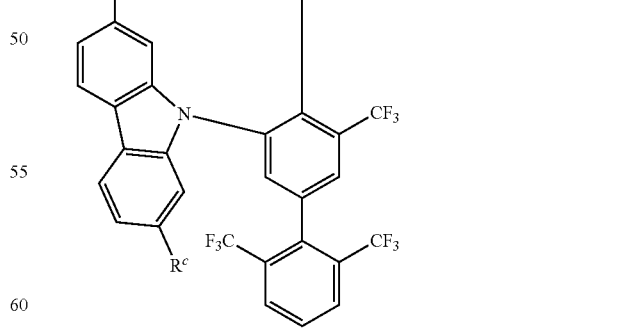

Formula VIIIc-2 wherein the abovementioned definitions apply.

In one embodiment, the organic molecules according to the invention comprise a structure of Formula VIIId-1 or Formula VIId-2 or consist thereof:

Formula VIIId-1

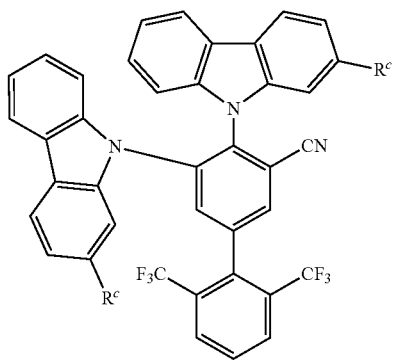

Formula VIIId-2

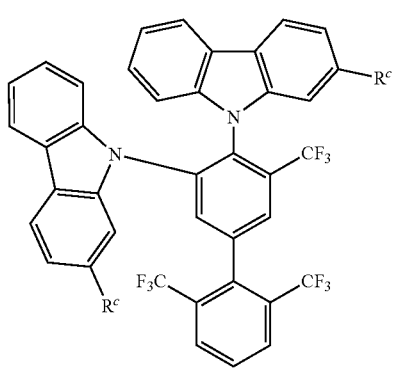

wherein the abovementioned definitions apply.

In one embodiment, in each occurrence $R^c$ is independently selected from the group consisting of
CN,
$CF_3$,
Me,
$^iPr$,
$^tBu$,
Ph, which can in each case be substituted with one or more radicals selected from CN, $CF_3$,
Me, $^iPr$, $^tBu$, CN, $CF_3$ or Ph,
1,3,5-triazinyl, which can in each case be substituted with one or more radicals selected from CN, $CF_3$, Me, $^iPr$, $^tBu$, CN, $CF_3$ or Ph, and
carbazolyl, which can in each case be substituted with one or more radicals selected from CN, $CF_3$, Me, $^iPr$, $^tBu$, or Ph.

In one embodiment, in each occurrence $R^c$ is independently selected from the group consisting of
Me,
$^tBu$,
Ph, which can in each case be substituted with one or more radicals selected from CN, $CF_3$, Me, $^iPr$, $^tBu$, CN, $CF_3$ or Ph, and
1,3,5-triazinyl, which can in each case be substituted with one or more radicals selected from CN, $CF_3$, Me, $^iPr$, $^tBu$, CN, $CF_3$ or Ph.

In the context of this invention, an aryl group contains 6 to 60 aromatic ring atoms; a heteroaryl group contains 5 to 60 aromatic ring atoms, at least one of which represents a heteroatom. The heteroatoms are, in particular, N, O and/or S. In the event that other definitions, which differ from the stated definitions, for example with respect to the number of aromatic ring atoms or the contained heteroatoms, are specified in the description of specific embodiments of the invention, then these definitions apply.

An aryl group or heteroaryl group is understood to be a simple aromatic ring, i.e. benzene, or a simple heteroaromatic ring, for example pyridine, pyrimidine or thiophene, or a heteroaromatic polycyclic compound, for example phenanthrene, quinoline or carbazole. In the context of the present application, a condensed (annelated) aromatic or heteroaromatic polycyclic compound consists of two or more simple aromatic or heteroaromatic rings which are condensed with one another.

An aryl or heteroaryl group, which can be respectively substituted with the abovementioned radicals and which can be linked to the aromatic or heteroaromatic group via any desired positions, are in particular understood to be groups which are derived from benzene, naphthalene, anthracene, phenanthrene, pyrene, dihydropyrene, chrysene, perylene, fluoranthene, benzanthracene, benzophenanthrene, tetracene, pentacene, benzopyrene, furan, benzofuran, isobenzofuran, dibenzofuran, thiophene, benzothiophene, isobenzothiophene, dibenzothiophene; pyrrole, indole, isoindole, carbazole, pyridine, quinoline, isoquinoline, acridine, phenanthridine, benzo-5,6-quinoline, isoquinoline, benzo-6,7-quinoline, benzo-7,8-quinoline, phenothiazine, phenoxazine, pyrazole, indazole, imidazole, benzimidazole, naphthimidazole, phenanthrimidazole, pyridimidazole, pyrazinimidazole, quinoxalinimidazole, oxazole, benzoxazole, napthoxazole, anthroxazole, phenanthroxazole, isoxazole, 1,2-thiazole, 1,3-thiazole, benzothiazole, pyridazine, benzopyridazine, pyrimidine, benzopyrimidine, quinoxaline, pyrazine, 1,3,5-triazine, phenazine, naphthyridine, azacarbazole, benzocarboline, phenanthroline, 1,2,3-triazole, 1,2,4-triazole, benzotriazole, 1,2,3-oxadiazole, 1,2,4-oxadiazole, 1,2,5-oxadiazole, 1,2,3,4-tetrazine, purine, pteridine, indolizine and benzothiadiazole or combinations of said groups.

A cyclic alkyl, alkoxy or thioalkoxy group is understood here to be a monocyclic, a bicyclic or a polycyclic group.

Within the scope of the present invention, a $C_1$ to $C_{40}$ alkyl group, in which individual H atoms or $CH_2$ groups can also be substituted with the groups mentioned above, are understood to be, for example, the radicals methyl, ethyl, n-propyl, i-propyl, cyclopropyl, n-butyl, i-butyl, s-butyl, t-butyl, cyclobutyl, 2-methylbutyl, n-pentyl, s-pentyl, t-pentyl, 2-pentyl, neopentyl, cyclopentyl, n-hexyl, s-hexyl, t-hexyl, 2-hexyl, 3-hexyl, neohexyl, cyclohexyl, 1-methylcyclopentyl, 2-methylpentyl, n-heptyl, 2-heptyl, 3-heptyl, 4-heptyl, cycloheptyl, 1-methylcyclohexyl, n-octyl, 2-ethyihexyl, cyclooctyl, 1-bicyclo[2,2,2]octyl, 2-bicyclo[2,2,2]-octyl, 2-(2,6-dimethyl)octyl, 3-(3,7-dimethyl)octyl, adamantyl, trifluoromethyl, pentafluorethyl, 2,2,2-trifluoroethyl, 1,1-dimethyl-n-hex-1-yl-, 1,1-dimethyl-n-hept-1-yl-, 1,1-dimethyl-n-oct-1-yl-, 1,1-dimethyl-n-dec-1-yl-, 1,1-dimethyl-n-dodec-1-yl-, 1,1-dimethyl-n-tetradec-1-yl-, 1,1-dimethyl-n-hexadec-1-yl-, 1,1-dimethyl-n-octadec-1-yl-, 1,1-diethyl-n-hex-1-yl-, 1,1-diethyl-n-hept-1-yl-, 1,1-diethyl-n-oct-1-yl-, 1,1-diethyl-n-dec-1-yl-, 1,1-diethyl-n-dodec-1-yl-, 1,1-diethyl-n-tetradec-1-yl-, 1,1-diethyln-n-hexadec-1-yl-, 1,1-diethyl-n-octadec-1-yl-, 1-(n-propyl)-cyclohex-1-yl-, 1-(n-butyl)-cyclohex-1-yl-, 1-(n-hexyl)-cyclohex-1-yl-, 1-(n-octyl)-cyclohex-1-yl- and 1-(n-decyl)-cyclohex-1-yl. An alkenyl group is understood to be ethenyl, propenyl, butenyl, pentenyl, cyclopentenyl, hexenyl, cyclohexenyl, heptenyl, cycloheptenyl, octenyl, cyclooctenyl or cyclooctadienyl, for example. An alkynyl group is understood to be ethinyl, propinyl, butinyl, pentinyl, hexinyl, heptinyl or octinyl, for example. A $C_1$ to $C_{40}$ alkoxy group is understood to be methoxy, trifluoromethoxy, ethoxy, n-propoxy, i-propoxy, n-butoxy, i-butoxy, s-butoxy, t-butoxy or 2-methylbutoxy, for example.

One embodiment of the invention relates to organic molecules having an $\Delta E(S_1-T_1)$ value between the lowest excited singlet ($S_1$) state and the triplet ($T_1$) state below it of no more than 5000 cm$^{-1}$, in particular no more than 3,000 cm$^{-1}$, or no more than 1500 cm$^{-1}$ or 1000 cm$^{-1}$, and/or an emission lifetime of at most 150 μs, in particular at most 100 μs, at most 50 μs, or at most 10 μs, in a film made of poly(methyl methacrylate) (PMMA) comprising 10 percent by mass of the organic molecule at room temperature and/or a main emission band having a full width at half maximum less than 0.55 eV, in particular less than 0.50 eV, less than 0.48 eV, or less than 0.45 eV, in a film of poly(methyl methacrylate) (PMMA) comprising 10 percent by mass of the organic molecule at room temperature.

In a further aspect, the invention relates to an OLED having an emission that is as close as possible to the CIEx and CIEy color coordinates of the primary color blue, which, according to Recommendation 2020, are suggested as CIEx (=0.131) and CIEy (=0.046) and are thus suitable for ultra high definition (UHD) screens, e.g. in UHD TVs.

Accordingly, a further aspect of the invention relates to an OLED, the emission of which is between the CIEx color coordinates 0.02 and 0.30, preferably between 0.08 and 0.18 and particularly preferably between 0.10 and 0.15, and/or between the CIEy color coordinates 0.00 and 0.45, preferably between 0.01 and 0.30, more preferably between 0.02 and 0.20 and particularly preferably between 0.03 and 0.15, and/or even between 0.04 and 0.10.

In a further aspect, the invention relates to an OLED having an emission that is as close as possible to the CIEx and CIEy color coordinates of the primary color green, which, according to Recommendation 2020, are suggested as CIEx (=0.170) and CIEy (=0.797) and are thus suitable for ultra high definition (UHD) screens, e.g. in UHD TVs.

Accordingly, a further aspect of the invention relates to an OLED, the emission of which is between the CIEx color coordinates 0.05 and 0.30, preferably between 0.10 and 0.20 and particularly preferably between 0.15 and 0.18, and/or between the CIEy color coordinates 0.35 and 1.25, preferably between 0.50 and 1.10, more preferably between 0.60 and 1.00 and particularly preferably between 0.65 and 0.95, and/or even between 0.70 and 0.90.

In a further aspect, the invention relates to a method for producing an organic molecule according to the invention of the type described here (with a possible subsequent reaction), wherein a 4,6-$R^1$-5-$R^2$-2-chloro/bromo-1,3-di(trifluoromethyl)benzene is used as the educt.

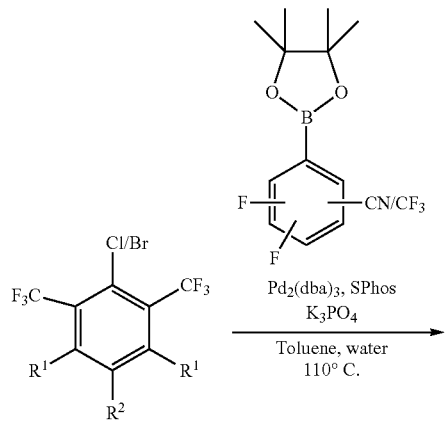

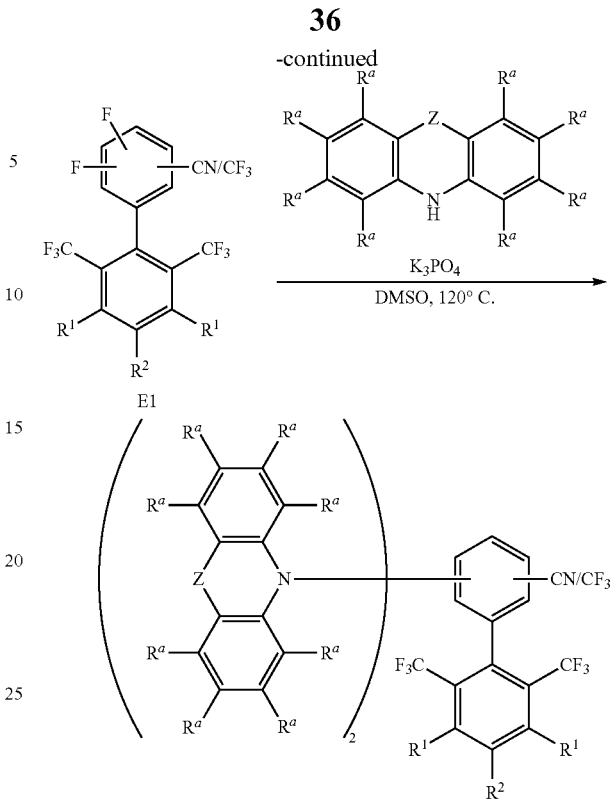

According to the invention, a boronic acid can be used in the reaction for the synthesis of E1 instead of a boronic acid ester.

In one embodiment, a 4,6-$R^1$-5-$R^2$-2-chloro/bromo-1,3-di(trifluoromethyl)benzene as the educt is reacted with a difluoro-cyano/trifluoromethyl-phenylboronic acid or a corresponding difluoro-cyano/trifluoromethyl-phenylboronic acid ester in a palladium-catalyzed cross-coupling reaction. According to the invention, 2,6-difluoro-4-cyano/trifluoromethyl-phenylboronic acid, 2,5-difluoro-4-cyano/trifluoromethyl-phenylboronic acid, 3,5-difluoro-4-cyano/trifluoromethyl-phenylboronic acid, 4,5-difluoro-3-cyano/trifluoromethyl-phenylboronic acid, 2,4-difluoro-3-cyano/trifluoromethyl-phenylboronic acid and 4,5-difluoro-2-cyano/trifluoromethyl-phenylboronic acid, for example, can be used. The product is obtained by deprotonation of the corresponding amine and subsequent nucleophilic substitution of the two fluorine groups. To do this, two nitrogen heterocyclic compounds are reacted with an educt E1 in the context of a nucleophilic aromatic substitution. Typical conditions include the use of a base, such as potassium phosphate tribasic or sodium hydride, in an aprotic polar solvent, such as dimethyl sulfoxide (DMSO) or N,N-dimethyl formamide (DMF).

In a further aspect, the invention relates to the use of the organic molecules as a luminescent emitter or as a host material in an optoelectronic device, in particular wherein the optoelectronic device is selected from the group consisting of:
organic light-emitting diodes (OLEDs),
light-emitting electrochemical cells,
OLED sensors, in particular in gas and vapor sensors which are not hermetically shielded to the outside,
organic diodes,
organic solar cells,
organic transistors, organic field-effect transistors,
organic lasers and
down-conversion elements.

In a further aspect, the invention relates to a composition comprising or consisting of:
(a) at least one organic molecule according to the invention, in particular as an emitter and/or host, and
(b) at least one, i.e. one or more emitter and/or host materials, that is or are different from the organic molecule according to the invention, and
(c) optionally one or more dyes and/or one or more organic solvents.

In one embodiment, the composition according to the invention consists of an organic molecule according to the invention and one or more host materials. In particular, the host material or materials possess triplet ($T_1$) and singlet ($S_1$) energy levels, which are energetically higher than the triplet ($T_1$) and singlet ($S_1$) energy levels of the organic molecule according to the invention. In one embodiment, in addition to the organic molecule according to the invention, the composition has an electron-dominant and a hole-dominant host material. The highest occupied orbital (HOMO) and the lowest unoccupied orbital (LUMO) of the hole-dominant host material are, in particular, energetically higher than that of the electron-dominant host material. The HOMO of the hole-dominant host material is energetically below the HOMO of the organic molecule according to the invention, while the LUMO of the electron-dominant host material is energetically above the LUMO of the organic molecule according to the invention. In order to avoid exciplex formation between emitter and host material or host materials, the materials should be selected such that the energy gaps between the respective orbitals are small. The distance between the LUMO of the electron-dominant host material and the LUMO of the organic molecule according to the invention is, in particular, less than 0.5 eV, preferably less than 0.3 eV, even more preferably less than 0.2 eV. The distance between the HOMO of the hole-dominant host material and the HOMO of the organic molecule according to the invention is in particular less than 0.5 eV, preferably less than 0.3 eV, even more preferably less than 0.2 eV.

In a further aspect, the invention relates to an optoelectronic device which comprises an organic molecule according to the invention or a composition according to the invention. The optoelectronic device is in particular formed as a device selected from the group consisting of organic light-emitting diode (OLED); light-emitting electrochemical cell; OLED sensor, in particular gas and vapor sensors which are not hermetically shielded to the outside; organic diode; organic solar cell; organic transistor; organic field-effect transistor; organic laser and down-conversion element.

An optoelectronic device consisting of or comprising
a substrate,
an anode and
a cathode, wherein the anode or the cathode are disposed on the substrate, and
at least one light-emitting layer, which is disposed between the anode and the cathode and which has an organic molecule according to the invention, represents a further embodiment of the invention.

In one embodiment, the optoelectronic device is an OLED. A typical OLED, for example, has the following layer structure:
1. Substrate (supporting material)
2. Anode
3. Hole injection layer (HIL)
4. Hole transport layer (HTL)
5. Electron blocking layer (EBL)
6. Emitting layer (EML)
7. Hole blocking layer (HBL)
8. Electron transport layer (ETL)
9. Electron injection layer (EIL)
10. Cathode.

The presence of specific layers is merely optional. A number of these layers can also be the same. Specific layers can also be present more than once in the component.

According to one embodiment, at least one electrode of the optoelectronic device is configured to be translucent. In this case, "translucent" describes a layer that is transmissive to visible light. The translucent layer can be clearly translucent, i.e. transparent, or at least partially light-absorbing and/or partially light-diffusing, so that the translucent layer can, for example, also be diffusely or milkily translucent. A layer referred to here as translucent is, in particular, configured to be as transparent as possible, so that in particular the absorption of light is as low as possible.

According to a further embodiment, the optoelectronic device, in particular an OLED, has an inverted structure. The inverted structure is characterized in that the cathode is located on the substrate and the other layers are disposed in a correspondingly inverted manner.
1. Substrate (supporting material)
2. Cathode
3. Electron injection layer (EIL)
4. Electron transport layer (ETL)
5. Hole blocking layer (HBL)
6. Emission layer or emitting layer (EML)
7. Electron blocking layer (EBL)
8. Hole transport layer (HTL)
9. Hole injection layer (HIL)
10. Anode The presence of specific layers is merely optional. A number of these layers can also be the same. Specific layers can also be present more than once in the component.

In one embodiment, in the inverted OLED, the anode layer of the typical structure e.g. an ITO layer (indium tin oxide), is connected as the cathode.

According to a further embodiment, the optoelectronic device, in particular an OLED, has a stacked structure. In this case, the individual OLEDs are arranged one above the other and not next to one another as usual. The production of mixed light can be made possible with the aid of a stacked structure. This structure can be used to produce white light, for example.

To produce said white light, the entire visible spectrum is typically imaged by combining the emitted light of blue, green and red emitters. Furthermore, with practically the same efficiency and identical luminance, significantly longer lifetimes can be achieved in comparison to conventional OLEDs. A so-called charge generation layer (CGL) between two OLEDs is optionally used for the stacked structure. Said layer consists of an n-doped and a p-doped layer, wherein the n-doped layer is typically disposed closer to the anode.

In one embodiment, a so-called tandem OLED, two or more emission layers occur between the anode and the cathode. In one embodiment, three emission layers are arranged one above the other, wherein one emission layer emits red light, one emission layer emits green light and one emission layer emits blue light, and additional charge generation, blocking or transport layers are optionally disposed between the individual emission layers. In a further embodiment, the respective emission layers are disposed directly adjacent to one another. In another embodiment, one respective charge generation layer is situated between the emission layers. Emission layers that are directly adjacent to one another and emission layers that are separated by charge generation layers can furthermore be combined in one OLED.

An encapsulation arrangement can furthermore be disposed above the electrodes and the organic layers as well. The encapsulation arrangement can, for example, be designed in the form of a glass cover or in the form of a thin-film encapsulation arrangement.

The supporting material of the optoelectronic device can, for example, be glass, quartz, plastic, metal, a silicon wafer or any other suitable solid or flexible, optionally transparent, material. The supporting material can, for example, have one or more materials in the form of a layer, a film, a plate or a laminate.

Transparent conductive metal oxides such as, for example, ITO (indium tin oxide), zinc oxide, tin oxide, cadmium oxide, titanium oxide, indium oxide or aluminum zinc oxide (AZO), $Zn_2SnO_4$, $CdSnO_3$, $ZnSnO_3$, $MgIn_2O_4$, $GaInO_3$, $Zn_2In_2O_5$ or $In_4Sn_3O_{12}$ or mixtures of different transparent conductive oxides, can be used as the anode of the optoelectronic device.

PEDOT:PSS (poly-3,4-ethylenedioxythiophene: polystyrene sulfonic acid), PEDOT (poly-3,4-ethylenedioxythiophene). m-MTDATA (4,4',4"-tris[phenyl(m-tolyl)amino]triphenylamine), Spiro-TAD (2,2',7,7'-tetrakis(N,N-diphenylamino)-9,9-spirobifluorene), DNTPD (4,4'-bis[N-[4-{N,N-bis(3-methyl-phenyl)amino}phenyl]-N-phenylamino]biphenyl), NPB (N,N'-bis-(1-naphthalenyl)-N,N'-bis-phenyl-(1,1'-biphenyl)-4,4'-diamine), NPNPB (N,N'-diphenyl-N,N'-di-[4-(N,N-diphenyl-amino)phenyl]benzene), MeO-TPD (N,N,N',N'-tetrakis(4-methoxyphenyl)benzene), HAT-CN (1,4,5,8,9,11-hexaazatriphenylene-hexacarbonitrile) or Spiro-NPD (N,N'-diphenyl-N,N'-bis-(1-naphthyl)-9,9'-spirobifluorene-2,7-diamine), for example, are suitable materials for an HIL. The layer thickness is 10-80 nm, for example. Small molecules (e.g. copper phthalocyanine (CuPc e.g. 10 nm thick)) or metal oxides, such as $MoO_3$, $V_2O_5$, can also be used.

Tertiary amines, carbazole derivatives, polyethylenedioxythiophene doped with polystyrene sulfonic acid, polyaniline poly-TPD (poly(4-butylphenyl-diphenyl-amine)) doped with camphor sulfonic acid, [alpha]-NPD (poly(4-butylphenyl-diphenyl-amine)), TAPC (4,4'-cyclohexylidene-bis[N,N-bis(4-methylphenyl)benzenamine]), TCTA (tris(4-carbazoyl-9-ylphenyl)amine), 2-TNATA (4,4',4"-tris [2-naphthyl(phenyl)amino]trphenylamine), Spiro-TAD, DNTPD, NPB, NPNPB, MeO-TPD, HAT-CN or Tris-Pcz (9,9'-diphenyl-6-(9-phenyl-9H-carbazole-3-yl)-9H,9'H-3,3'-bicarbazole) can be used as materials for an HTL. The layer thickness is 10 nm to 100 nm, for example.

The HTL can have a p-doped layer comprising an inorganic or organic dopant in an organic hole transporting matrix. Transition metal oxides such as vanadium oxide, molybdenum oxide or tungsten oxide, for example, can be used as the inorganic dopant. Tetrafluorotetracyanoquinodimethane (F4-TCNQ), copper pentafluorobenzoate (Cu(I) pFBz) or transition metal complexes, for example, can be used as the organic dopants. The layer thickness is 10 nm to 100 nm, for example.

MCP (1,3-bis(carbazole-9-yl)benzene), TCTA, 2-TNATA, mCBP (3,3-Di(9H-carbazole-9-yl)biphenyl), tris-Pcz (9,9'-diphenyl-6-(9-phenyl-9H-carbazole-3-yl)-9H, 9'H-3,3'-bicarbazole), CzSi (9-(4-tert-butylphenyl)-3,6-bis (triphenylsilyl)-9H-carbazole) or DCB (N,N'-dicarbazolyl-1,4-dimethylbenzene) can, for example, be used as the materials of an electron blocking layer. The layer thickness is 10 nm to 50 nm, for example.

The emitter layer EML or emission layer consists of or contains emitter material or a mixture having at least two emitter materials and optionally one or more host materials. Suitable host materials are, for example, mCP, TCTA, 2-TNATA, mCBP, CBP (4,4'-Bis-(N-carbazolyl)-biphenyl), Sif87 (dibenzo[b,d]thiophene-2-yltriphenylsilane), Sif88 (dibenzo[b,d]thiophene-2-yl)diphenylsilane), DPEPO (bis [2-((oxo)diphenylphosphino)phenyl]ether), 9-[3-(dibenzofuran-2-yl)phenyl]-9H-carbazole, 9-[3-(dibenzofuran-2-yl) phenyl]-9H-carbazole, 9-[3-(dibenzothiophene-2-yl) phenyl]-9H-carbazole, 9-[3,5-bis(2-dibenzofuranyl) phenyl]-9H-carbazole, 9-[3,5-bis(2-dibenzothiophenyl) phenyl]-9H-carbazole, T2T (2,4,6-tris(biphenyl-3-yl)-1,3,5-triazine), T3T (2,4,6-tris(triphenyl-3-yl)-1,3,5-triazine) or TST (2,4,6-tris(9,9'-spirobifluorene-2-yl)-1,3,5-triazine). The common matrix materials, such as CBP, are suitable for emitter material emitting in the green or in the red range or for a mixture having at least two emitter materials. UHG matrix materials (ultra-high energy gap materials) (see, for example, M. E. Thompson et al., Chem. Mater. 2004, 16, 4743) or other so-called wide-gap matrix materials can be used for emitter material emitting in the blue range or a mixture having at least two emitter materials. The layer thickness is 10 nm to 250 nm, for example.

The hole blocking layer HBL can, for example, comprise BCP (2,9-dimethyl-4,7-diphenyl-1,10-phenanthroline=bathocuproine), bis-(2-methyl-8-hydroxyquinolinato)-(4-phenylphenolato)-aluminum(III) (BAlq), Nbphen (2,9-bis(naphthalene-2-yl)-4,7-diphenyl-1,10-phenanthroline), Alq3 (aluminum-tris(8-hydroxyquinoline)). TSPO1 (diphenyl-4-triphenylsilyl-phenylphosphine oxide) or TCB/TCP (1,3,5-tris(N-carbazolyl)benzene/1,3,5-tris(carbazole)-9-yl)benzene). The layer thickness is 10 nm to 50 nm, for example.

The electron transport layer ETL can, for example, comprise materials based on $AlQ_3$, TSPO1, BPyTP2 (2,7-di(2, 2'-bipyridine-5-yl)triphenyl), Sif87, Sif88, BmPyPhB (1,3-bis[3,5-di(pyridine-3-yl)phenyl]benzene) or BTB (4,4'-bis-[2-(4,6-diphenyl-1,3,5-triazinyl)]-1,1'-biphenyl). The layer thickness is 10 nm to 200 nm, for example.

CsF, LiF, 8-hydroxyquinolinolatolithium (Liq), $Li_2O$, $BaF_2$, MgO or NaF can be used as materials for a thin electron injection layer EIL.

Metals or alloys, for example Al, Al>AlF, Ag, Pt, Au, Mg, Ag:Mg, can be used as materials of the cathode layer. Typical layer thicknesses are 100 nm to 200 nm. In particular, one or more metals are used, which are stable when exposed to air and/or are self-passivating, for example by forming a thin protective oxide layer.

Aluminum oxide, vanadium oxide, zinc oxide, zirconium oxide, titanium oxide, hafnium oxide, lanthanum oxide, tantalum oxide, for example, are suitable materials for encapsulation.

In one embodiment of the optoelectronic device according to the invention, the organic molecule according to the invention is used as the emission material in a light-emitting layer EML, wherein it is used either as a pure layer or in combination with one or more host materials.

One embodiment of the invention relates to optoelectronic devices having an external quantum efficiency (EQE) at 1000 $cd/m^2$ greater than 5%, in particular greater than 8%, in particular greater than 10%, or greater than 13%, or greater than 16% and in particular greater than 20%, and/or an emission maximum at a wavelength between 420 nm and 500 nm, in particular between 430 nm and 490 nm, or between 440 nm and 480 nm, and in particular between 450 nm and 470 nm, and/or an LT80 value at 500 cd/m² greater than 30 h, in particular greater than 70 h, or greater than 100 h, or greater than 150 h and in particular greater than 200 h.

In another embodiment, the mass fraction of the organic molecule according to the invention in the emitter layer EML of a light-emitting layer in devices emitting optical light, in particular in OLEDs, is between 1% and 80%. In one embodiment of the optoelectronic device according to the invention, the light-emitting layer is disposed on a substrate, whereby an anode and a cathode are preferably disposed on the substrate and the light-emitting layer is disposed between the anode and the cathode.

In one embodiment, the light-emitting layer can have only one organic molecule according to the invention in 100% concentration, whereby the anode and the cathode are disposed on the substrate, and the light-emitting layer is disposed between the anode and the cathode.

In one embodiment of the optoelectronic device according to the invention, a hole- and electron-injecting layer is disposed between the anode and the cathode, and a hole- and electron-transporting layer is disposed between the hole- and electron-injecting layer, and the light-emitting layer is disposed between the hole- and electron-transporting layer.

In another embodiment of the invention, the optoelectronic device comprises: a substrate, an anode, a cathode and at least one respective hole- and electron-injecting layer, and at least one respective hole- and electron-transporting layer, and at least one light-emitting layer, which comprises the organic molecule according to the invention and one or more host materials, the triplet ($T_1$) and singlet ($S_1$) energy levels of which are energetically higher than the triplet ($T_1$) and singlet ($S_1$) energy levels of the organic molecule, whereby the anode and the cathode are disposed on the substrate, and the hole- and electron-injecting layer is disposed between the anode and the cathode, and the hole- and electron-transporting layer is disposed between the hole- and electron-injecting layer, and the light-emitting layer is disposed between the hole- and electron-transporting layer.

In a further aspect, the invention relates to a method for producing an optoelectronic device. To do this, an organic molecule according to the invention is used.

In one embodiment, the production method comprises the processing of the organic molecule according to the invention by means of a vacuum evaporation method or from a solution.

The invention also relates to a method for producing an optoelectronic device according to the invention, in which at least one layer of the optoelectronic device
- is coated using a sublimation process,
- is coated using an OVPD (organic vapor phase deposition) process,
- is coated using a carrier-gas sublimation, and/or
- is produced from solution or using a pressure process.

Known methods are used for the production of the optoelectronic device according to the invention. The layers are generally disposed individually onto a suitable substrate in successive deposition method steps. The common methods, such as thermal evaporation, chemical vapor deposition (CVD), physical vapor deposition (PVD) can be used for the vapor deposition. For active matrix OLED (AMOLED) displays, deposition takes place onto an AMOLED backplane as the substrate.

Layers can alternatively be deposited from solutions or dispersions in suitable solvents. Spin coating, dip coating and jet pressure methods are examples of suitable coating methods.

According to the invention, the individual layers can be produced via the same as well as via respective different coating methods.

EXAMPLES

General Synthesis Scheme I

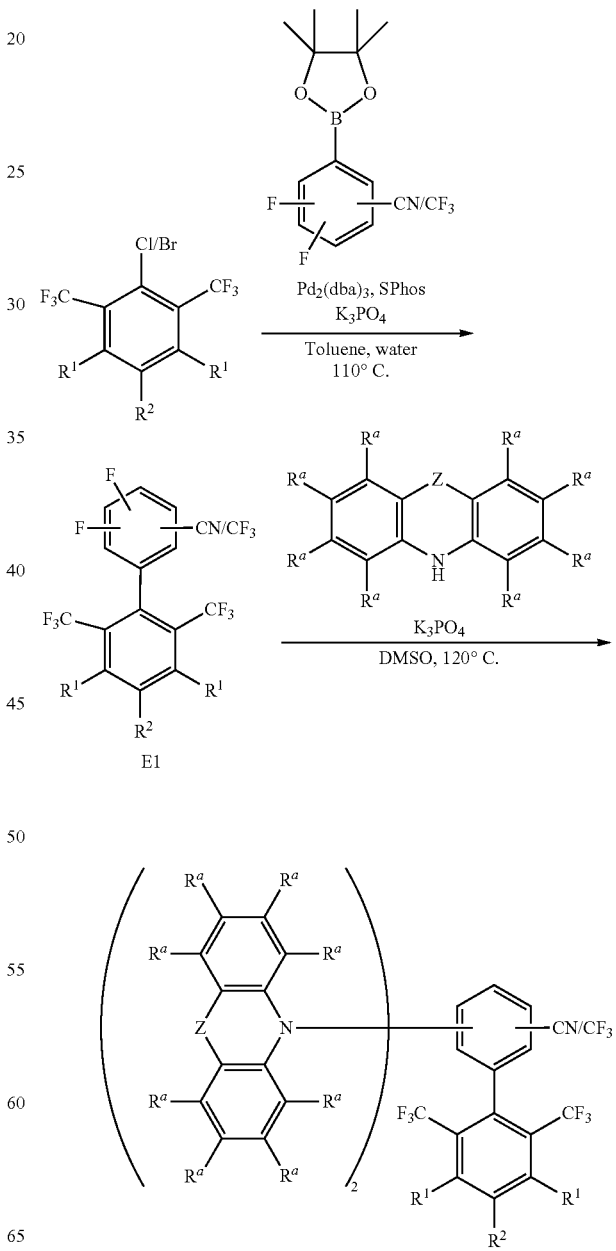

General Synthesis Specification AAV1

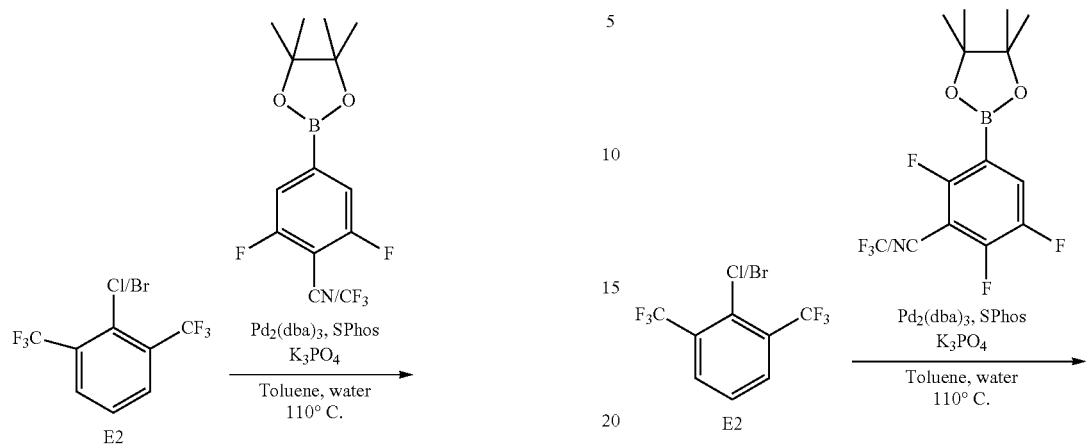

2,6-bis(trifluoromethyl)chloro/bromobenzene E2 (1.00 equivalent), 4-cyano(trifluoromethyl)-3,5-difluorophenyl-boronic acid ester (1.10 equivalent), Pd$_2$(dba)$_3$ (0.01 equivalent), 2-dicyclohexylphosphino-2',6'-dimethoxybiphenyl-SPhos) (0.04 equivalent) and potassium) (phosphate tribasic (2.50 equivalent are stirred under nitrogen in a toluene/water mixture (ratio 10:1) at 110° C. for 16 hours. After cooling to RT, the reaction mixture is filtered. The filtrate is mixed with saturated NaCl solution and the phases are separated. The organic phase is dried over MgSO$_4$, filtered and freed from solvent under reduced pressure. The residue is purified by recrystallization from ethanol/chloroform or by column chromatography.

The product is obtained as a solid.

A corresponding boronic acid can be used instead of a boronic acid ester.

General Synthesis Specification AAV2

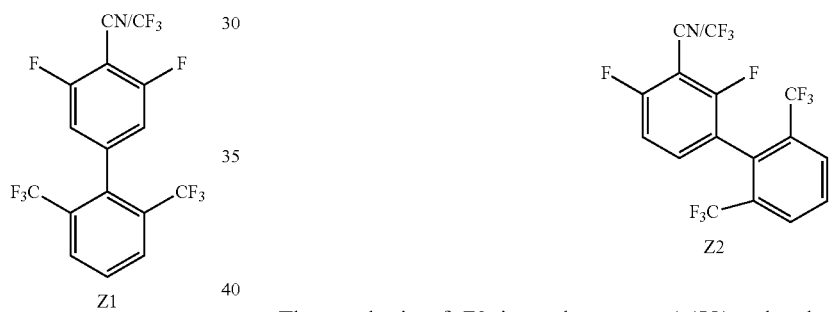

The synthesis of Z2 is analogous to AAV1, whereby 2-chloro/bromo-1,3-di(trifluoromethyl)benzene is reacted with 2,4-difluoro-3-cyano/trifluoromethyl-phenylboronic acid pinacol ester.

General Synthesis Specification AAV3

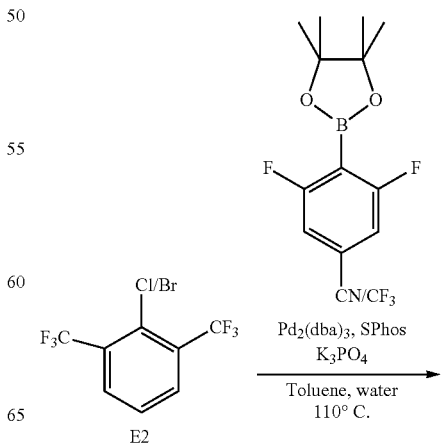

45

-continued

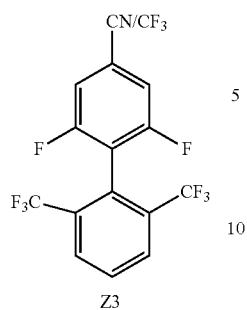
Z3

The synthesis of Z3 is analogous to AAV1, whereby 2-chloro/bromo-1,3-di(trifluoromethyl)benzene is reacted with 2,6-difluoro-4-cyano/trifluoromethyl-phenylboronic acid pinacol ester.

General Synthesis Specification AAV4

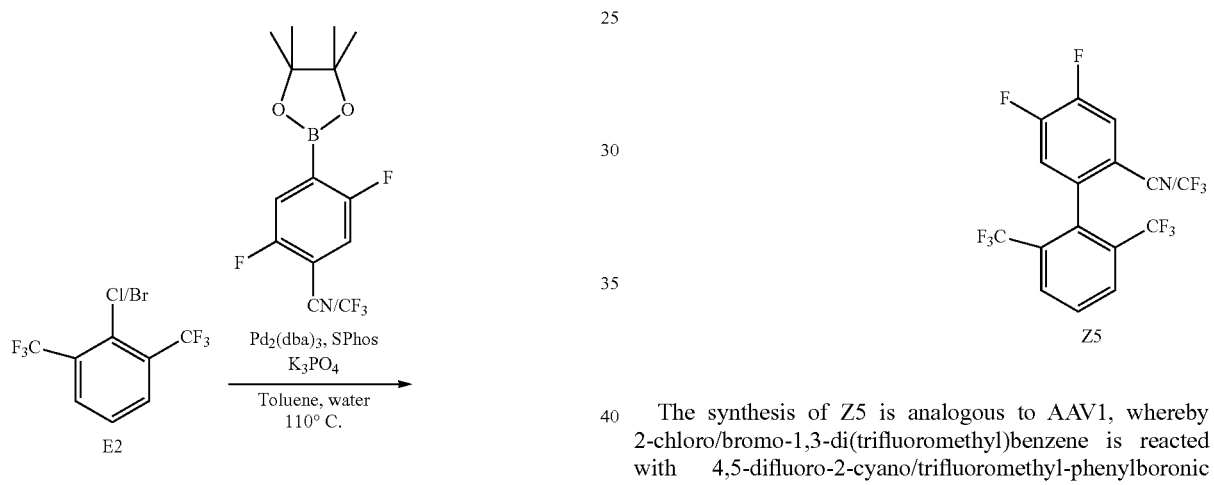

The synthesis of Z4 is analogous to AAV1, whereby 2-chloro/bromo-1,3-di(trifluoromethyl)benzene is reacted with 2,5-difluoro-4-cyano/trifluoromethyl-phenylboronic acid pinacol ester.

46

General Synthesis Specification AAV5

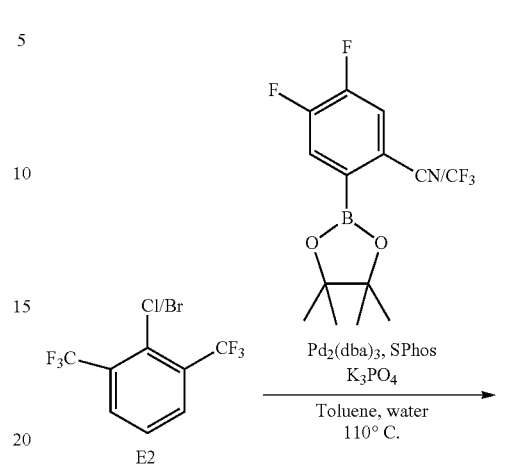

Z5

The synthesis of Z5 is analogous to AAV1, whereby 2-chloro/bromo-1,3-di(trifluoromethyl)benzene is reacted with 4,5-difluoro-2-cyano/trifluoromethyl-phenylboronic acid pinacol ester.

General Synthesis Specification AAV6

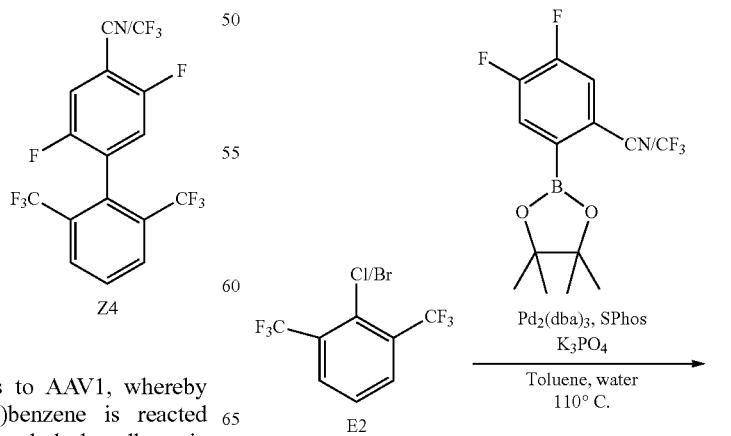

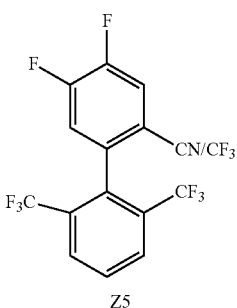
Z5
The synthesis of Z6 is analogous to AAV1, whereby 2-chloro/bromo-1,3-di(trifluoromethyl)benzene is reacted with 4,5-difluoro-3-cyano/trifluoromethyl-phenylboronic acid pinacol ester.
General Synthesis Specification AAV7
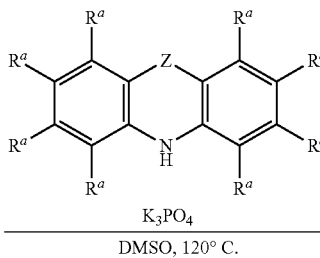
Z1
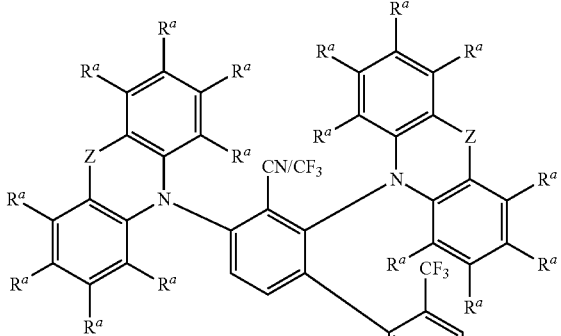
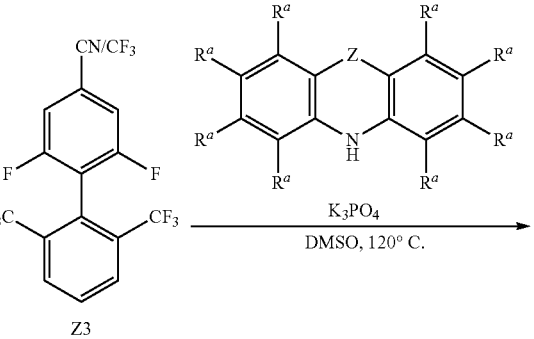
Z3
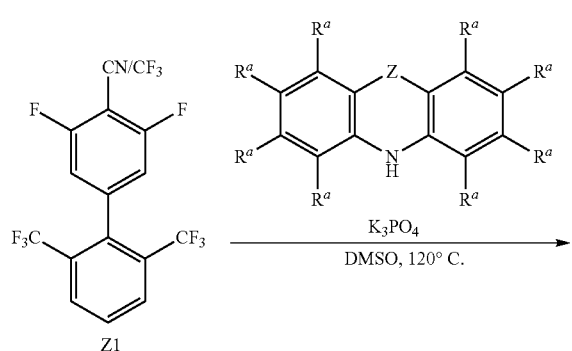
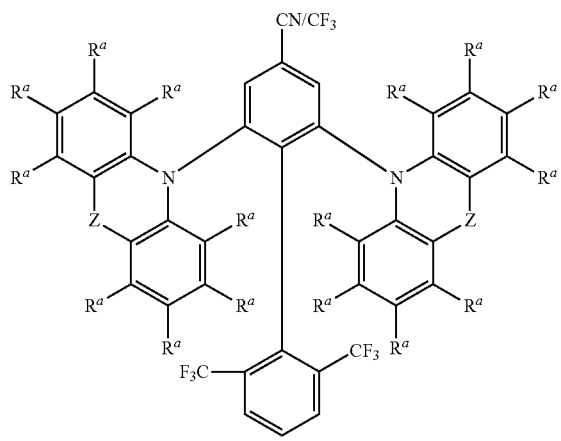
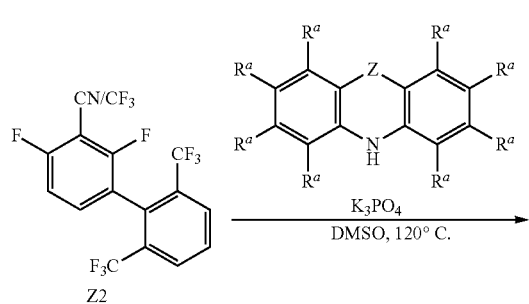
Z2
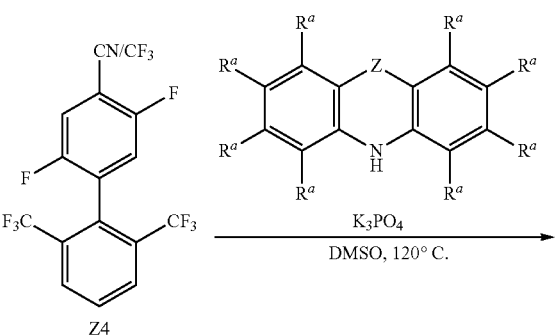
Z4

-continued

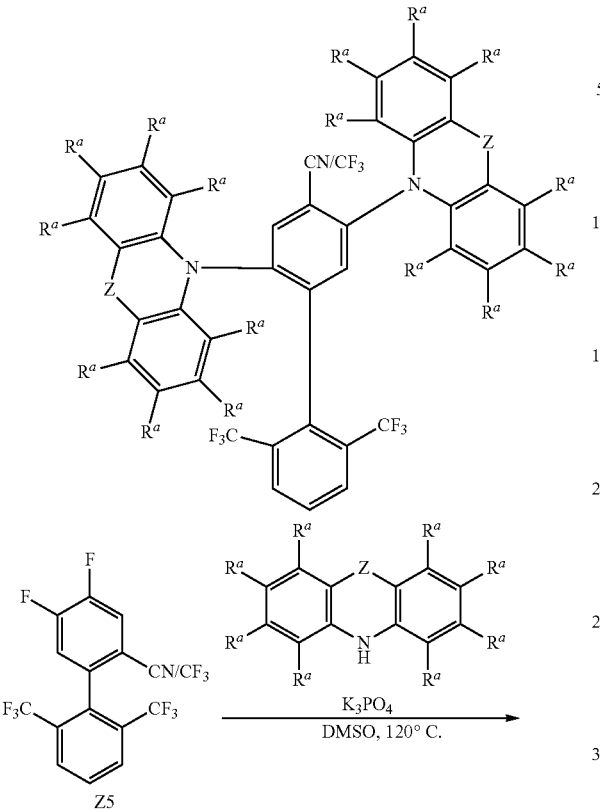

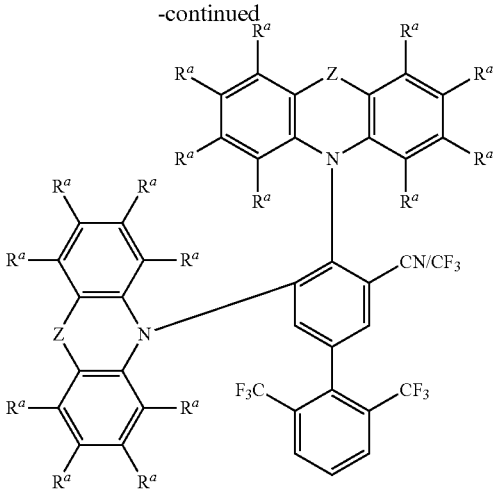

Z1, Z2, Z3, Z4, Z5 or Z6 (respectively 1.00 equivalent), the corresponding donor molecule D-H (2.00 equivalent) and potassium phosphate tribasic (4.00 equivalent) are suspended in DMSO under nitrogen and stirred at 120° C. (16 h). The reaction mixture is then added to saturated sodium chloride solution and extracted three times with dichloromethane. The combined organic phases are washed twice with saturated sodium chloride solution, dried over magnesium sulfate, and the solvent is subsequently removed. Lastly, the crude product was purified by recrystallization from toluene or by means of flash chromatography. The product is obtained as a solid.

D-H in particular corresponds to a 3,6-substituted carbazole (e.g. 3,6-dimethylcarbazole, 3,6-diphenylcarbazole, 3,6-di-tert-butylcarbazole), a 2,7-substituted carbazole (e.g. 2,7-dimethylcarbazole, 2,7-diphenylcarbazole, 2,7-di-tert-butylcarbazole), an 1,8-substituted carbazole (e.g. 1,8-dimethylcarbazole, 1,8-diphenylcarbazole, 1,8-di-tert-butylcarbazole), a 1-substituted carbazole (e.g. 1-methylcarbazole, 1-phenylcarbazole, 1-tert-butylcarbazole), a 2-substituted carbazole (e.g. 2-methylcarbazole, 2-phenylcarbazole, 2-tert-butylcarbazole) or a 3-substituted carbazole (e.g. 3-methylcarbazole, 3-phenylcarbazole, 3-tert-butylcarbazole). In particular, a halocarbazole, in particular 3-bromocarbazole or 3,6-dibromocarbazole, can be used as DH, which in a subsequent reaction for example in a corresponding boronic acid, for example (carbazole-3-yl) boronic acid, or in a corresponding boronic acid ester, for example (carbazole-3-yl) boronic acid ester is reacted, for example, by reaction with bis (pinacol) boronic acid ester (CAS No. 73183-34-3). In a subsequent reaction, one or more radicals $R^a$, which is used as halogenated educt $R^a$-Hal, preferably $R^a$—Cl and $R^a$—Br, is introduced via a coupling reaction in place of the boronic acid group or the boronic acid ester group. Alternatively, one or more radicals $R^a$ can be introduced by reaction of the previously introduced halocarbazole with boronic acids of the radical $R^a$ ($R^a$—B(OH)$_2$) or corresponding boronic acid esters can be introduced.

Photophysical Measurements
Sample Preparation, Film: Spin Coating
Device: Spin150, SPS Euro.
The sample concentration corresponded to 10 mg/ml, prepared in a suitable solvent.
Program: 1) 3 s at 400 rpm; 2) 20 s at 1000 rpm at 1000 rpm/s. 3) 10 s at 4,000 rpm at 1000 rpm/s. After coating, the films were dried for 1 min at 70° C. in air.

Photoluminescence Spectroscopy and TCSPC

Steady-state emission spectroscopy was carried out using a fluorescence spectrometer of the Horiba Scientific company, Model Fluoromax-4, equipped with a 150 W xenon arc lamp, excitation and emission monochromators and a Hamamatsu R928 photomultiplier tube, as well as a "time-correlated single photon counting" (TCSPC) option. The emission and excitation spectra were corrected by means of standard correction curves.

The emission decay times were likewise measured on this system, using the TCSPC method with the FM-2013 accessories and a TCSPC hub of the Horiba Yvon Jobin company.

Excitation Sources:

NanoLED 370 (wavelength: 371 nm, pulse duration: 1.1 ns)

NanoLED 290 (wavelength: 294 nm, pulse duration: <1 ns)

SpectraLED 310 (wavelength: 314 nm)

SpectraLED 355 (wavelength: 355 nm).

The analysis (exponential fitting) was performed using the DataStation software package and the DAS6 analysis software. The fit was specified with the aid of the chi square method.

Quantum Efficiency Determination

The measurement of the photoluminescence quantum yield (PLQY) was carried out by means of an Absolute PL Quantum Yield Measurement C9920-03G system of the company Hamamatsu Photonics. The analysis of the quantum efficiency and the CIE coordinates was carried out using the software U6039-05 Version 3.6.0.

The emission maximum is measured in nm, the quantum yield Q is measured in % and the CIE color coordinates are stated as x, y values.

The photoluminescence quantum yield was determined according to the following protocol:

1) Implementation of quality assurance measures: Anthracene in ethanol at a known concentration serves as the reference material.

2) Determination of the excitation wavelength: The absorption maximum of the organic molecule was determined first and excitation was carried out with said wavelength.

3) Implementation of the sample measurement:

The absolute quantum yield of degassed solutions and films was determined under a nitrogen atmosphere.

The calculation was performed within the system according to the following equation:

$$\Phi_{PL} = \frac{n_{photon}, \text{emitted}}{n_{photon}, \text{absorbed}} = \frac{\int \frac{\lambda}{hc}[Int_{emitted}^{sample}(\lambda) - Int_{absorbed}^{sample}(\lambda)]d\lambda}{\int \frac{\lambda}{hc}[Int_{emitted}^{reference}(\lambda) - Int_{absorbed}^{reference}(\lambda)]d\lambda}$$

with the photon number n, and the intensity Int.

Production and Characterization of Organic Electroluminescence Devices from the Gas Phase With the organic molecules according to the invention, OLED devices can be produced by means of vacuum sublimation techniques. If a layer contains multiple components, the ratio of said components is stated in percent by mass.

These not yet optimized OLEDs can be characterized in the usual manner. To do this, the electroluminescence spectra, the external quantum efficiency (measured in %) as a function of the brightness and calculated from the light detected by the photodiode, and the current are recorded. The lifetime of the OLEDs can be determined from the time profile of the electroluminescence spectra. The LT50 value corresponds to the time at which the luminance has fallen to 50% of the starting value. The LT70 value analogously corresponds to the time at which the luminance has fallen to 70% of the starting value.

The values are obtained from the average of the various pixels of an OLED.

HPLC-MS:

HPLC-MS spectroscopy was measured using an HPLC system of the company Agilent (1100 series) with a connected MS detector (Thermo LTQ XL). An RP column 4.6 mm×150 mm and a Waters' particle size of 5.0 μm was used for the HPLC. This was carried out without a precolumn and at room temperature using the solvents acetonitrile, water and tetrahydrofuran in the following concentrations:

Solvent A: $H_2O$ (90%) MeCN (10%)

Solvent B: $H_2O$ (10%) MeCN (90%)

Solvent C: THF (50%) MeCN (50%)

An injection volume of 15 μL and a concentration of 0.5 mg/ml were used.

| Flow [ml/min] | Time [min] | A[%] | B[%] | C[%] |
| --- | --- | --- | --- | --- |
| 3 | 0 | 40 | 50 | 10 |
| 3 | 10 | 15 | 25 | 60 |
| 3 | 14 | 15 | 25 | 60 |
| 3 | 14.01 | 40 | 50 | 10 |
| 3 | 18 | 40 | 50 | 10 |
| 3 | 19 | 40 | 50 | 10 |

The sample is ionized by means of APCI (atmospheric pressure chemical ionization).

Example 1

Example 1 was produced in accordance with AAV1 (Yield 68%) and AAV7 (Yield 57%).

MS (HPLC-MS), m/z (retention time): 949.48, (10.89 min)

FIG. 1 shows the emission spectrum of Example 1 (10% in PMMA). The emission maximum is at 455 nm. The photoluminescence quantum yield (PLQY) is 69%, the full width at half maximum is 0.46 eV and the emission lifetime is 6.1 μs. The resulting CIE-Coordinate is 0.16 and the resulting $CIE_y$-Coordinate is 0.17.

Examples of Molecules According to the Invention
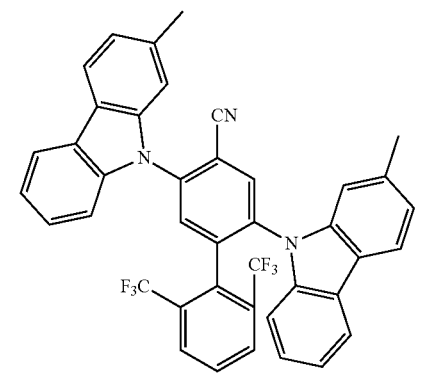
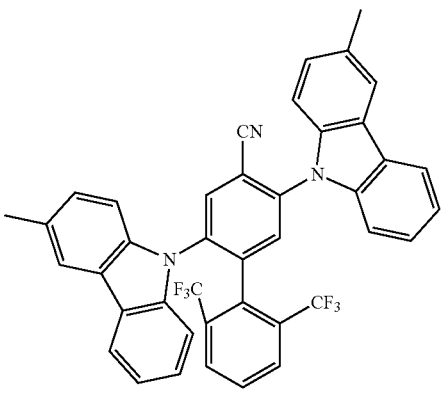
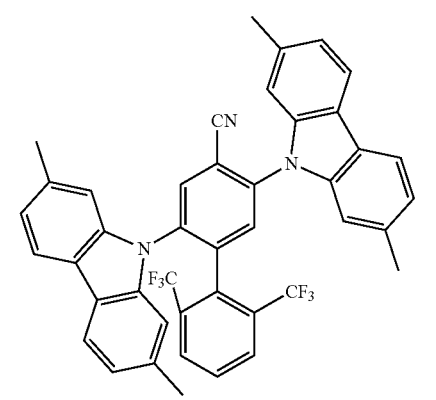
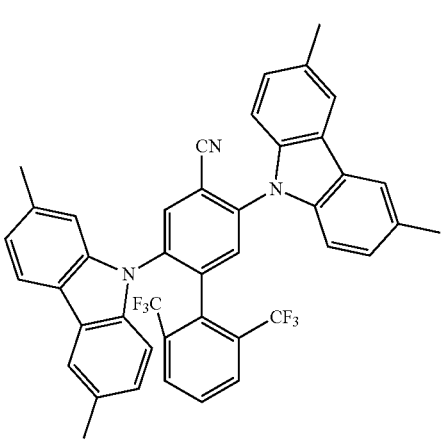
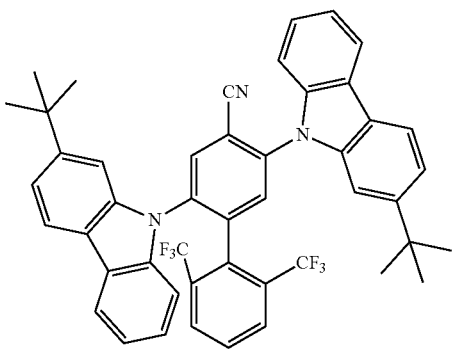
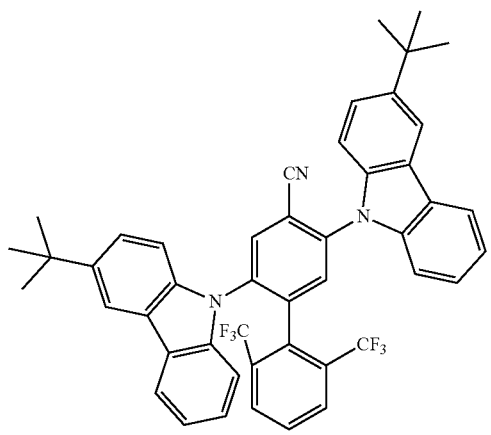
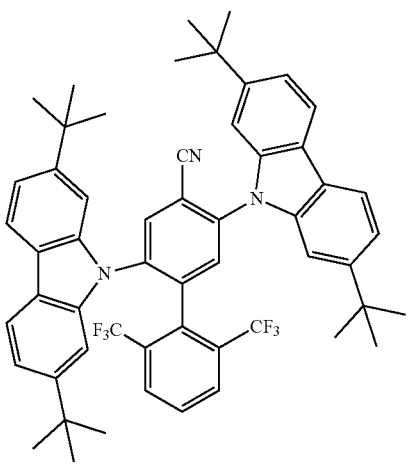

55
-continued
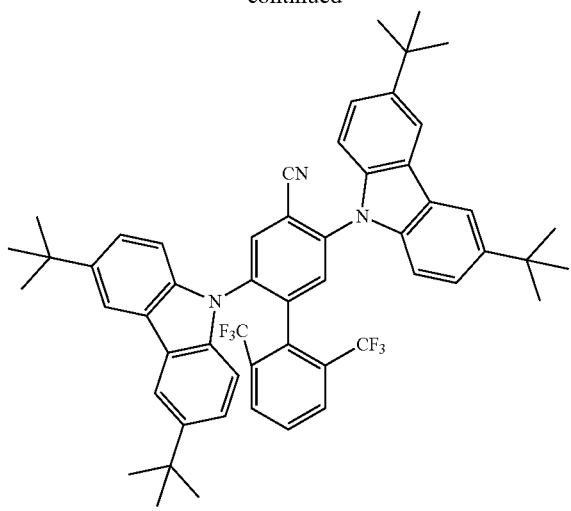
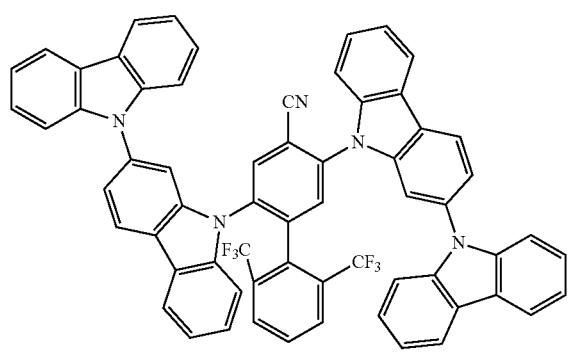
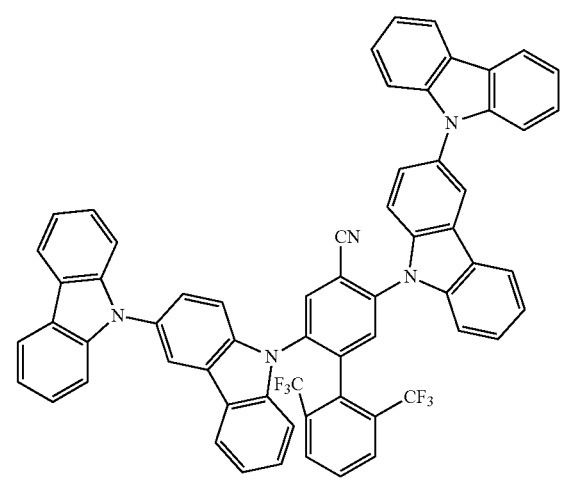
56
-continued
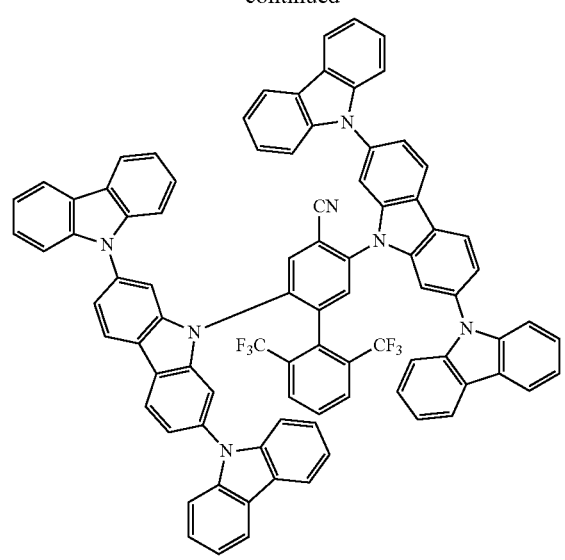
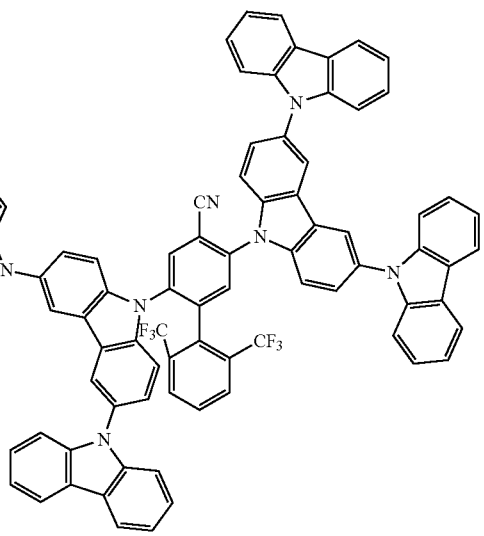
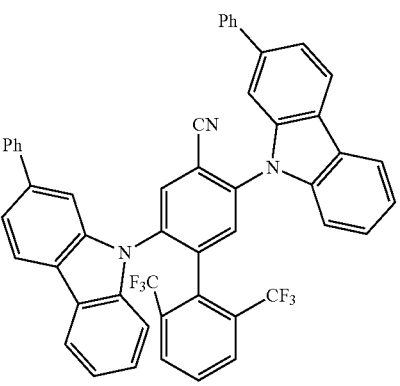

-continued
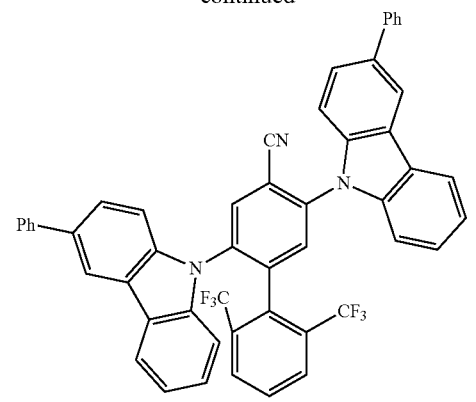
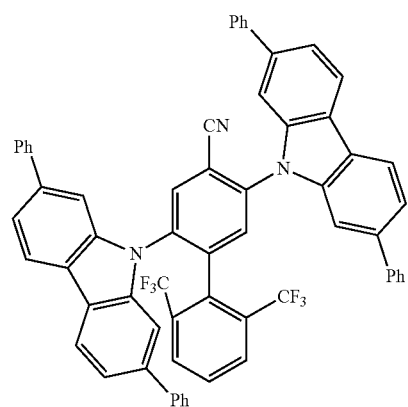
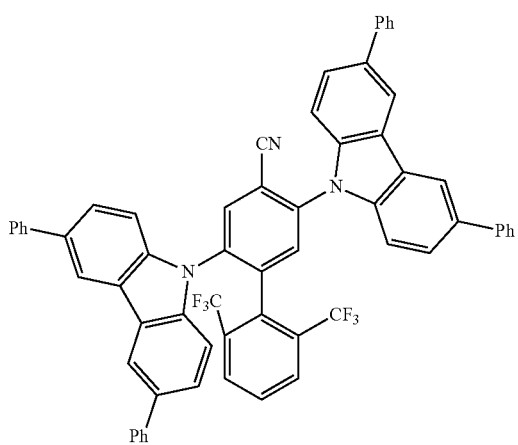
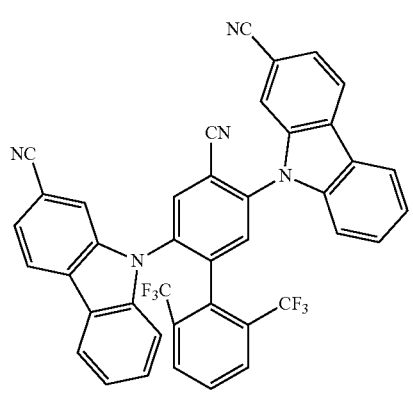
-continued
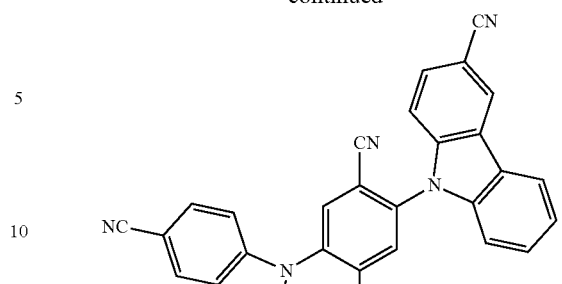
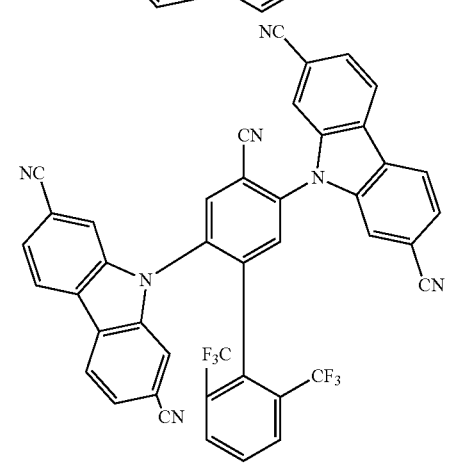
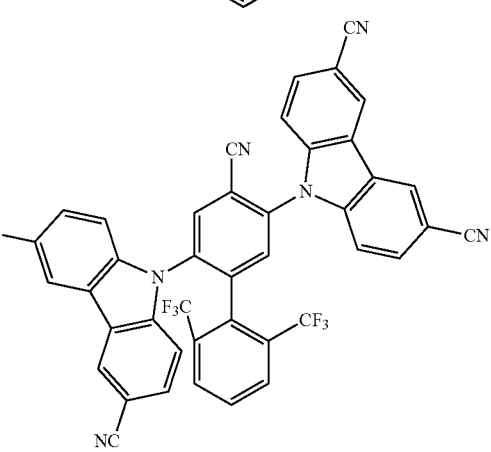
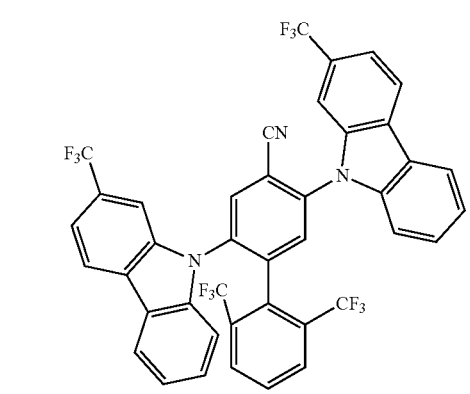

59
-continued
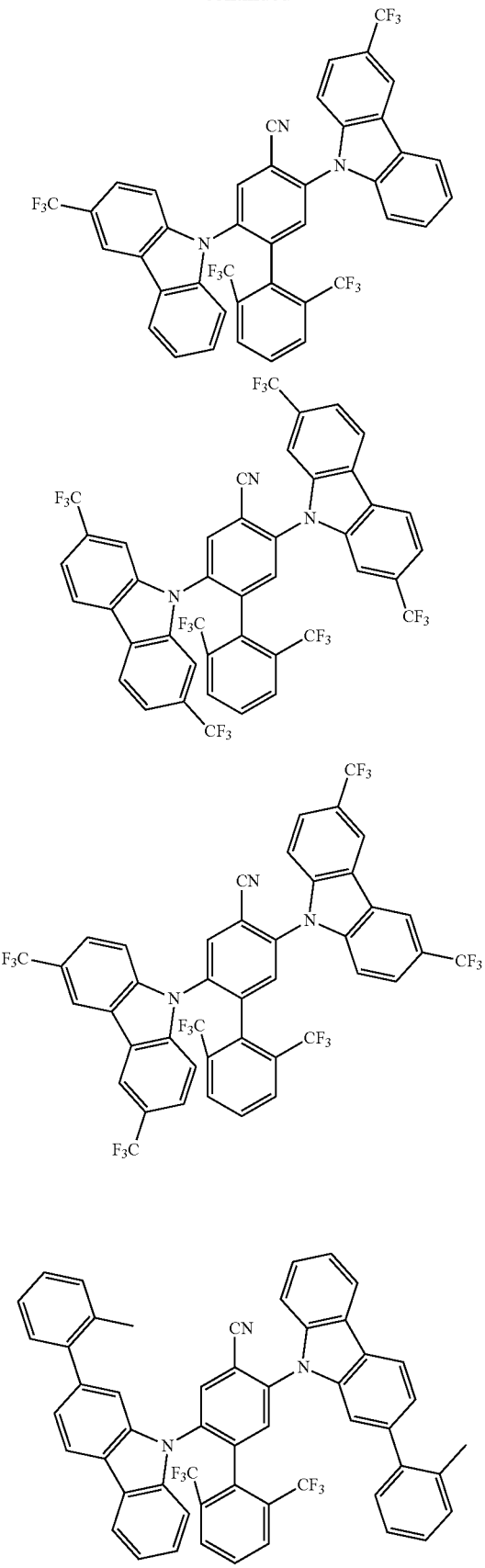
60
-continued
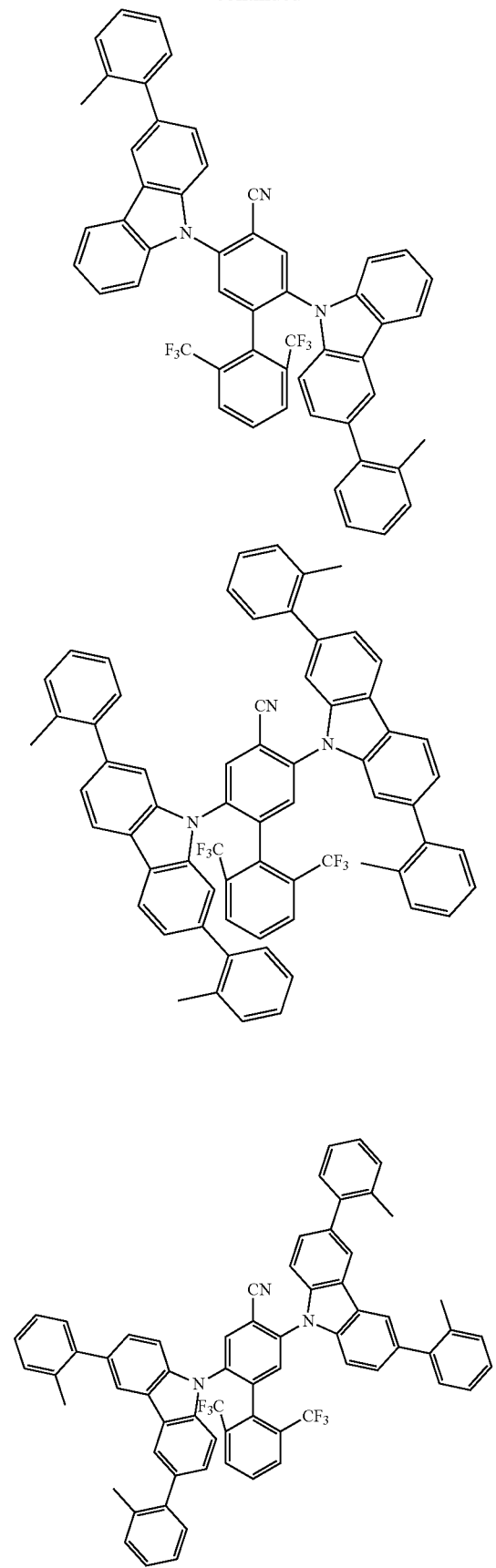

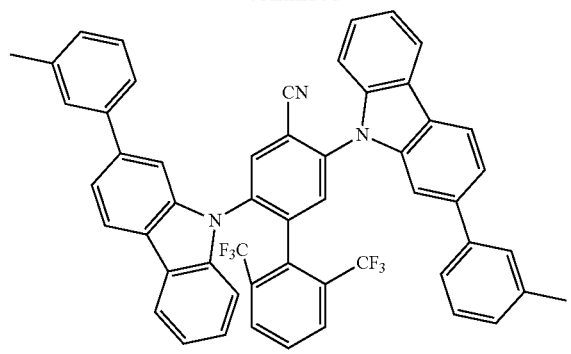
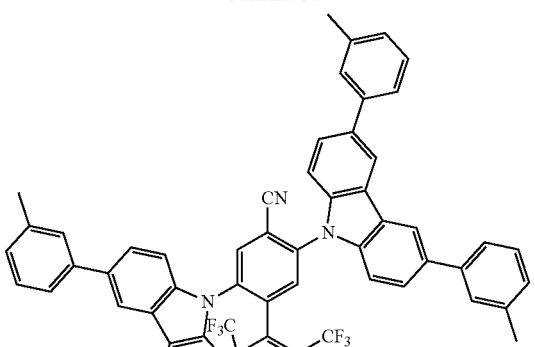
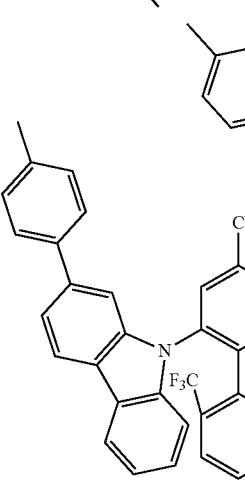
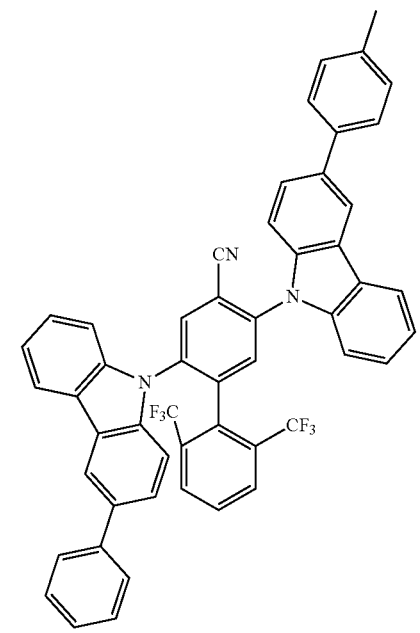

-continued
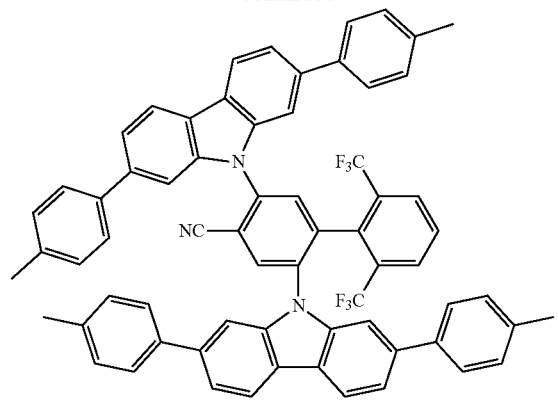
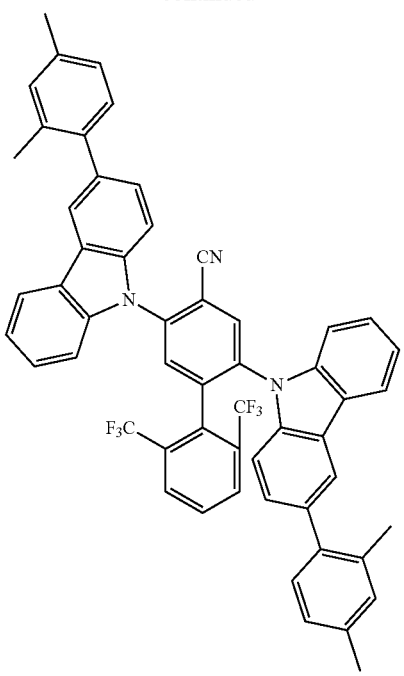
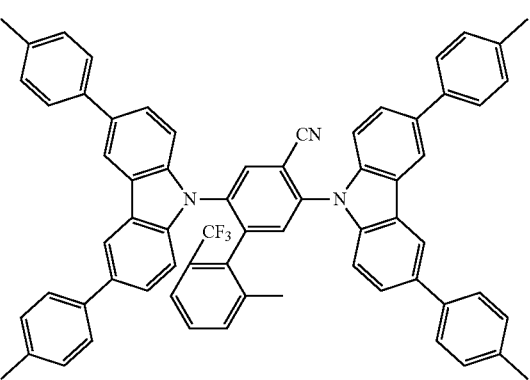
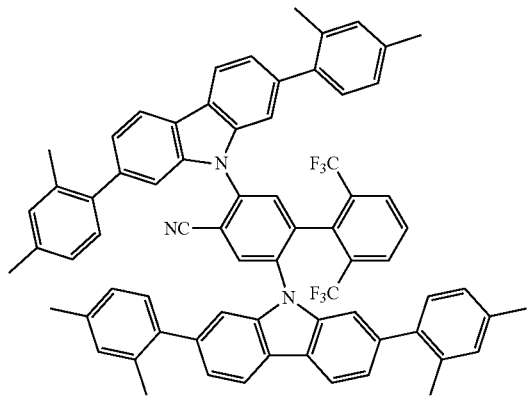
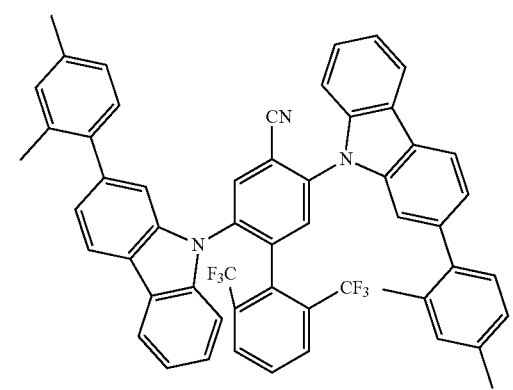
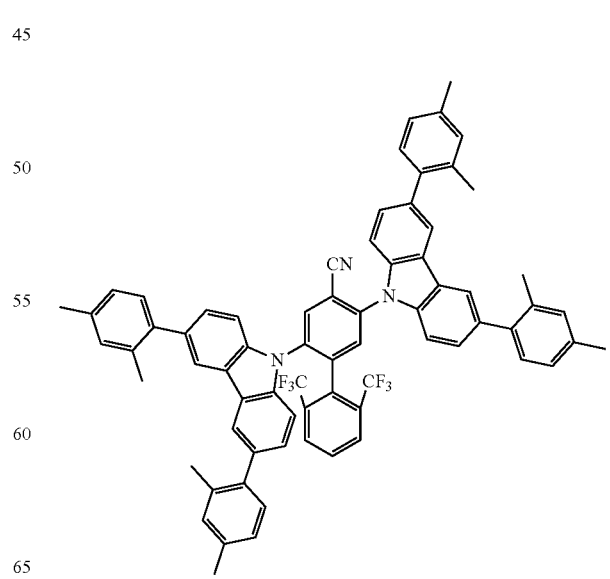

-continued
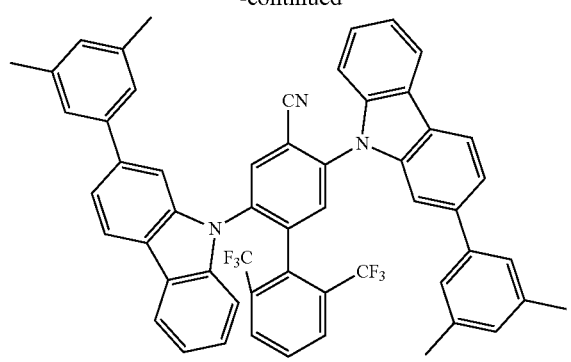
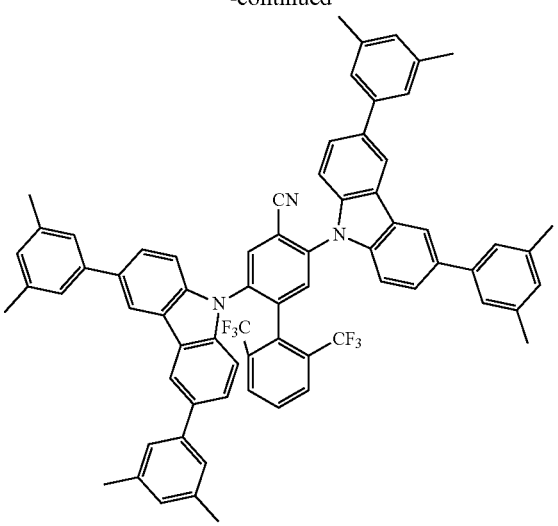
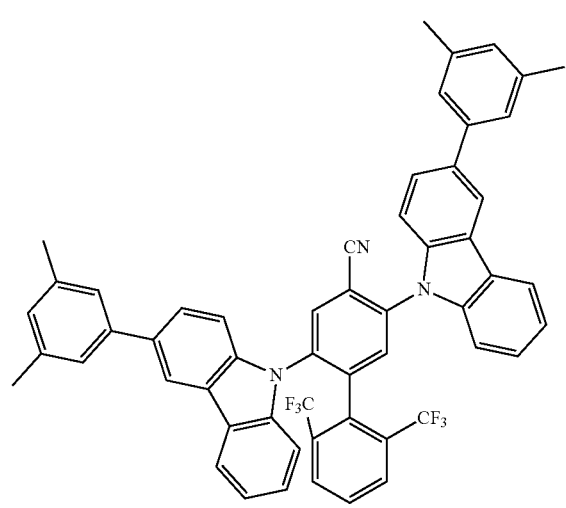
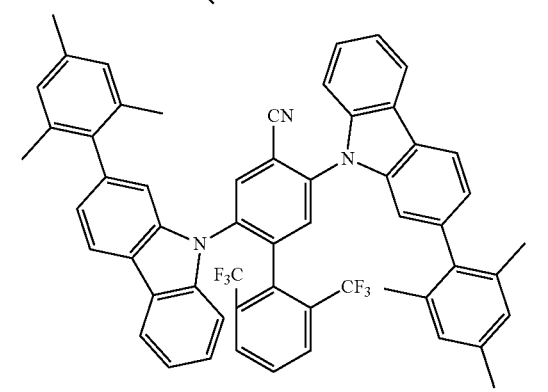
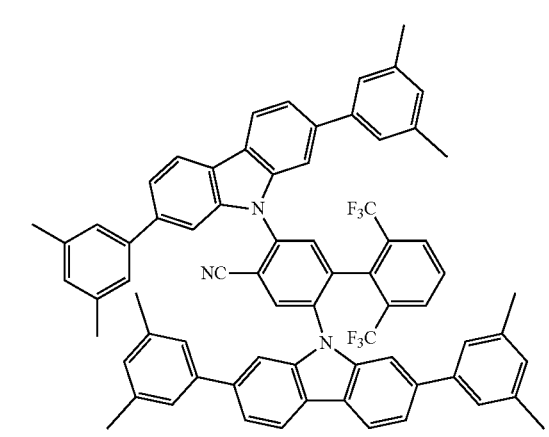
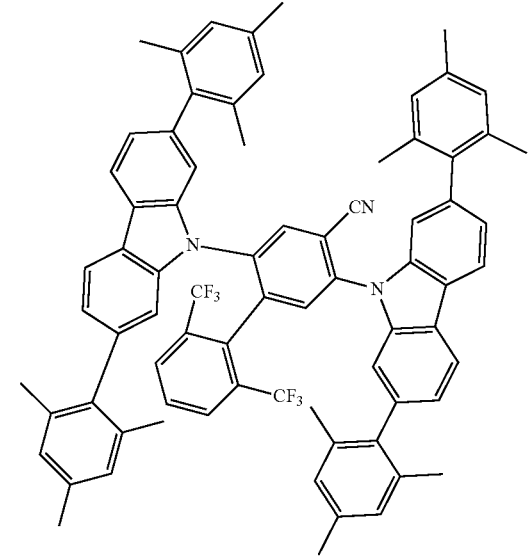

67
-continued
68
-continued
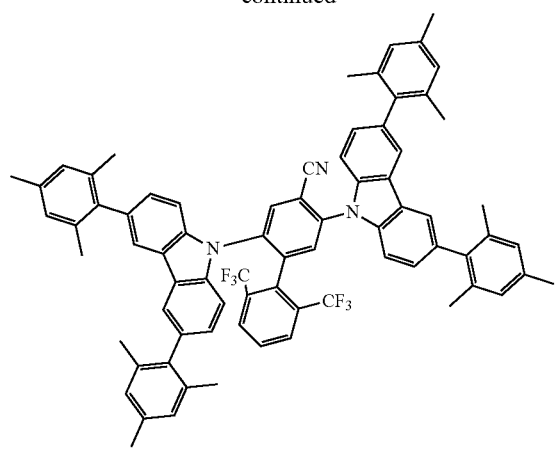
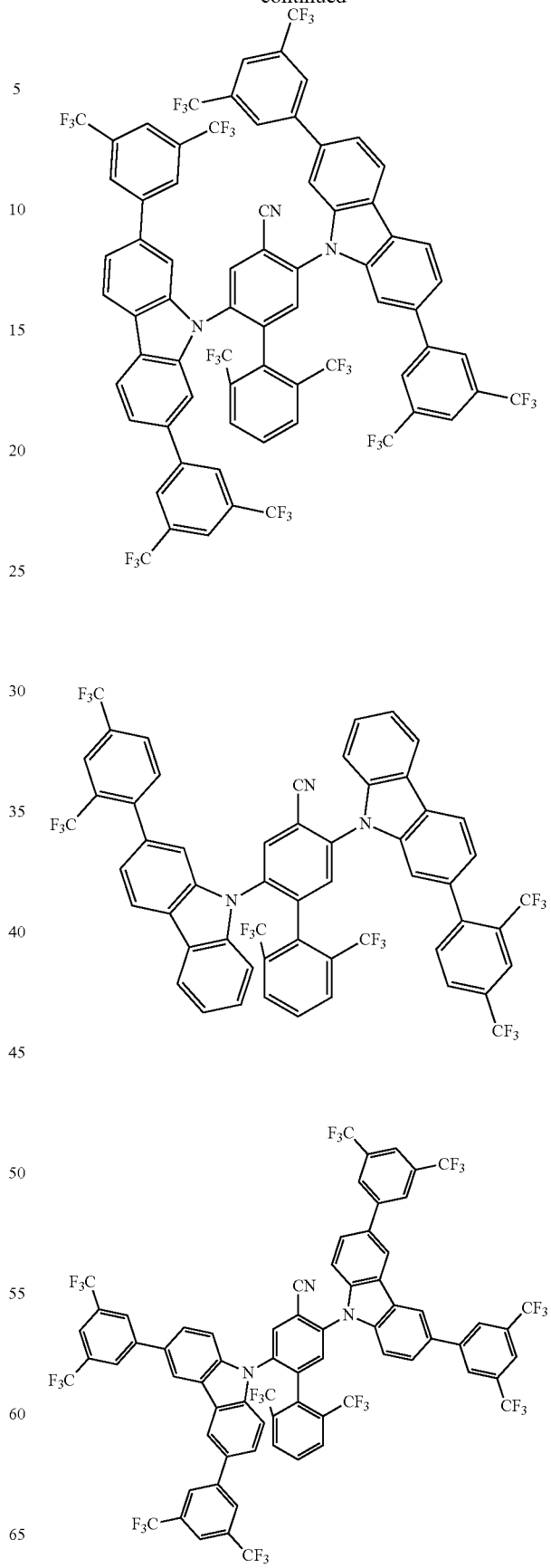

-continued
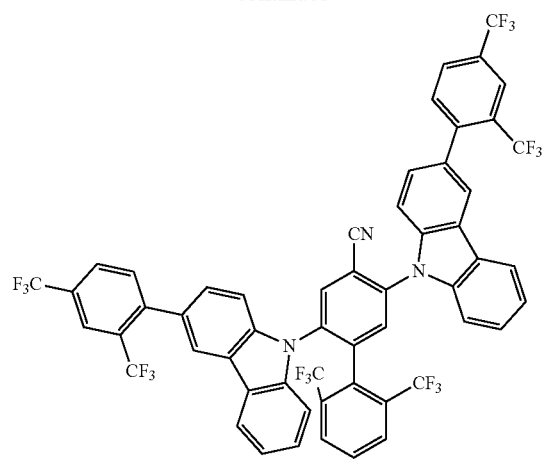
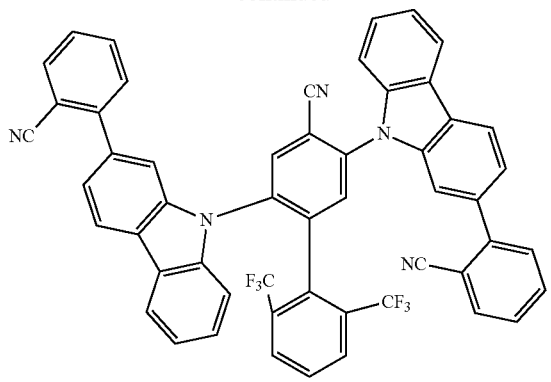
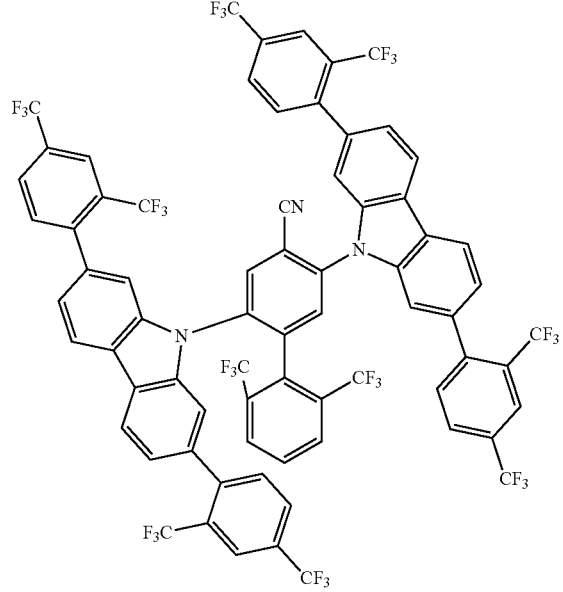
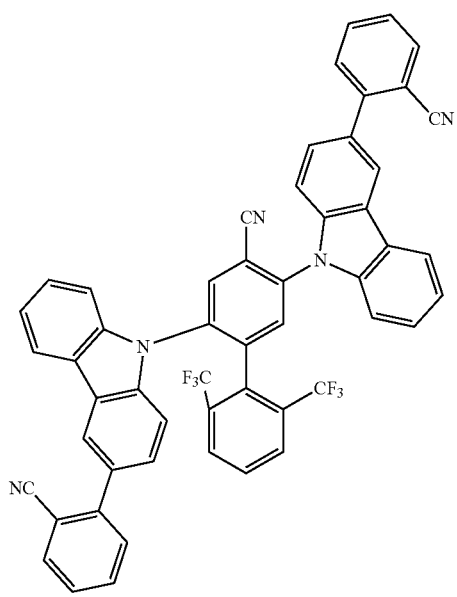
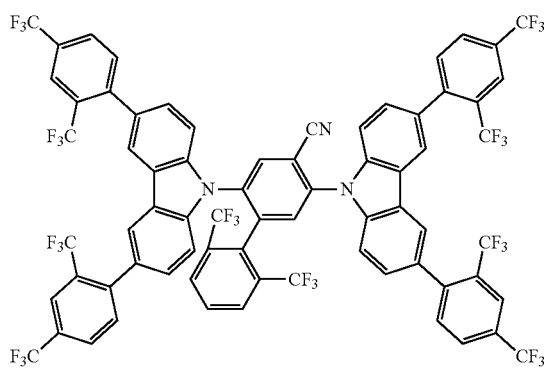
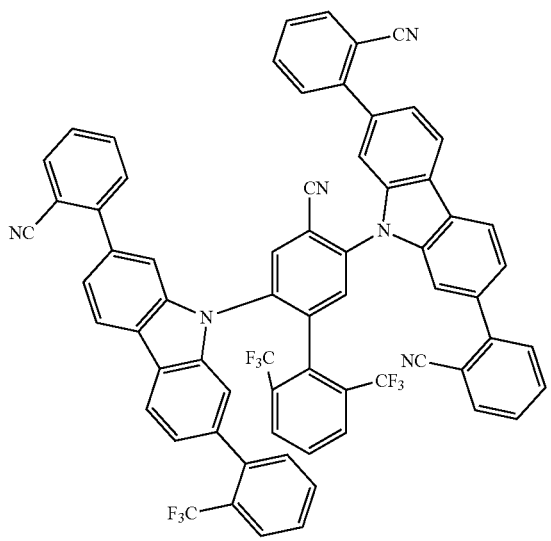

71
-continued
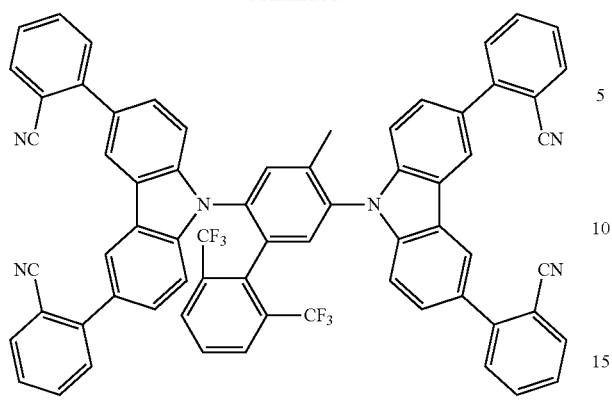
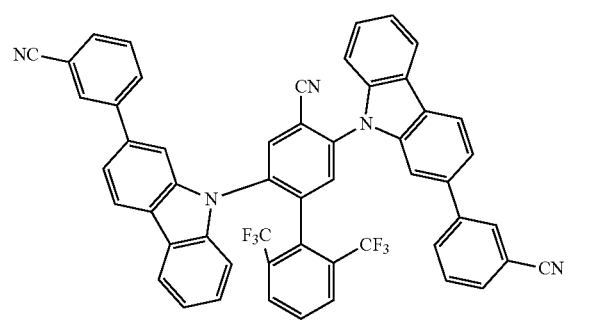
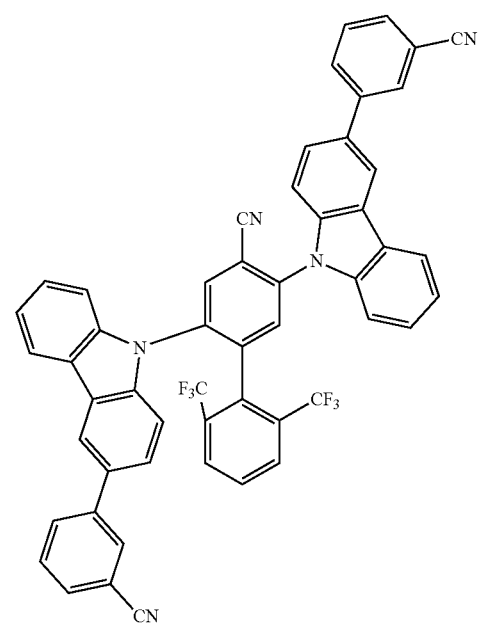
72
-continued
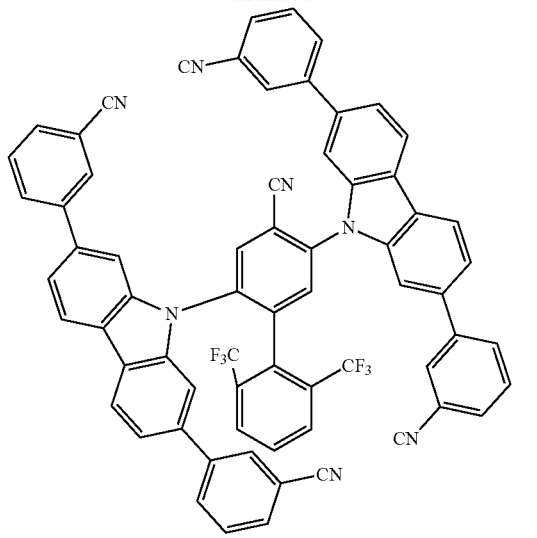
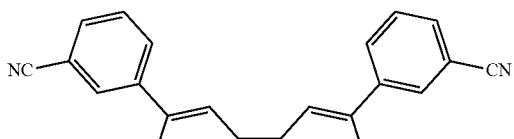
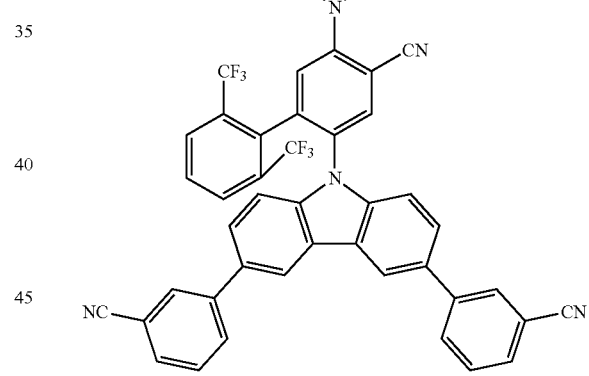
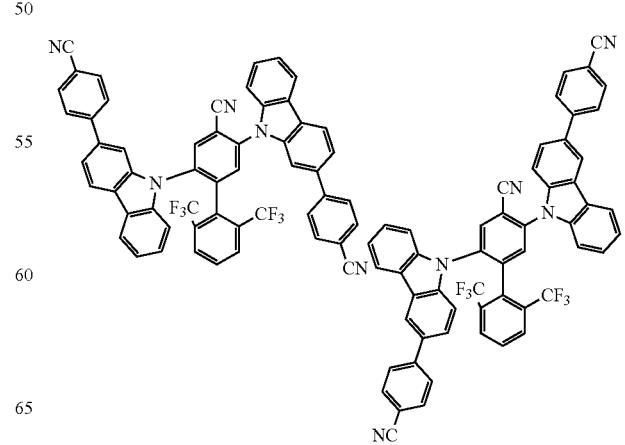

| 73 | 74 |
|---|---|
| -continued | -continued |
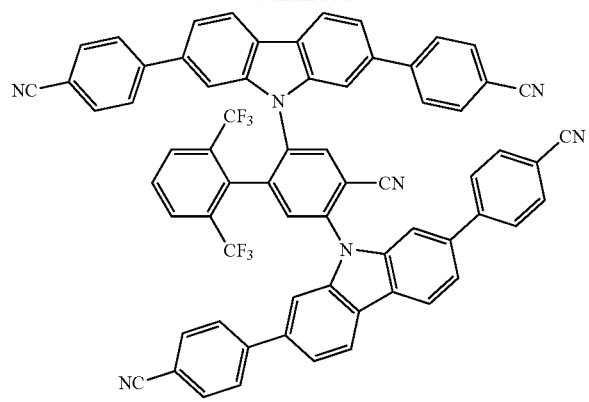
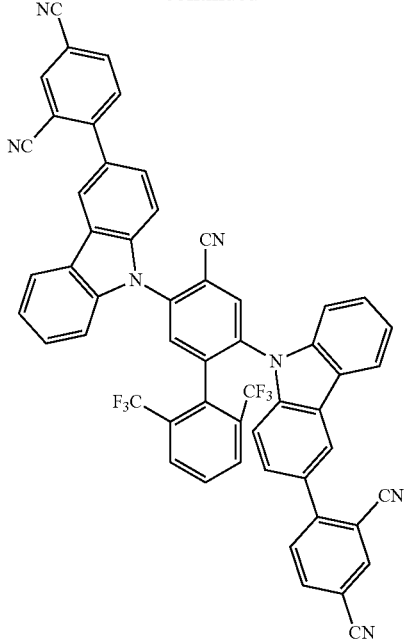
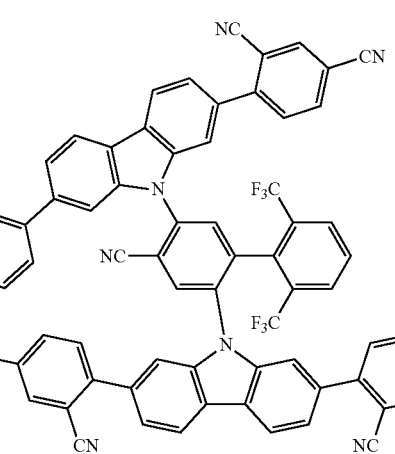
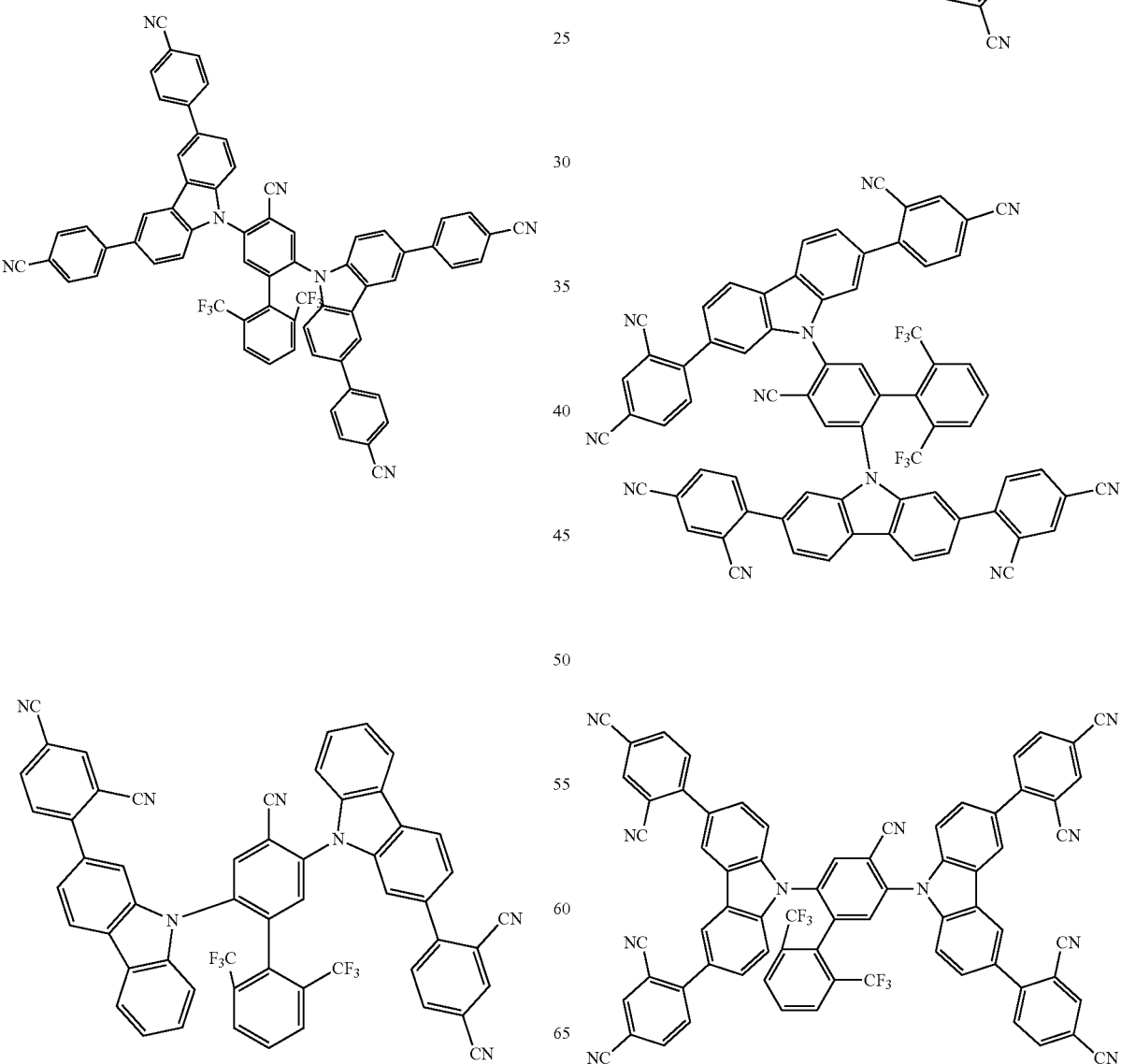

75
-continued
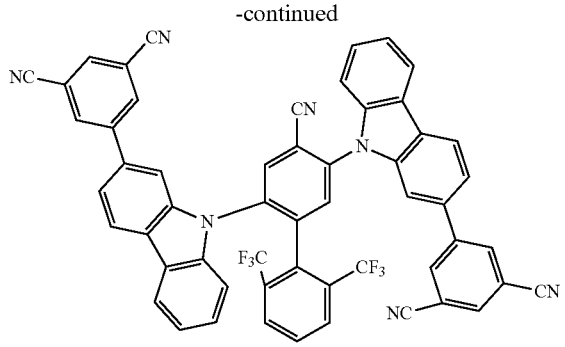
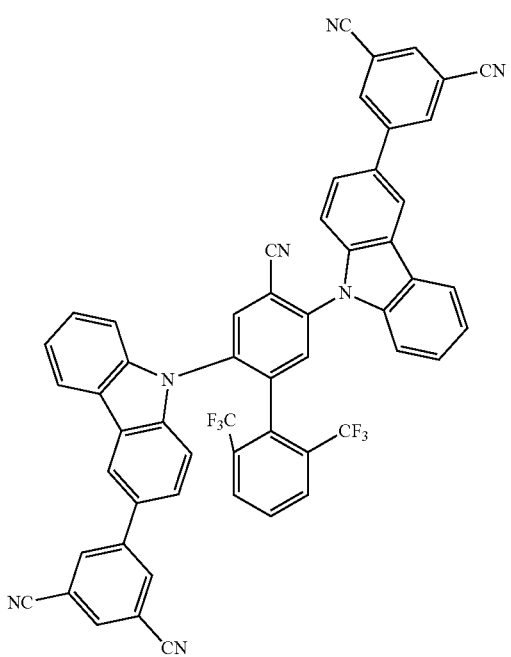
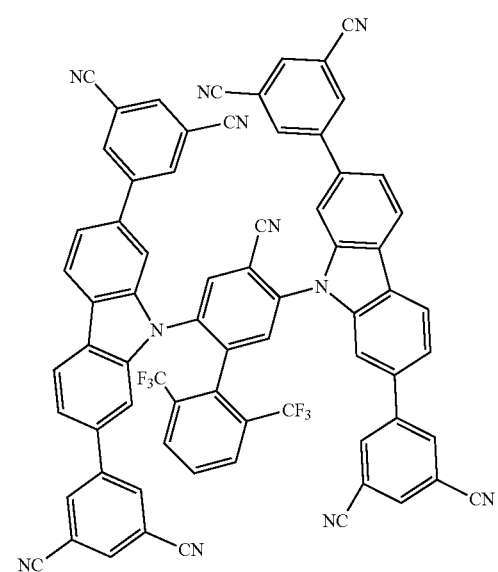
76
-continued
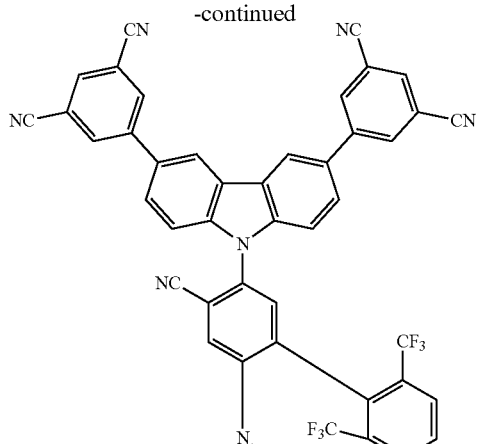
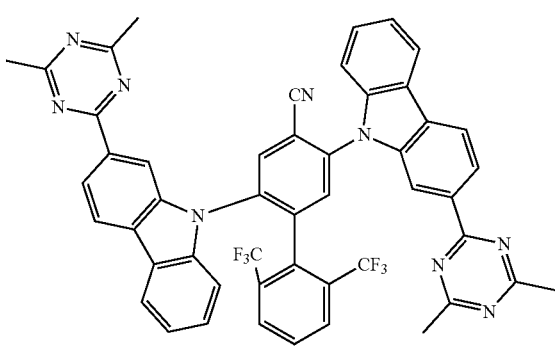
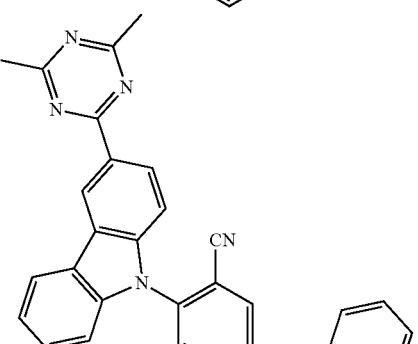
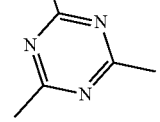

77
-continued
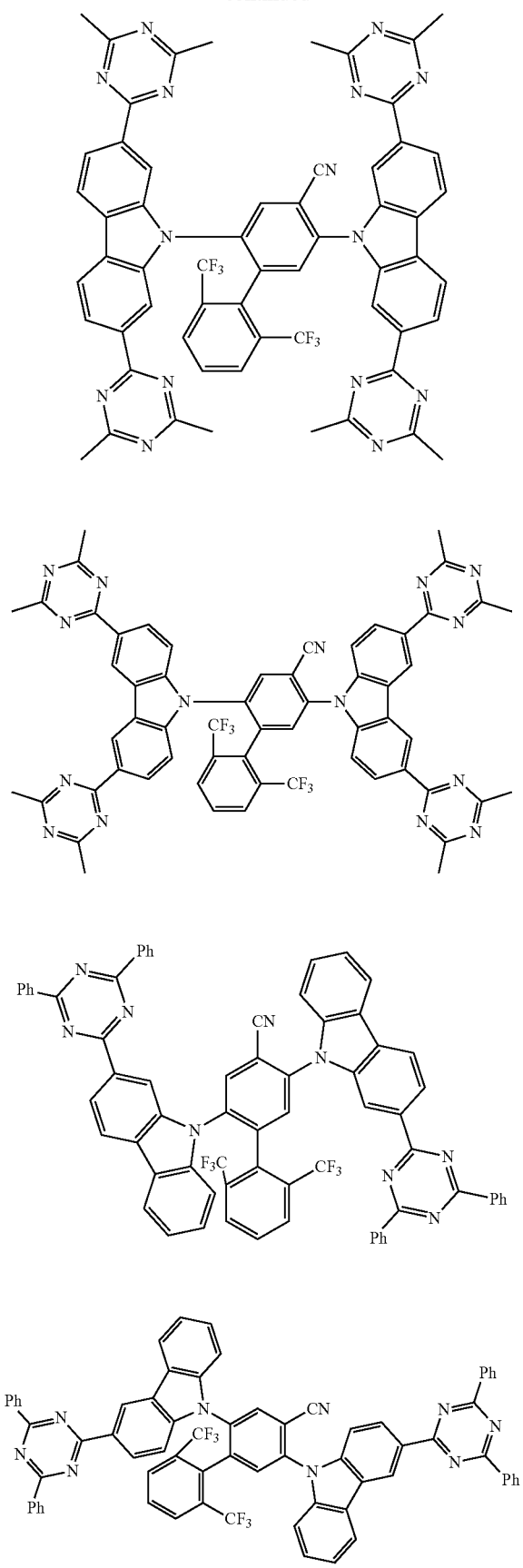
78
-continued
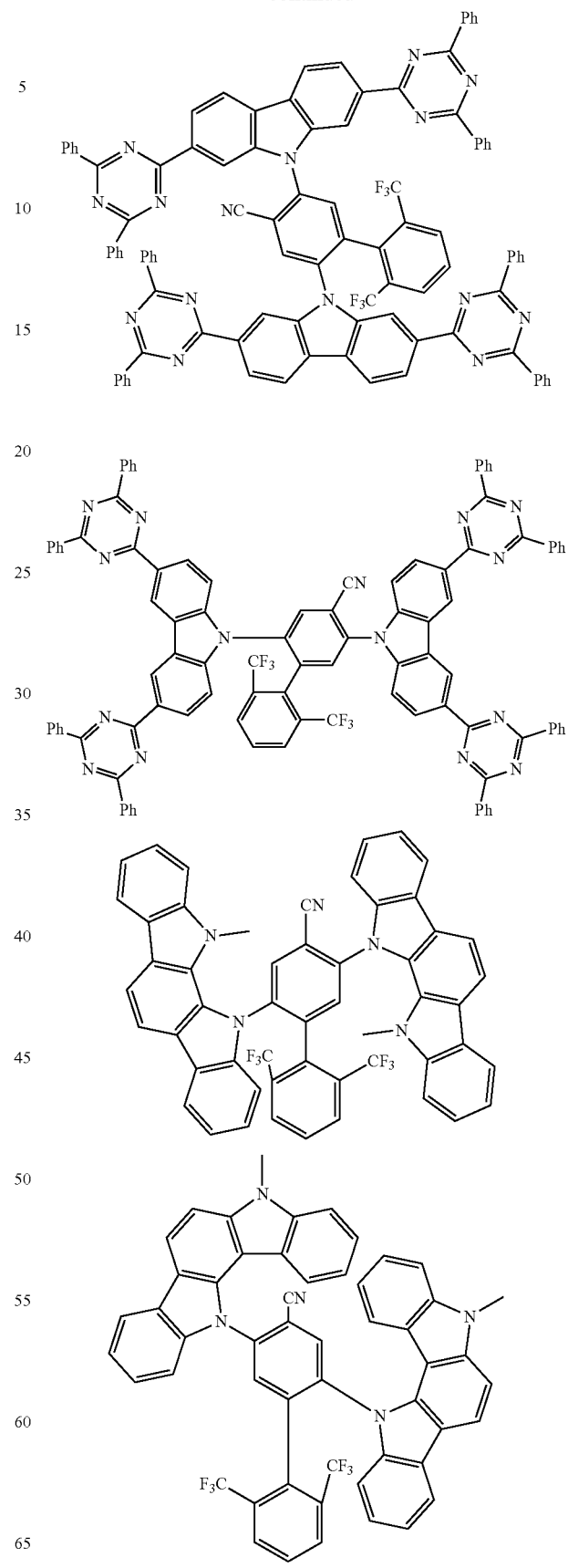

-continued
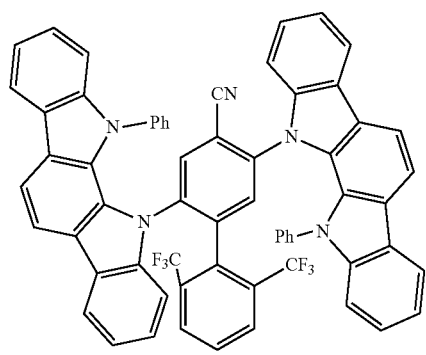
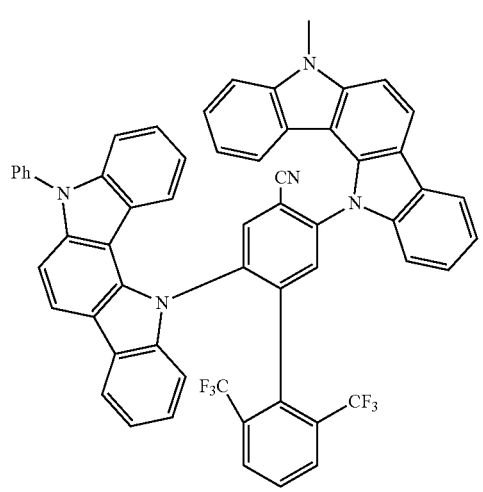
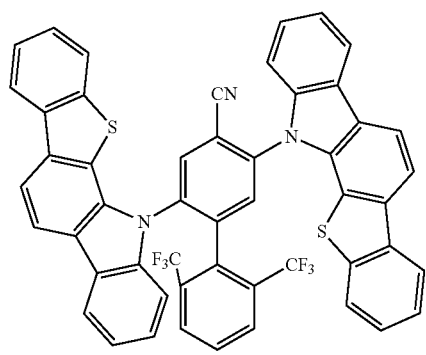
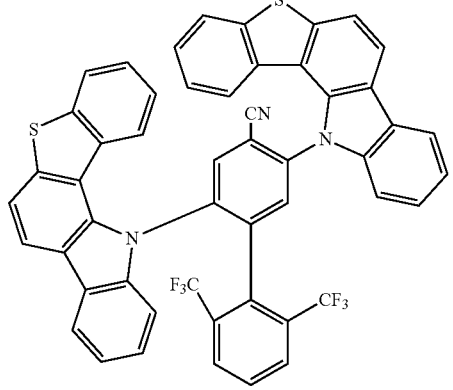
-continued
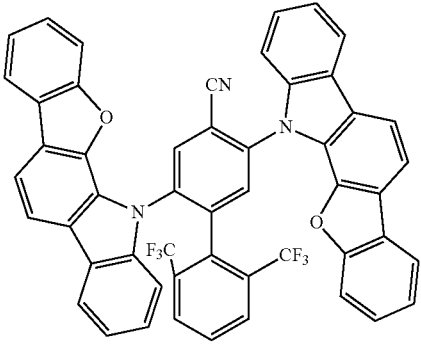
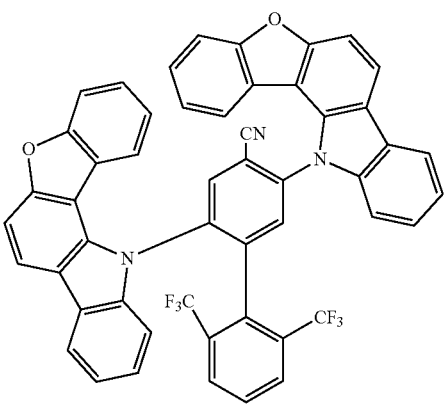
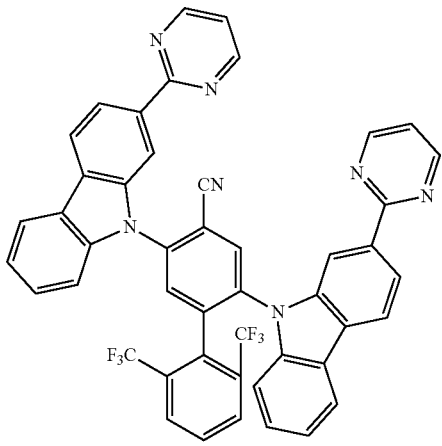
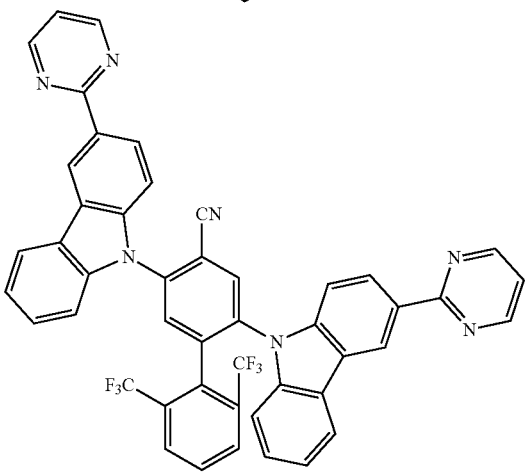

81
-continued
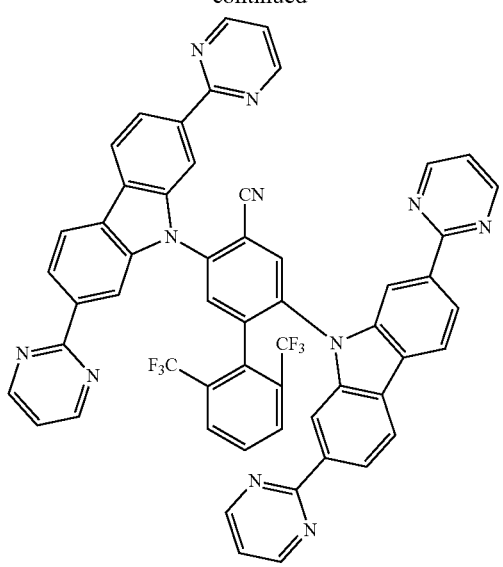
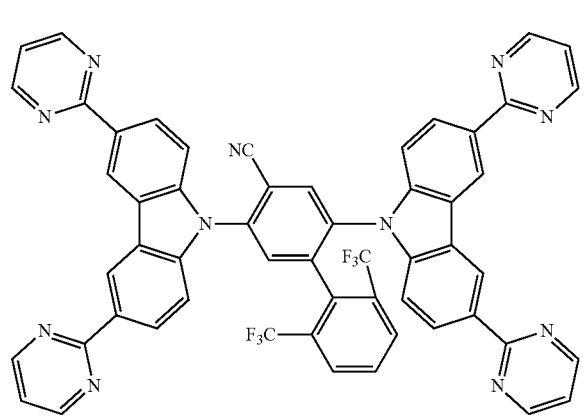
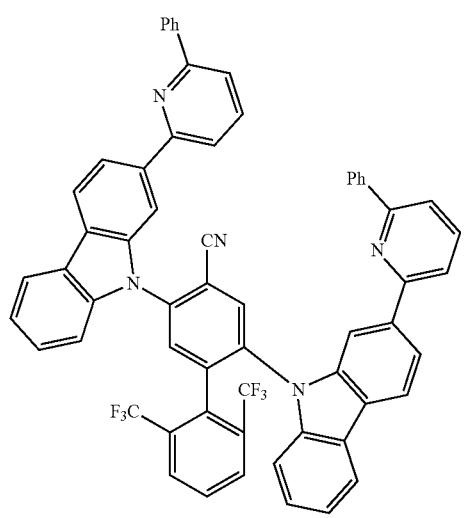
82
-continued
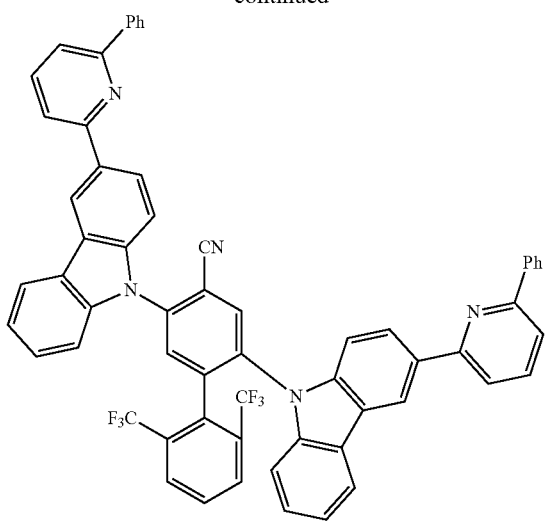
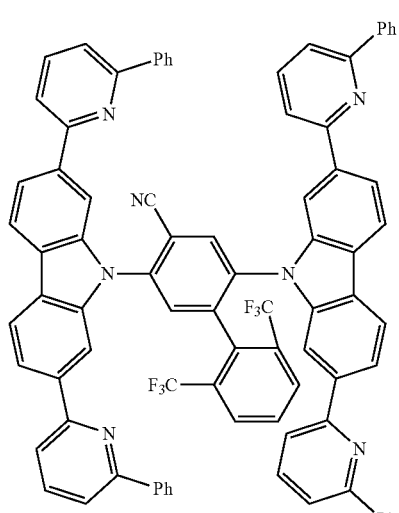
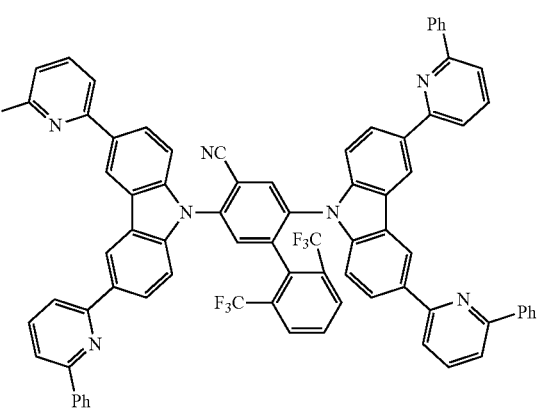

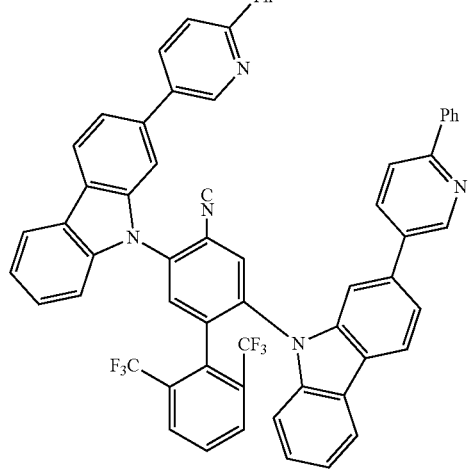
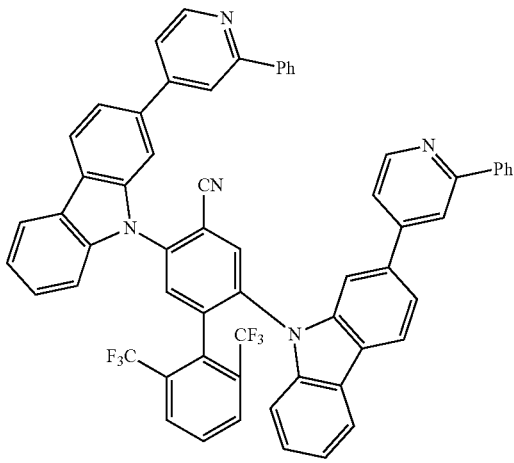
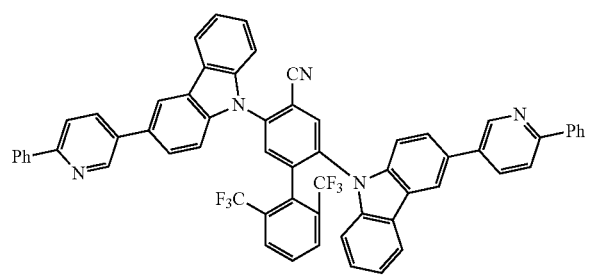
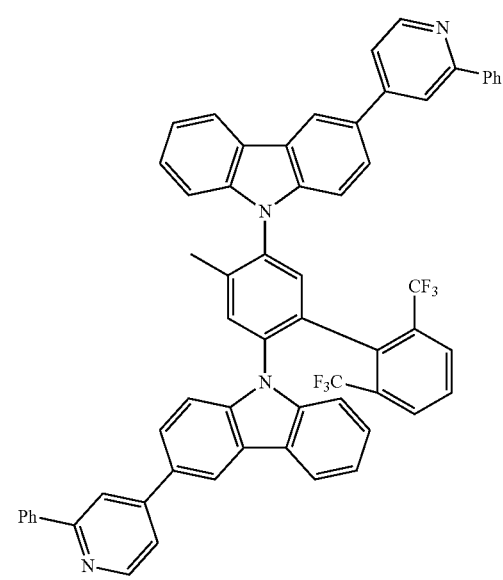
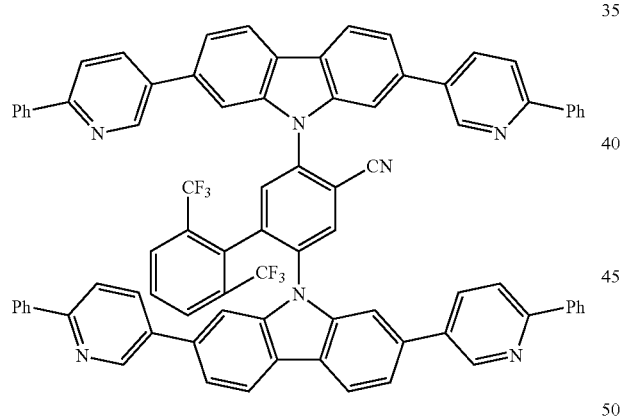
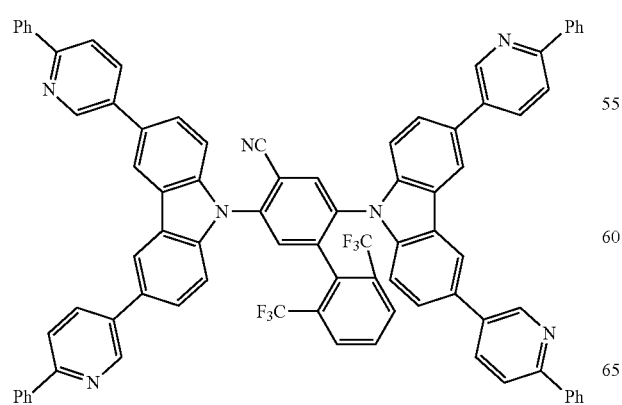
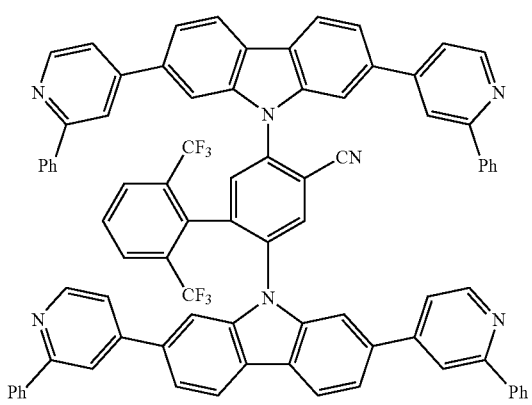

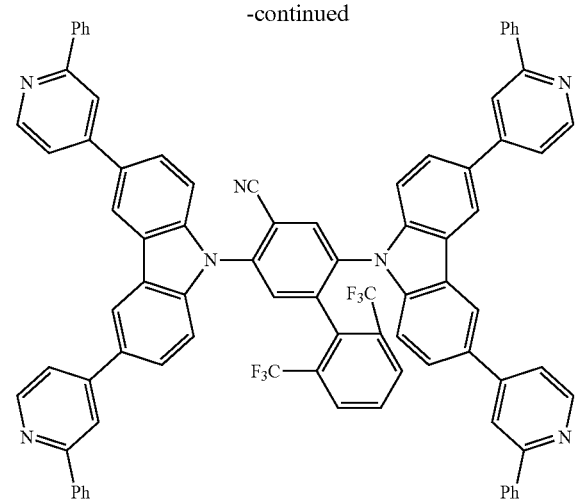
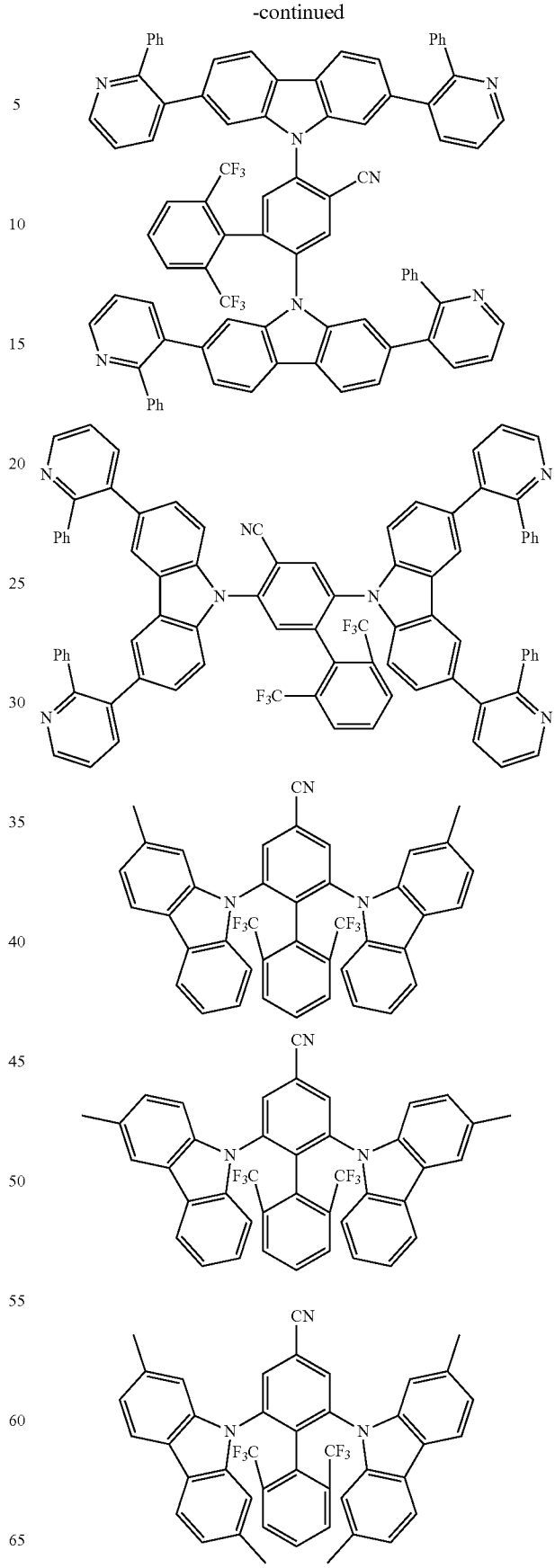

-continued
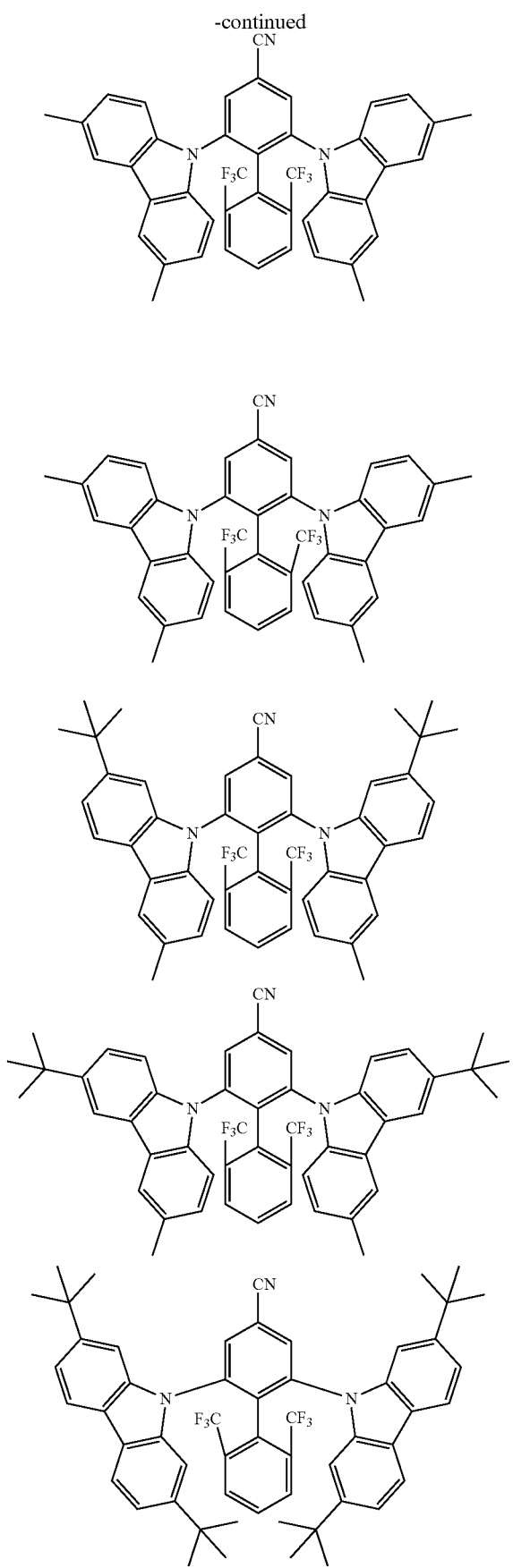
-continued
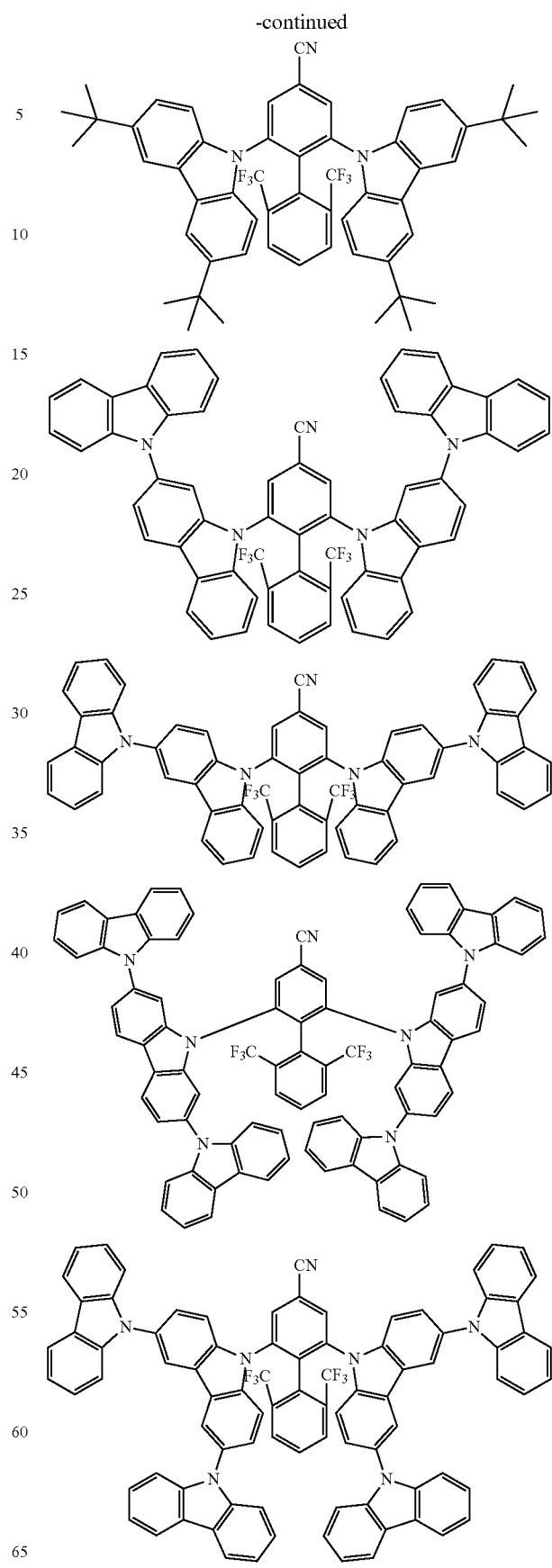

89
-continued
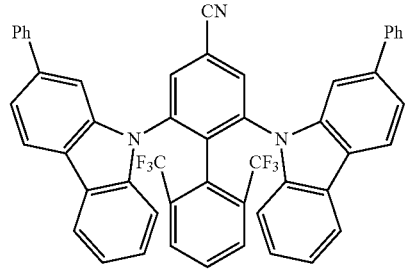
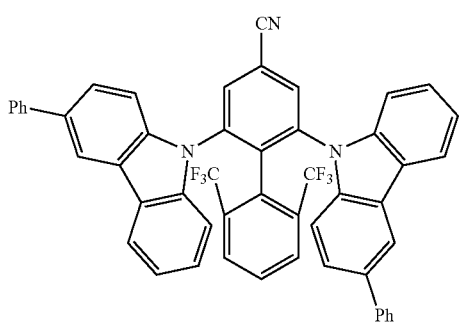
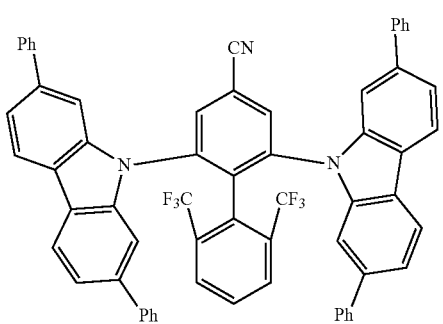
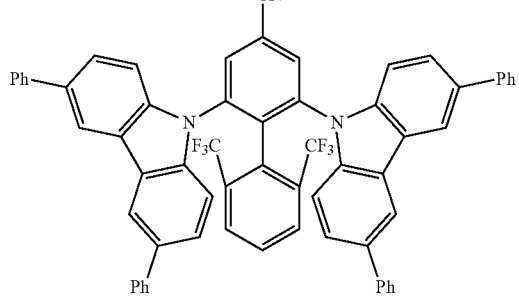
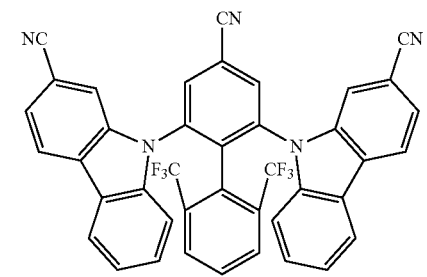
90
-continued
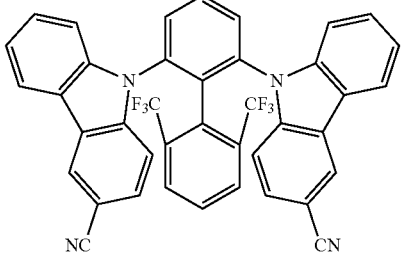
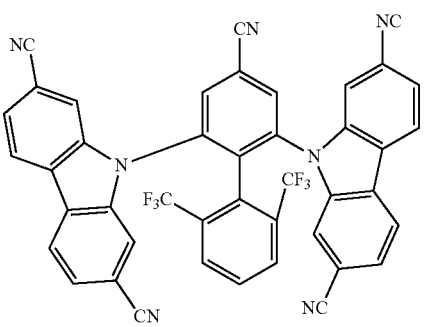
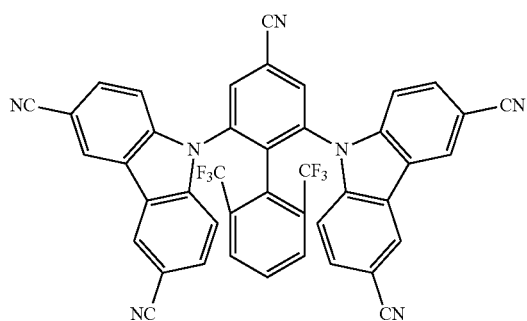
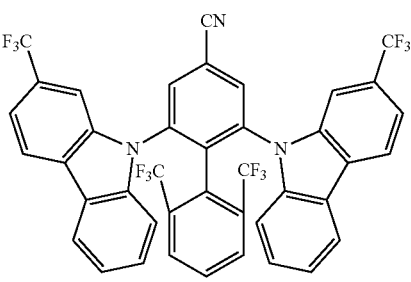
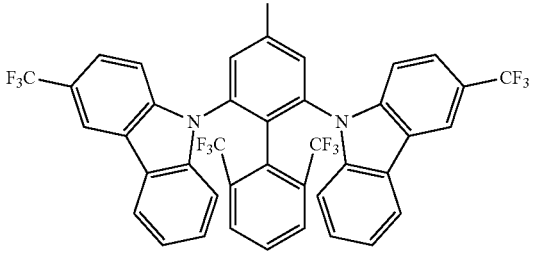

91
-continued
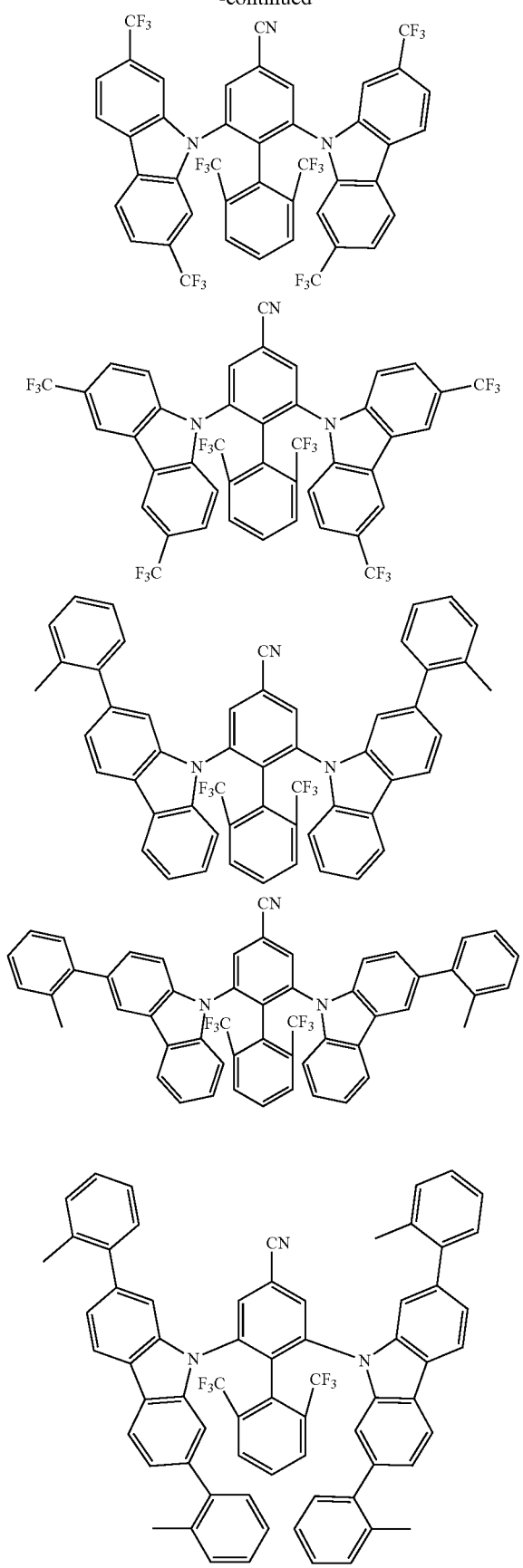
92
-continued
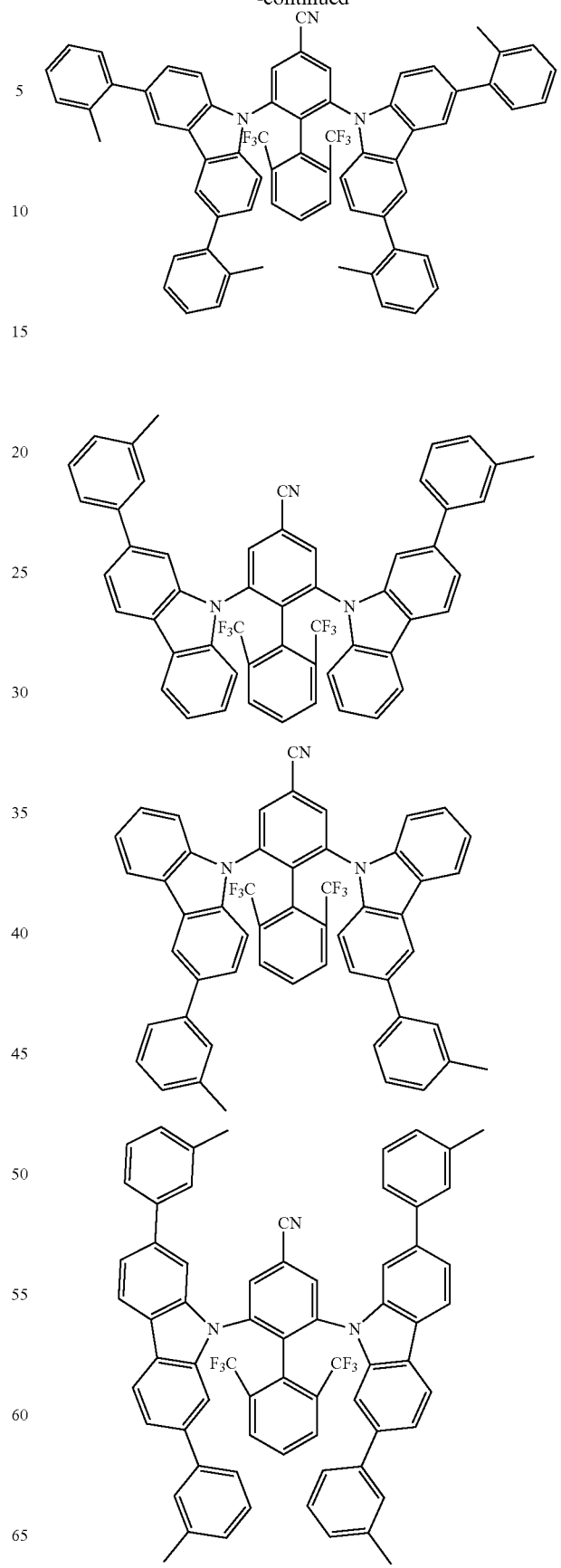

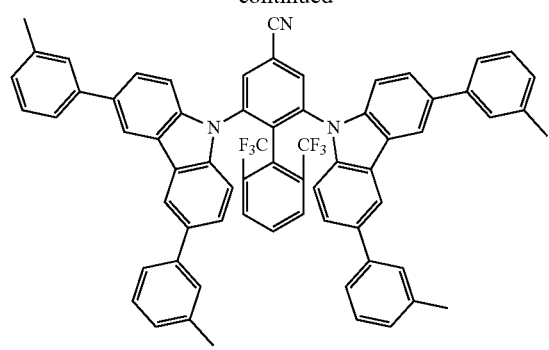
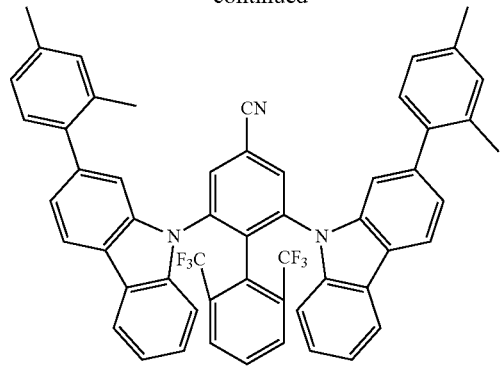
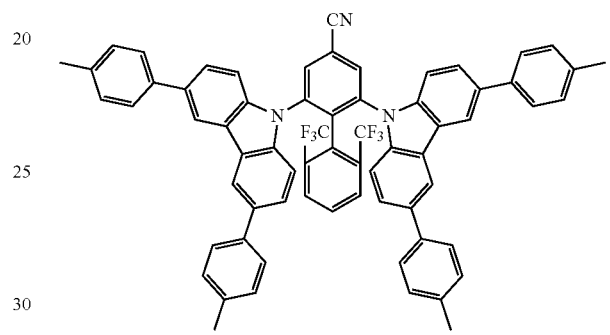
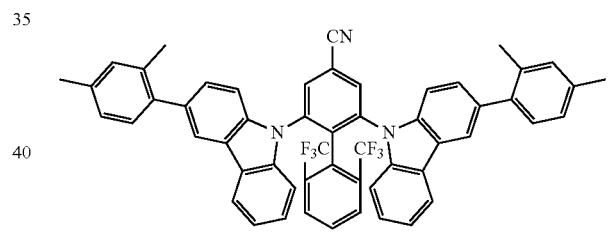
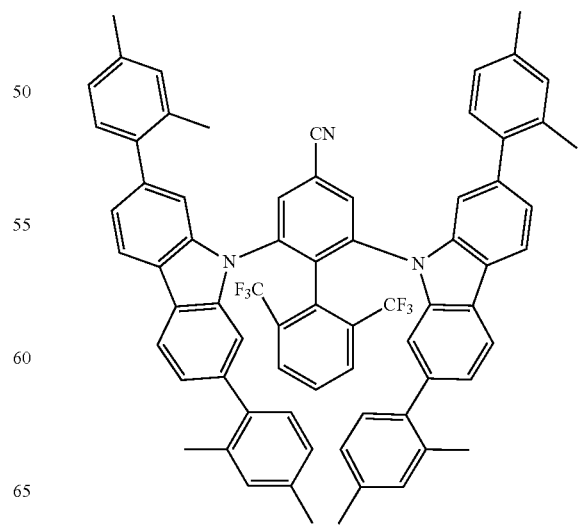

95
96
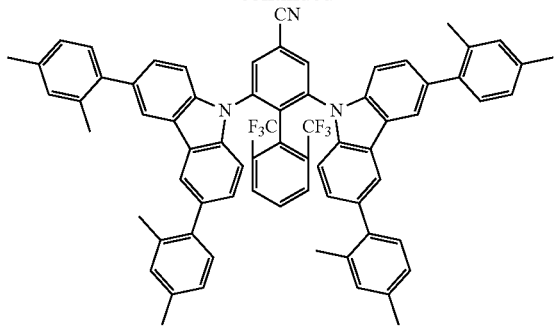
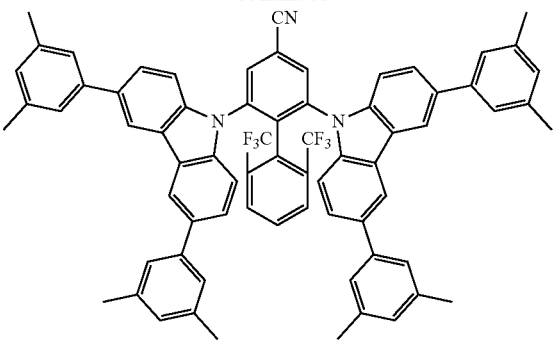
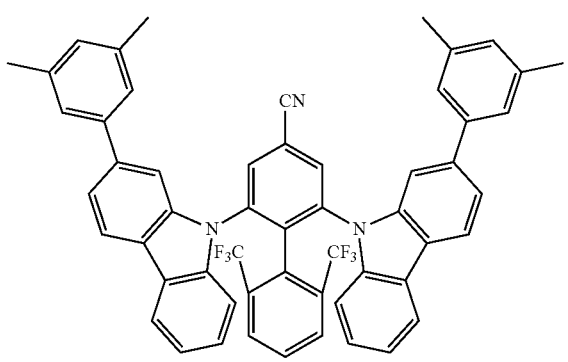
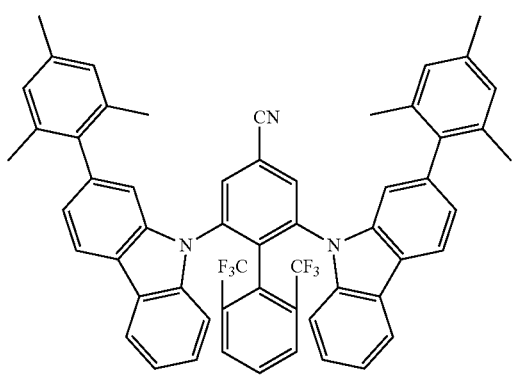
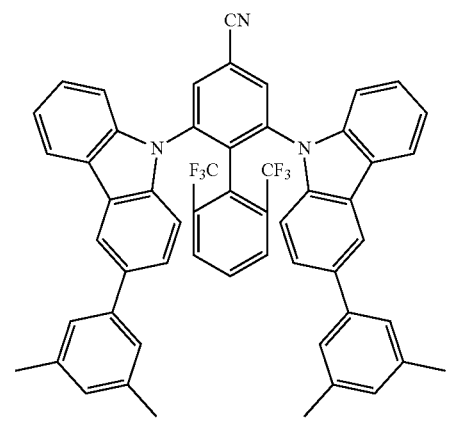
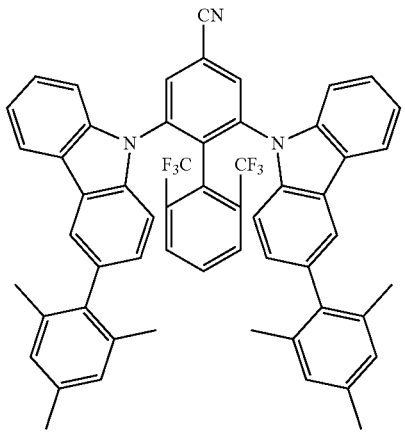
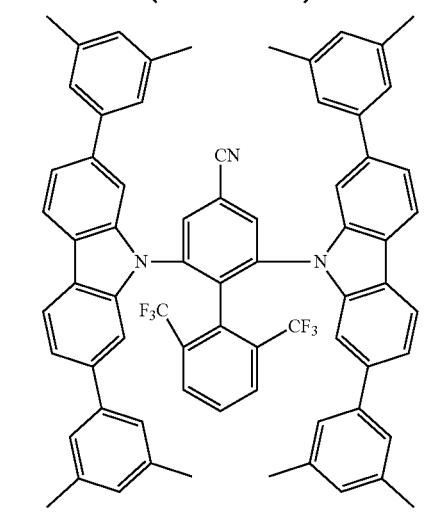
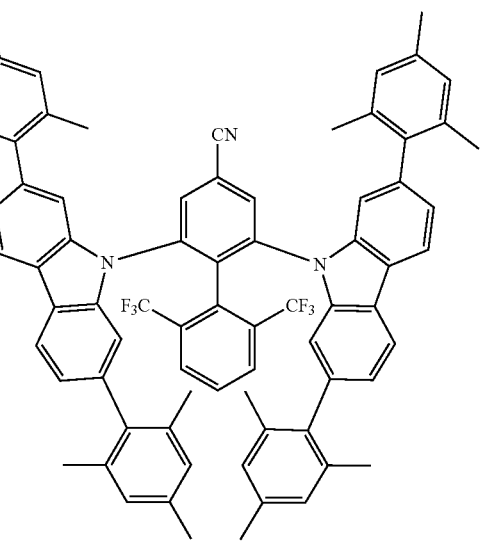

-continued
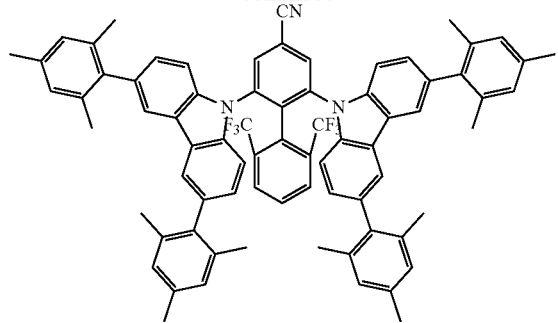
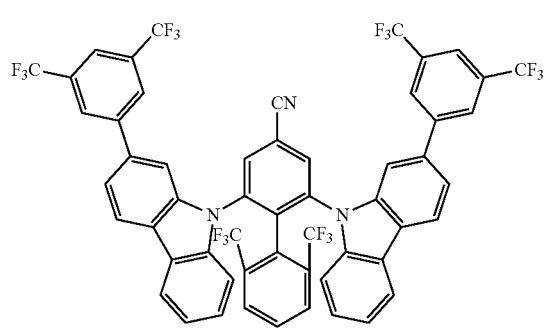
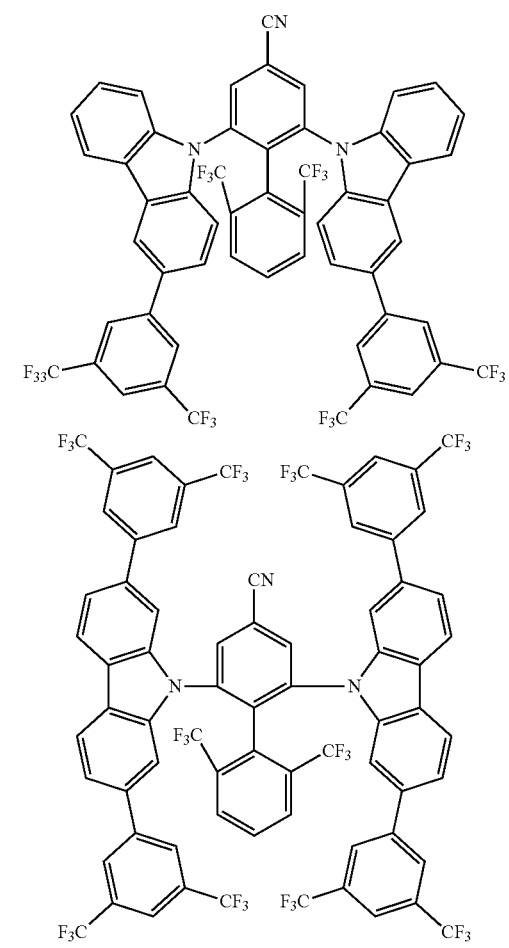
-continued
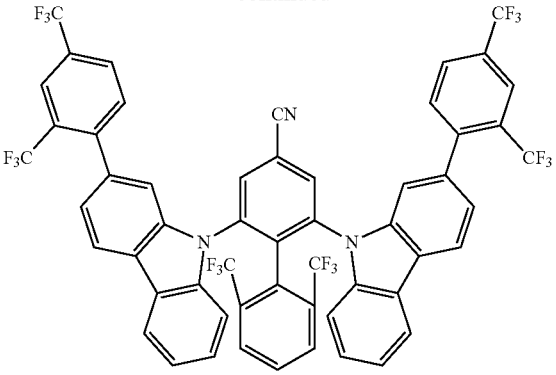
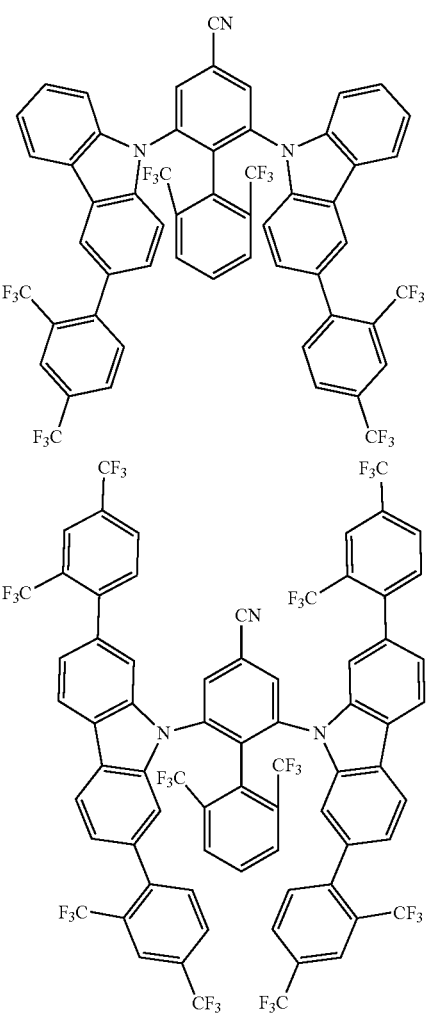

99
-continued
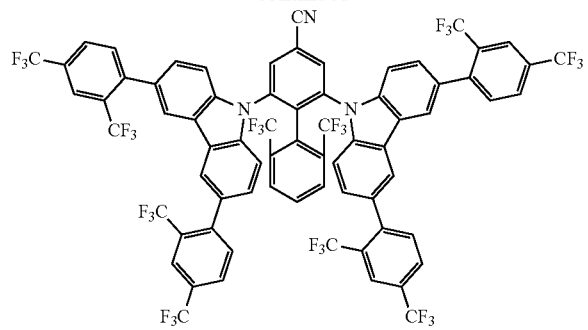
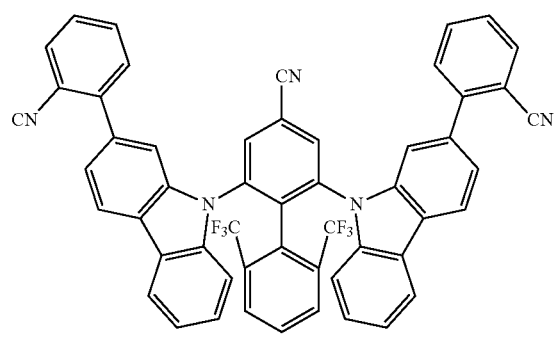
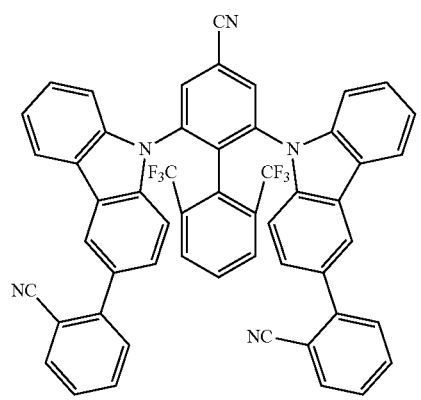
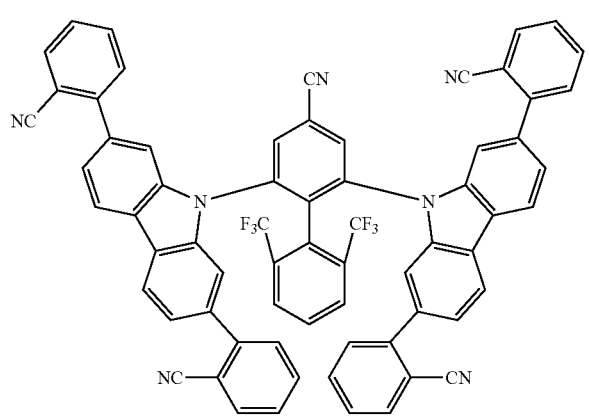
100
-continued
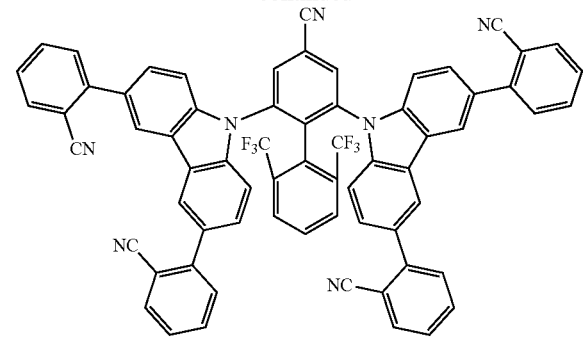
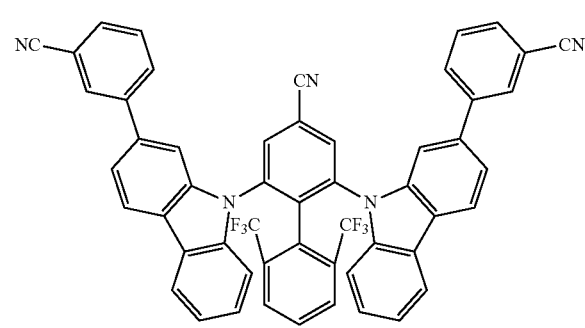
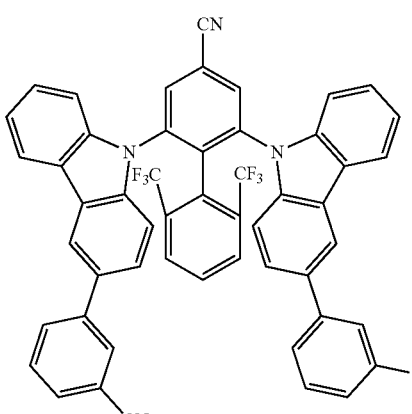
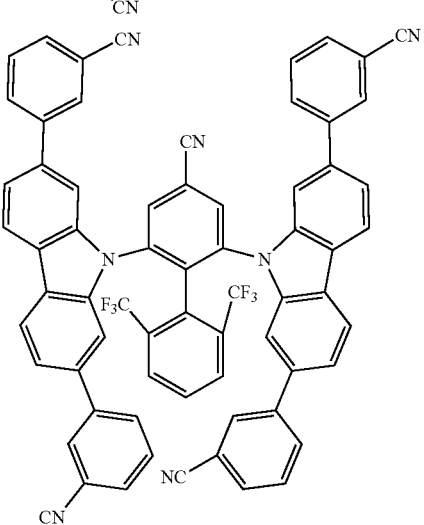

101
-continued
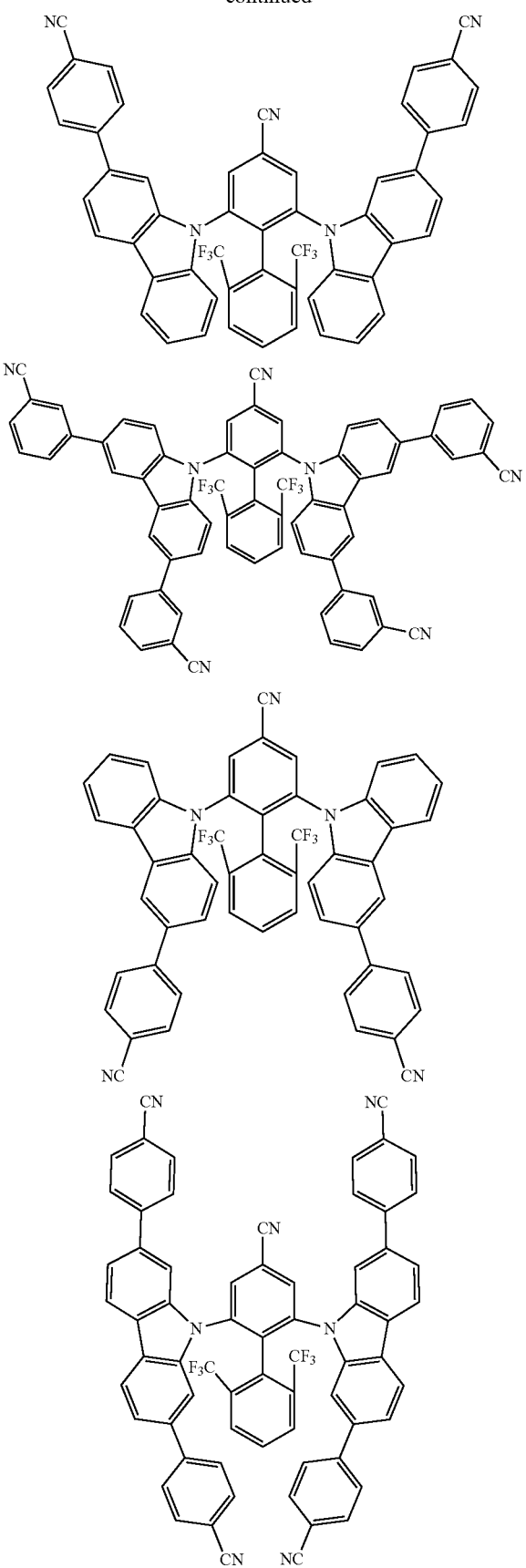
102
-continued
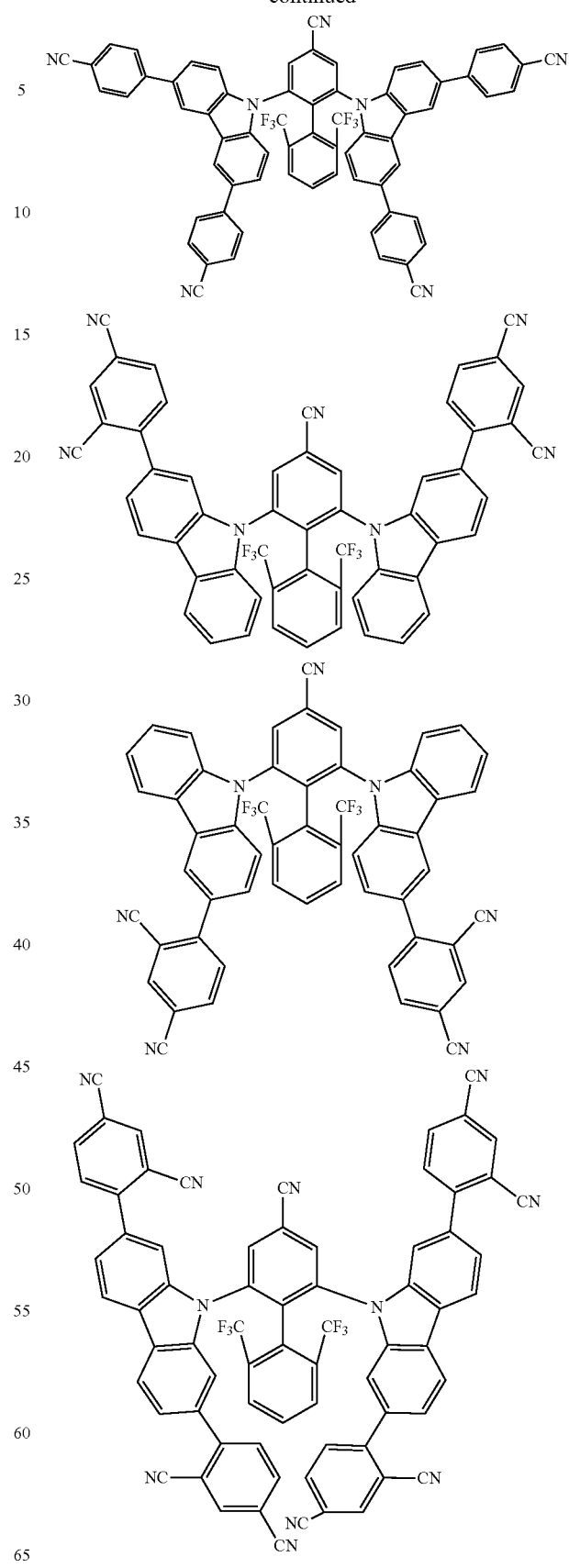

103
-continued
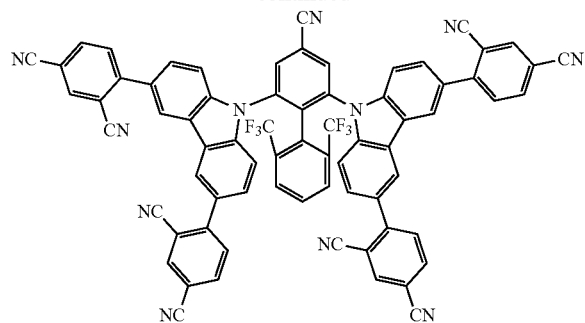
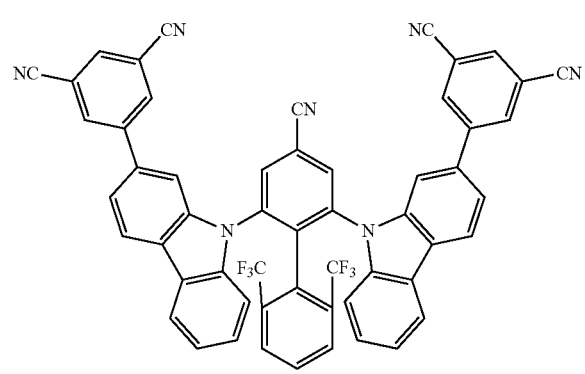
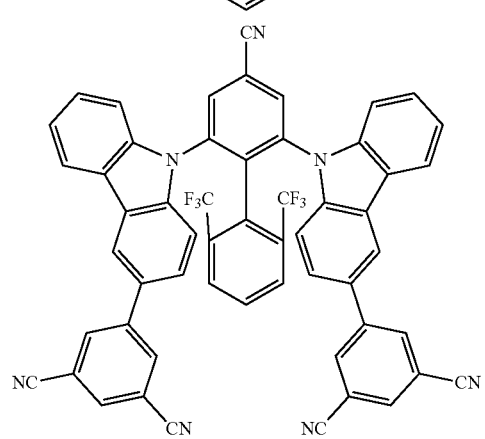
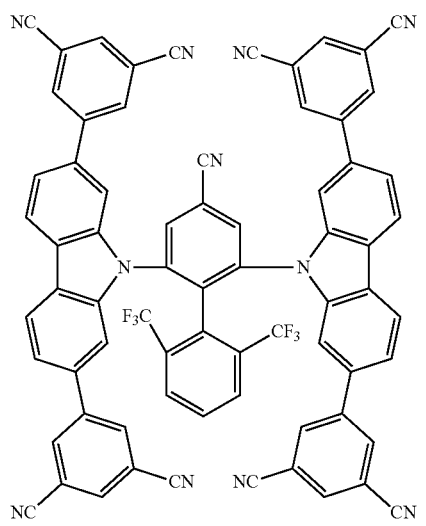
104
-continued
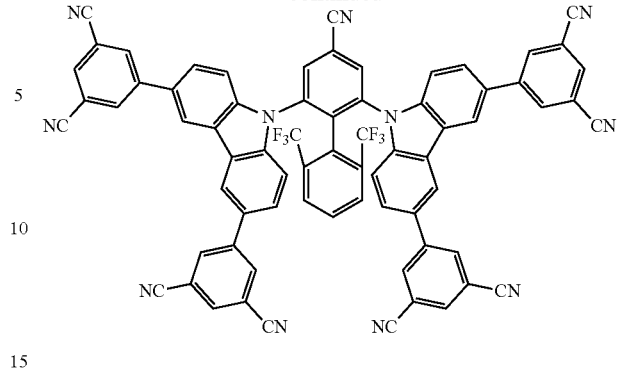
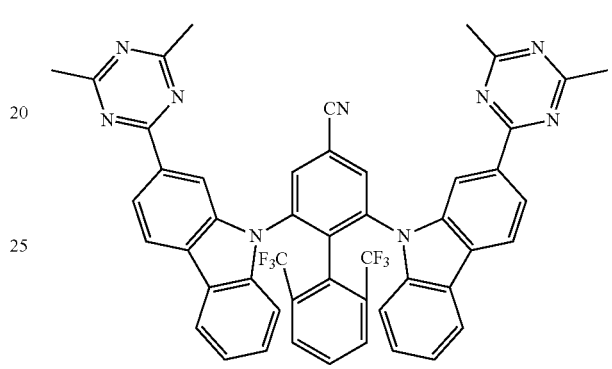
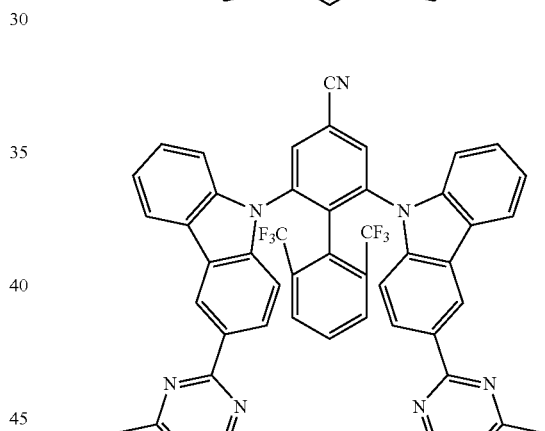
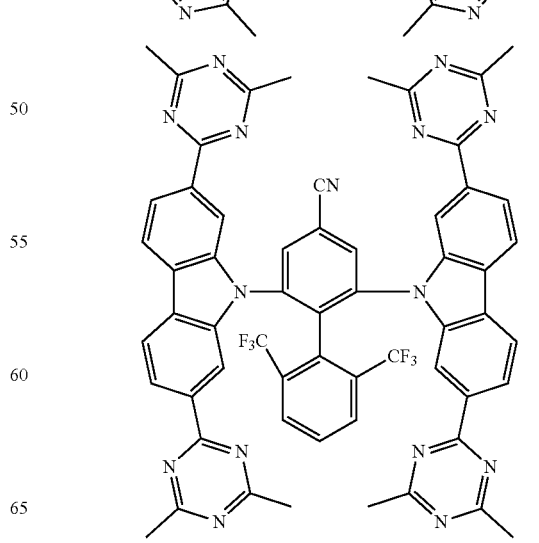

-continued
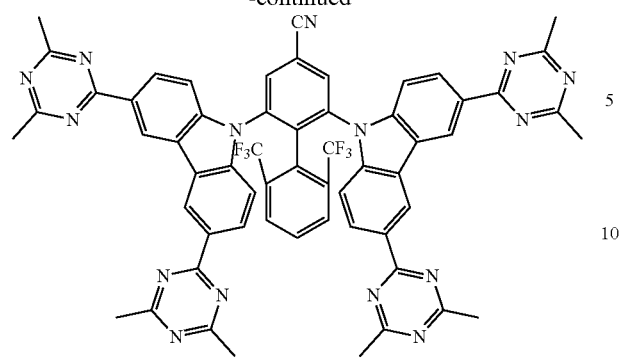
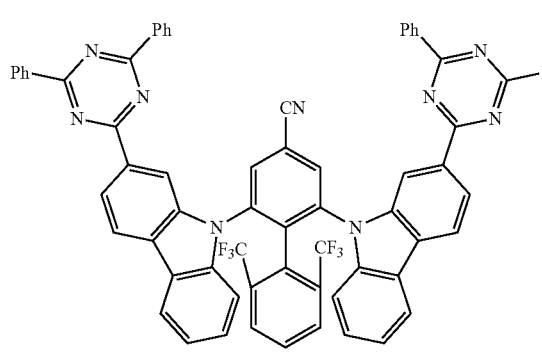
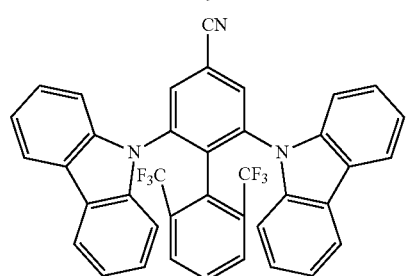
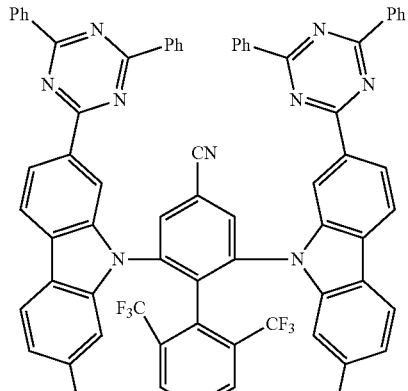
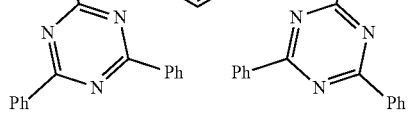
-continued
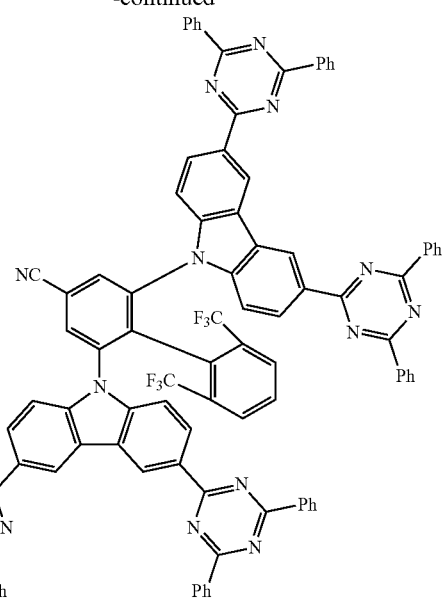
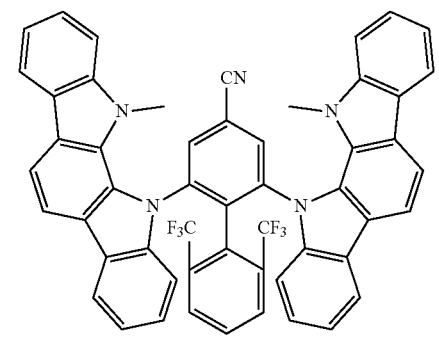
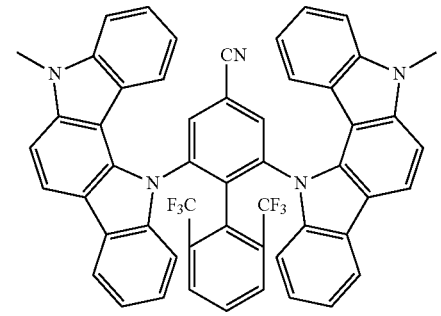
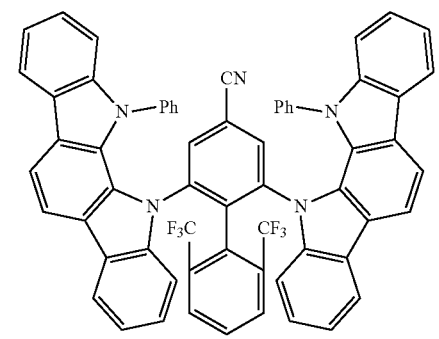

107
-continued
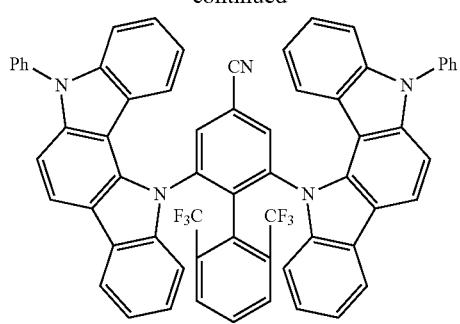
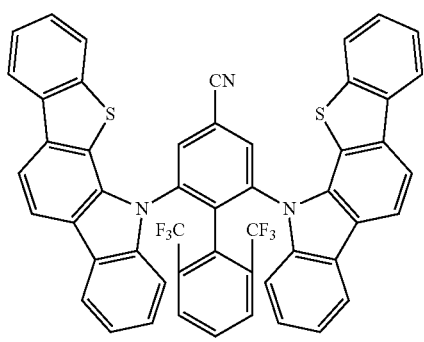
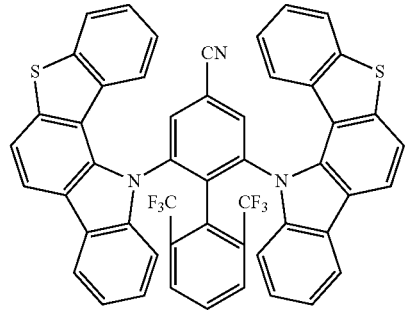
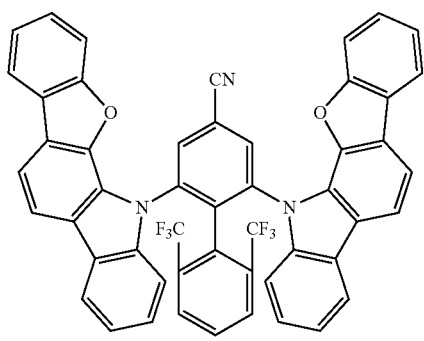
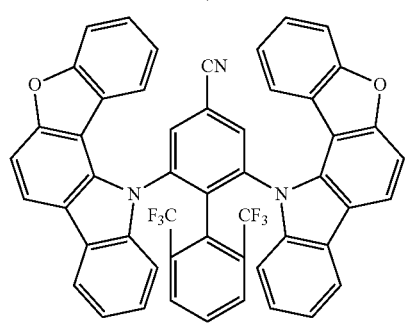
108
-continued
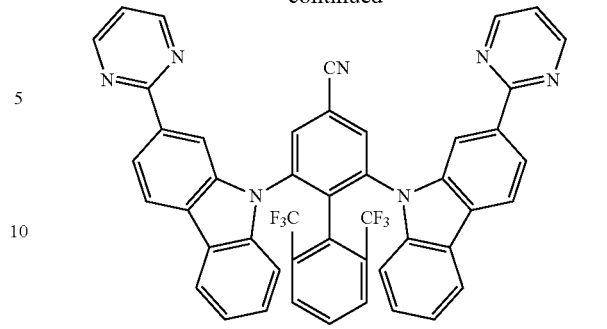
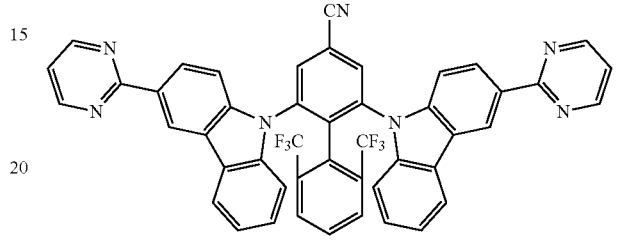
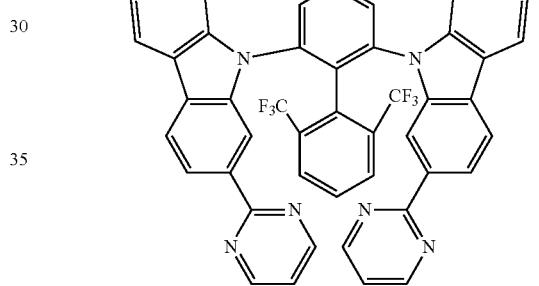
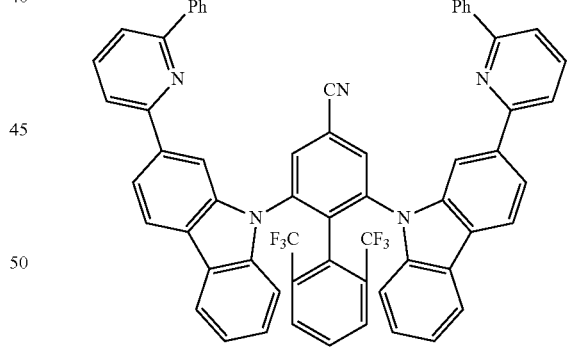
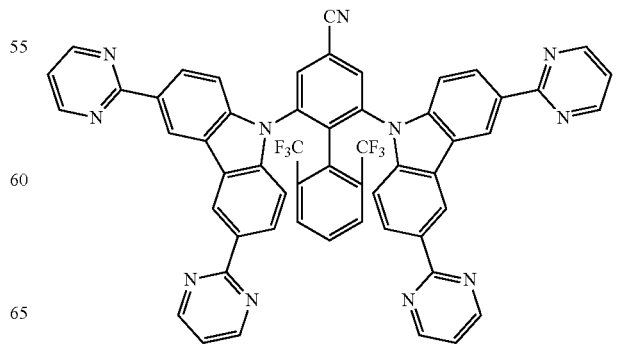

109
-continued
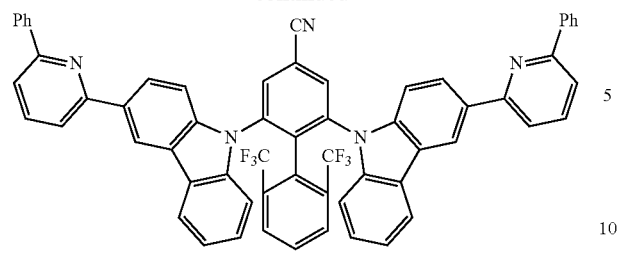
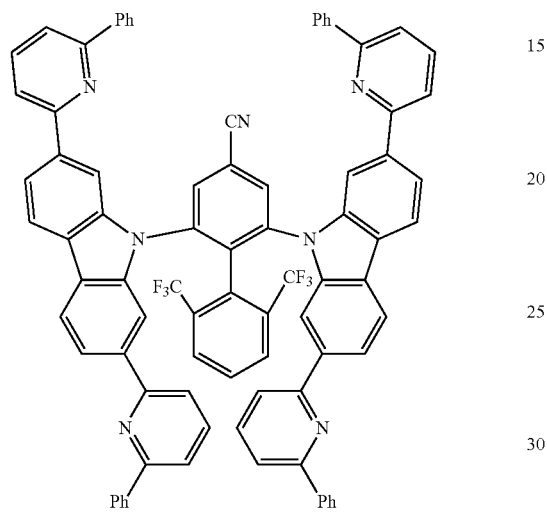
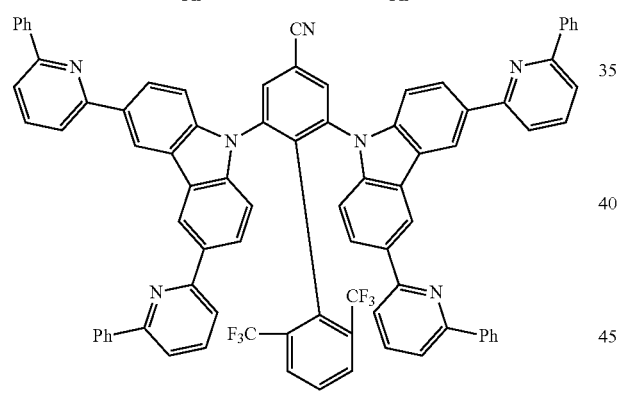
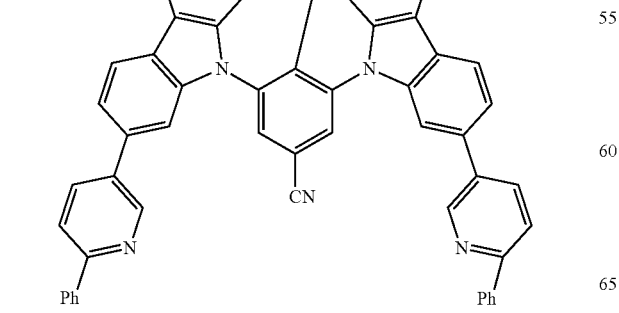
110
-continued
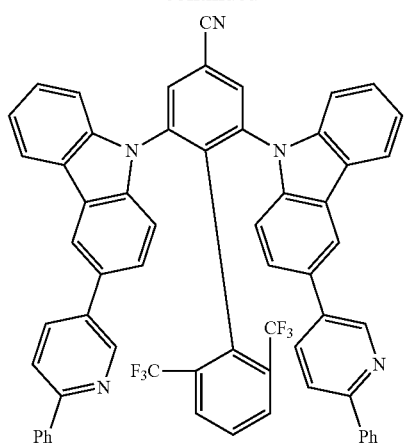
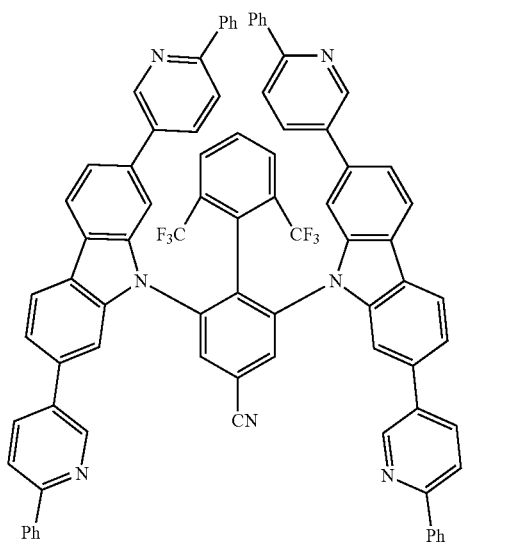
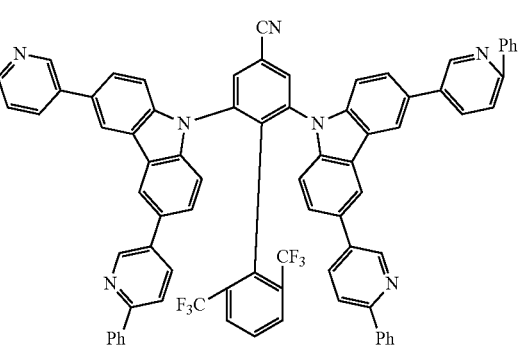

111
-continued
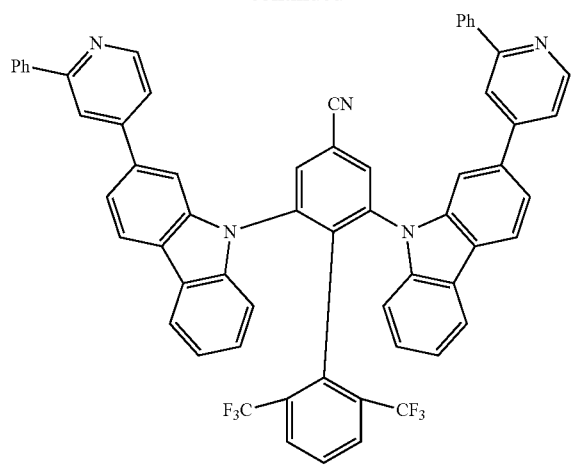
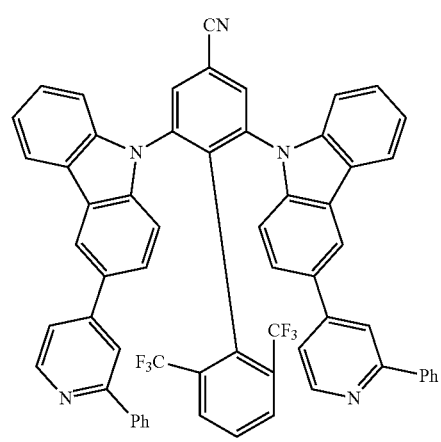
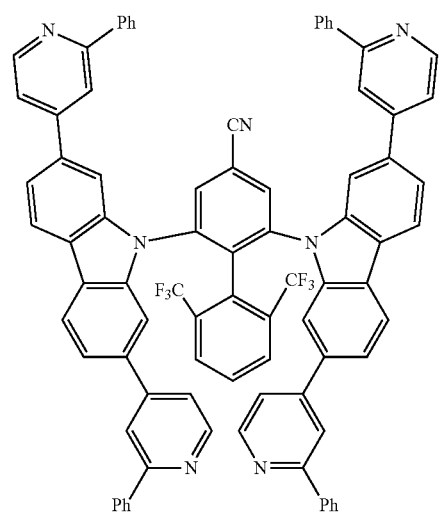
112
-continued
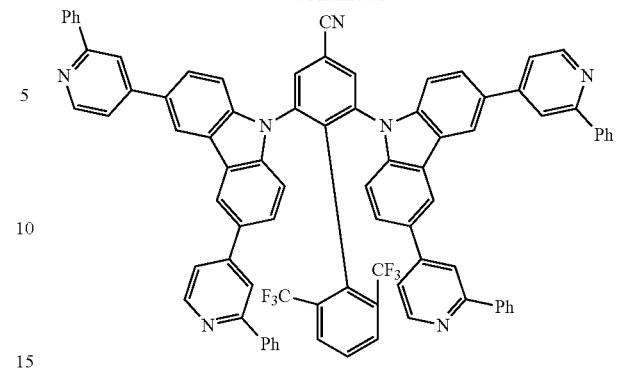
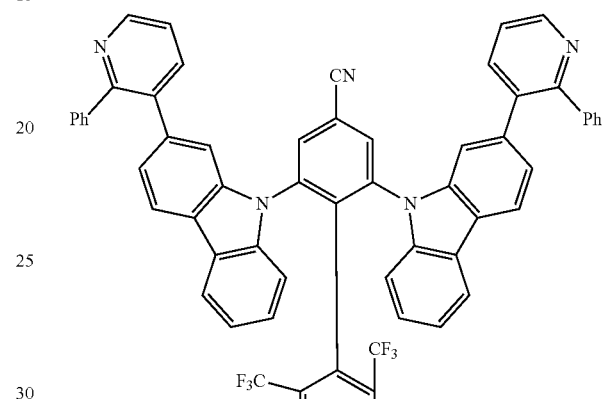
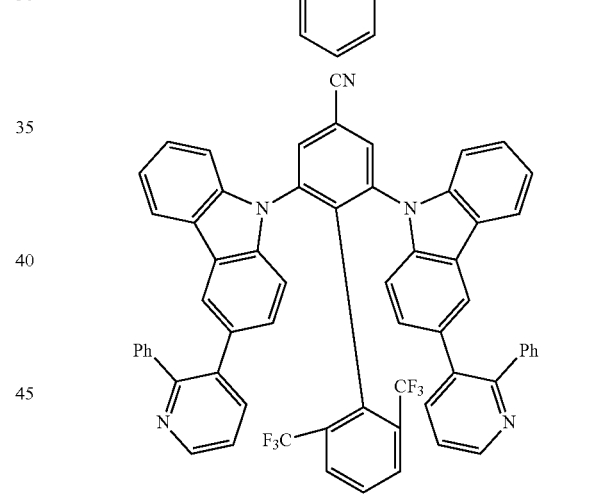
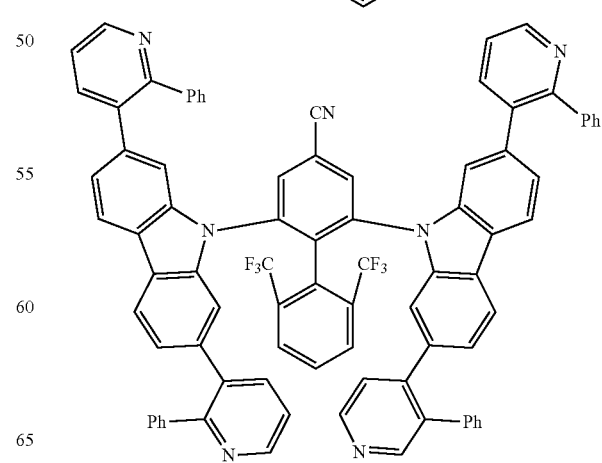

113
-continued
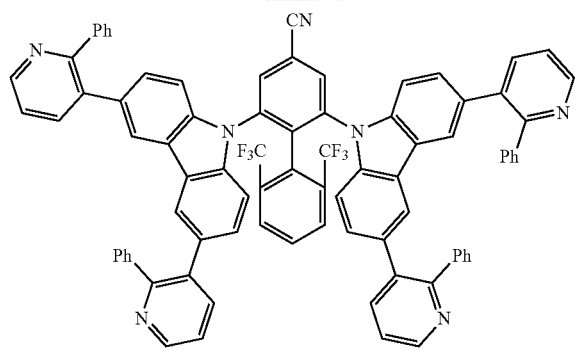
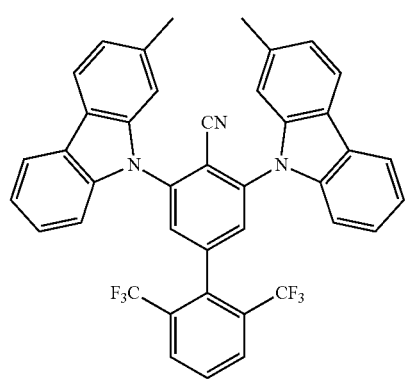
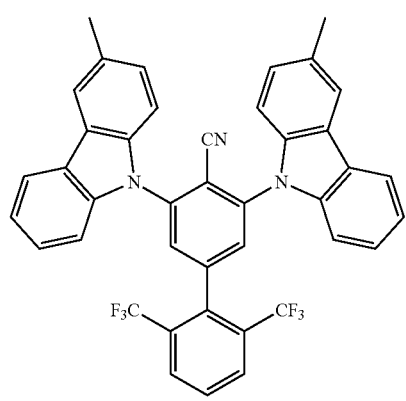
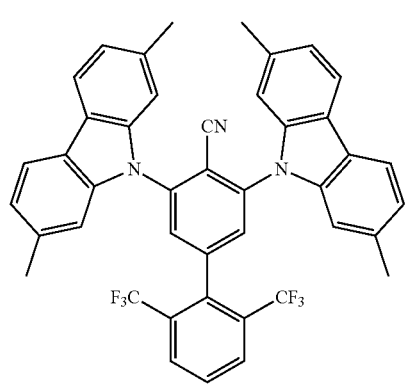
114
-continued
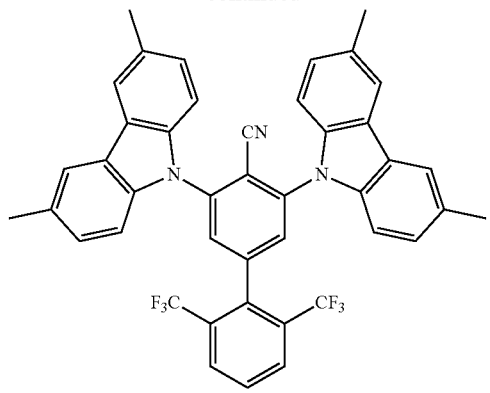
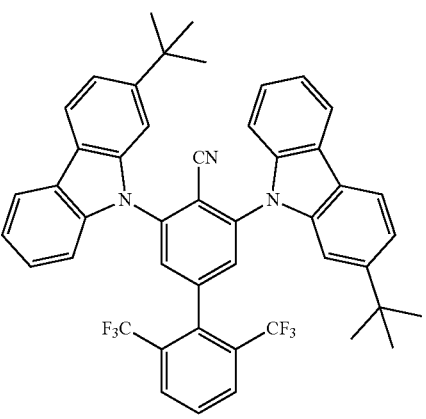
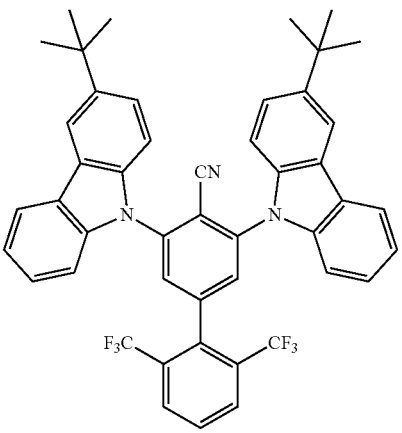
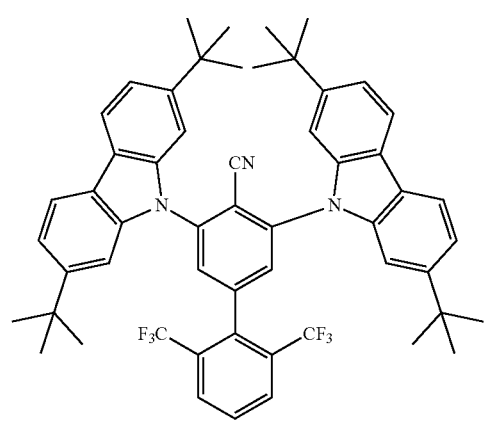

115
-continued
116
-continued
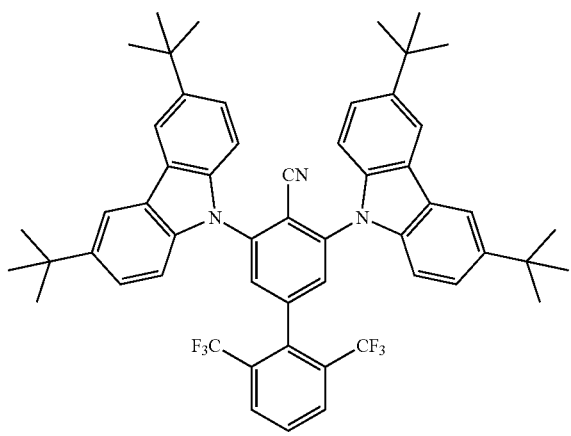
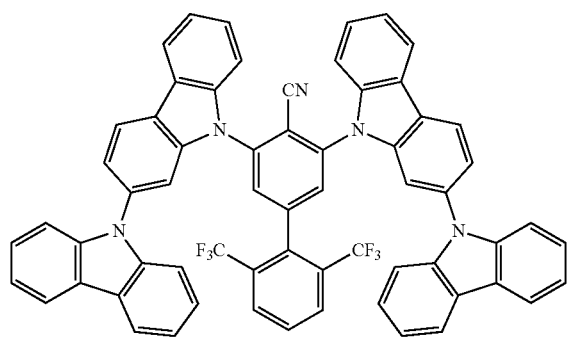
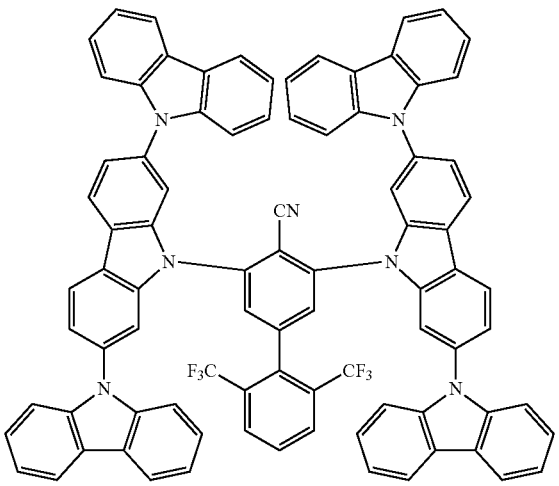
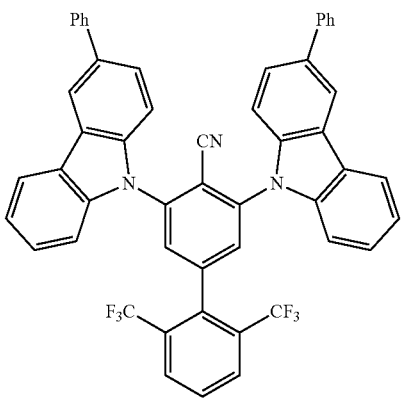

117
-continued
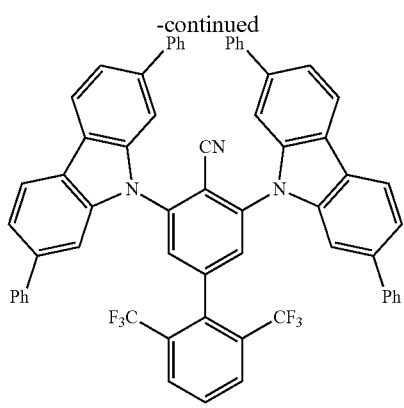
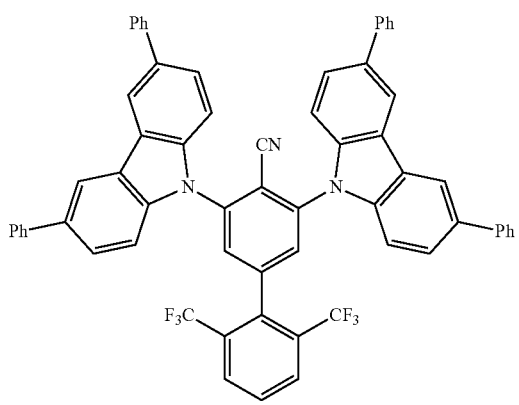
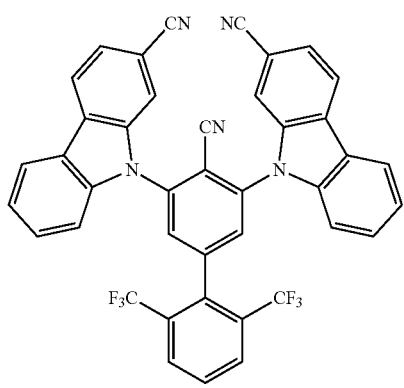
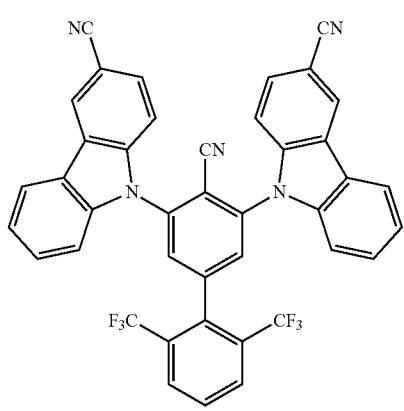
118
-continued
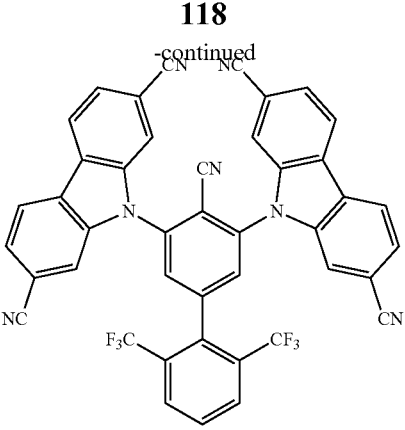
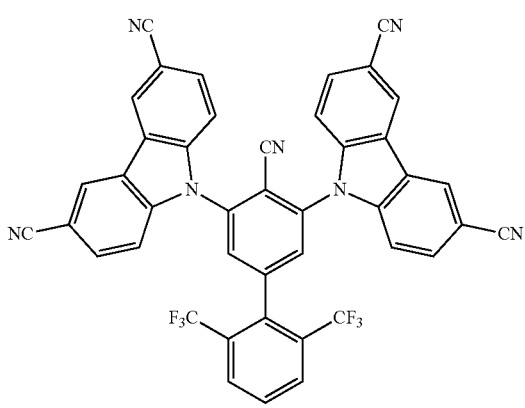
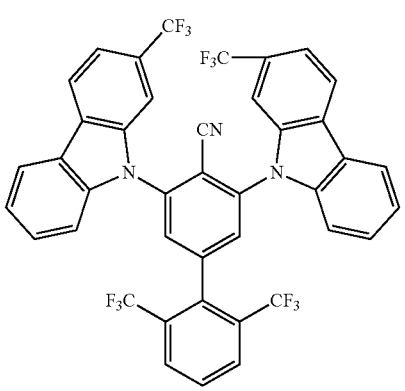
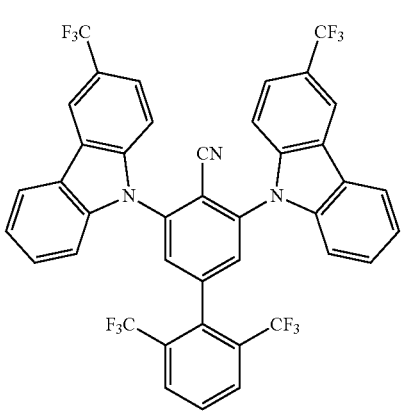

119
-continued
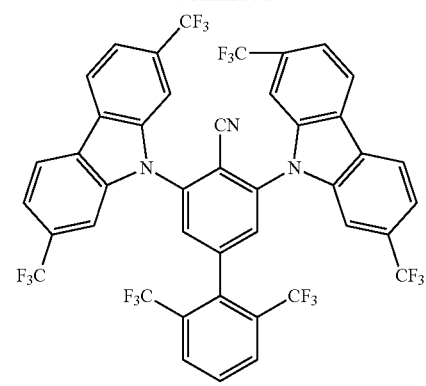
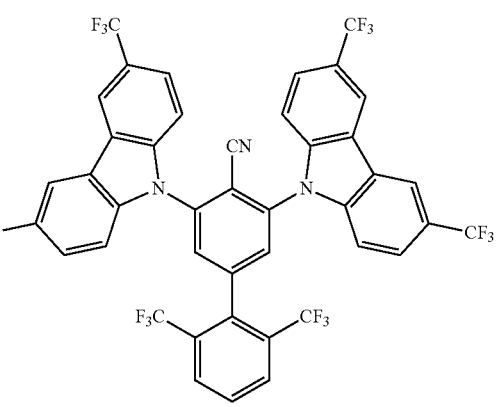
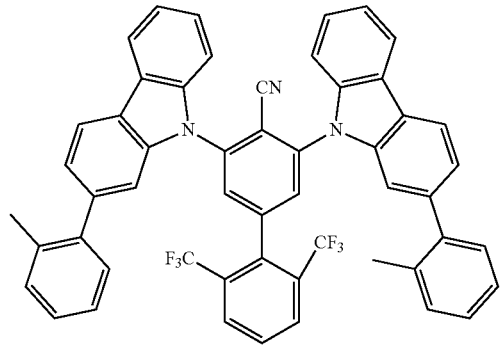
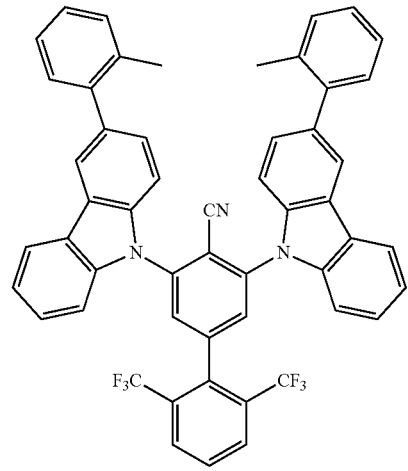
120
-continued
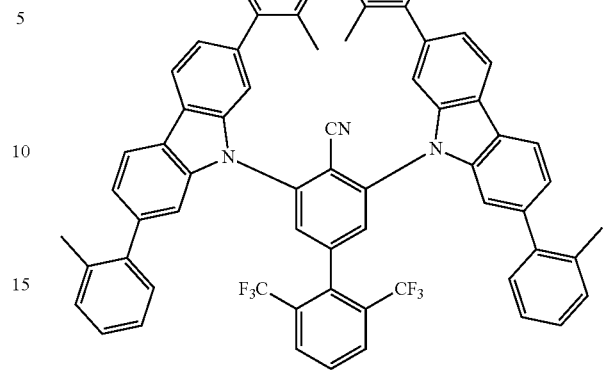
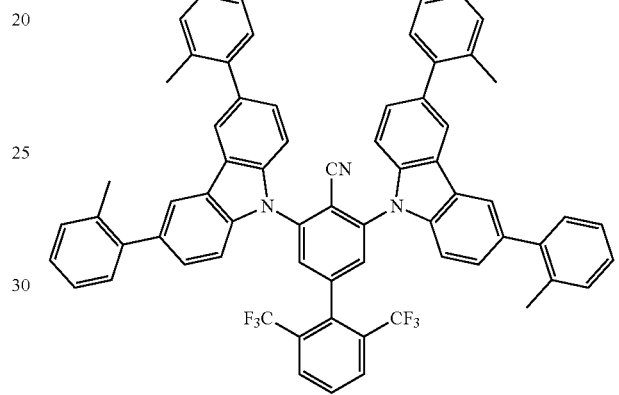
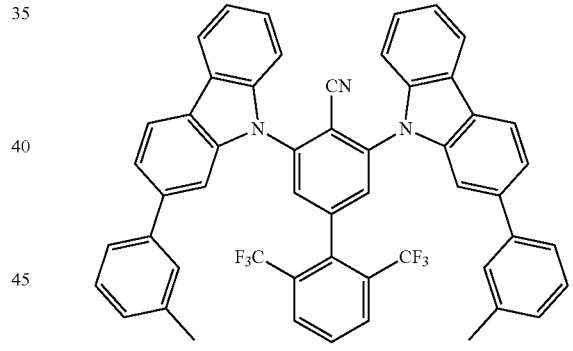
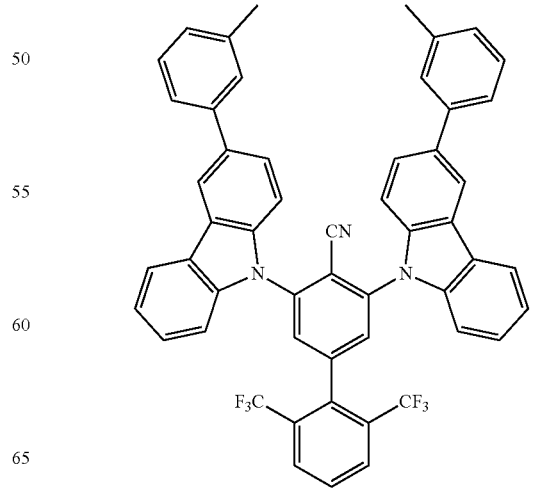

121
-continued
122
-continued
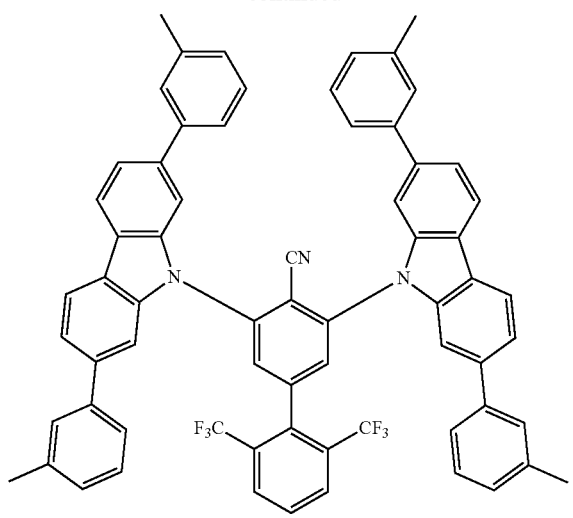
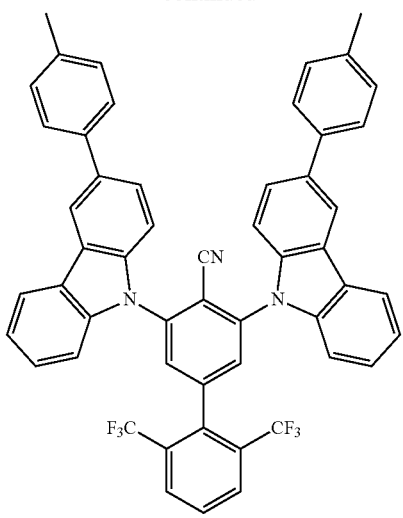
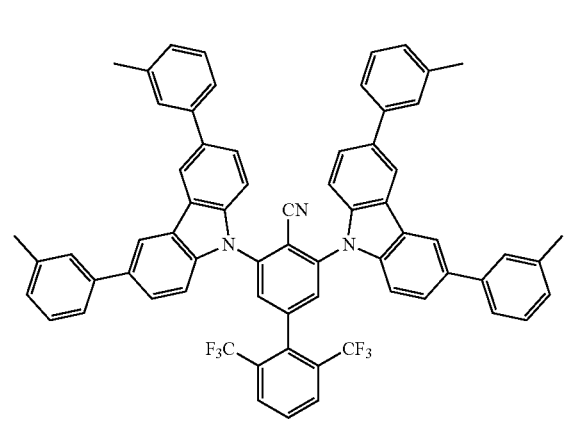
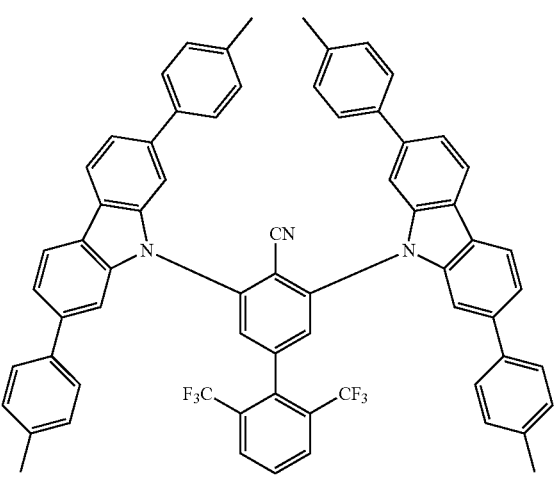
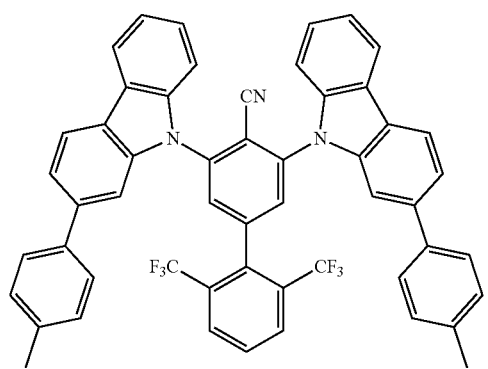
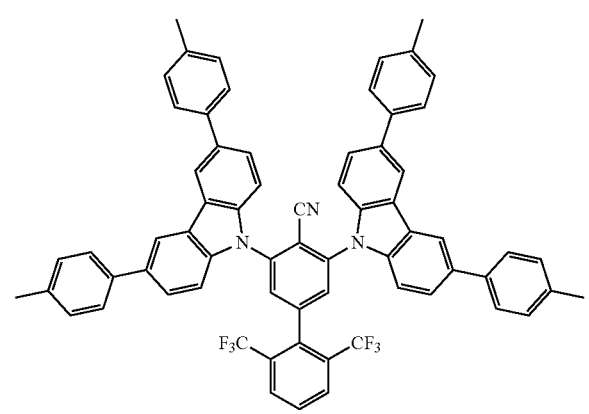

123
-continued
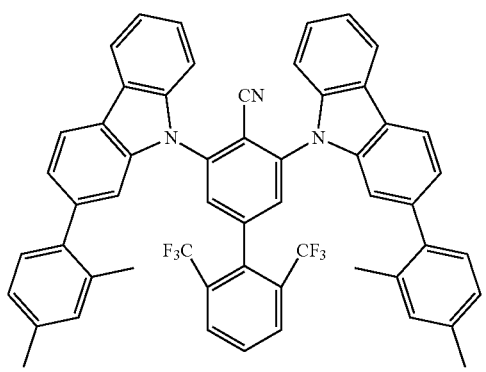
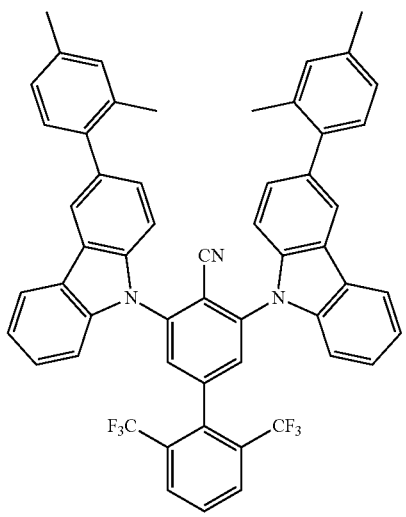
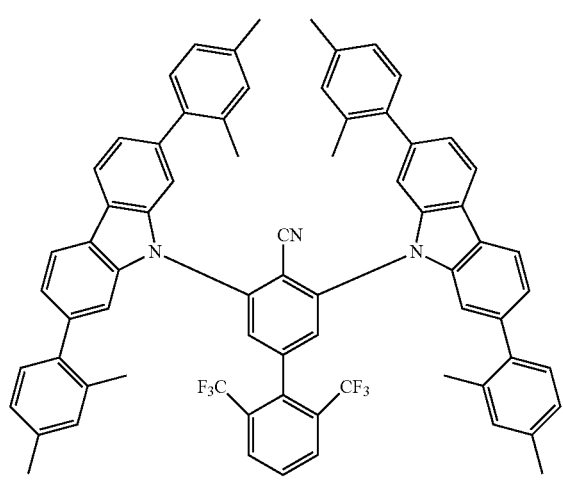
124
-continued
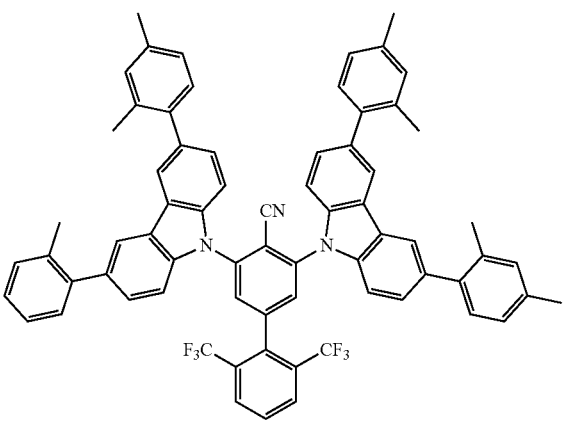
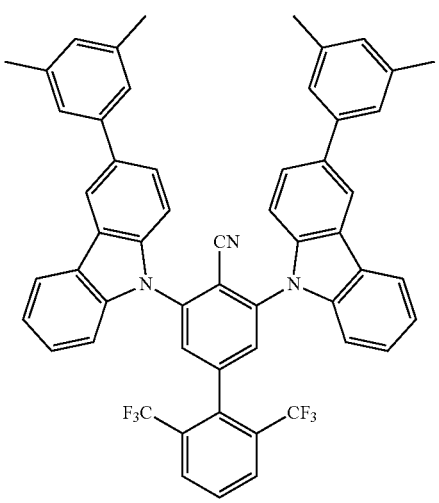

125
-continued
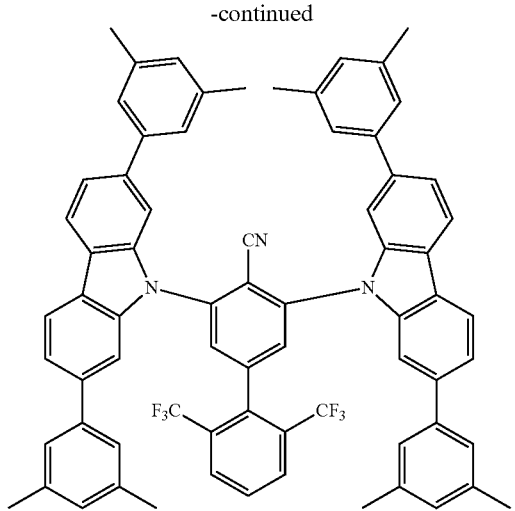
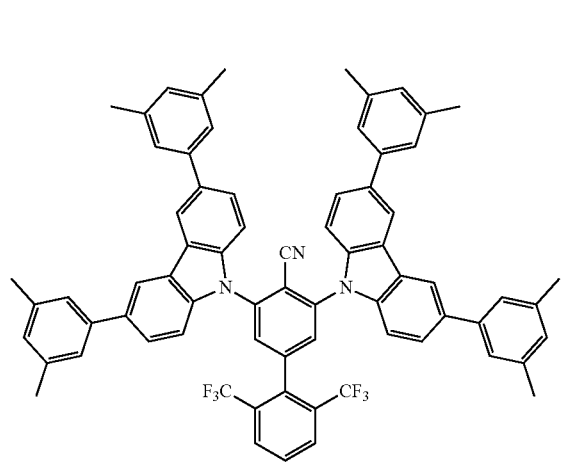
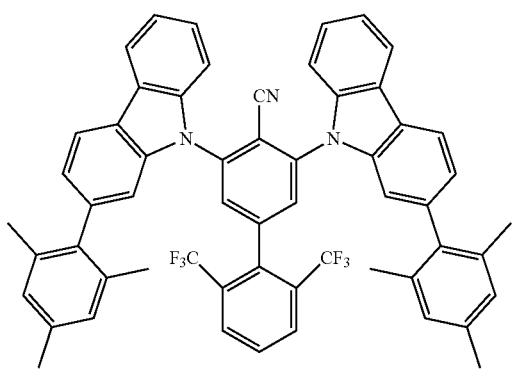
126
-continued
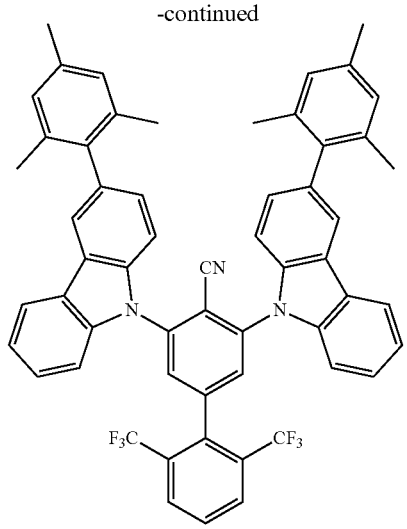
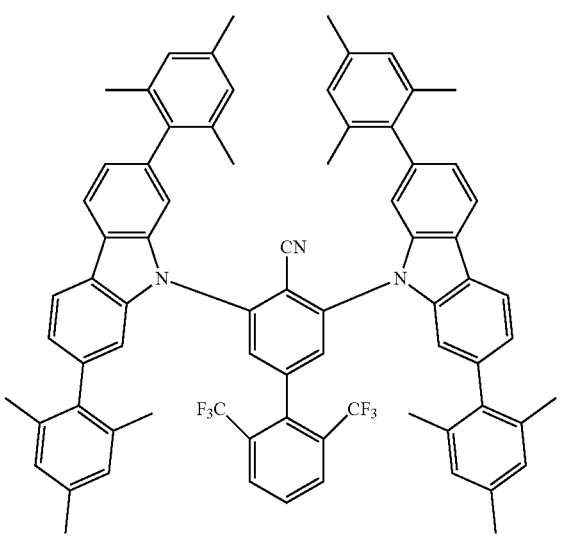
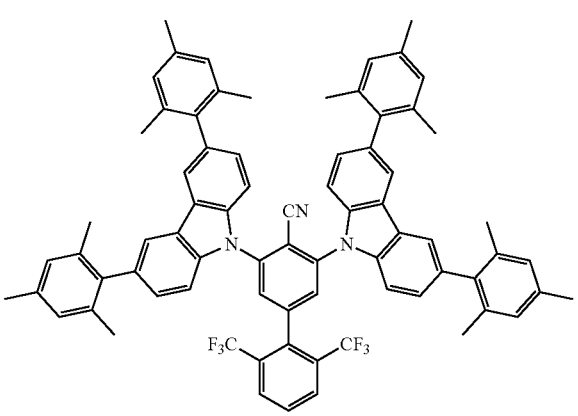

127
-continued
128
-continued
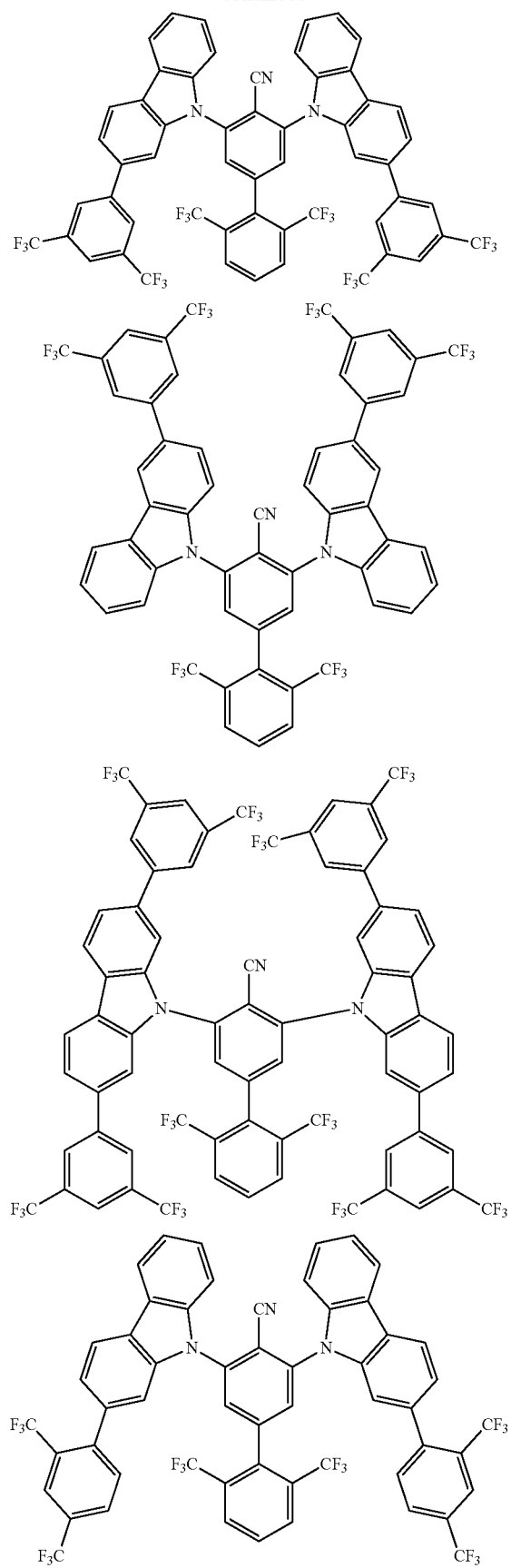
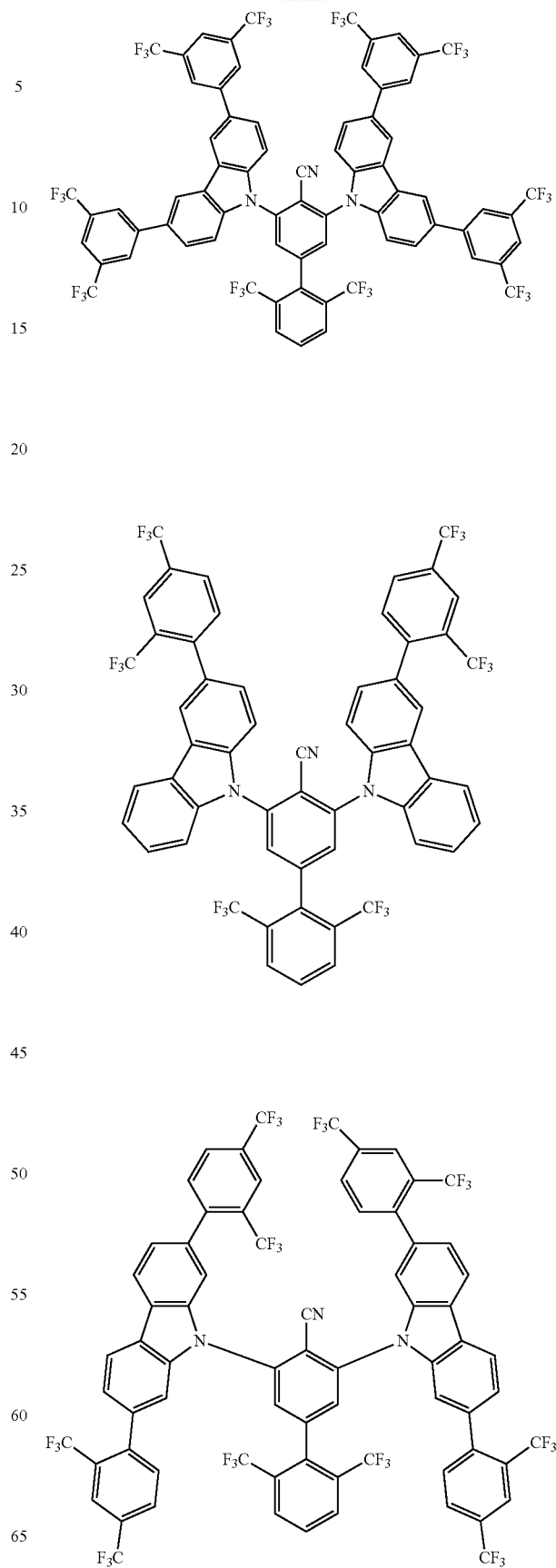

129
-continued
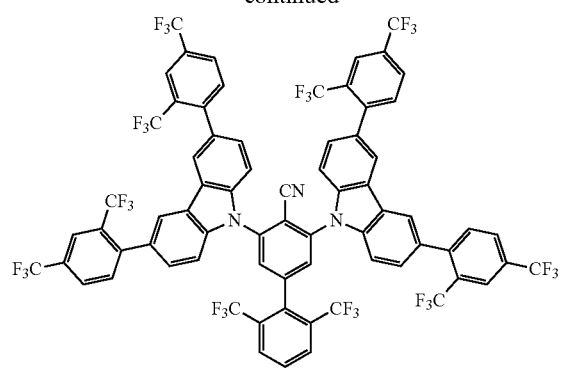
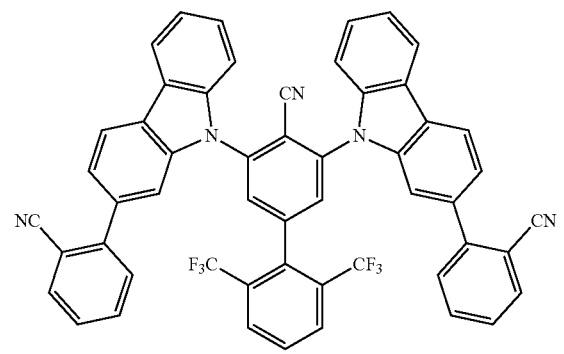
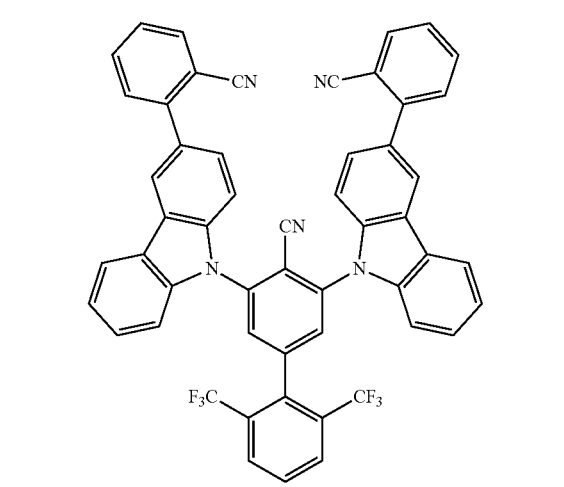
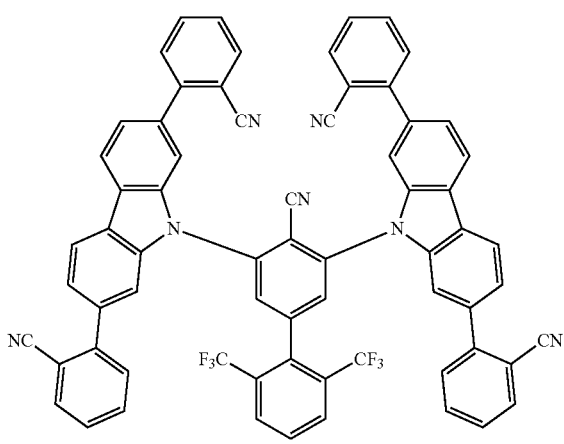
130
-continued
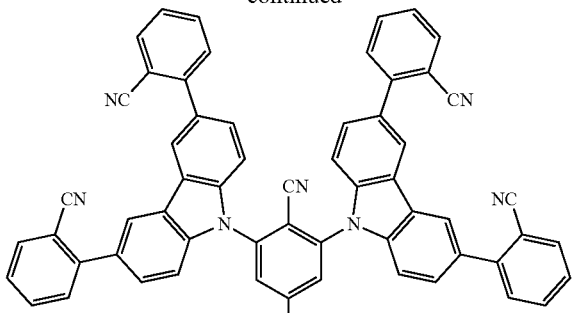
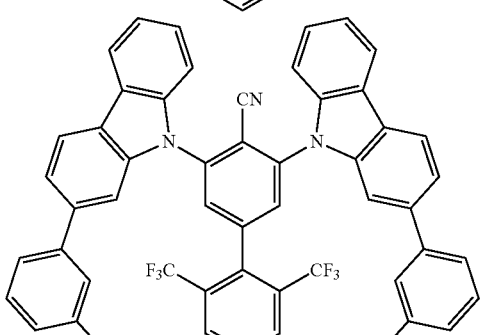
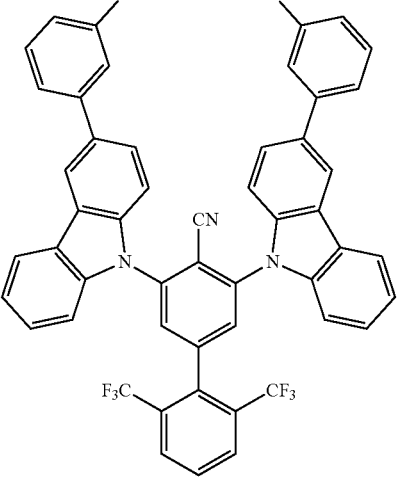
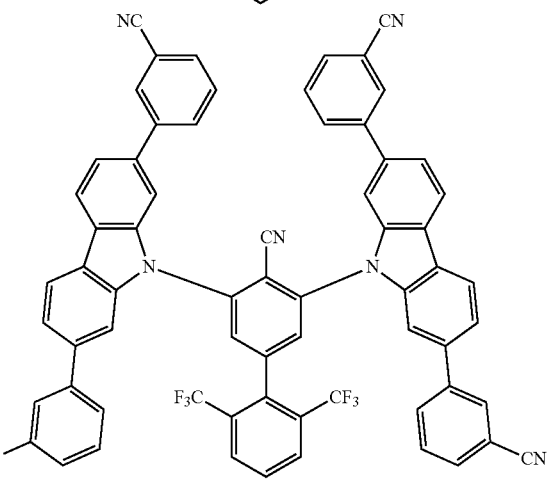

131
-continued
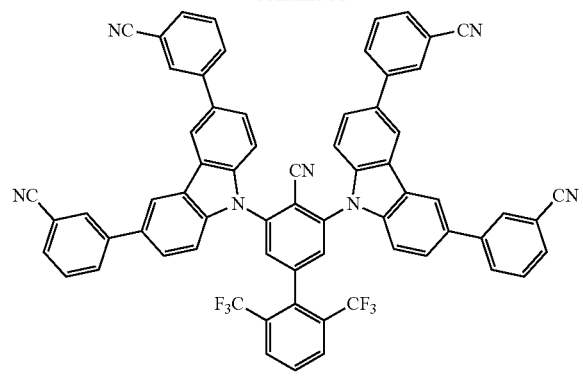
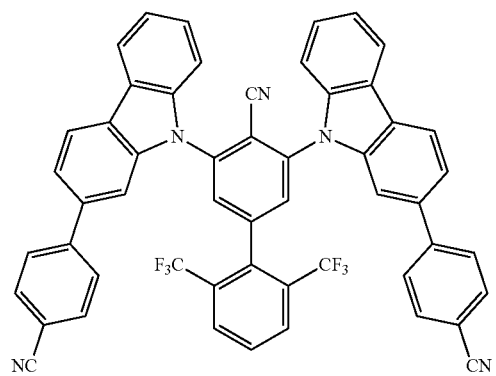
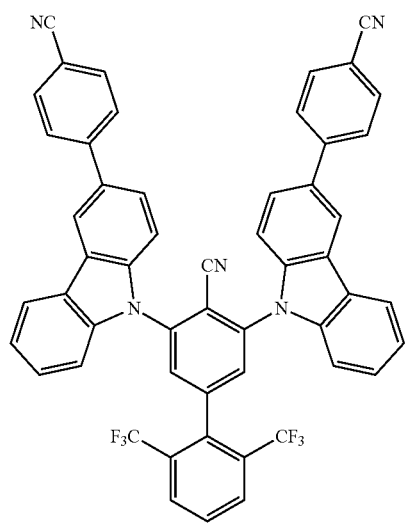
132
-continued
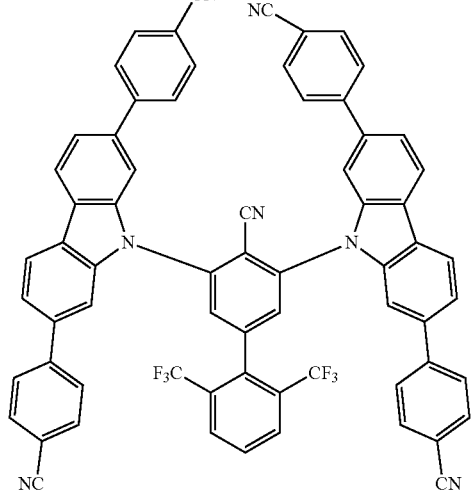
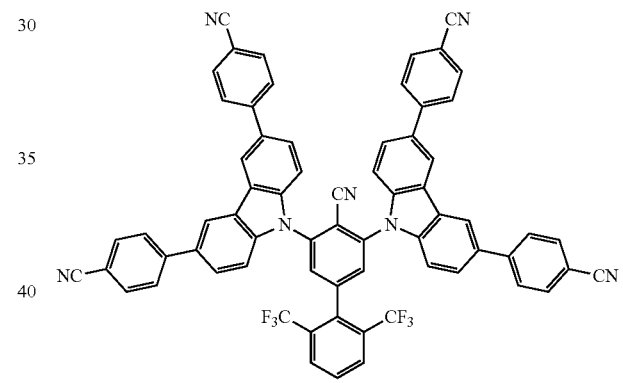
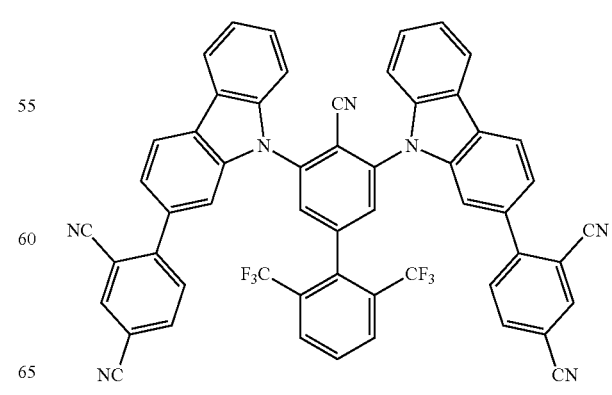

| 133 -continued | 134 -continued |
|---|---|
| 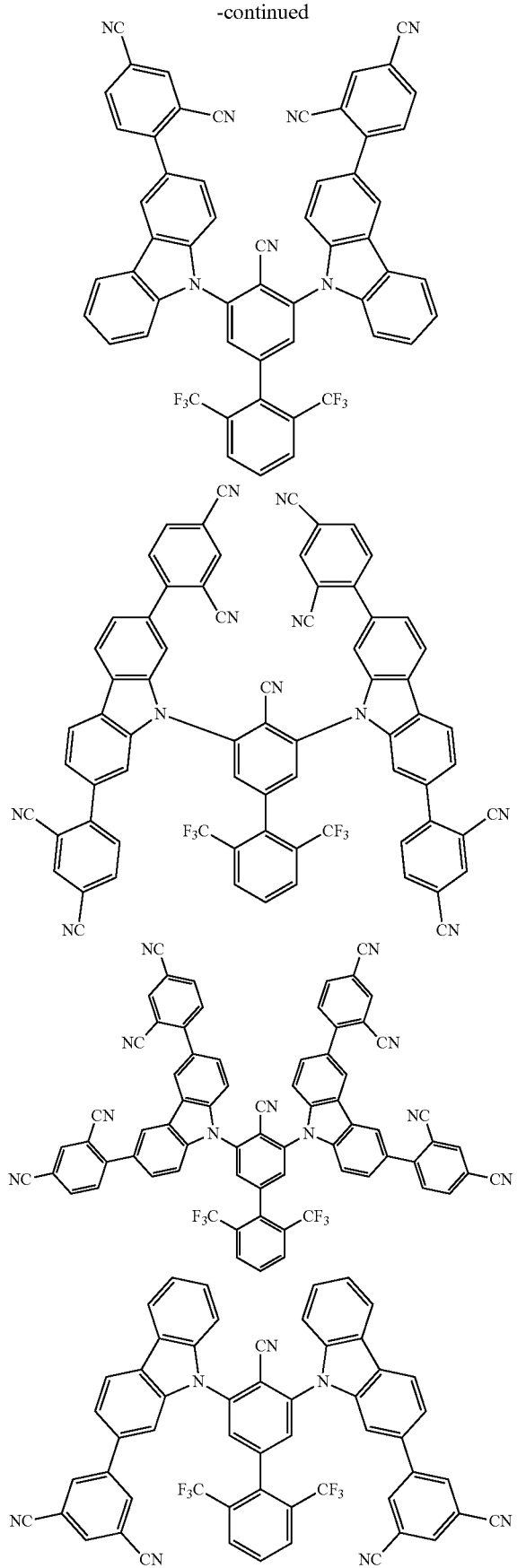 | 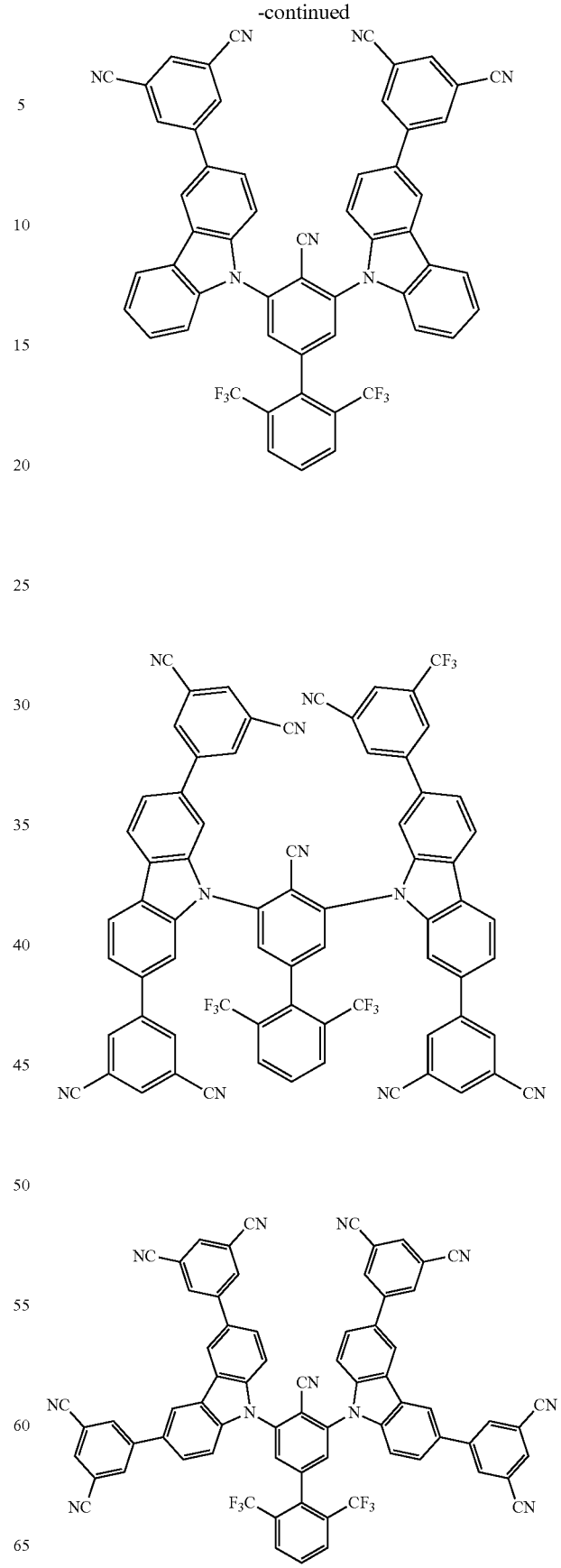 |

135
-continued
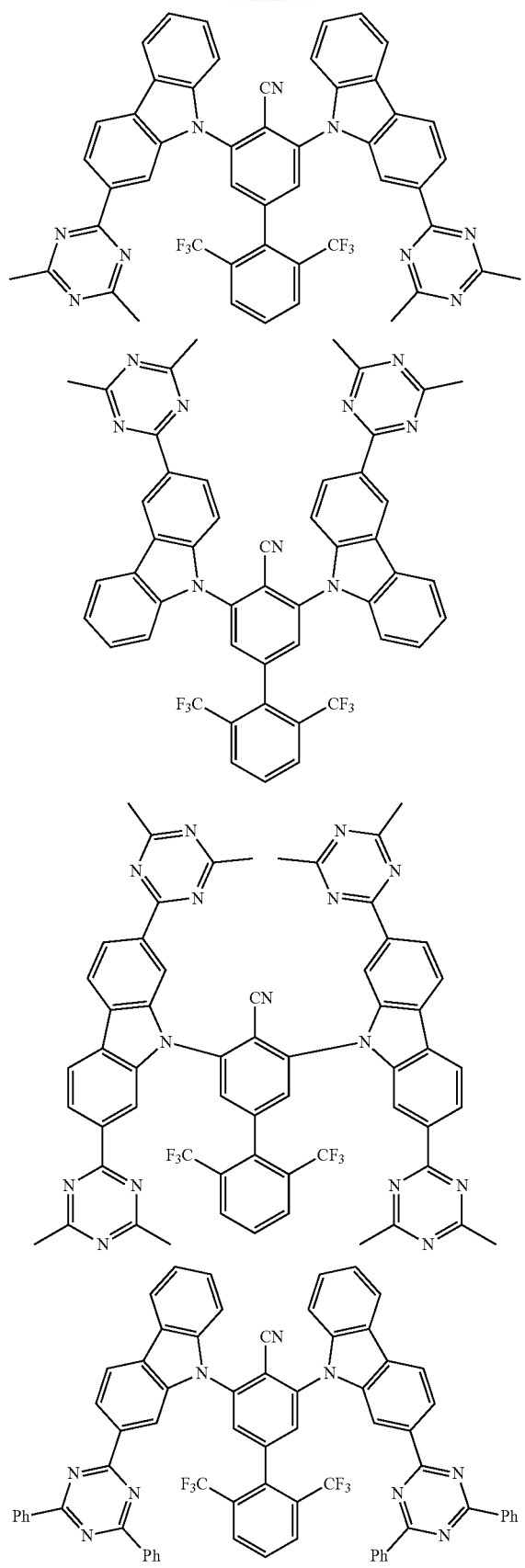
136
-continued
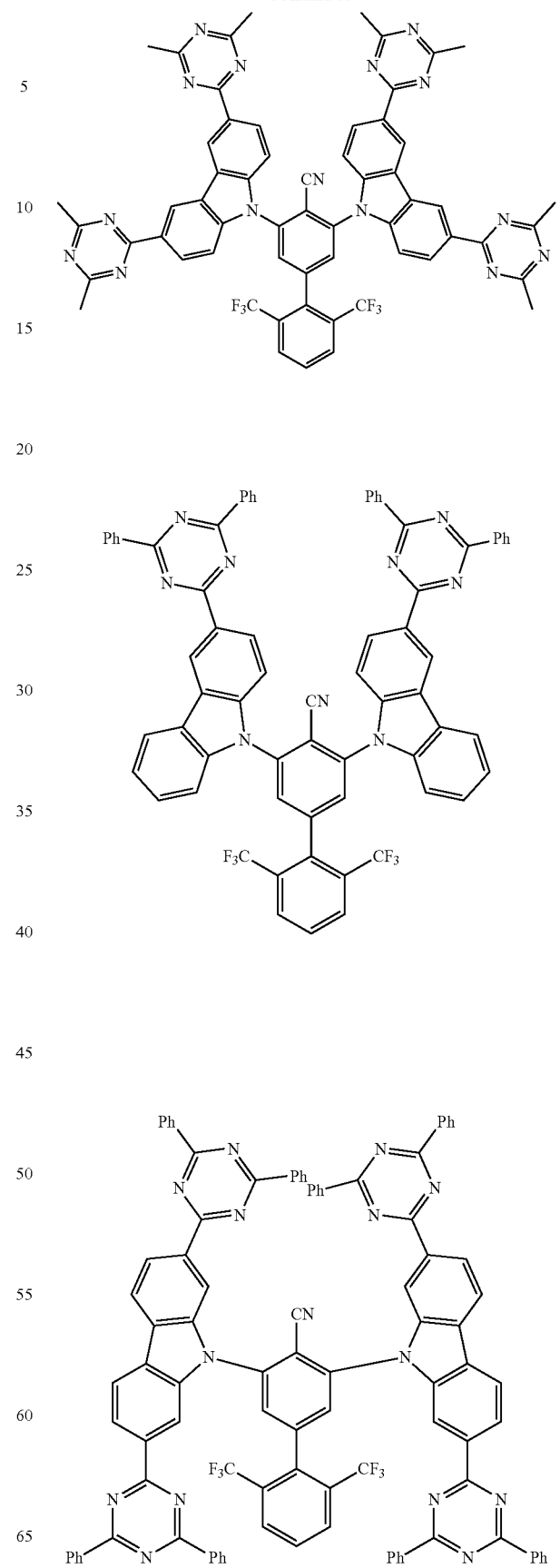

137
-continued
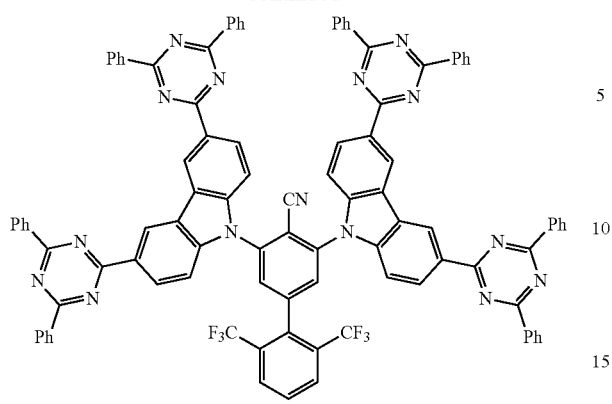
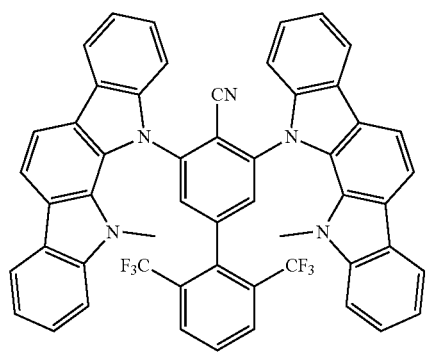
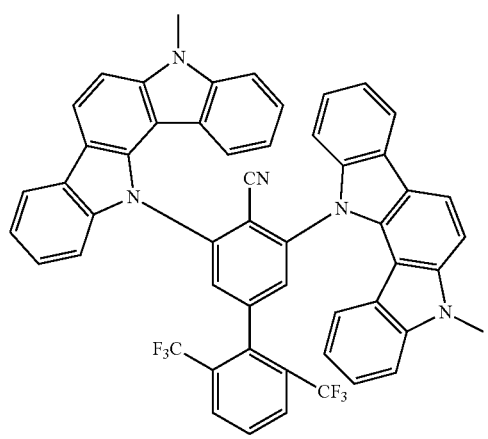
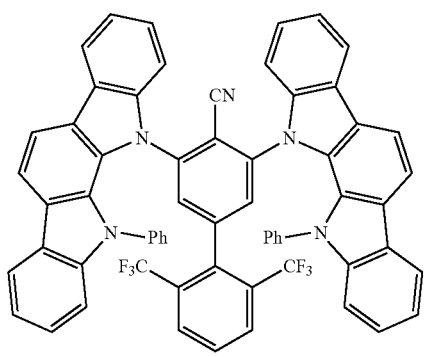
138
-continued
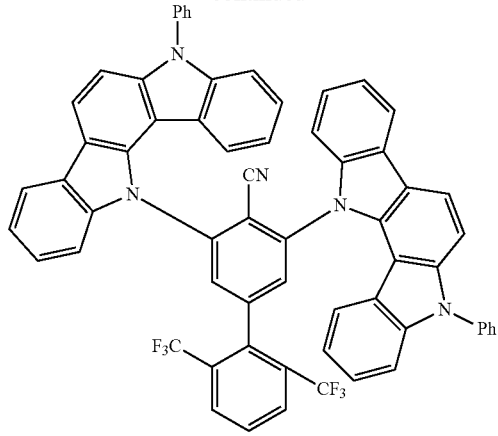
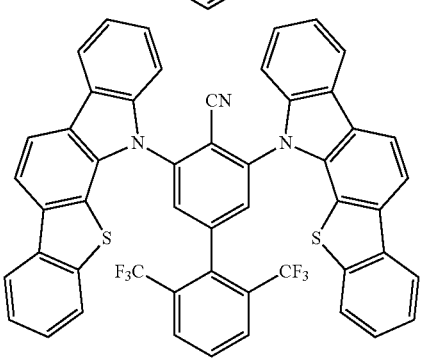
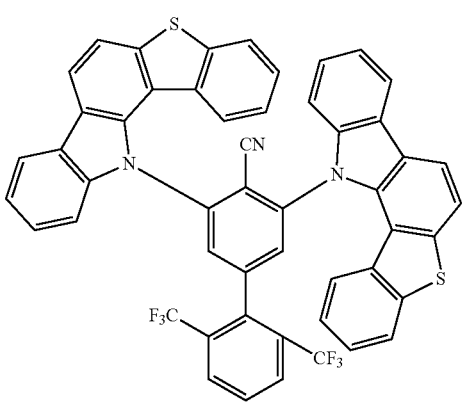
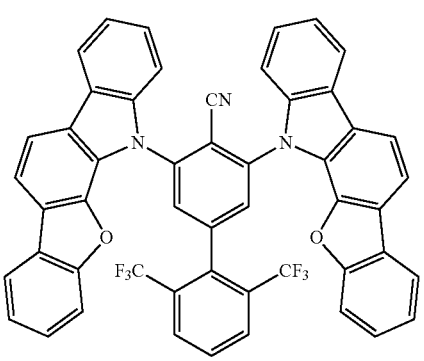

139
-continued
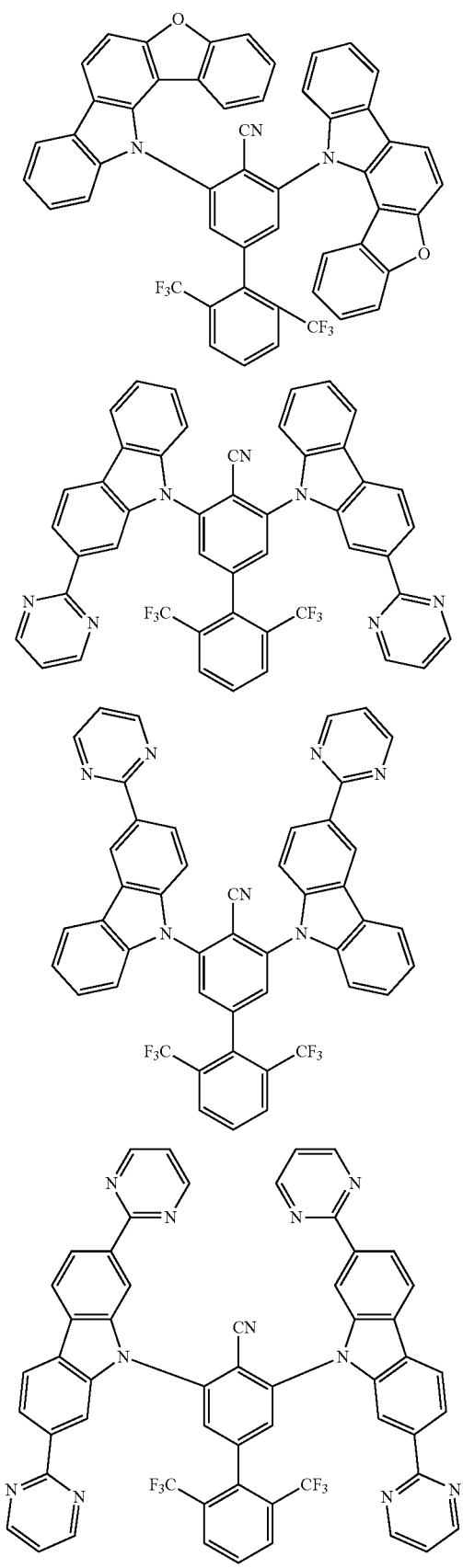
140
-continued
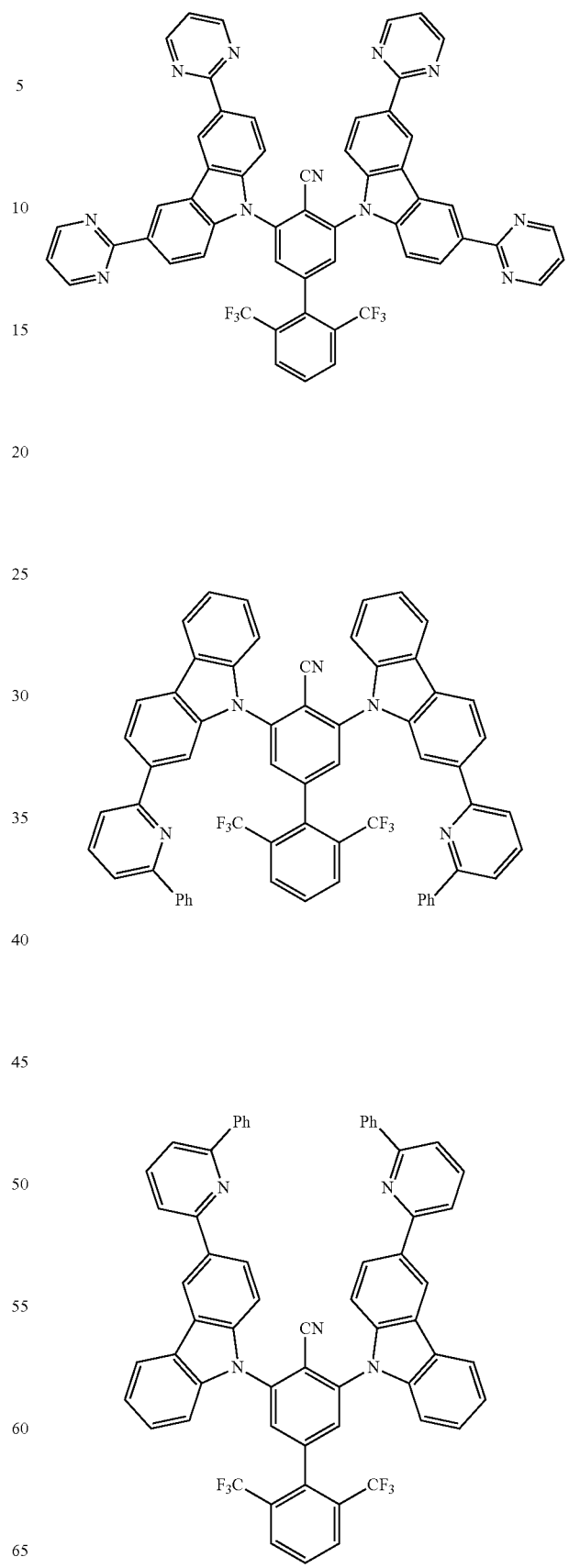

141
-continued
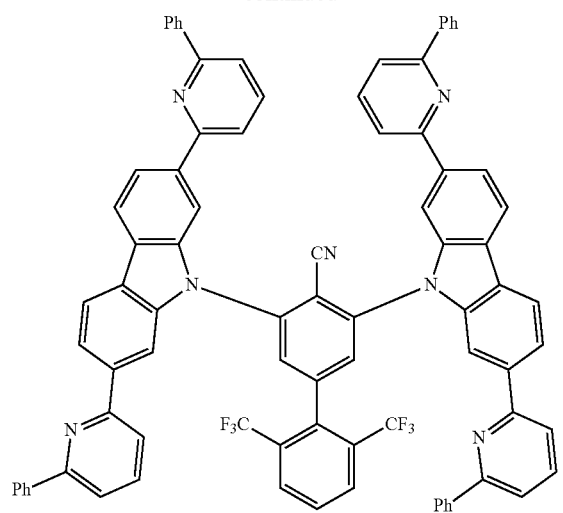
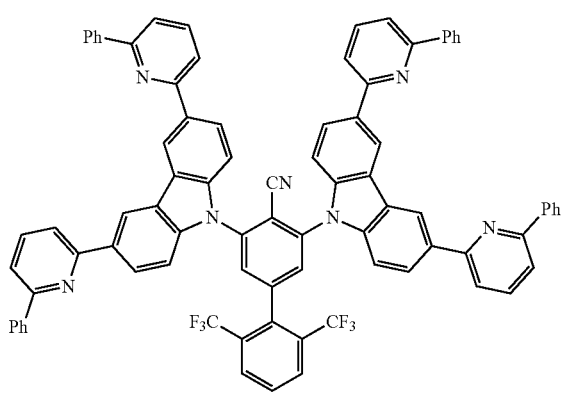
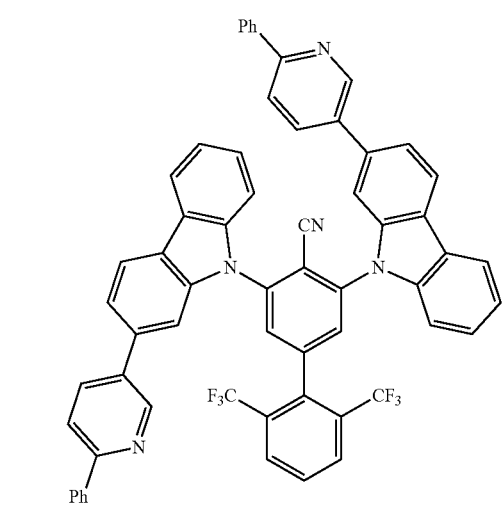
142
-continued
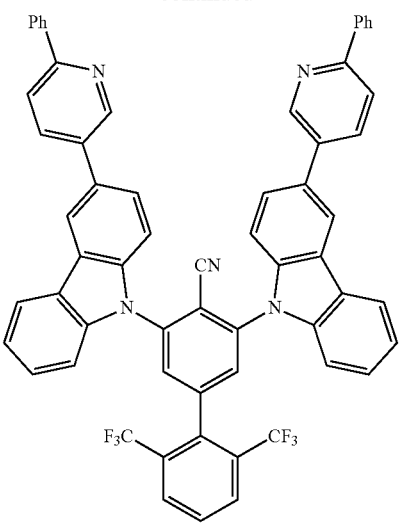
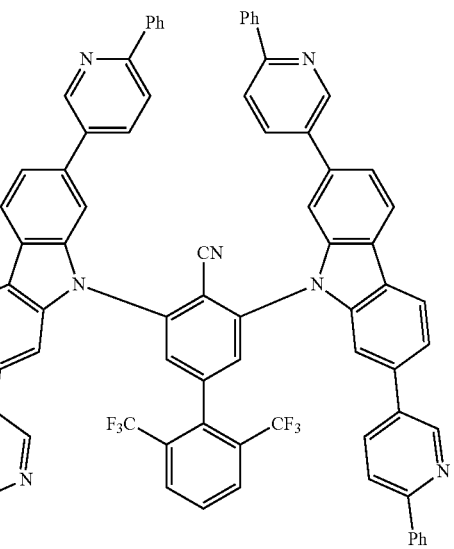
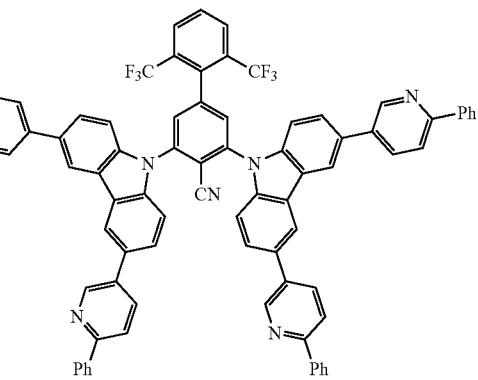

143
-continued
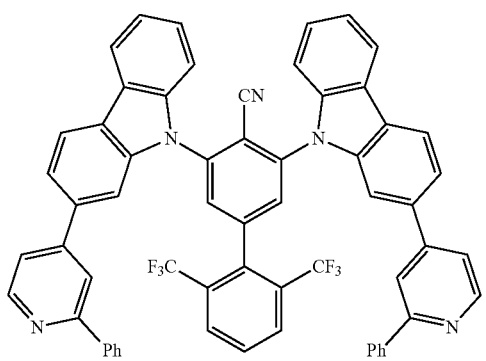
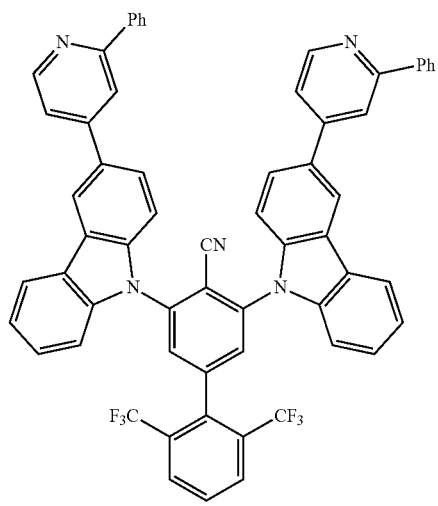
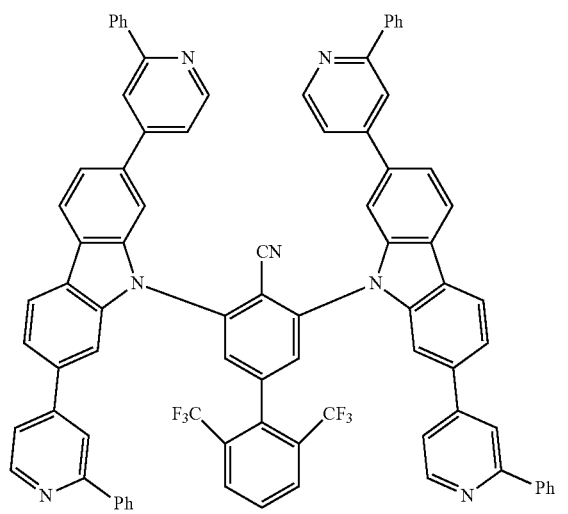
144
-continued
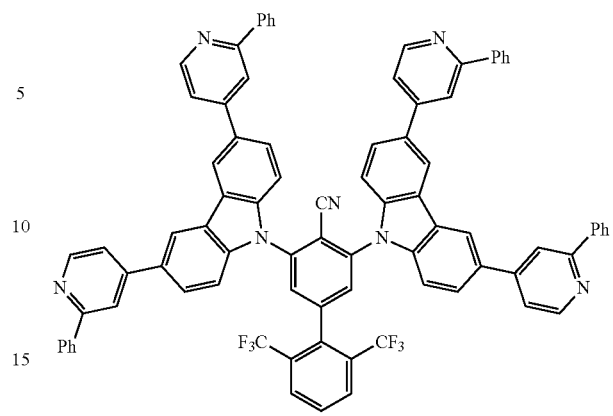
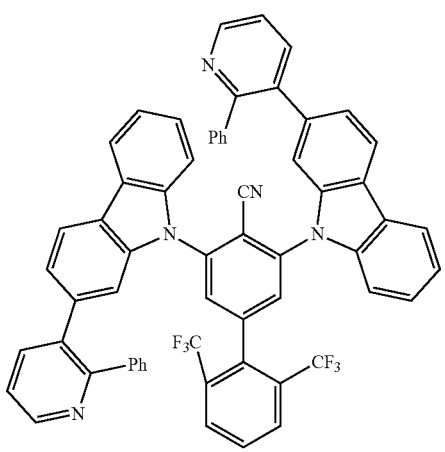
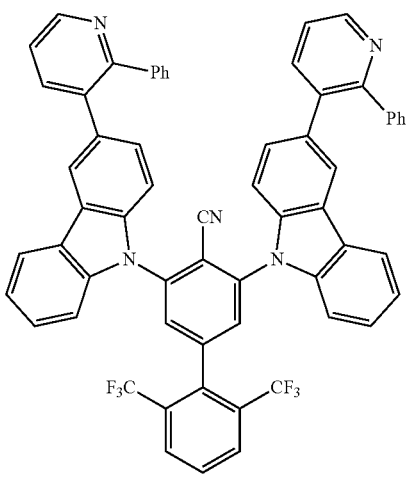

-continued
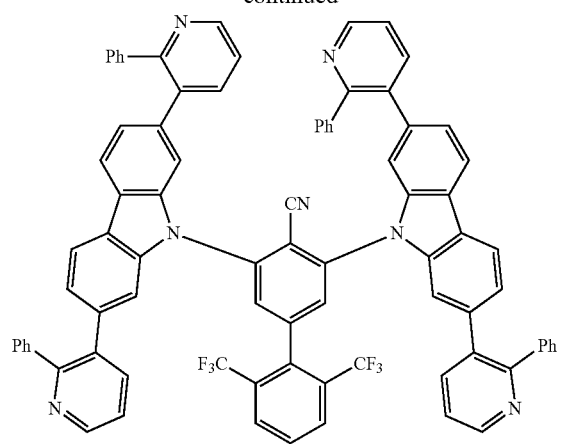
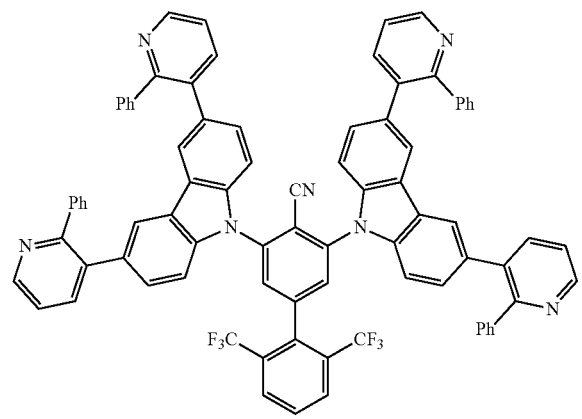
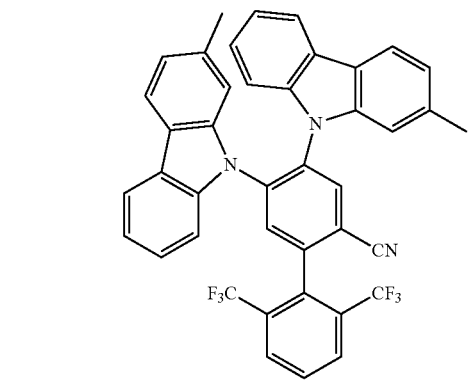
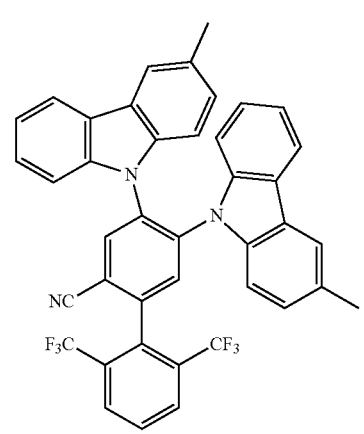
-continued
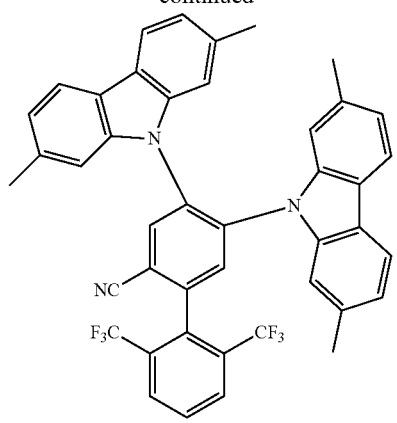
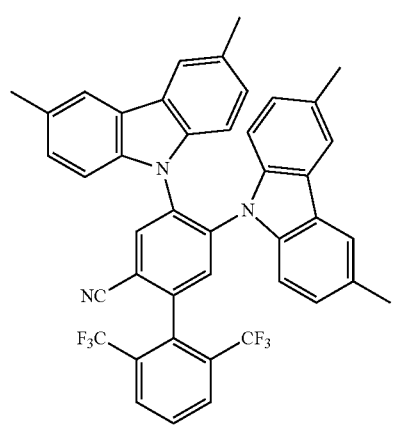
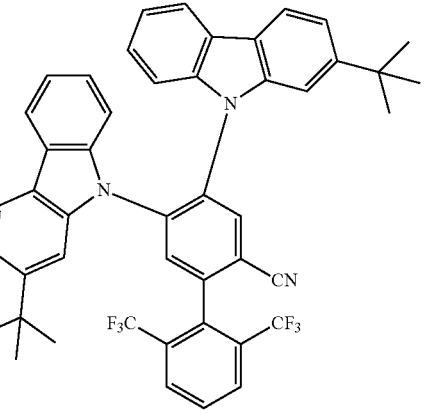
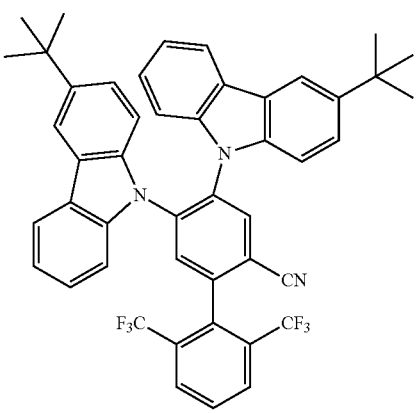

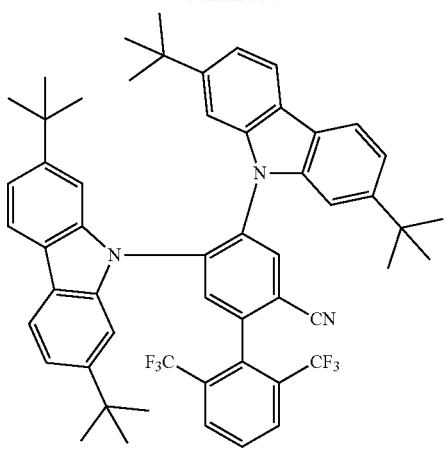
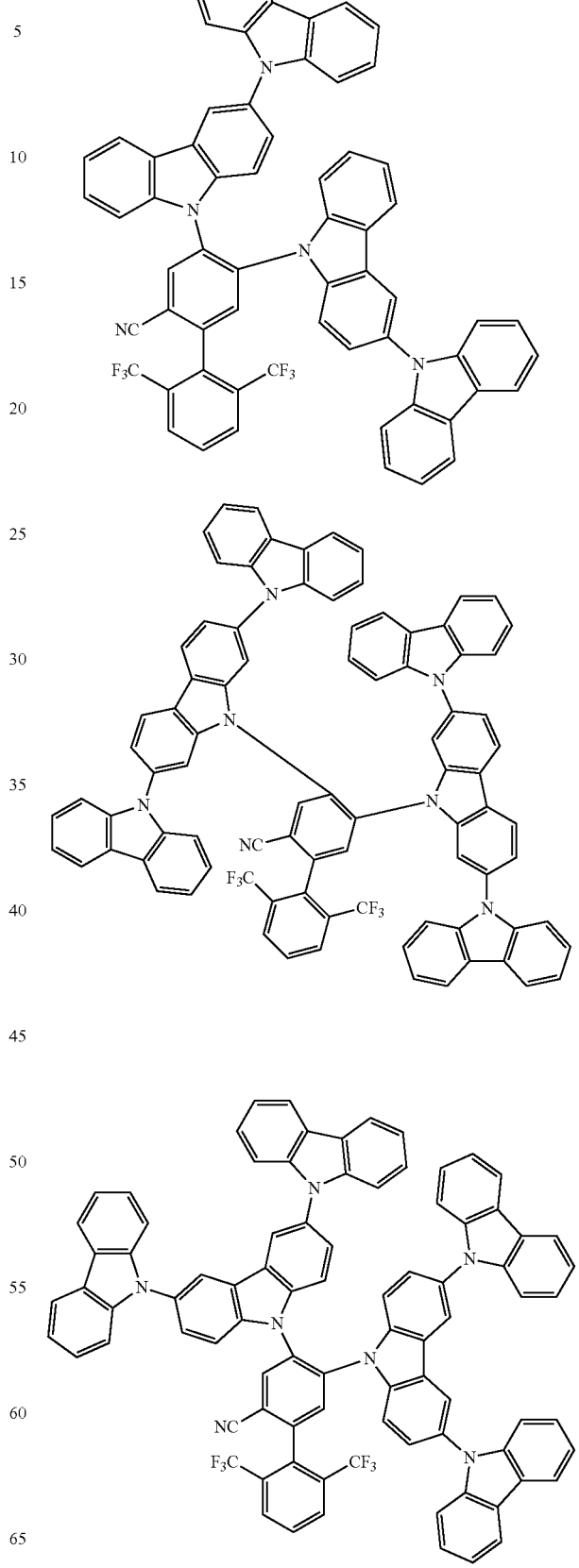

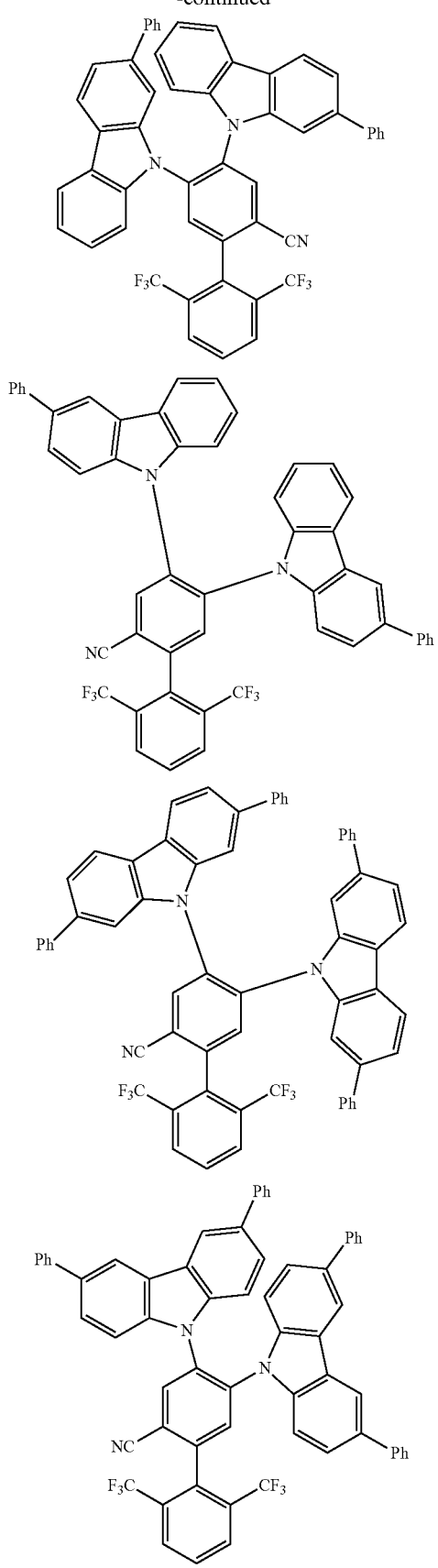
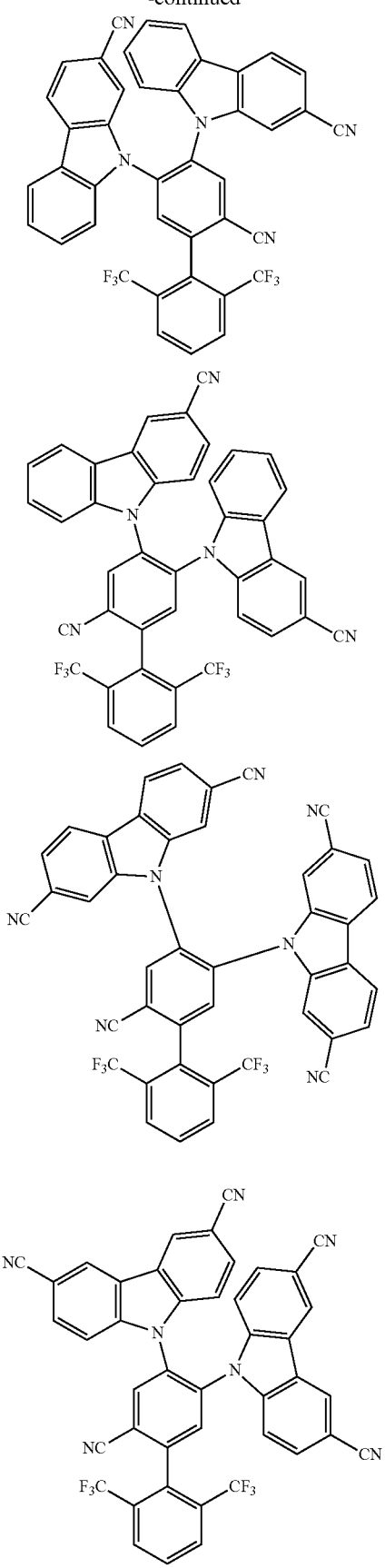

151
-continued
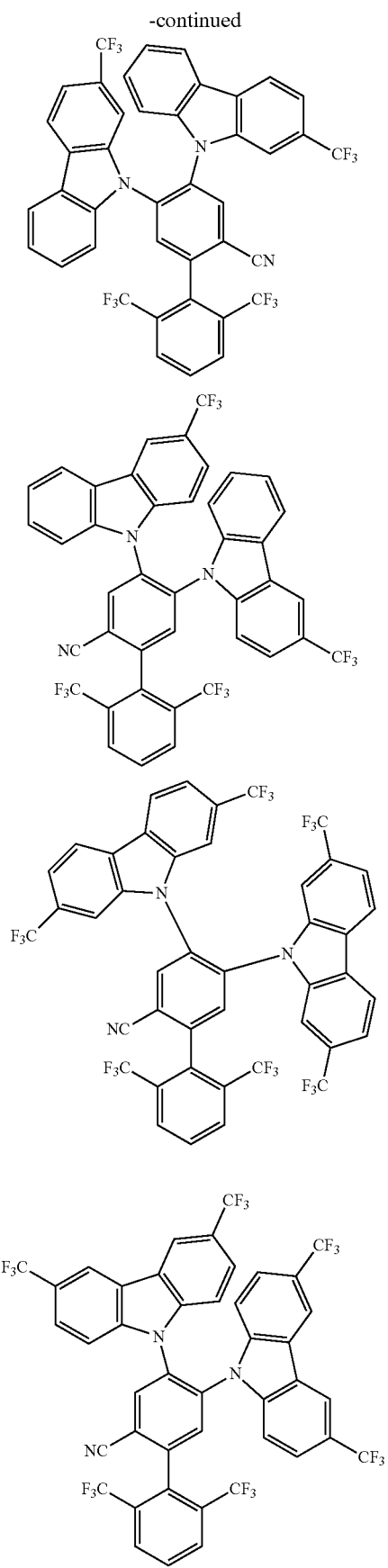
152
-continued
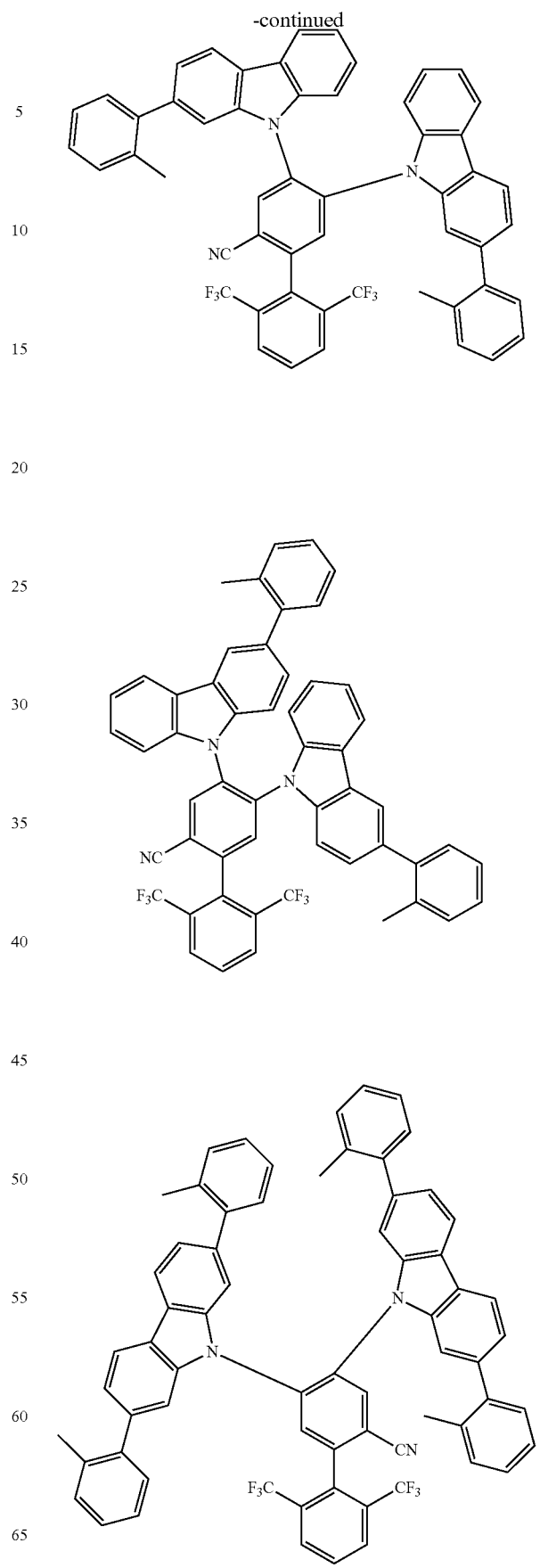

153
-continued
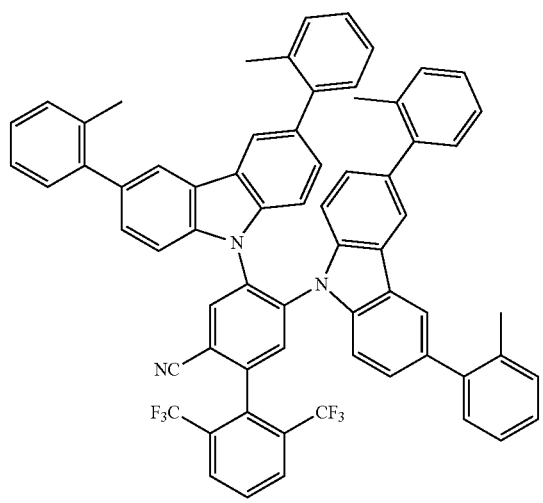
154
-continued
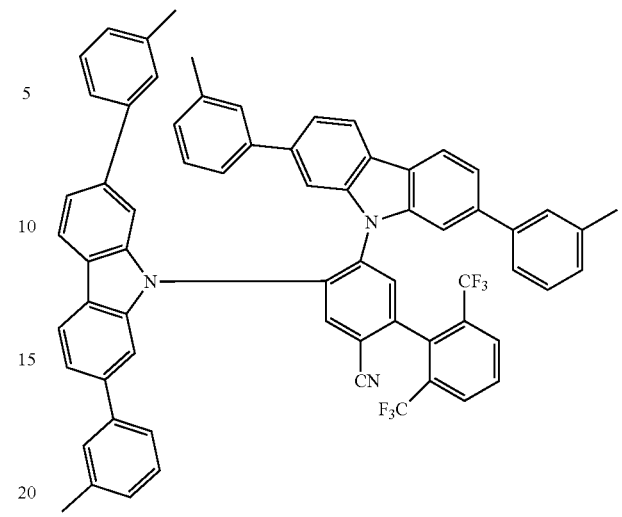
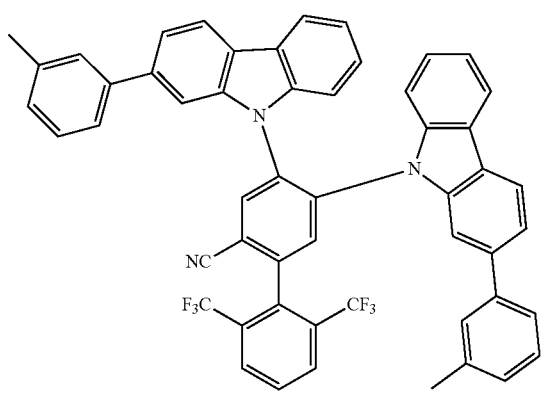
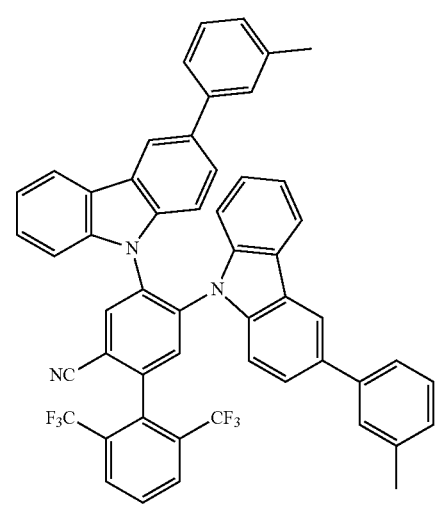
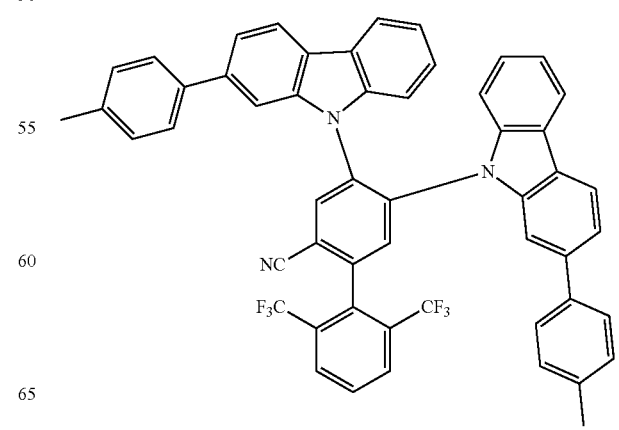

155
-continued
156
-continued
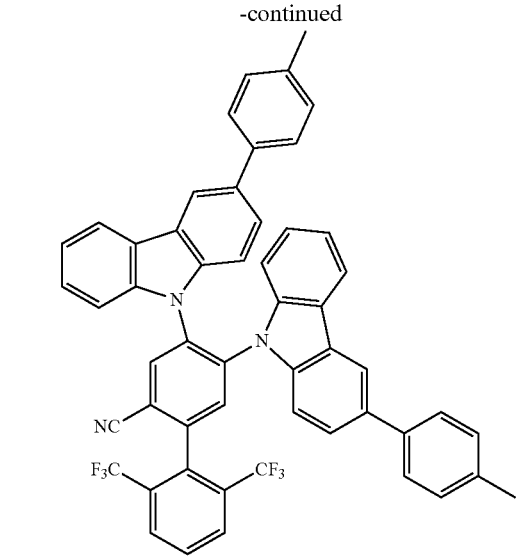
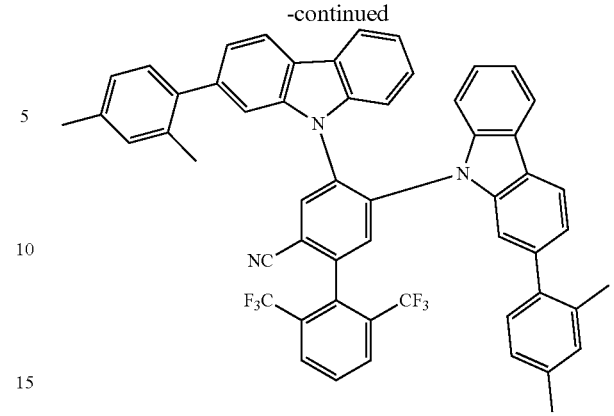
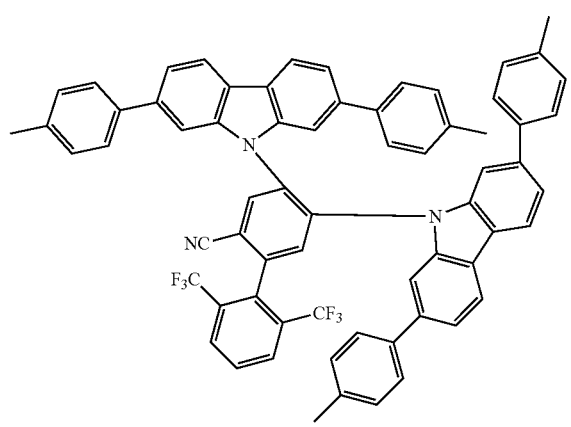
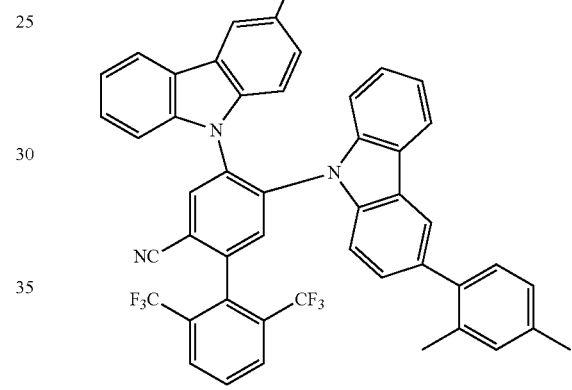
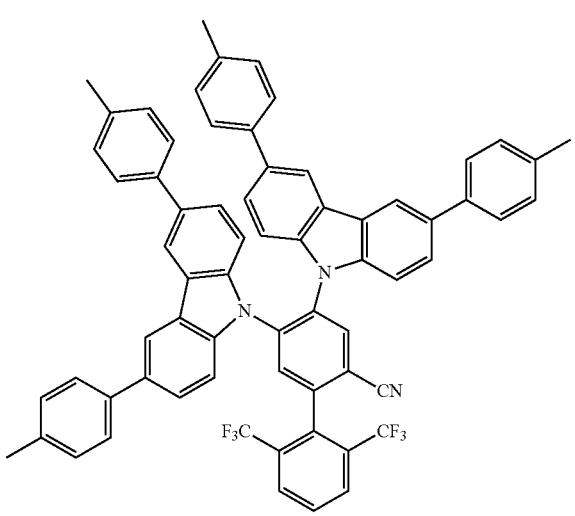
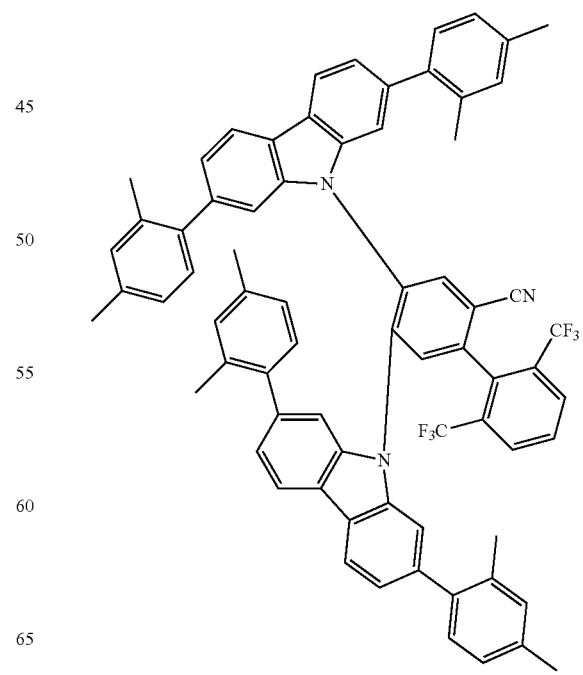

157
-continued
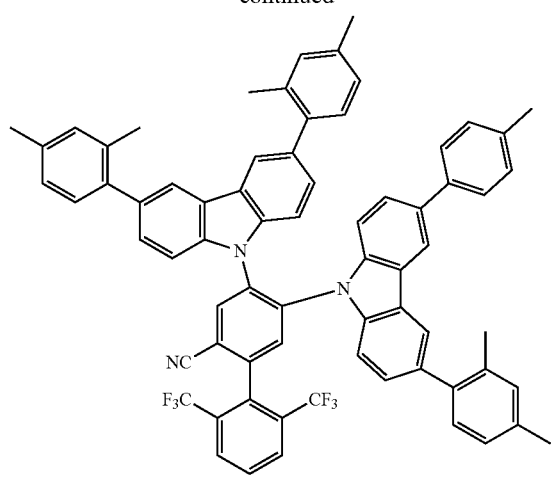
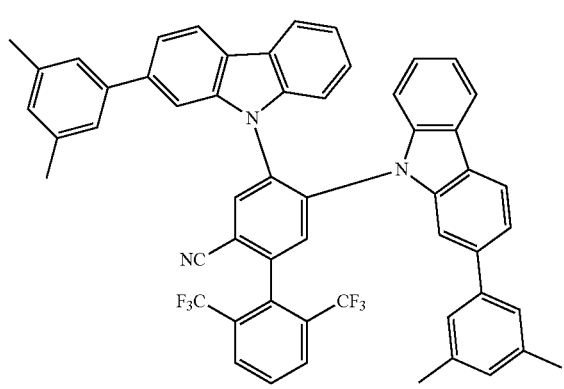
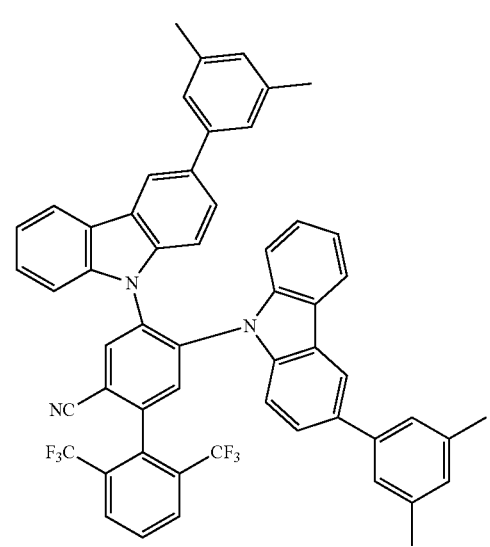
158
-continued
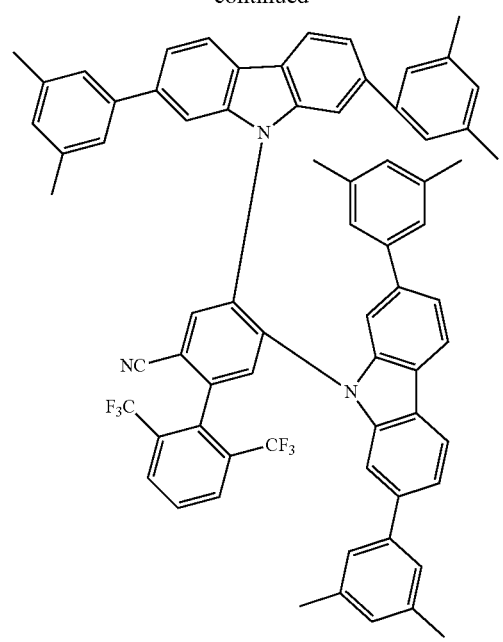
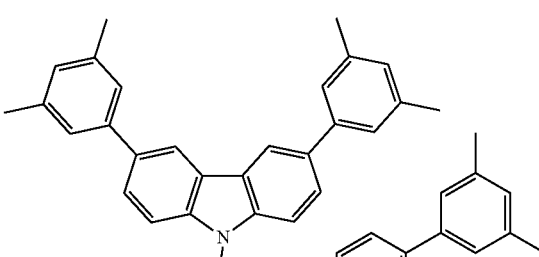
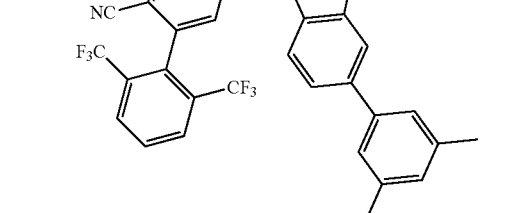
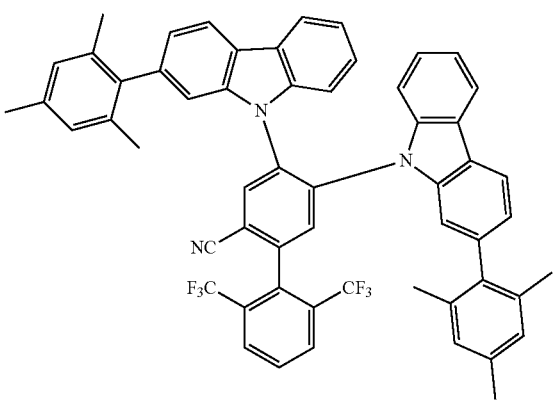

159
-continued
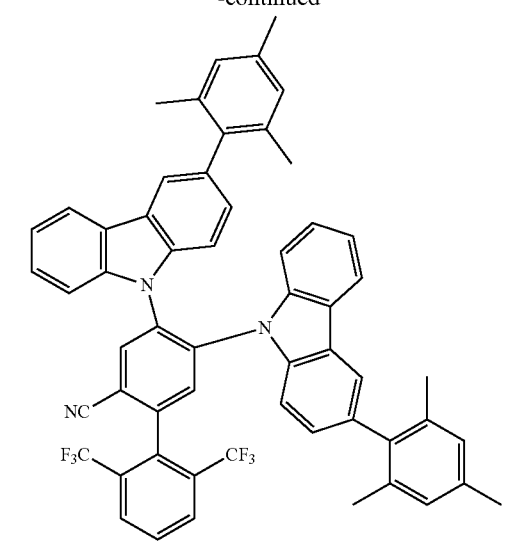
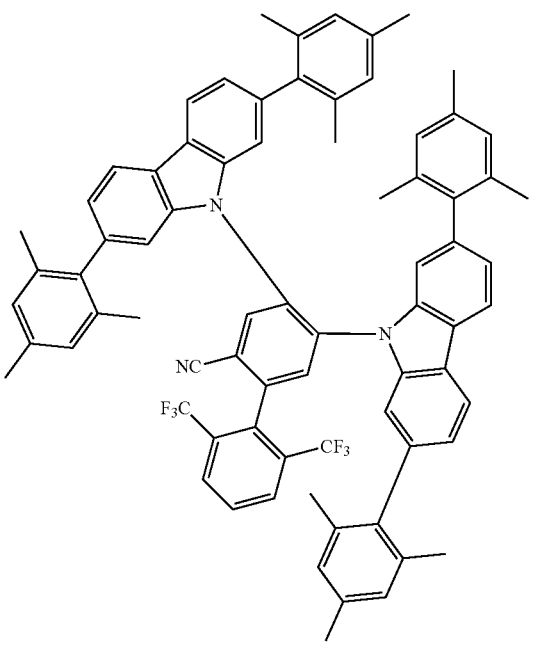
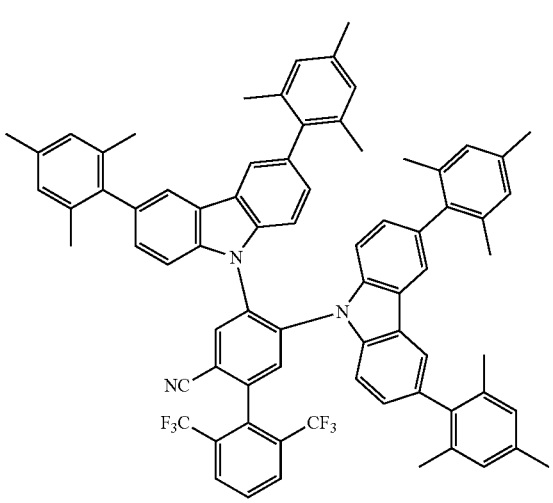
160
-continued
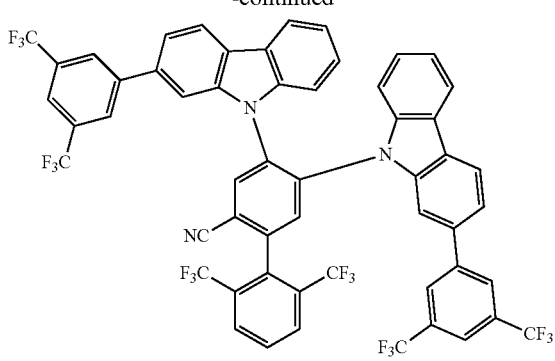
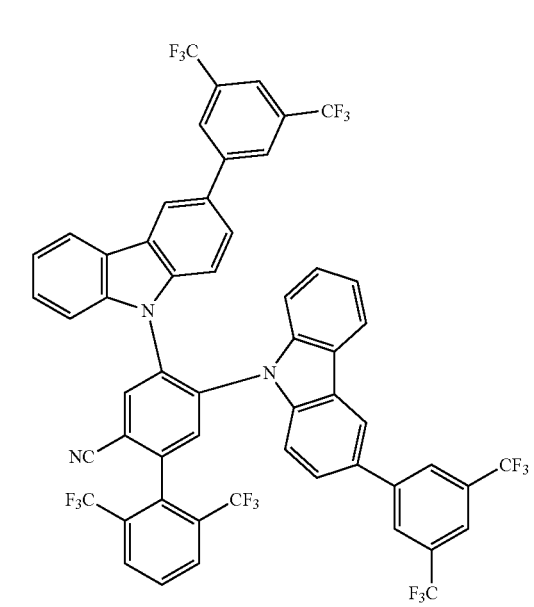
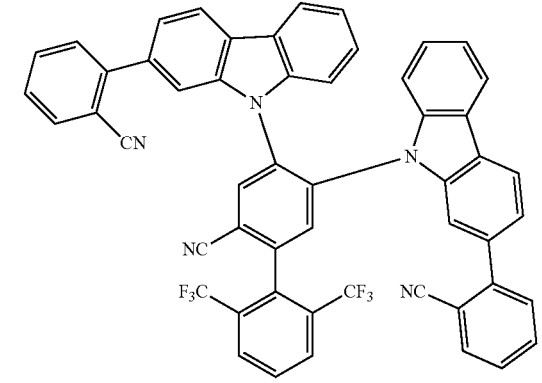

161
-continued
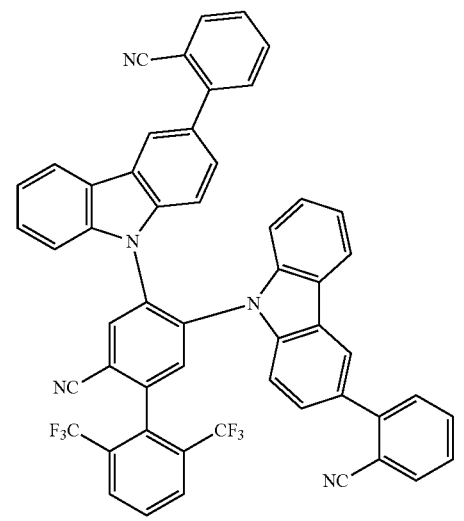
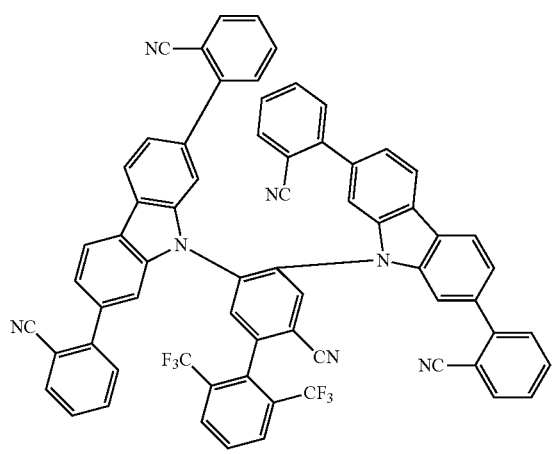
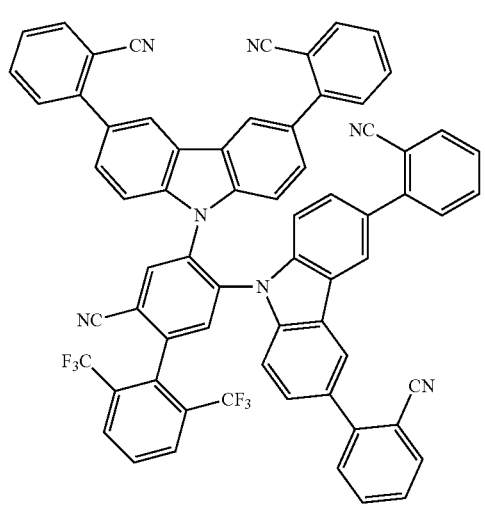
162
-continued
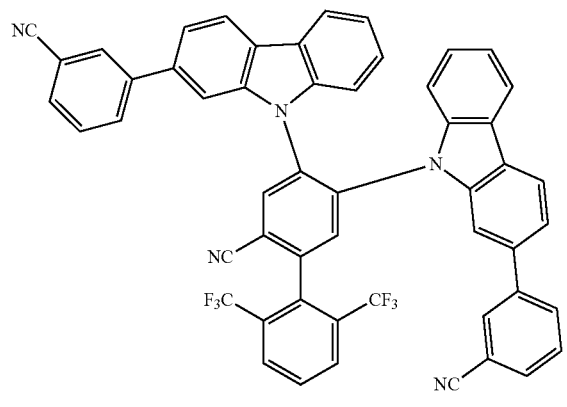
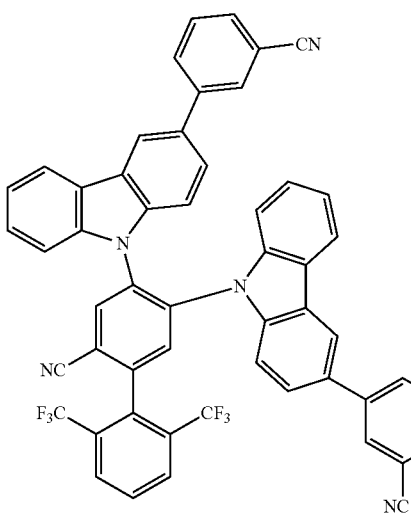
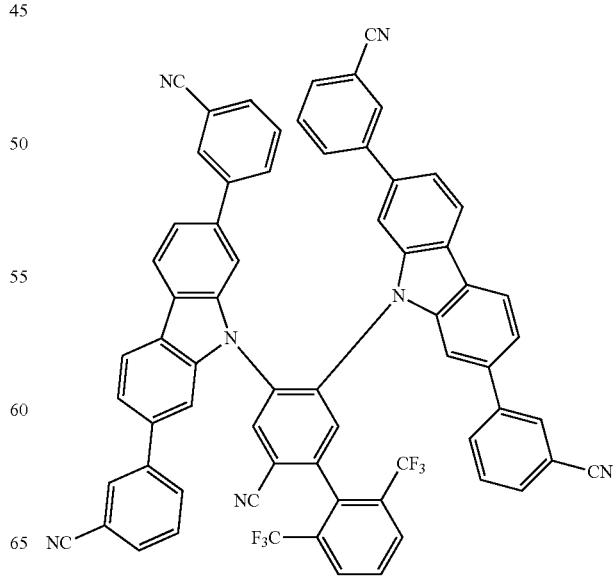

163
-continued
164
-continued
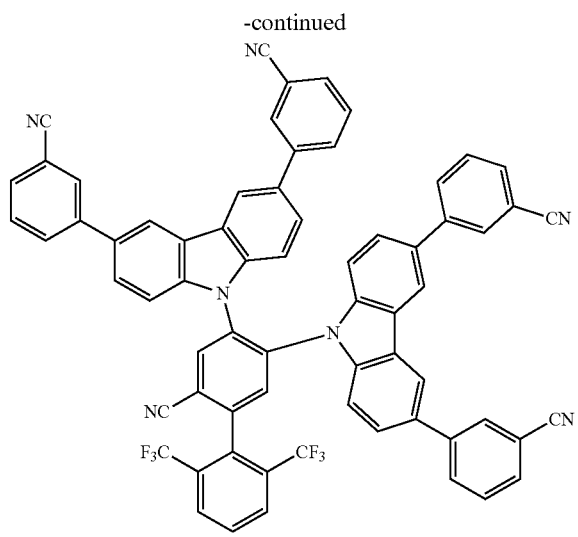
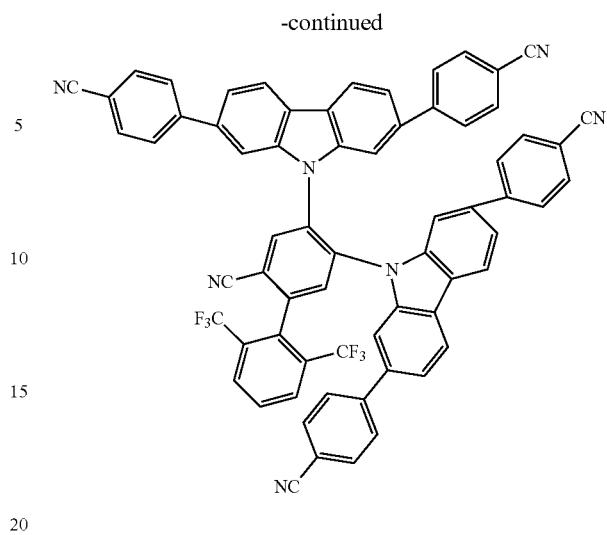
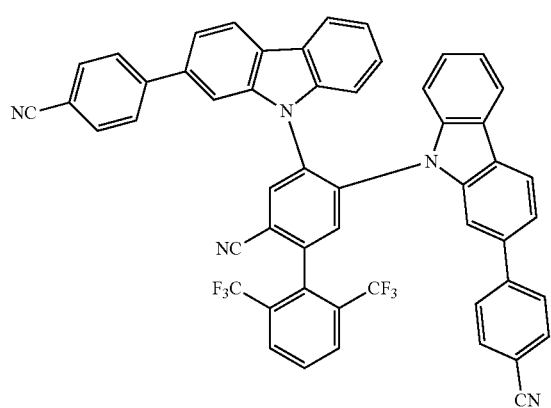
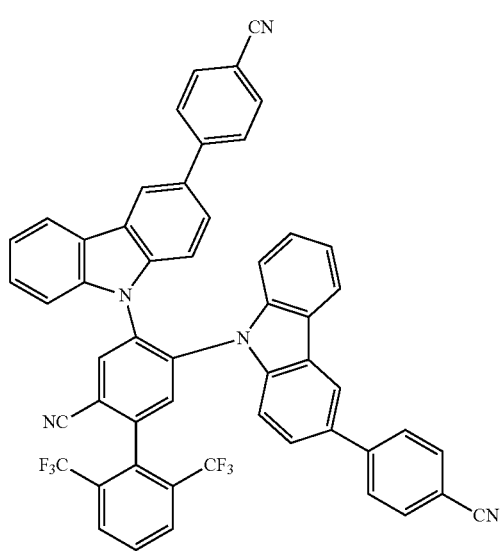
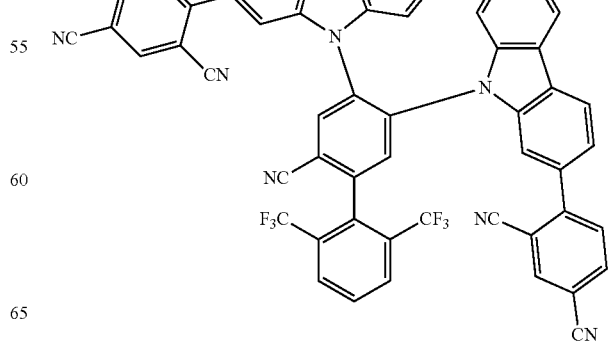

165
-continued
166
-continued
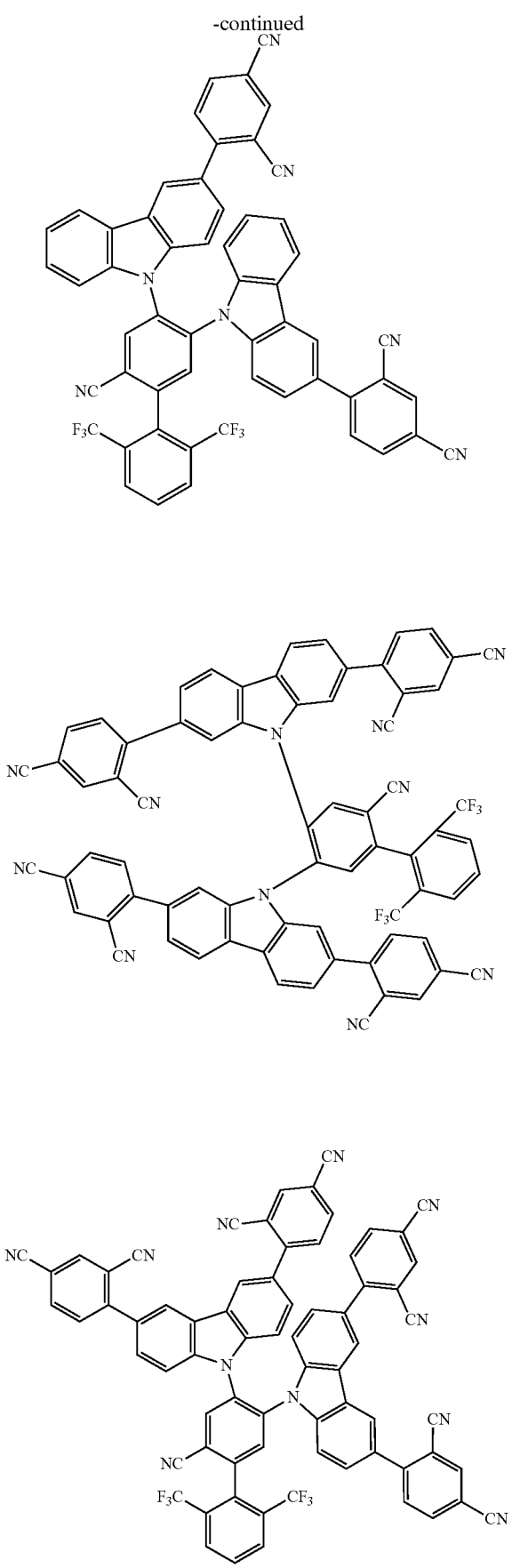
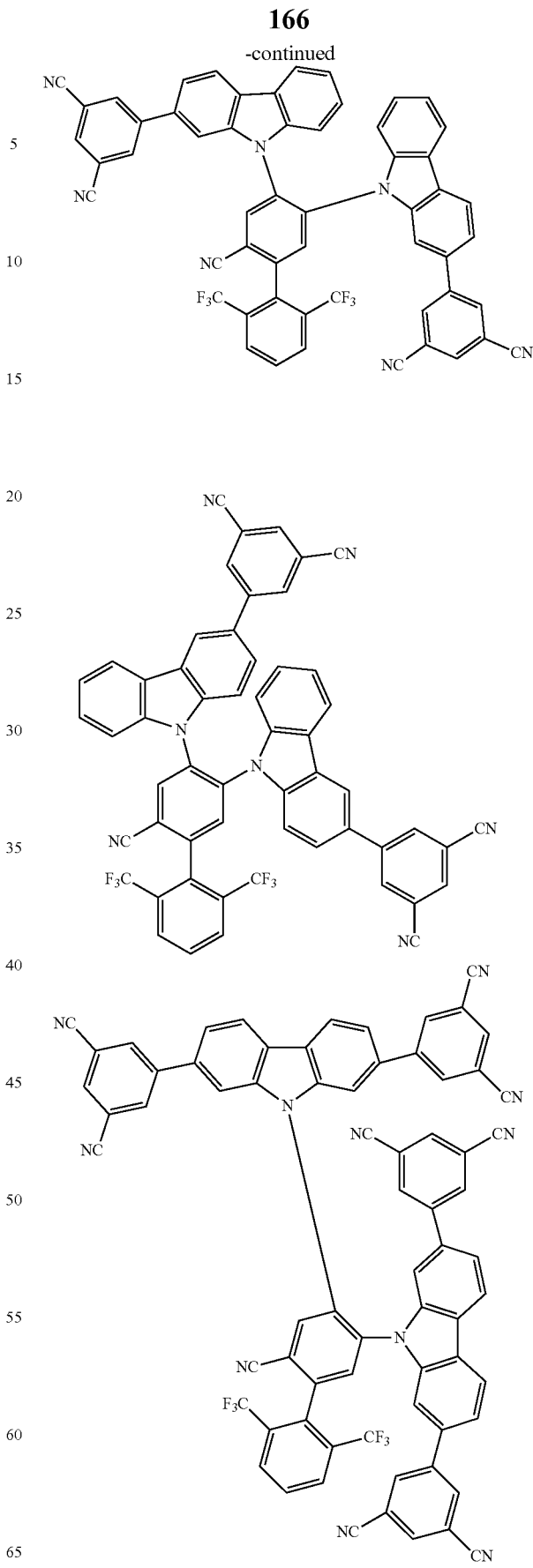

-continued
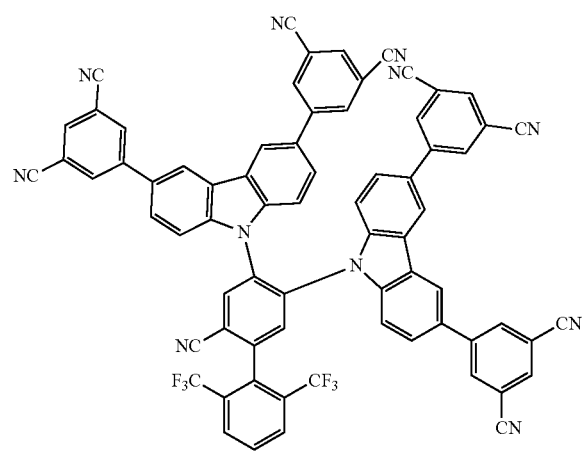
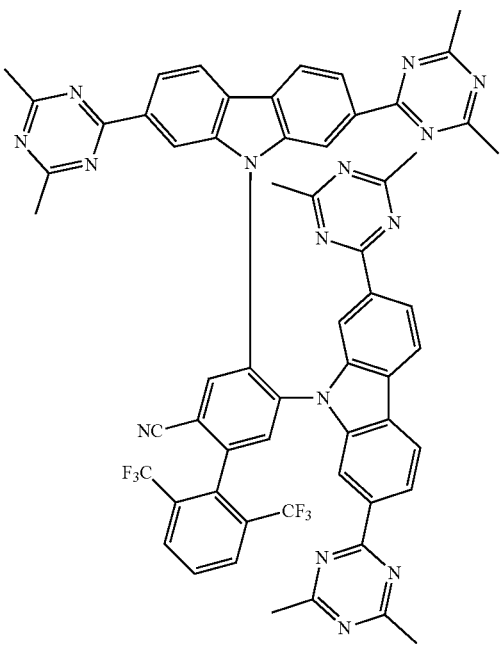
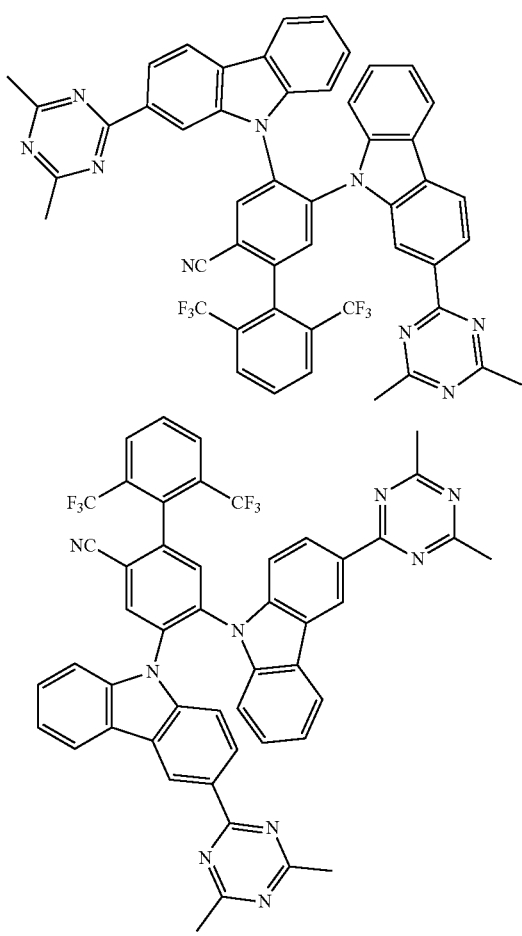
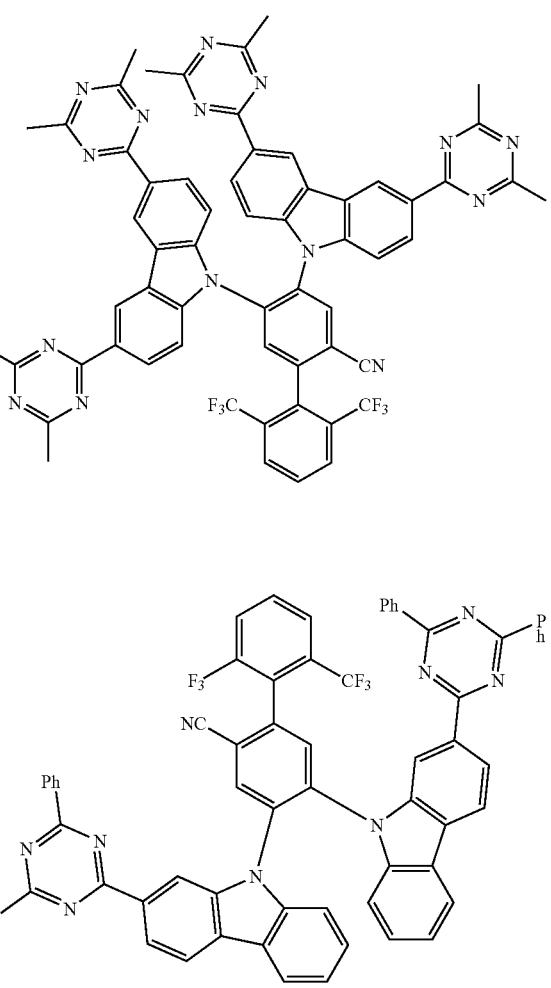

169
-continued
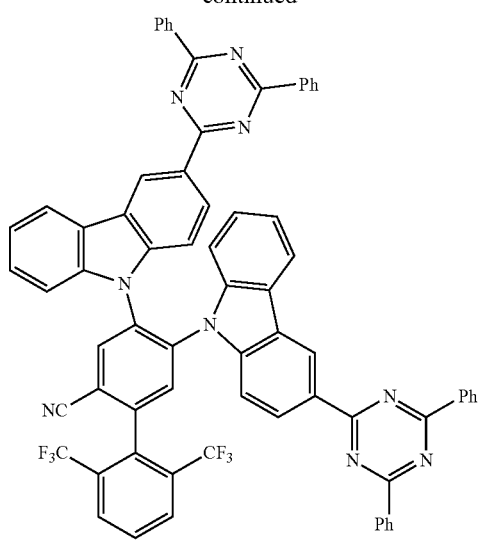
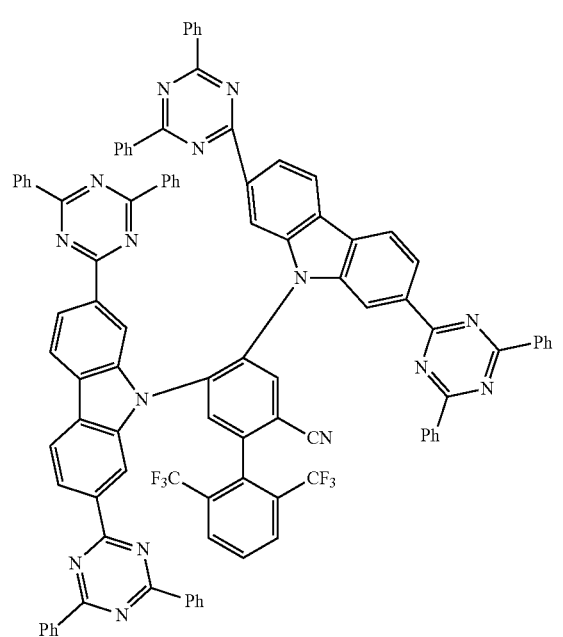
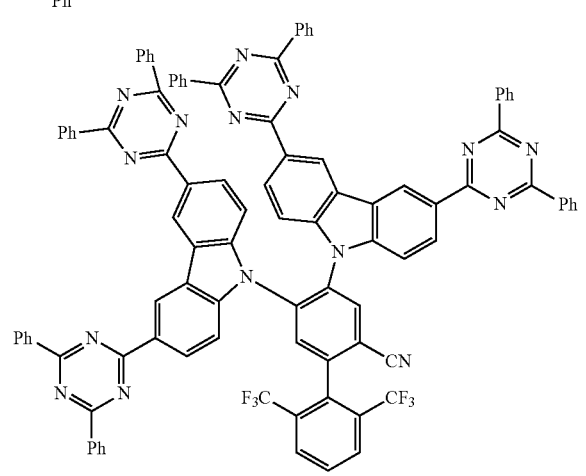
170
-continued
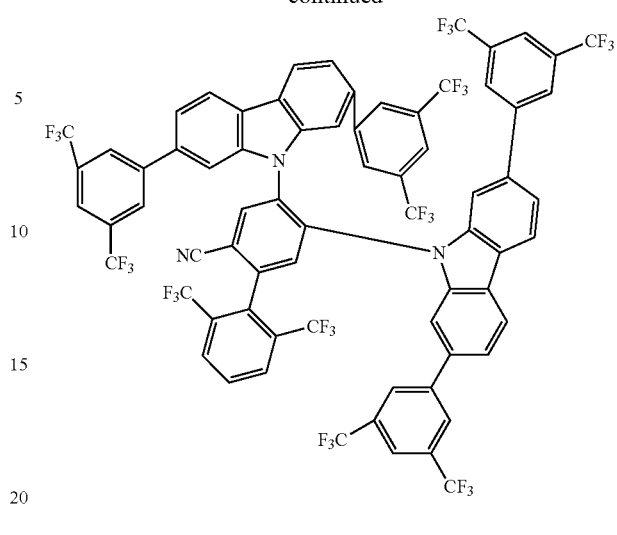
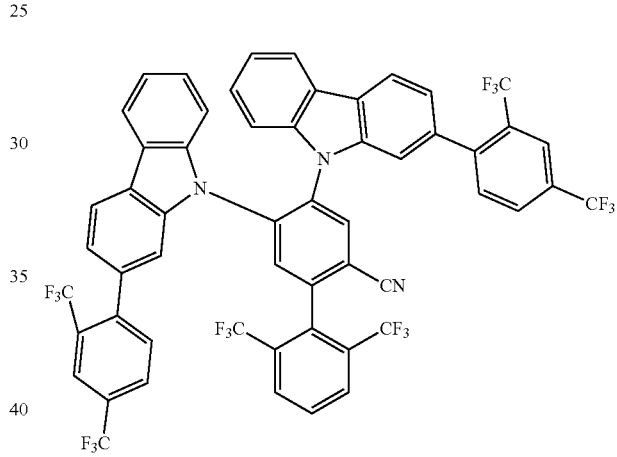
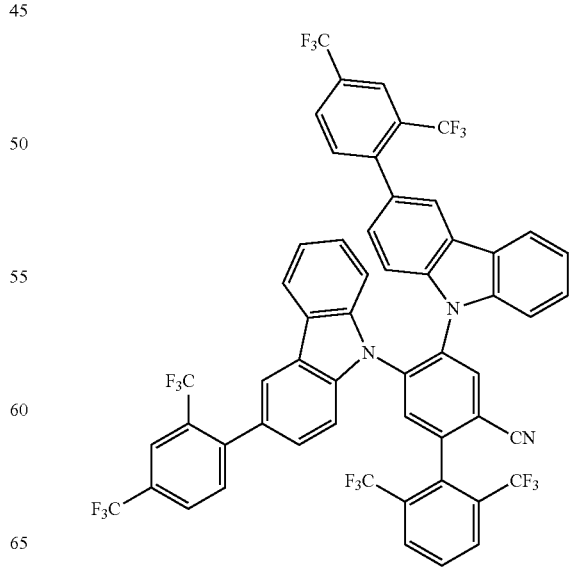

-continued
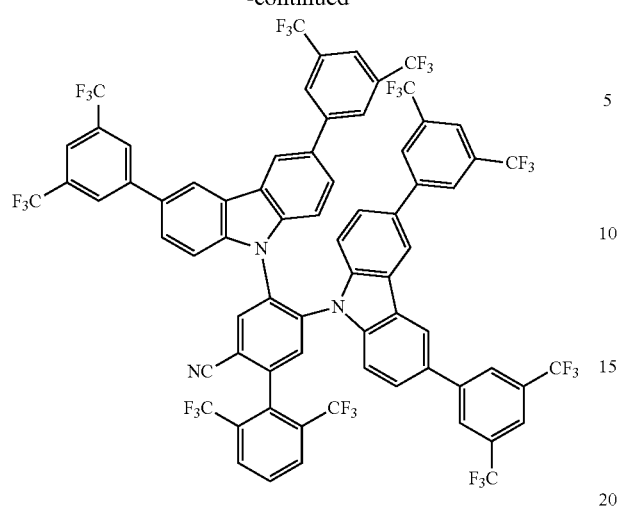
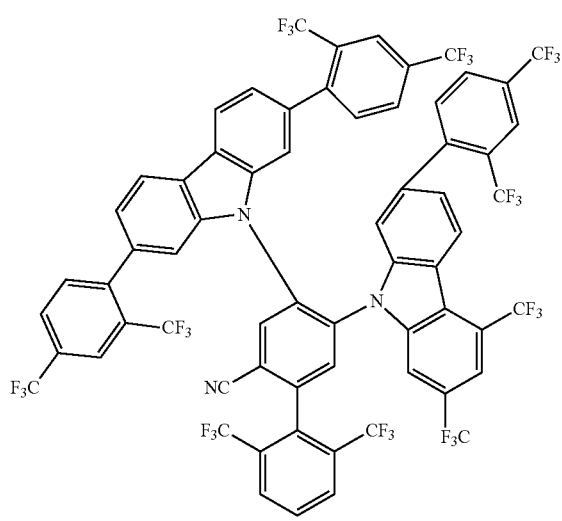
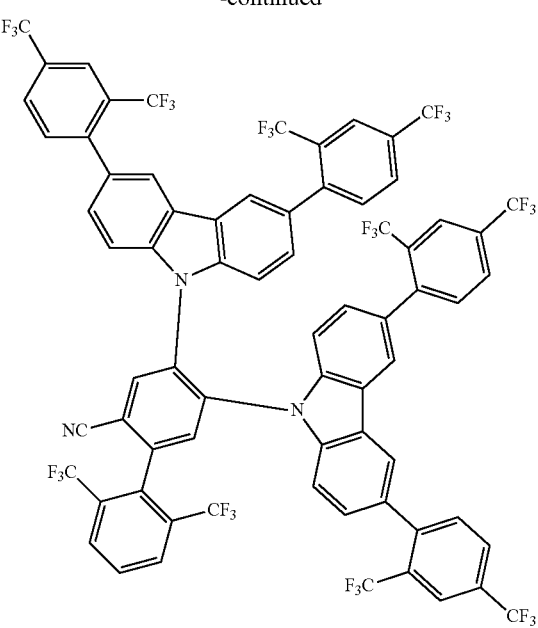
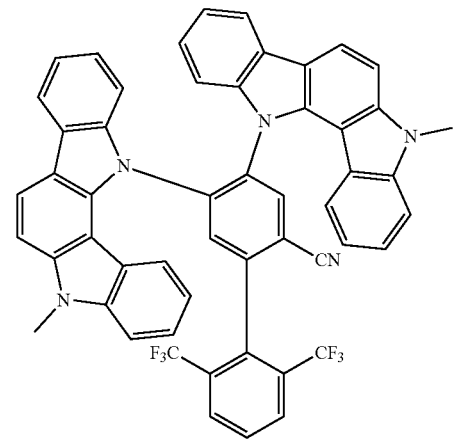
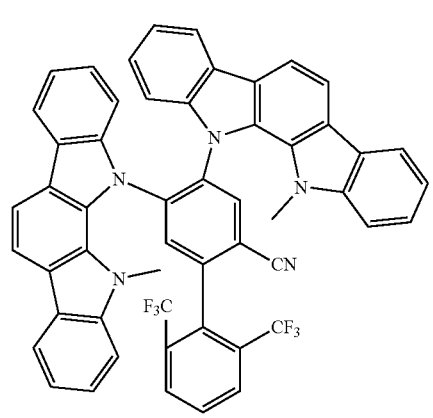
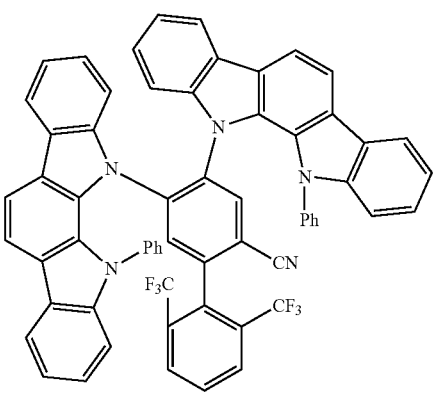

173
-continued
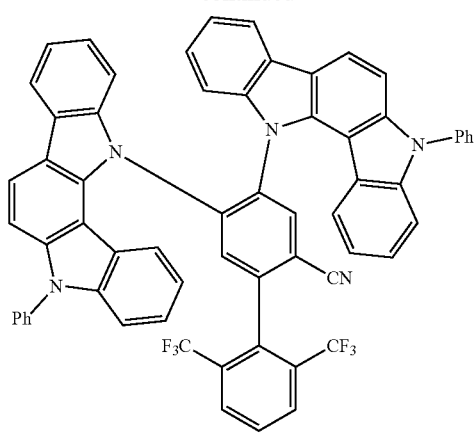
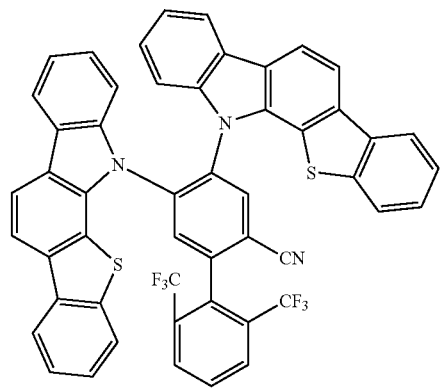
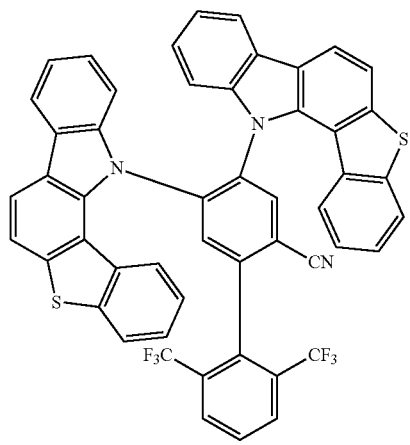
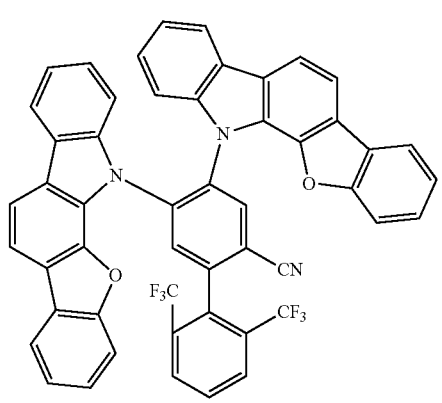
174
-continued
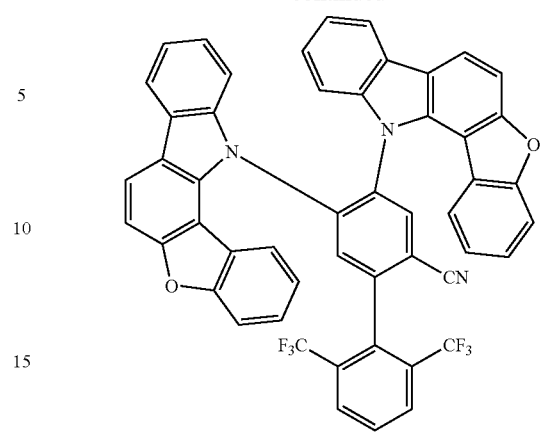
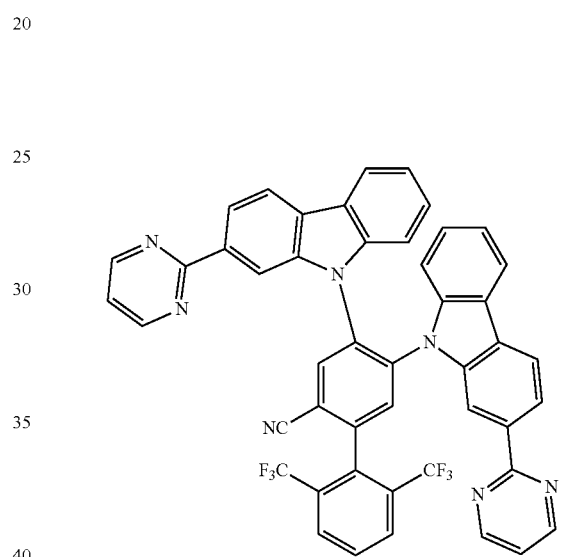
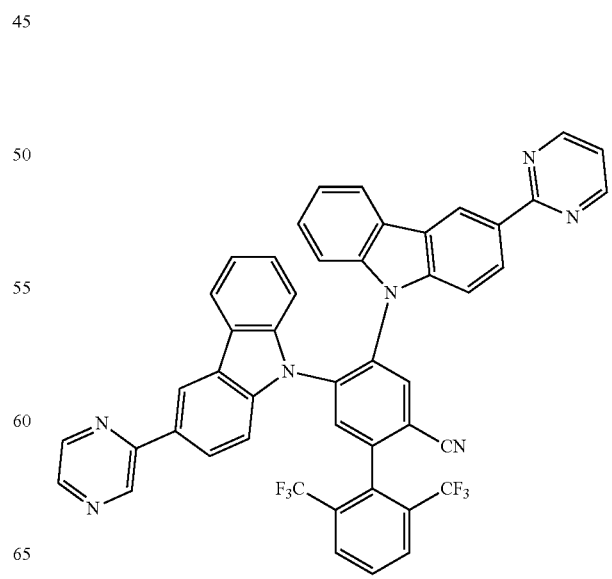

175
-continued
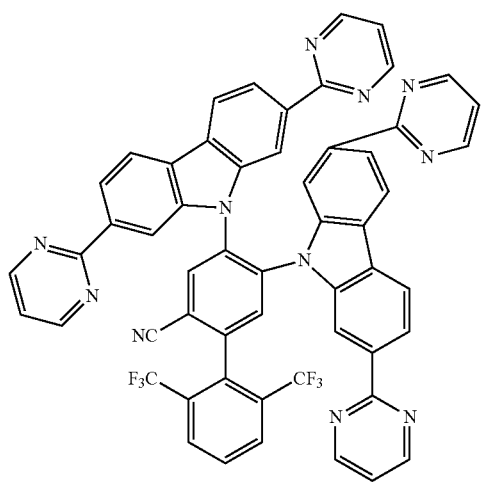
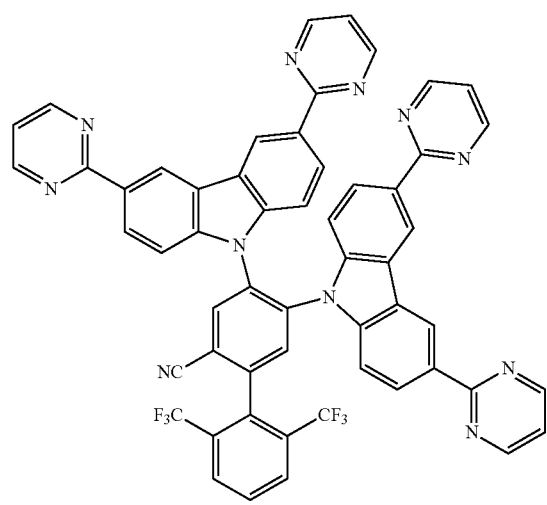
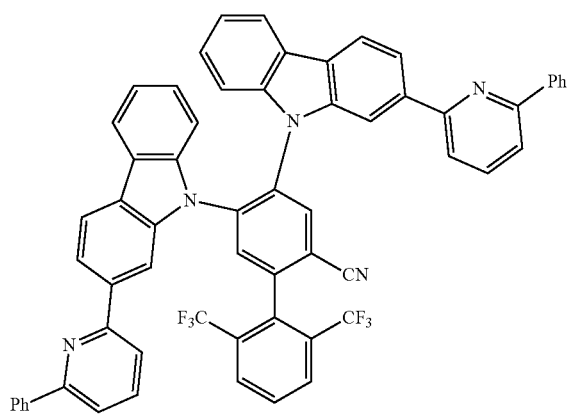
176
-continued
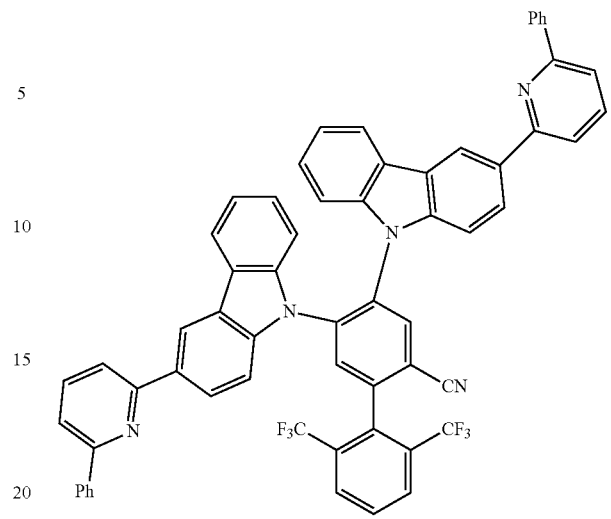
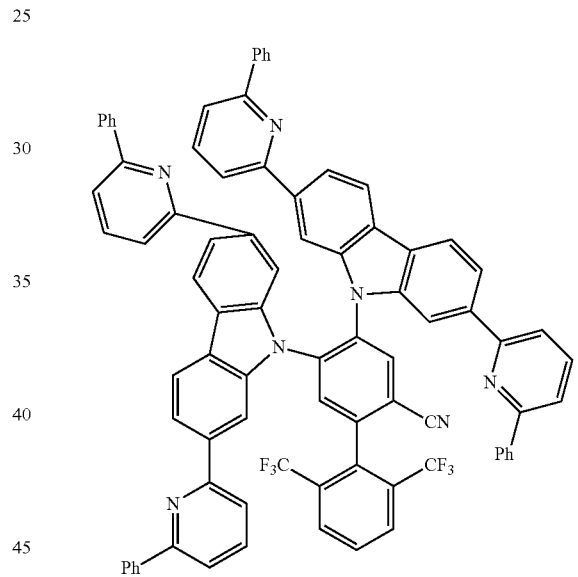
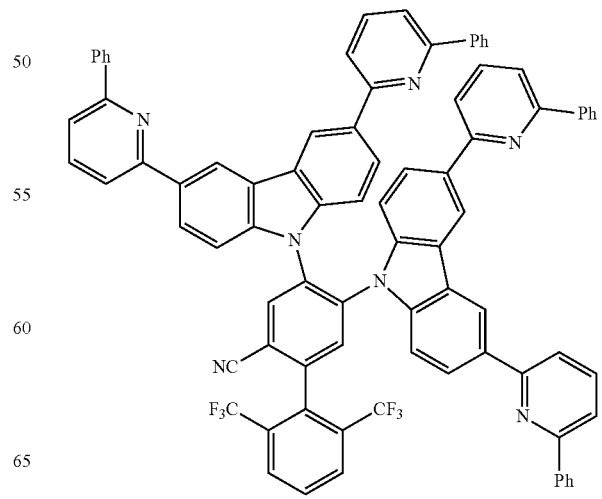

177
-continued
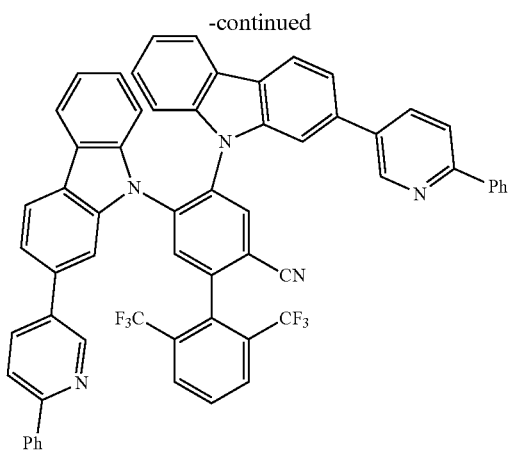
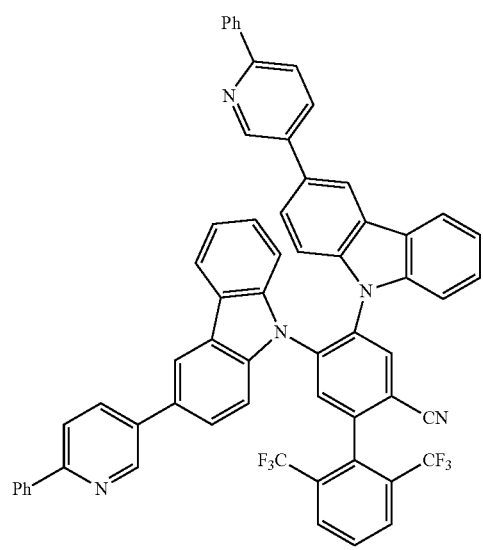
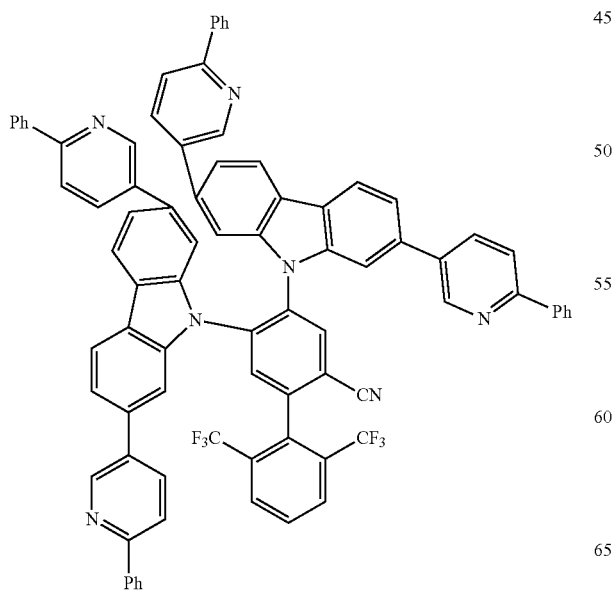
178
-continued
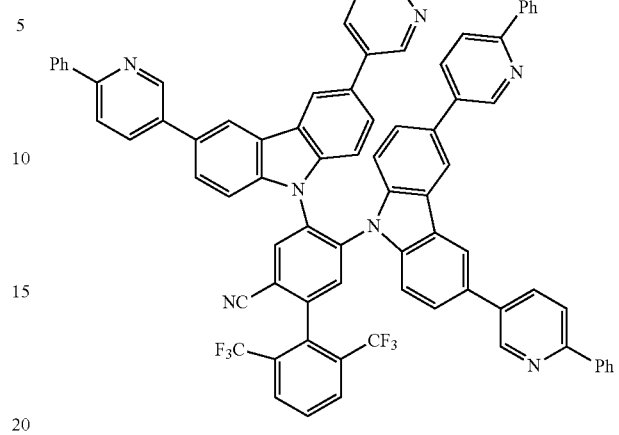
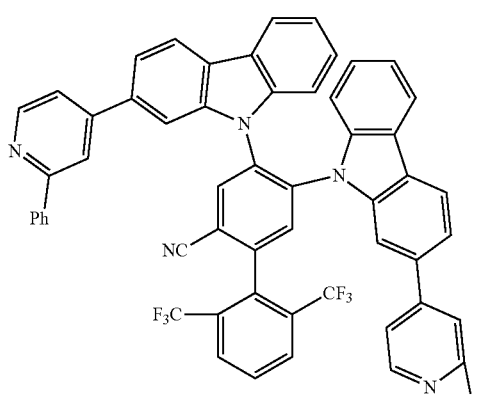
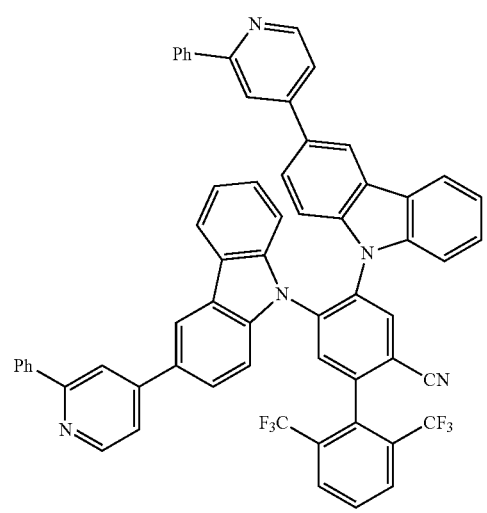

179
-continued
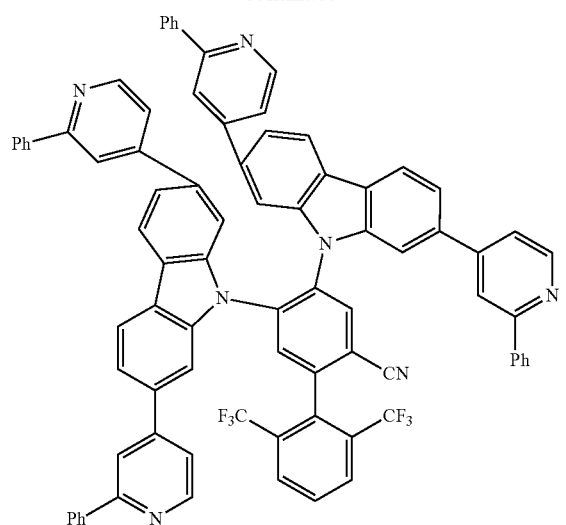
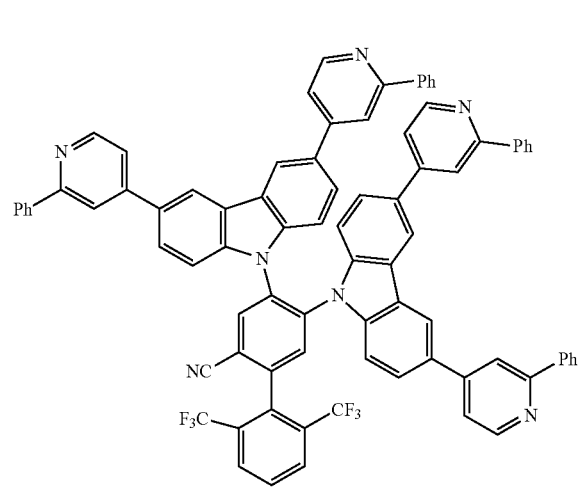
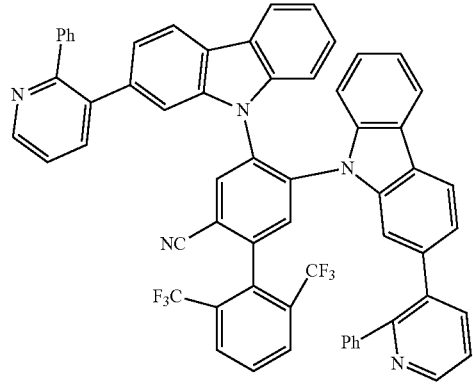
180
-continued
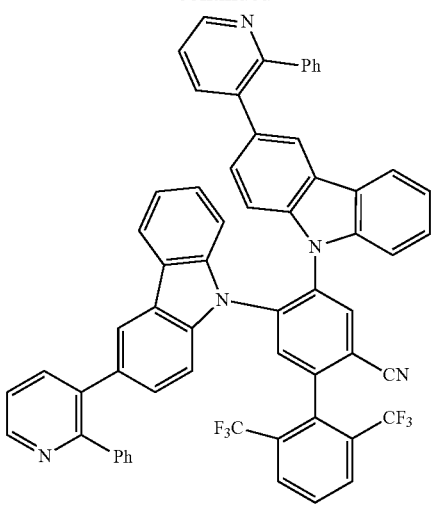
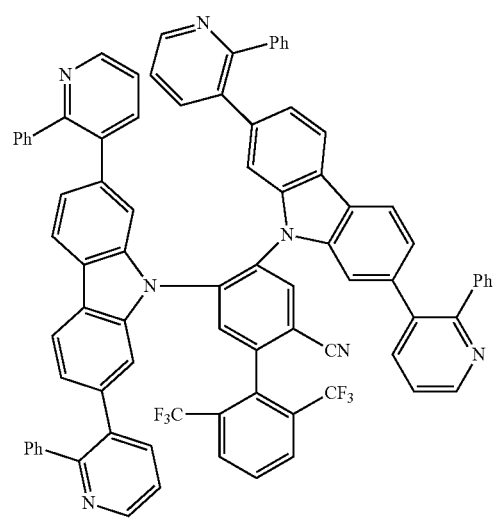
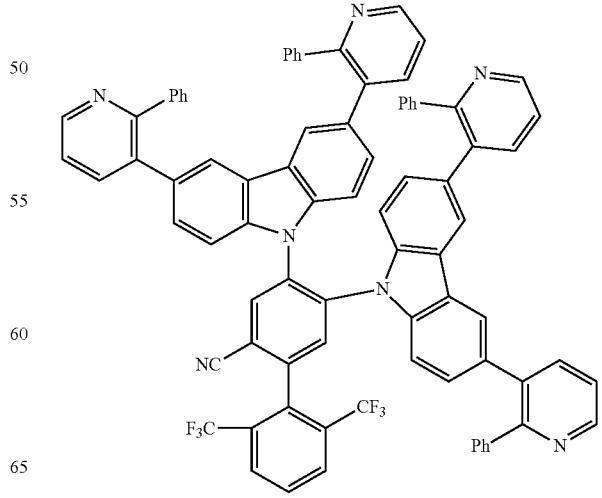

181
-continued
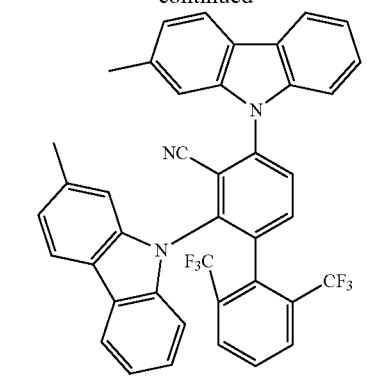
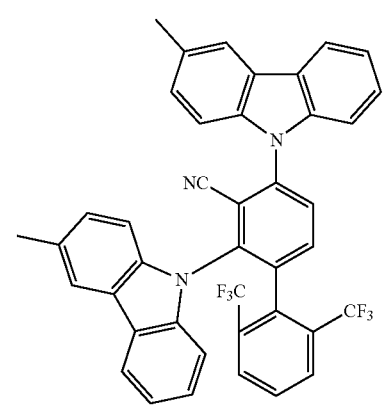
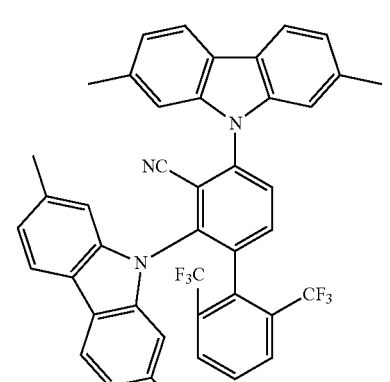
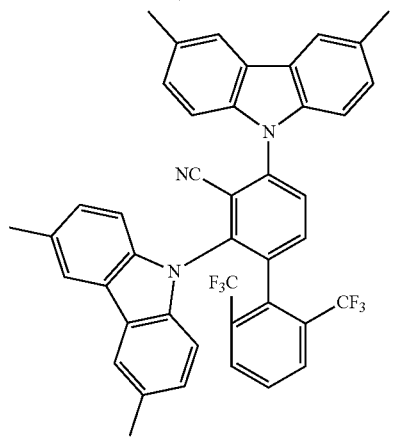
182
-continued
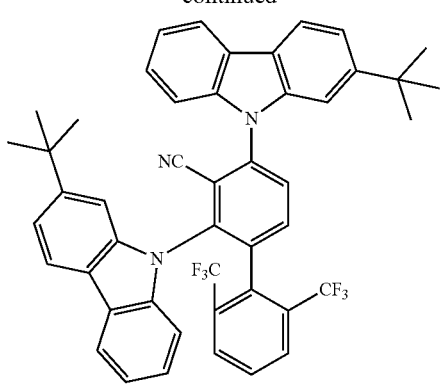
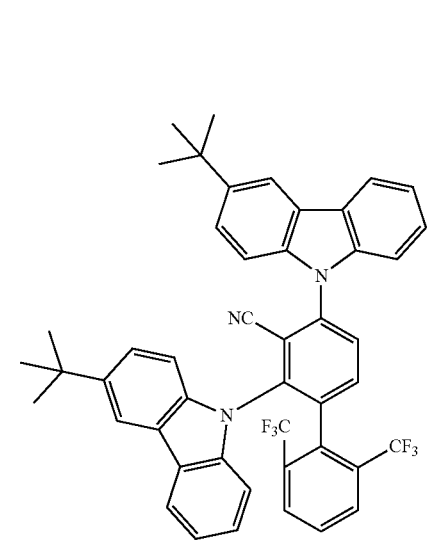
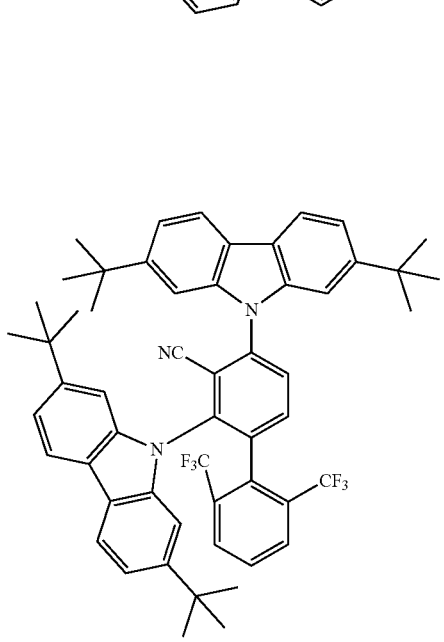

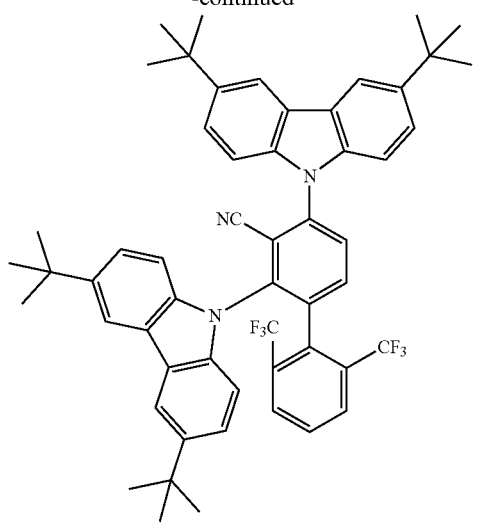
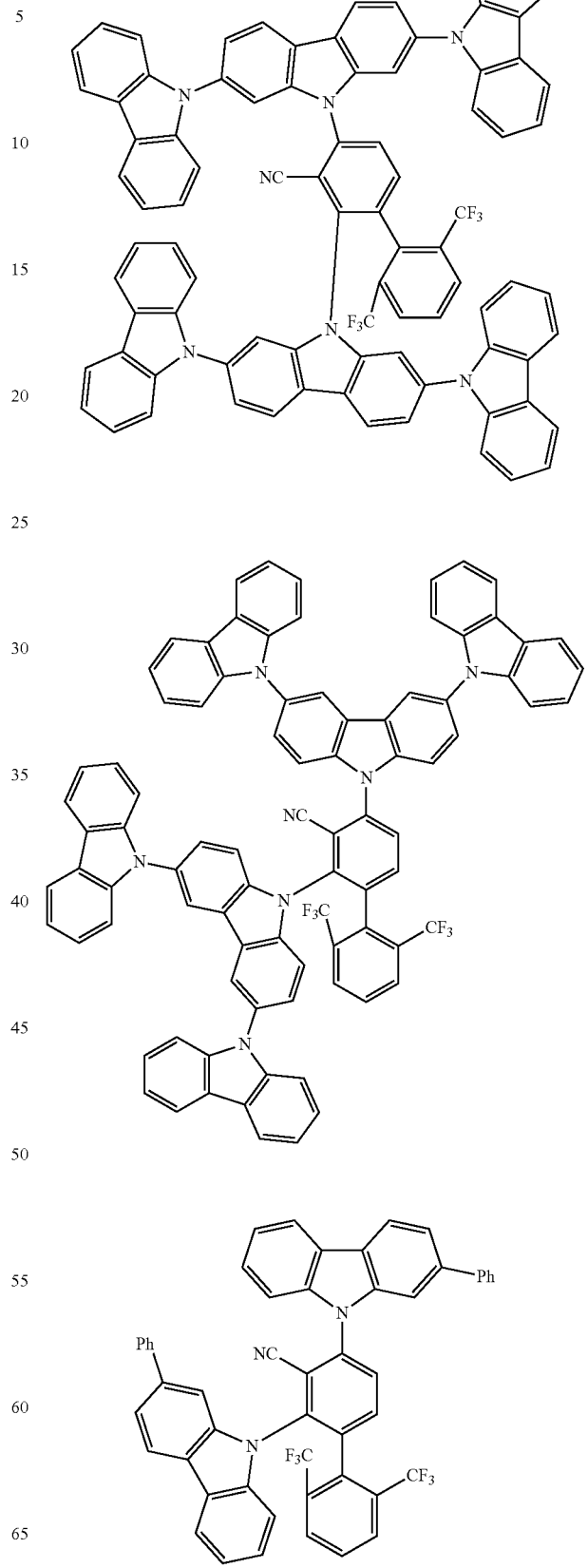

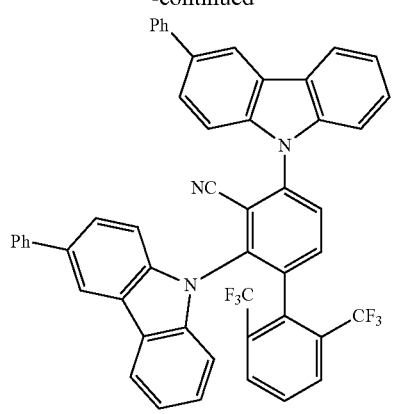
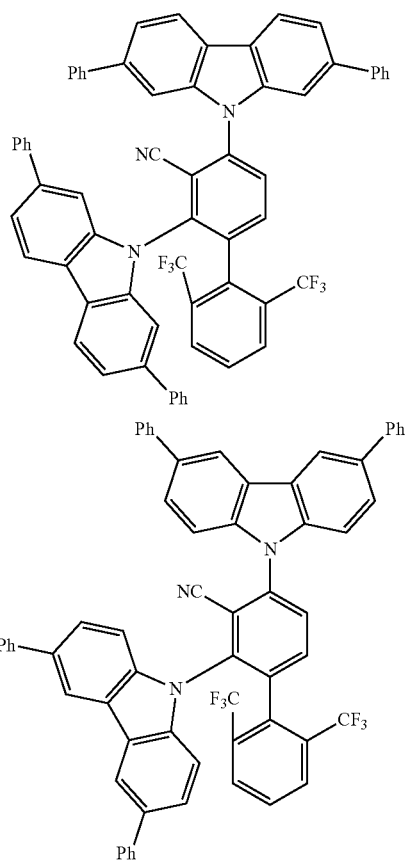
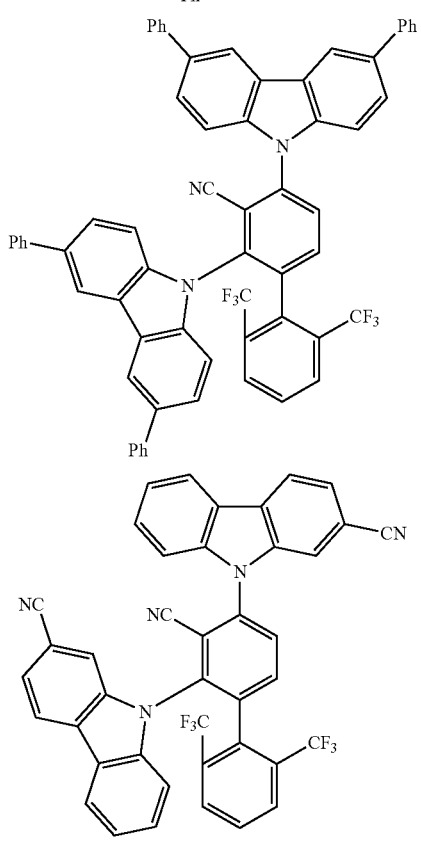
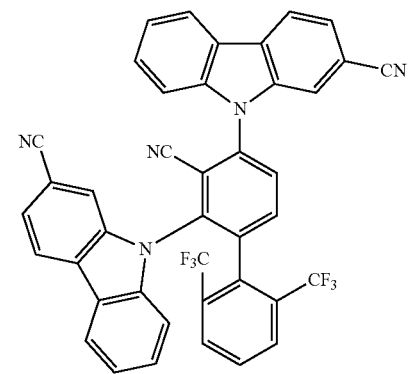
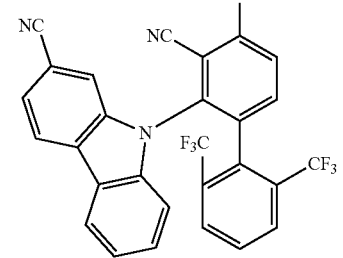
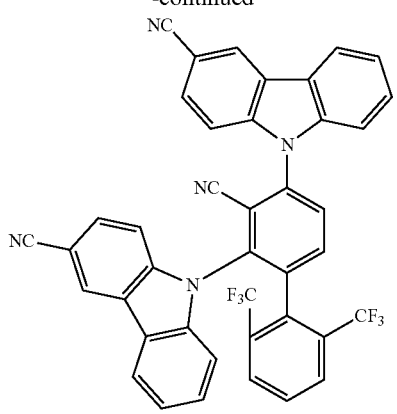
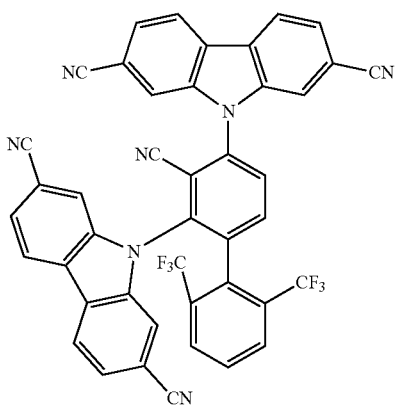
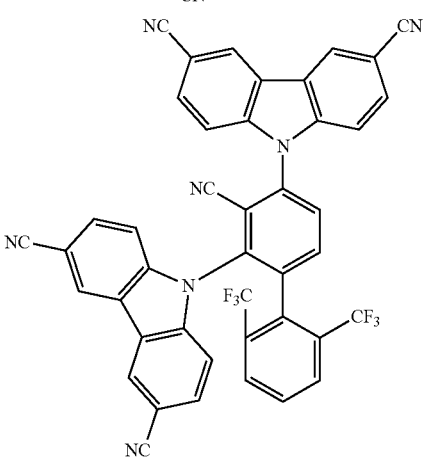
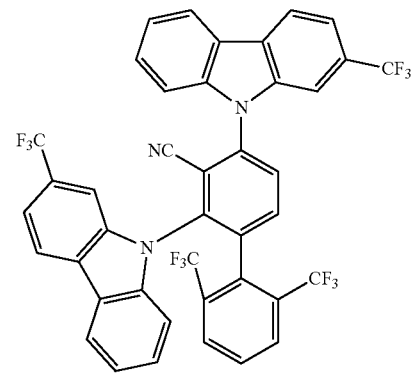

187
-continued
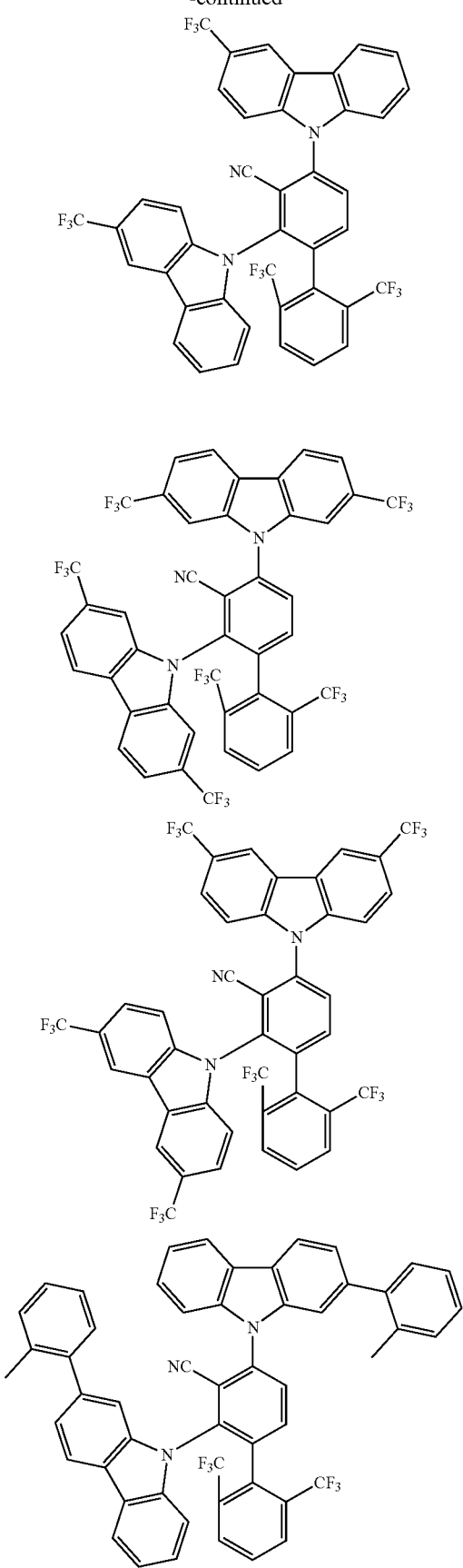
188
-continued
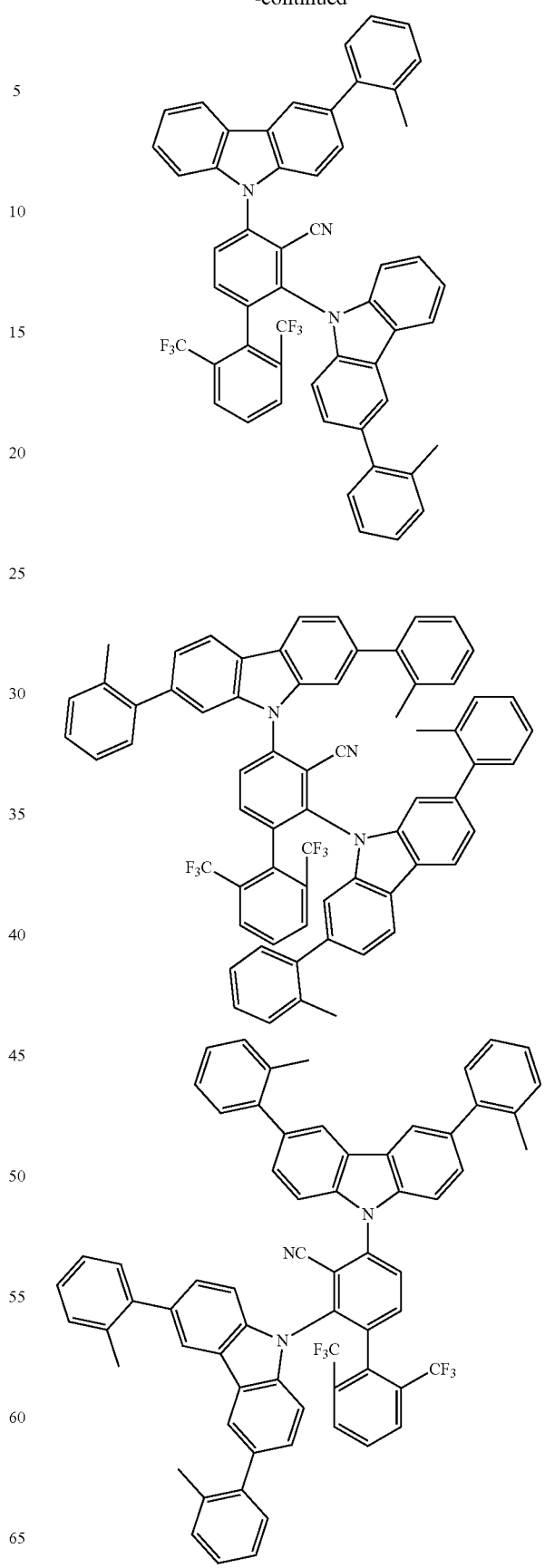

189
-continued
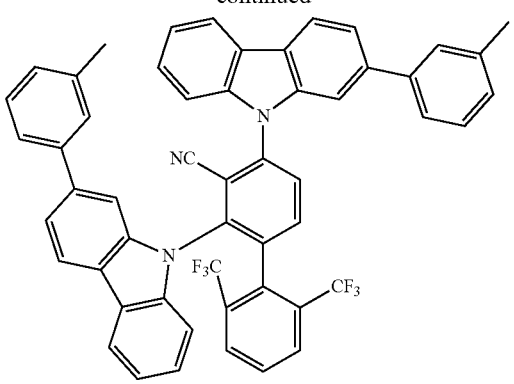
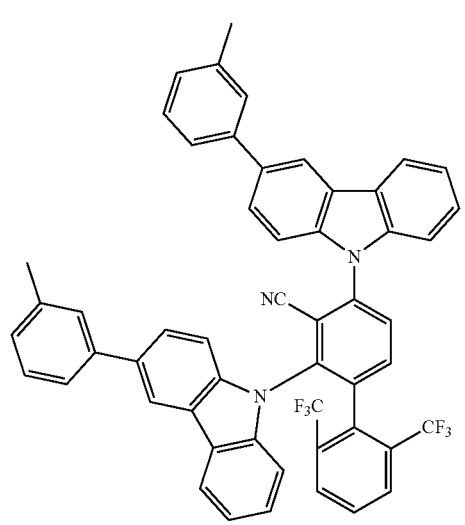
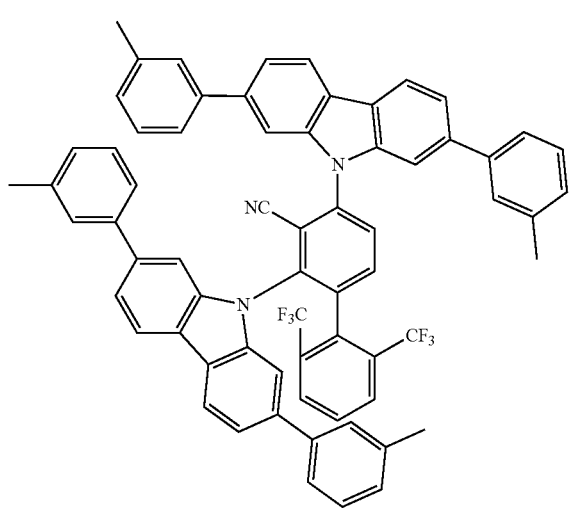
190
-continued
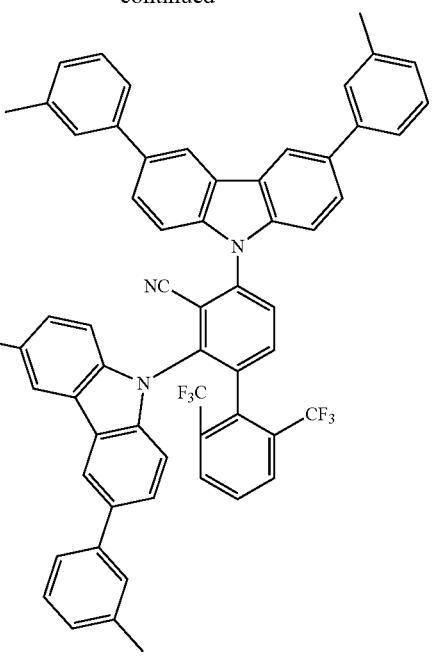
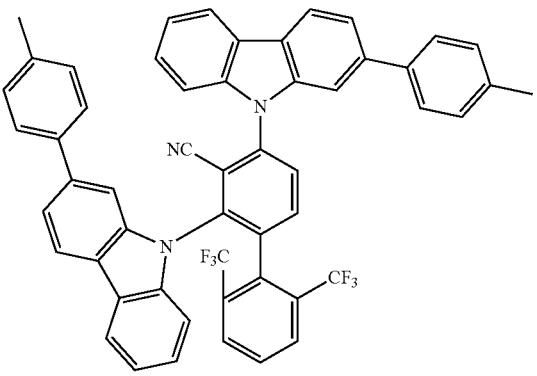
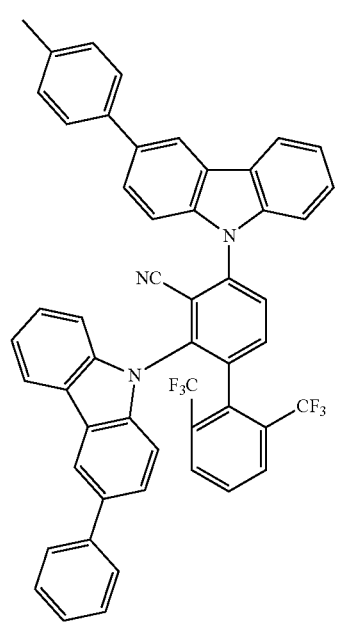

191
-continued
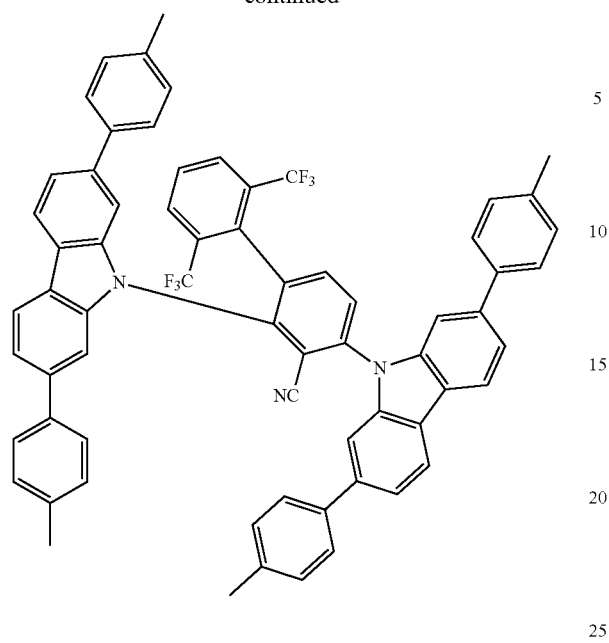
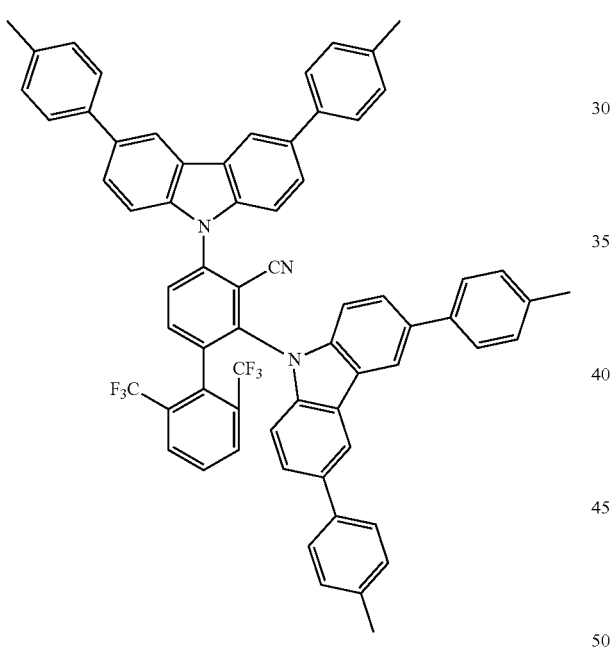
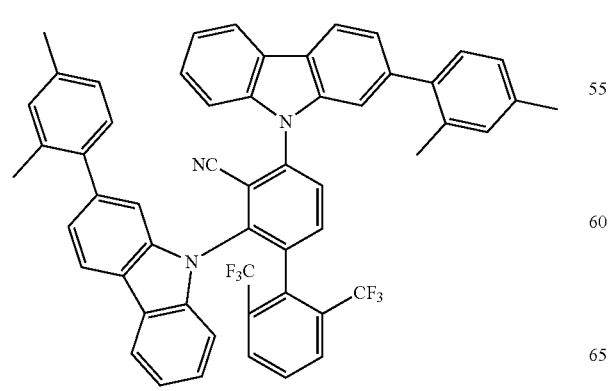
192
-continued
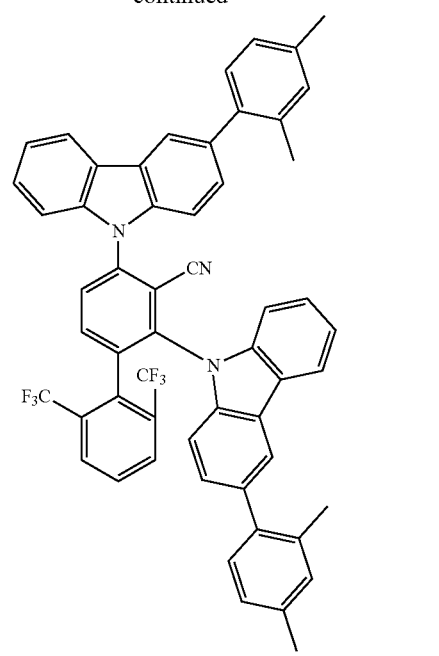
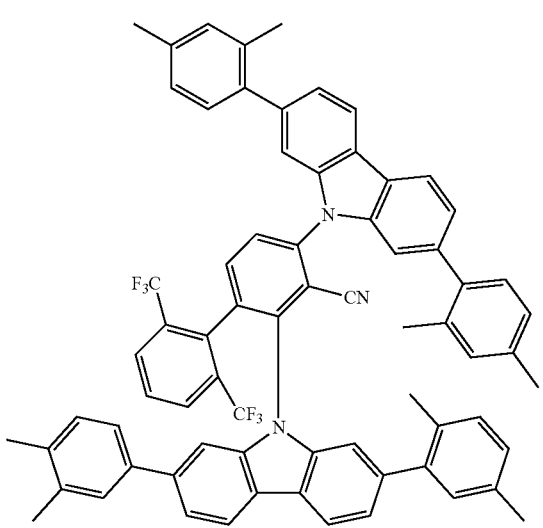

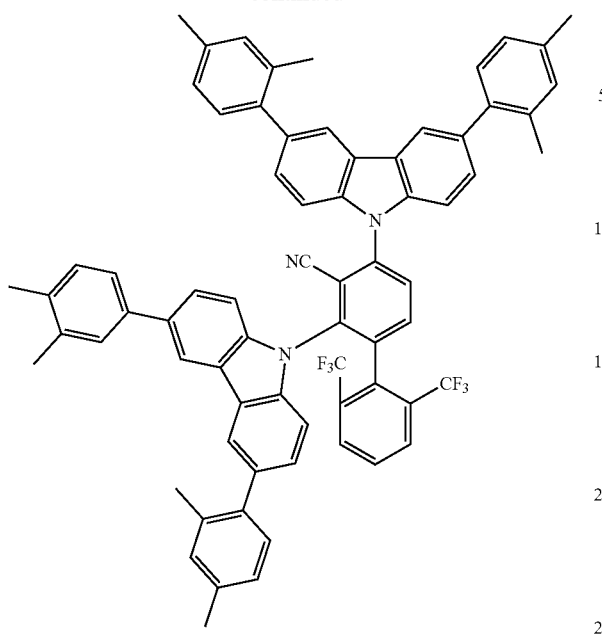
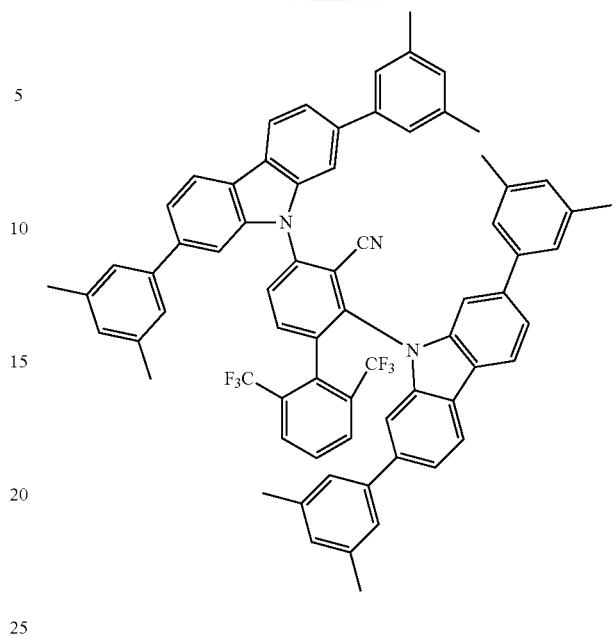
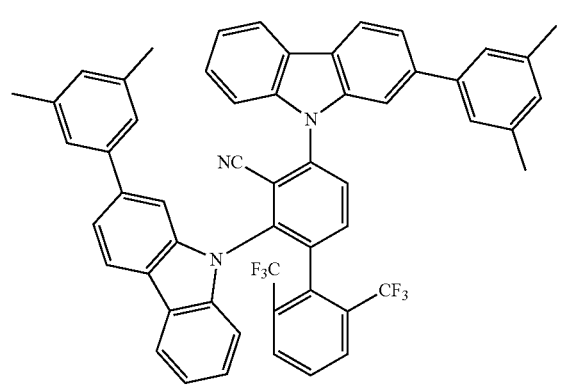
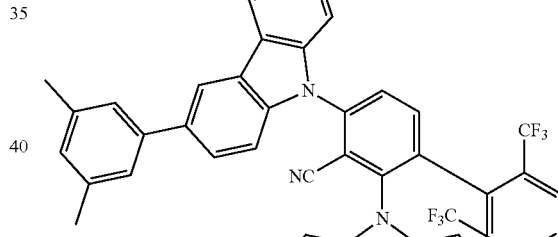
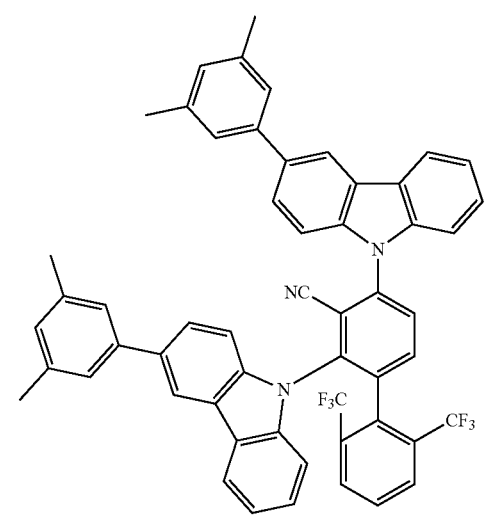
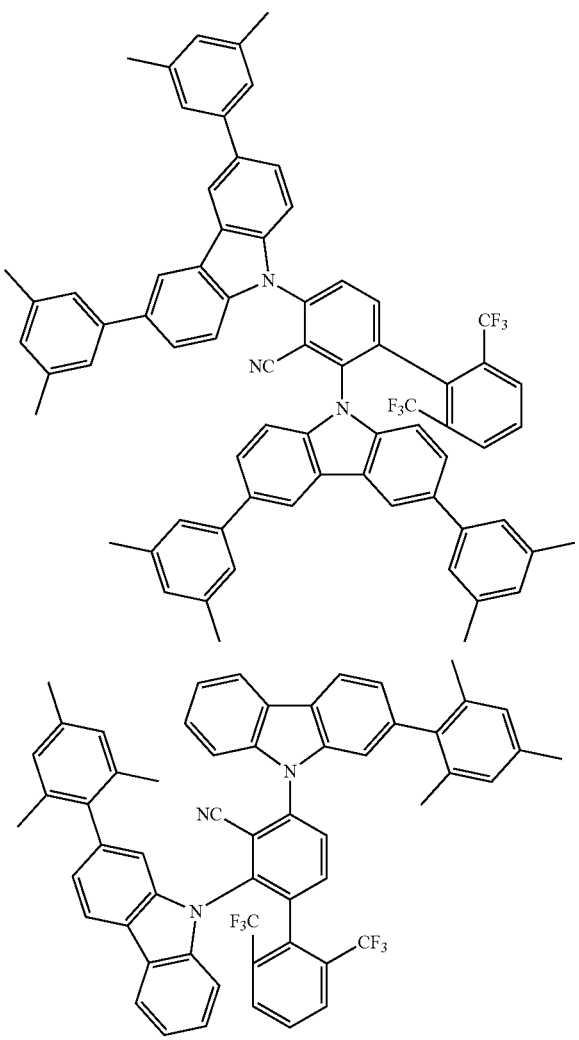

195
-continued
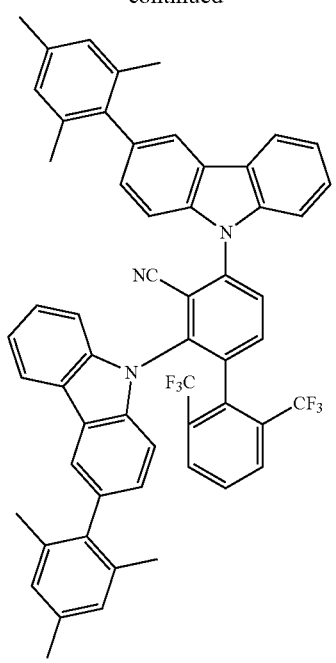
196
-continued
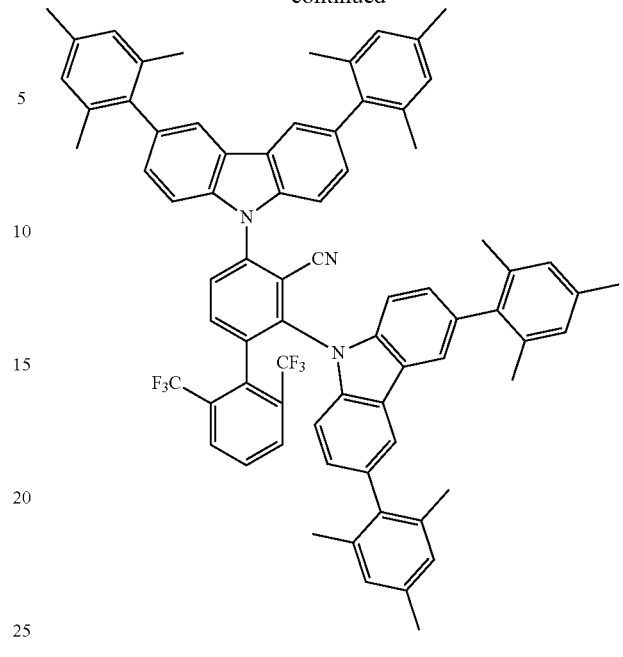
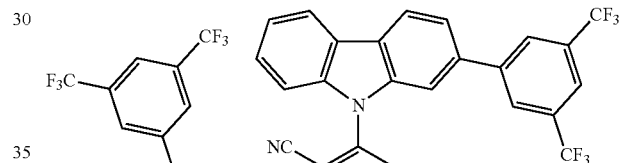
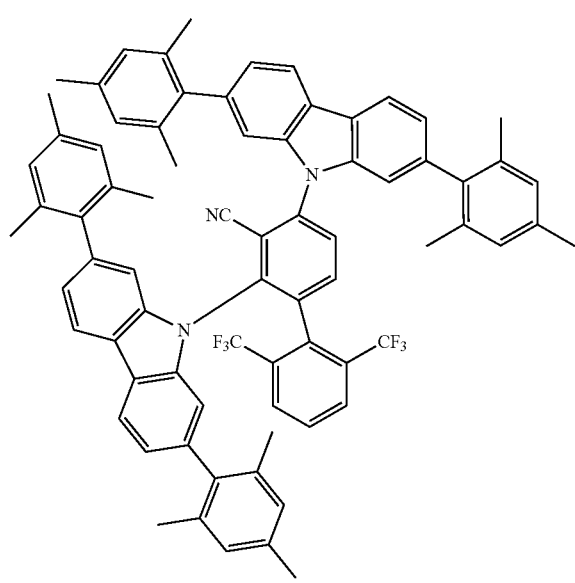
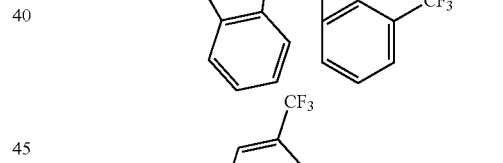
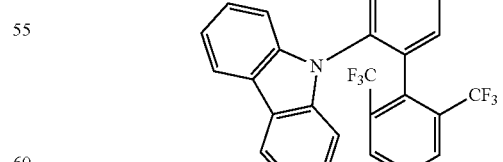
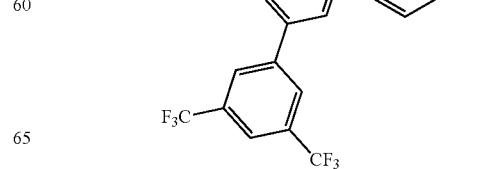

| 197 -continued | 198 -continued |
|---|---|
| 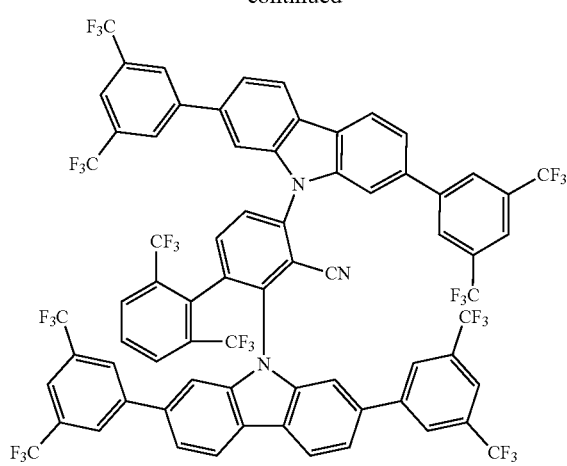 | 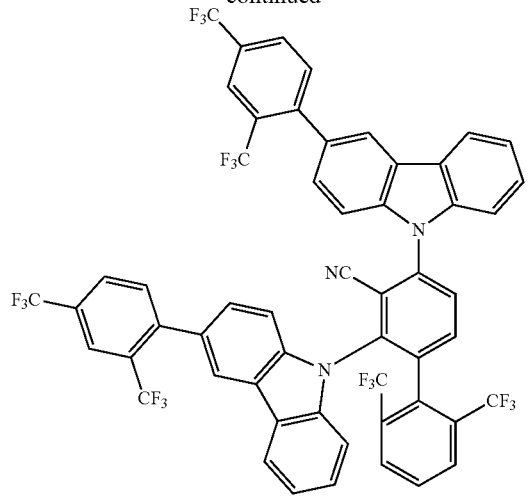 |
| 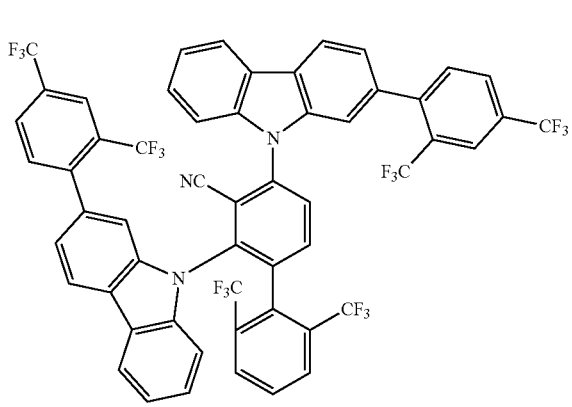 | 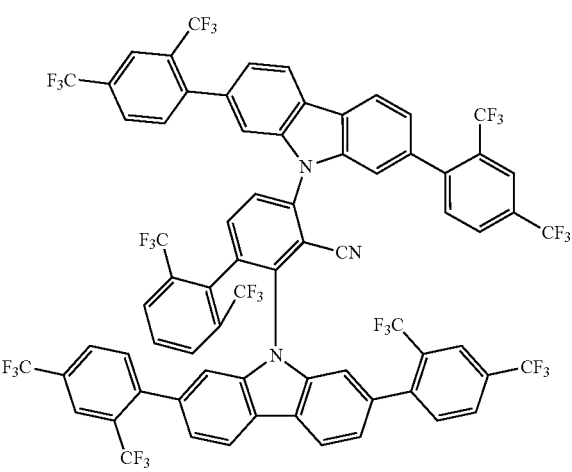 |
| 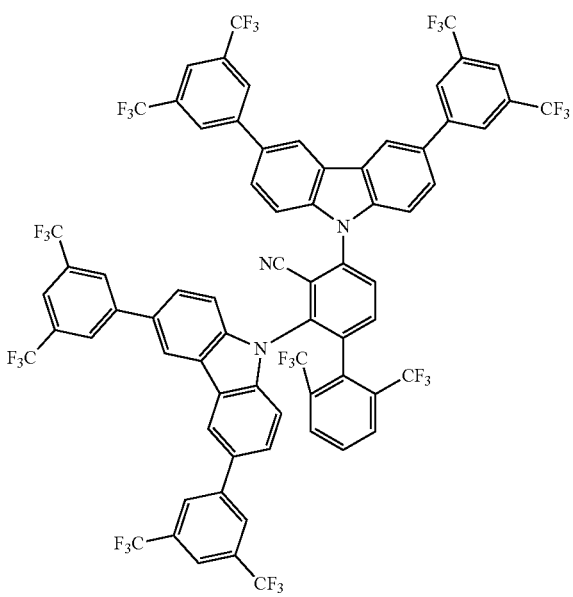 | 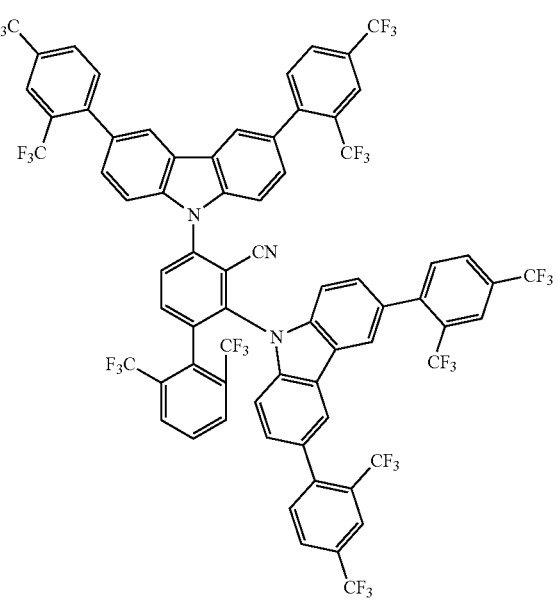 |

-continued
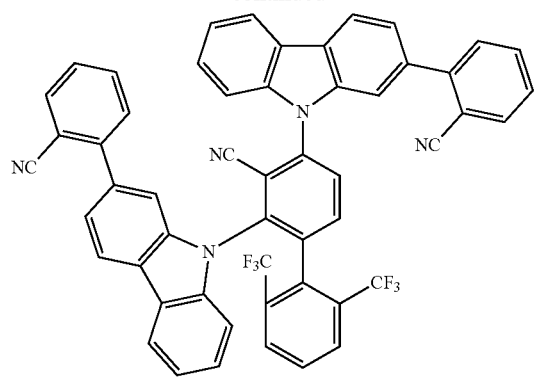
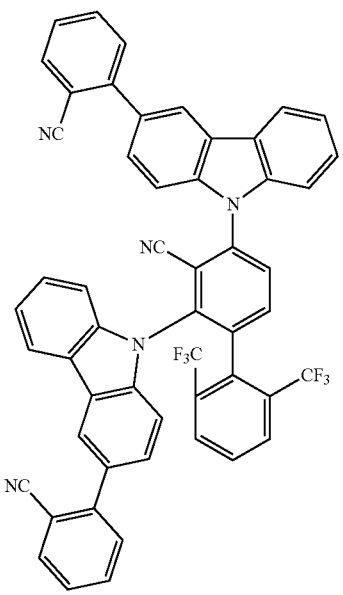
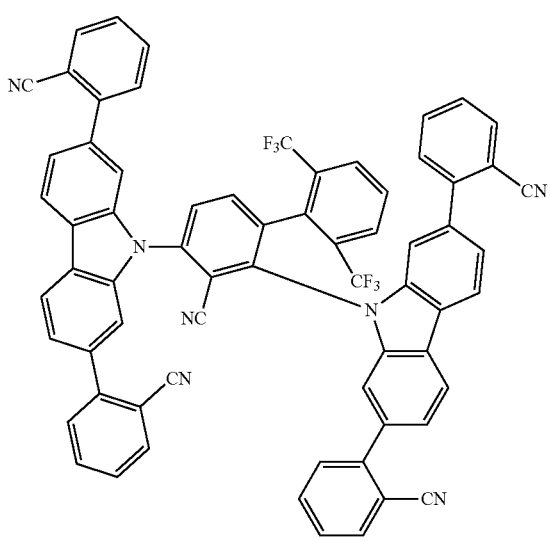
-continued
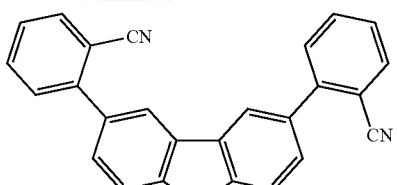
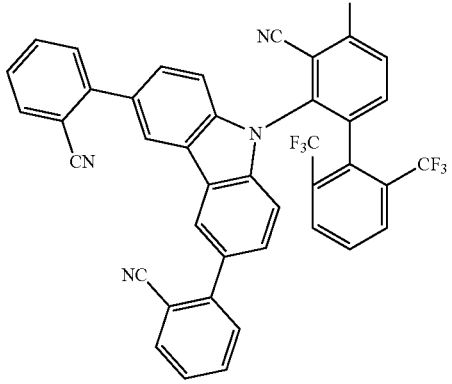
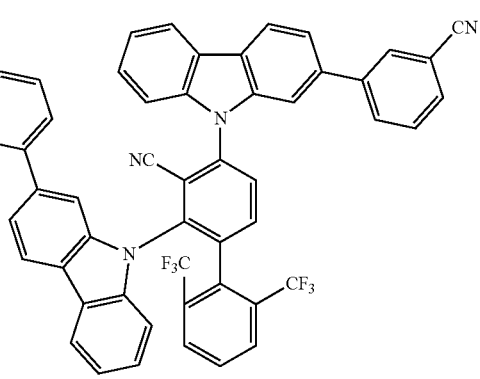
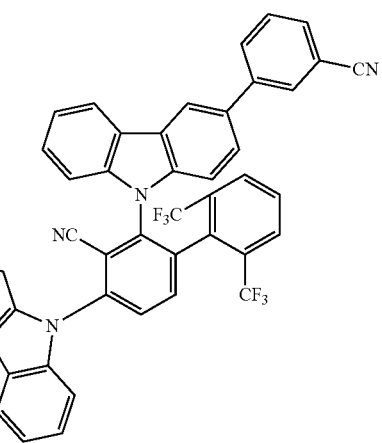

201
-continued
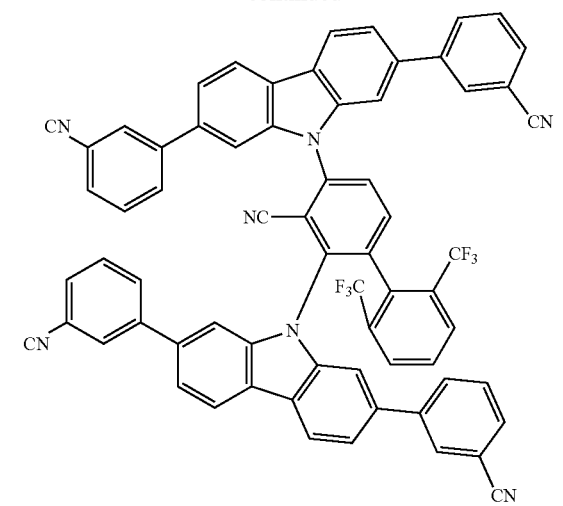
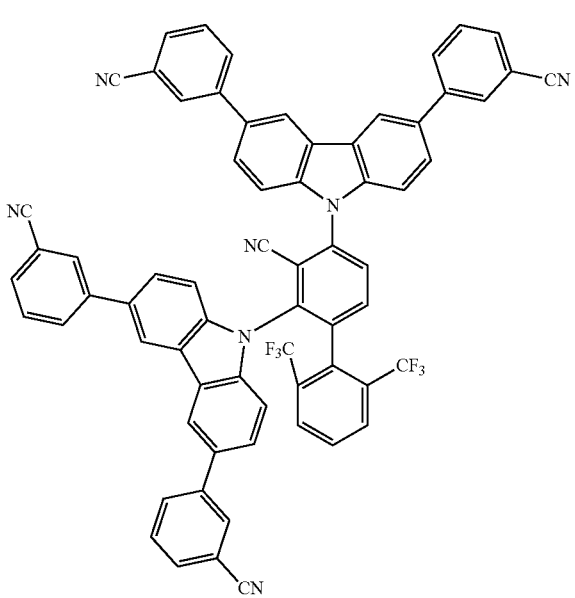
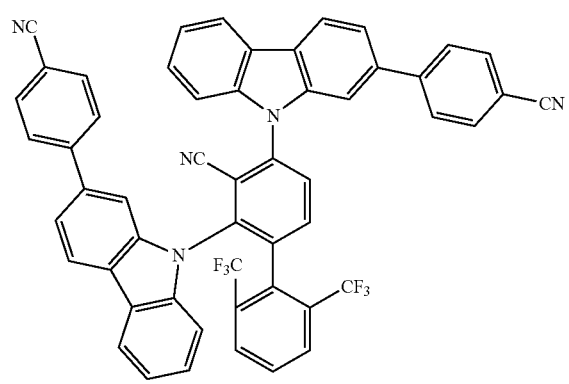
202
-continued
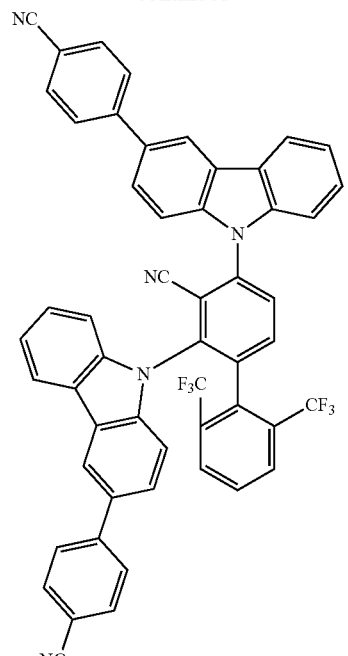
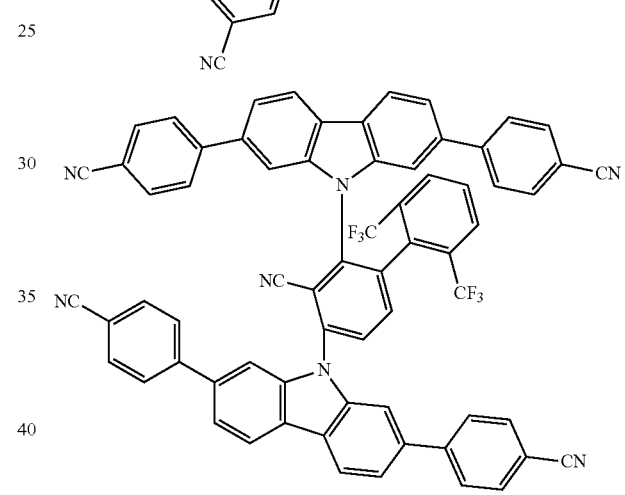
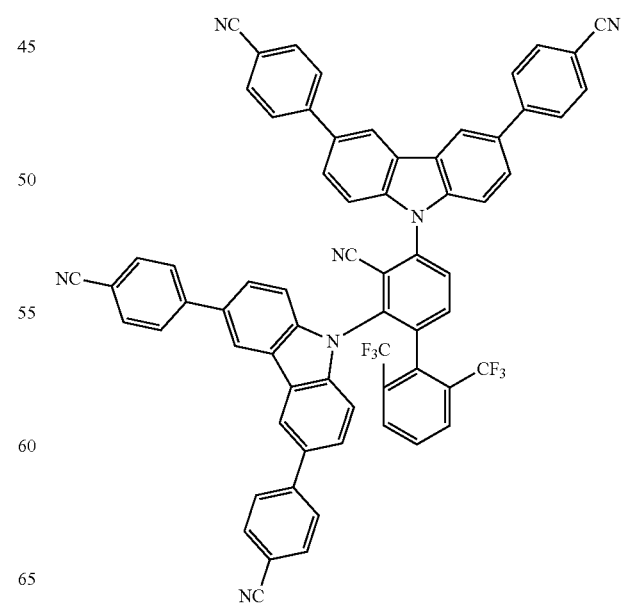

203
-continued
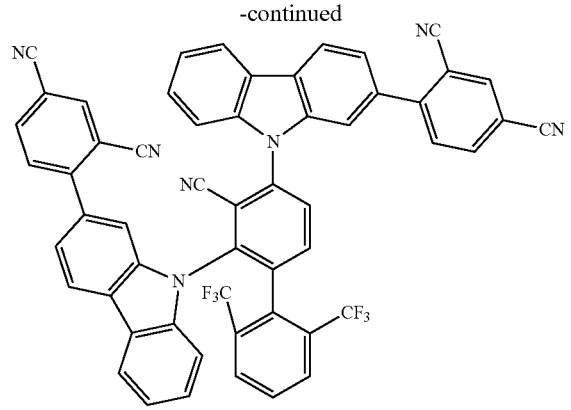
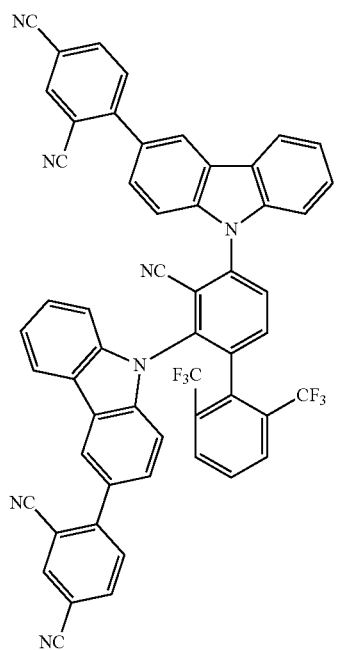
204
-continued
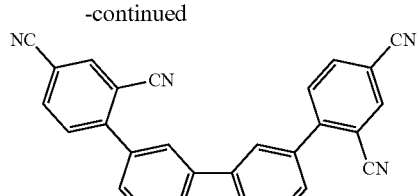
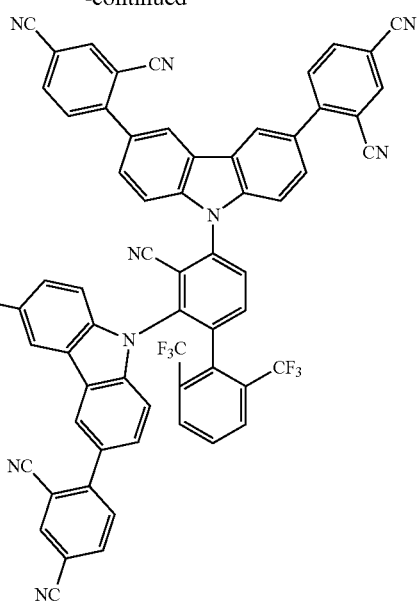
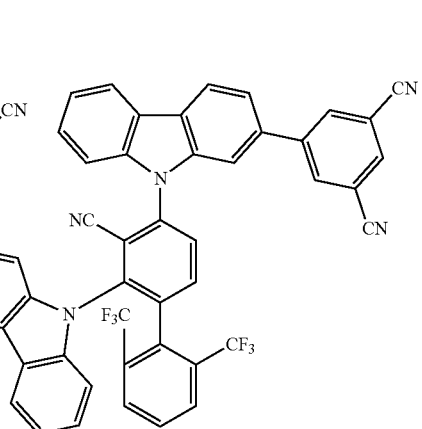
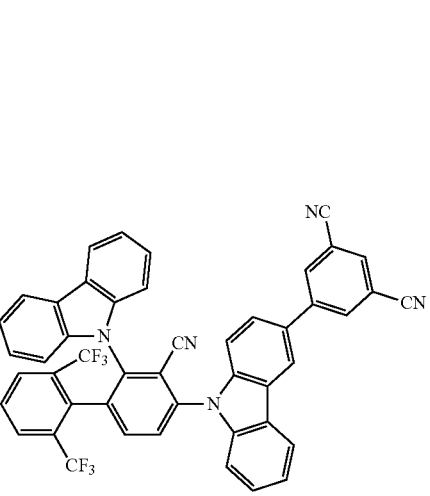

205
-continued
206
-continued
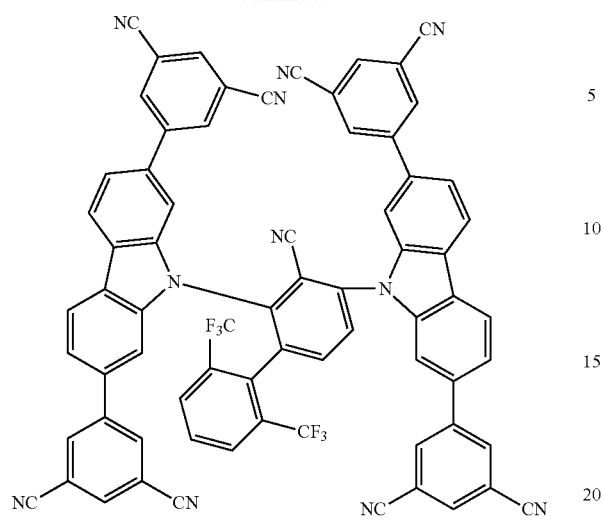
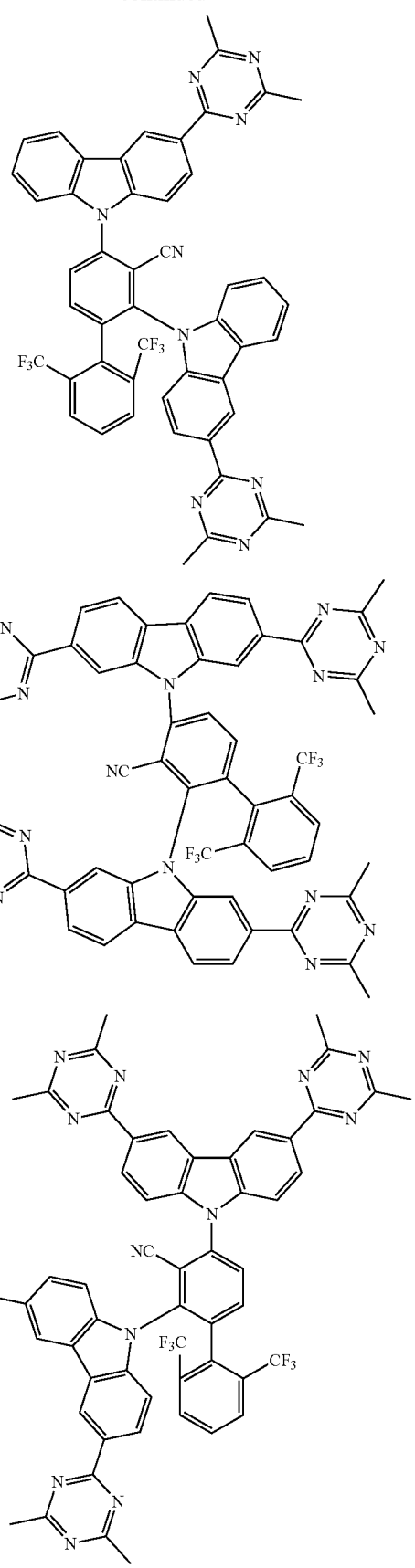

207
-continued
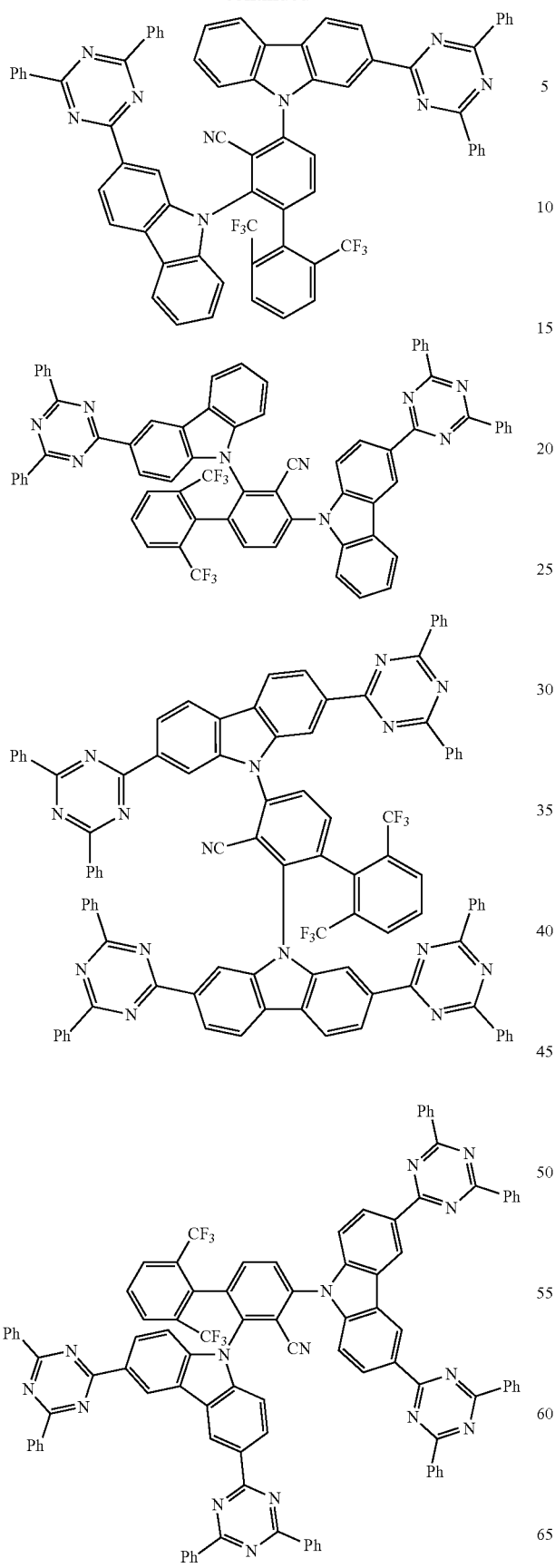
208
-continued
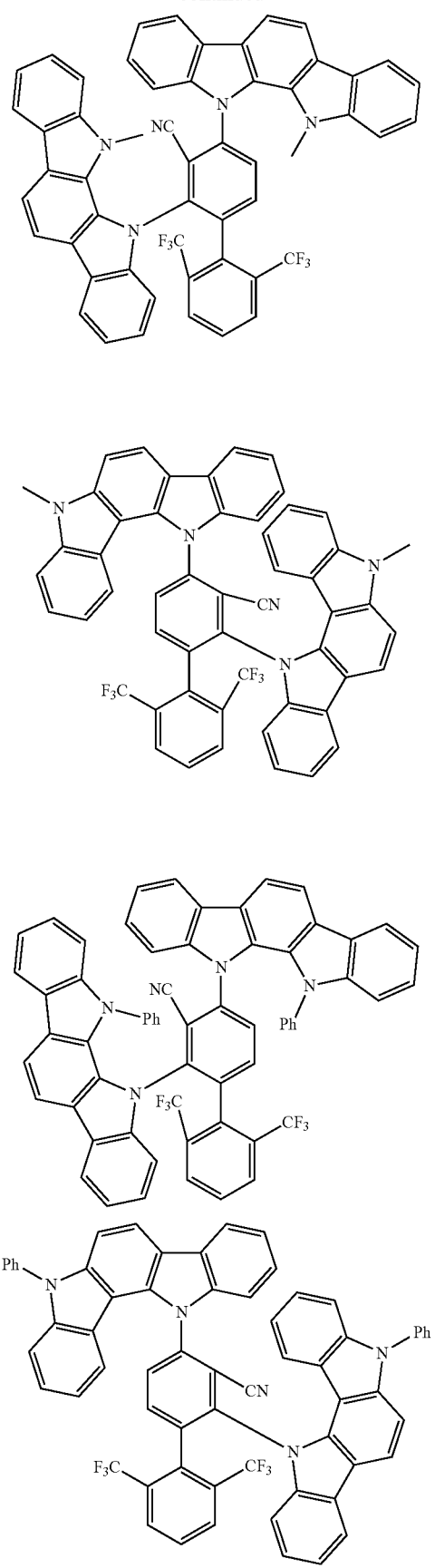

-continued
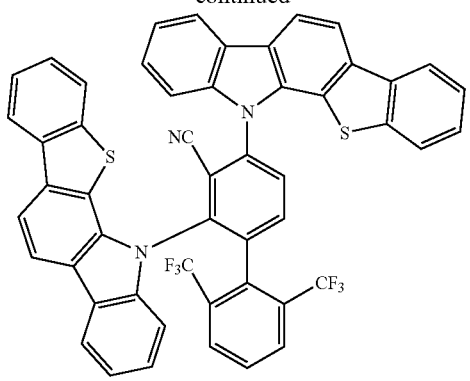
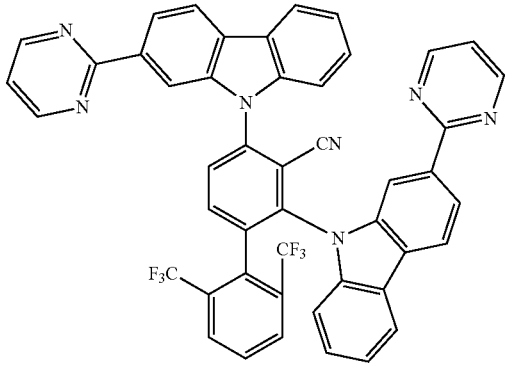
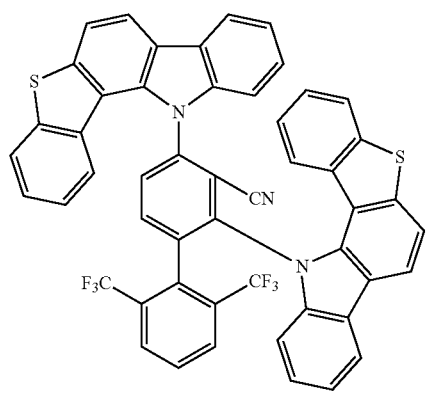
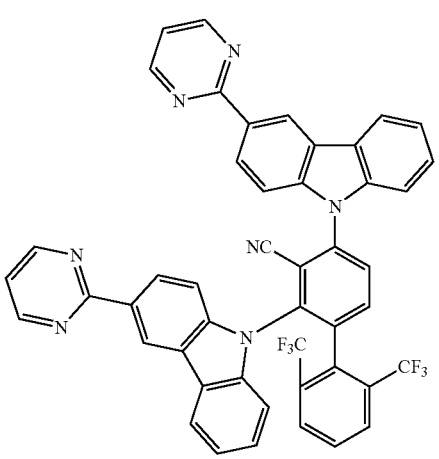
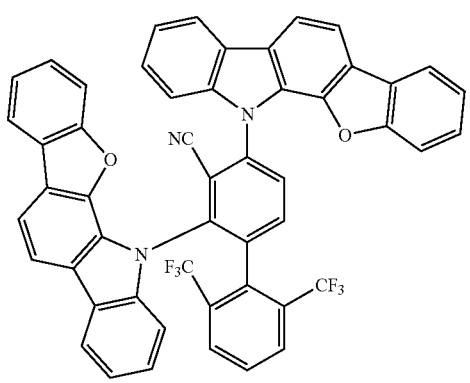
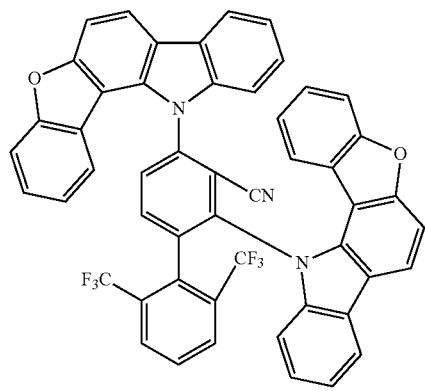
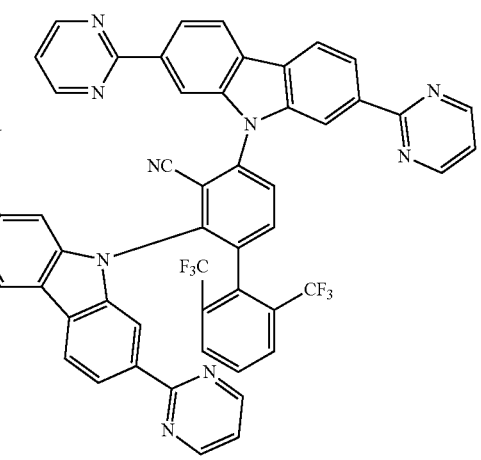

211
-continued
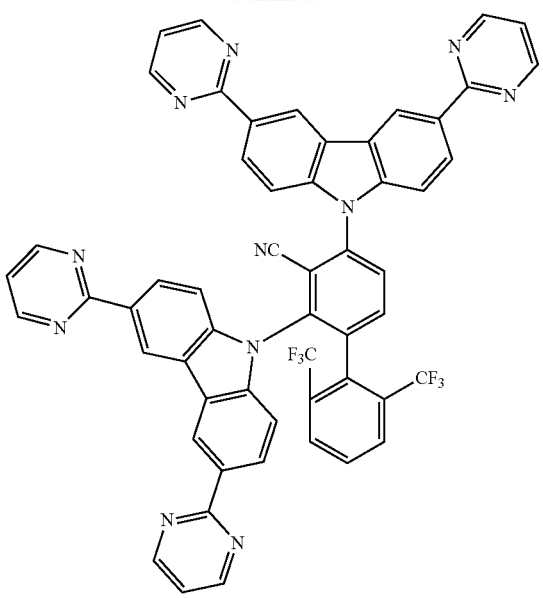
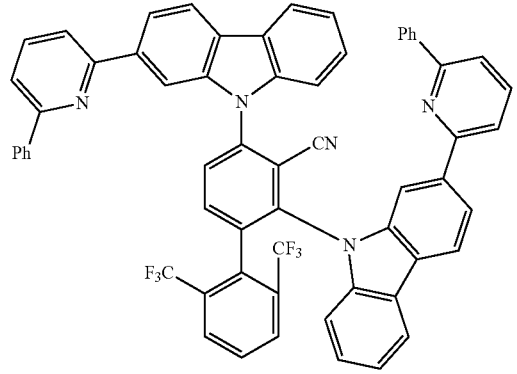
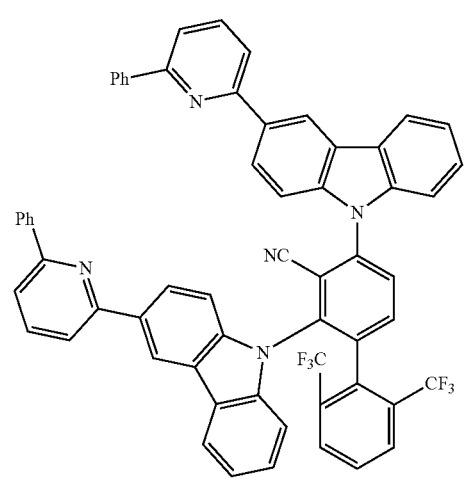
212
-continued
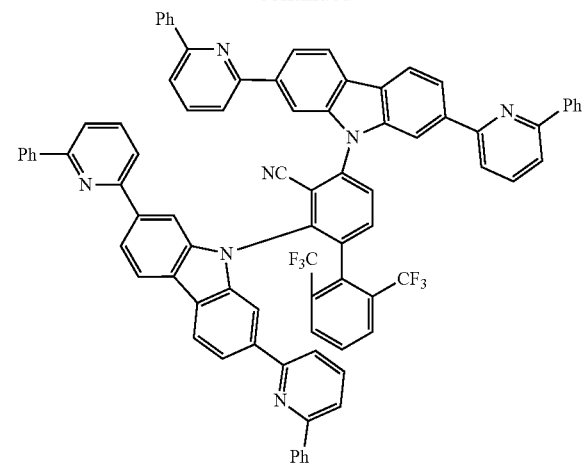
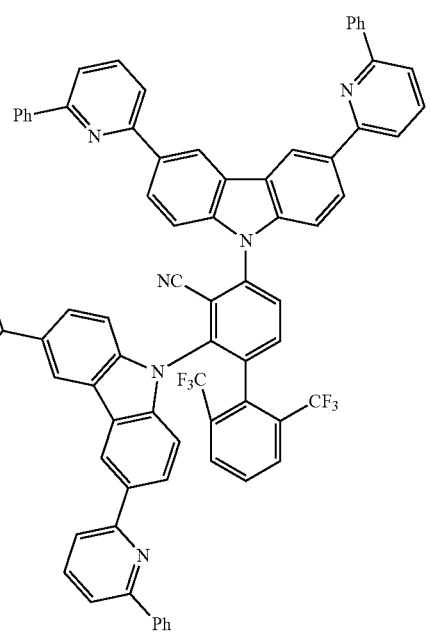
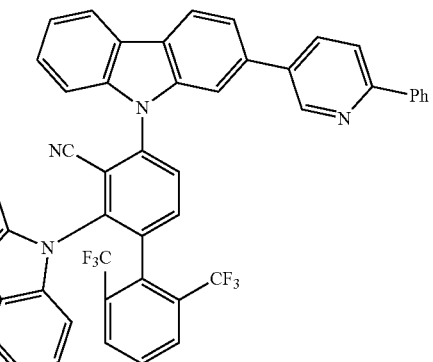

-continued
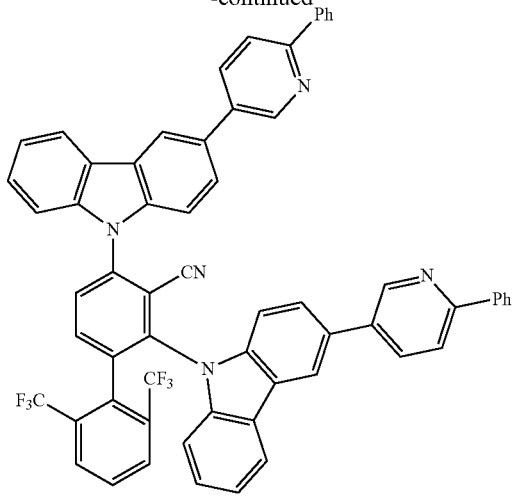
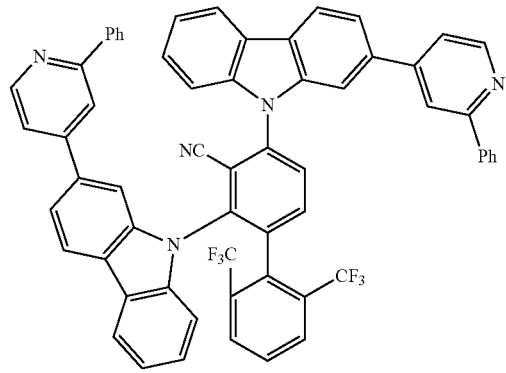
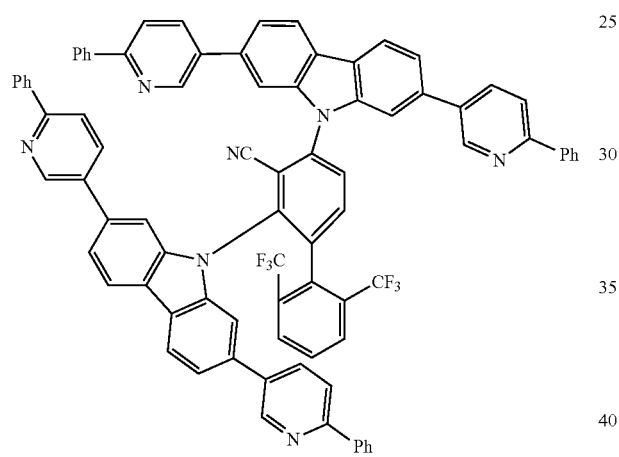
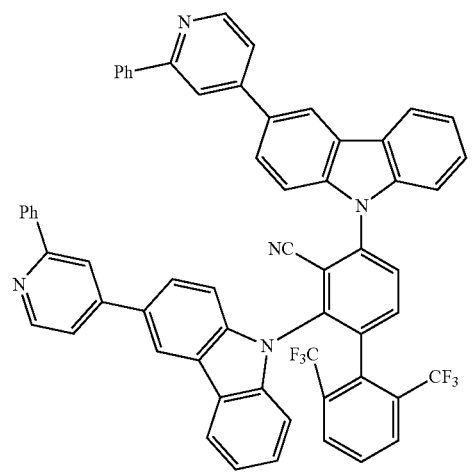
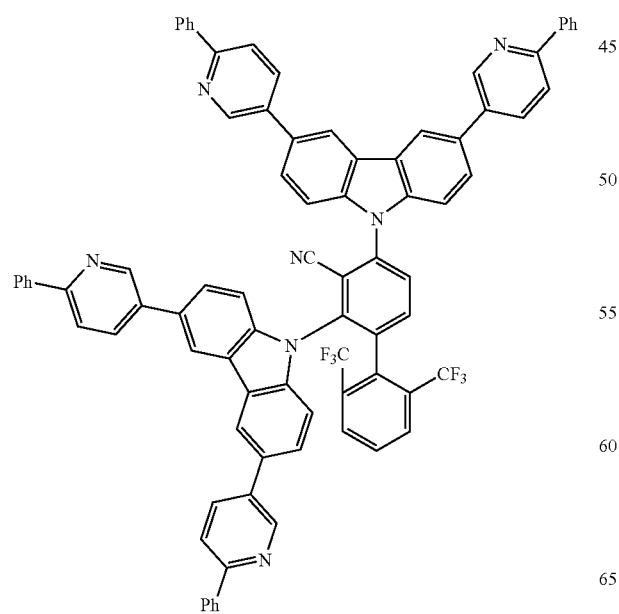
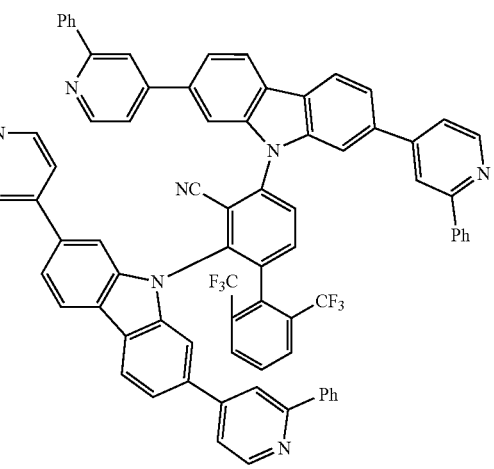

215
-continued

216
-continued

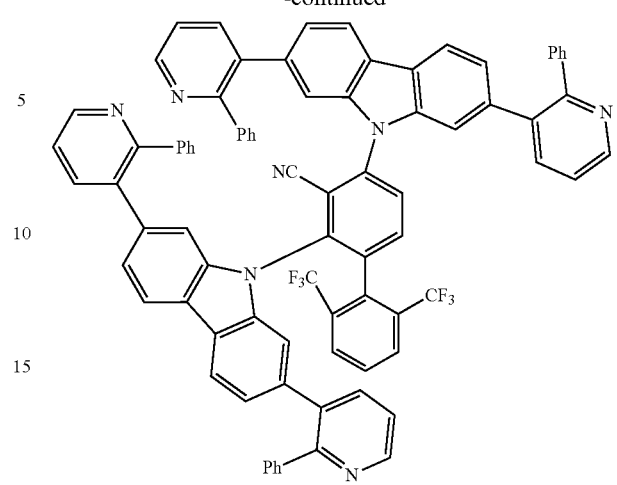

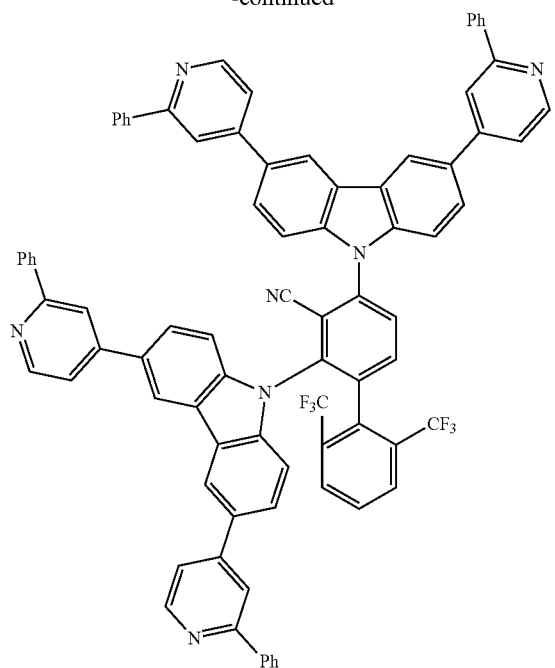

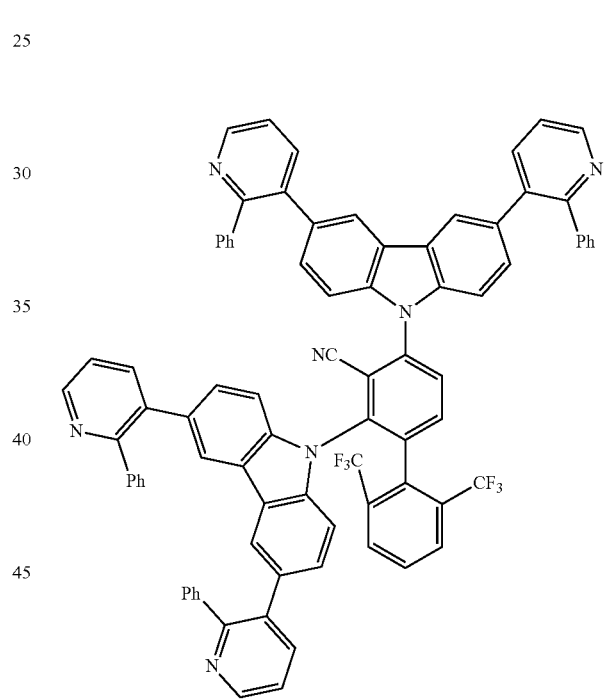

Although illustrative embodiments of the present invention have been described herein with reference to the accompanying drawings, it is to be understood that the invention is not limited to those precise embodiments, and that various other changes and modifications may be made by one skilled in the art without departing from the scope or spirit of the invention.

FIGURES

FIG. 1 shows the emission spectrum of Example 1 (10% in PMMA).

The invention claimed is:
1. An organic molecule, comprising:
a first chemical unit comprising a structure according to Formula I:

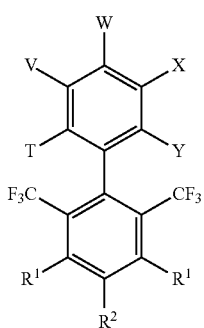

Formula I and
two second chemical units, which are respectively the same or different in each occurrence, comprising a structure according to Formula II:

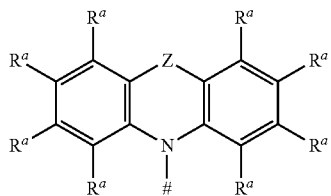

Formula II wherein, in each case, the first chemical unit is connected to the two second chemical units via a single bond;
wherein
T is the point of attachment of the single bond between the first chemical unit and a second chemical unit or is H;
V is the point of attachment of the single bond between the first chemical unit and a second chemical unit or is H;
W is the point of attachment of the single bond between the first chemical unit and a second chemical unit or is selected from the group consisting of H, CN and $CF_3$;
X is the point of attachment of the single bond between the first chemical unit and a second chemical unit or is selected from the group consisting of H, CN and $CF_3$;
Y is the point of attachment of the single bond between the first chemical unit and a second chemical unit or is selected from the group consisting of H, CN and $CF_3$;
identifies the point of attachment of the single bond between a second chemical unit and the first chemical unit;
Z is the same or different in each occurrence, is a direct bond or is selected from the group consisting of $CR^3R^4$, $C=CR^3R^4$, $C=O$, $C=NR^3$, $NR^3$, O, $SiR^3R^4$, S, S(O) and $S(O)_2$;
$R^1$ is the same or different in each occurrence and is selected from the group consisting of:
H, deuterium;
a linear alkyl group having 1 to 5 C atoms, a linear alkenyl or alkynyl group having 2 to 8 C atoms, a branched or cyclic alkyl, alkenyl or alkynyl group having 3 to 10 C atoms, wherein one or more H atoms in the aforementioned groups can be replaced by deuterium; and
an aromatic ring system having 6 to 15 aromatic ring atoms, which can in each case be substituted with one or more radicals $R^6$;
$R^2$ is selected from the group consisting of H and deuterium;
$R^a$, $R^3$ and $R^4$ is the same or different in each occurrence and is selected from the group consisting of:
H, deuterium, $N(R^5)_2$, OH, $Si(R^5)_3$, $B(OR^5)_2$, $OSO_2R^5$, $CF_3$, CN, F, Br, I;
a linear alkyl, alkoxy or thioalkoxy group having 1 to 40 C atoms, which can in each case be substituted with one or more radicals $R^5$, wherein one or more non-adjacent $CH_2$ groups can be replaced by $R^5C=CR^5$, $C\equiv C$, $Si(R^5)_2$, $Ge(R^5)_2$, $Sn(R^5)_2$, $C=O$, $C=S$, $C=Se$, $C=NR^5$, $P(=O)(R^5)$, SO, $SO_2$, $NR^5$, O, S or $CONR^5$ and wherein one or more H atoms can be replaced by deuterium, CN, $CF_3$ or $NO_2$;
a linear alkenyl or alkynyl group having 2 to 40 C atoms, which can in each case be substituted with one or more radicals $R^5$, wherein one or more non-adjacent $CH_2$ groups can be replaced by $R^5C=CR^5$, $C\equiv C$, $Si(R^5)_2$, $Ge(R^5)_2$, $Sn(R^5)_2$, $C=O$, $C=S$, $C=Se$, $C=NR^5$, $P(=O)(R^5)$, SO, $SO_2$, $NR^5$, O, S or $CONR^5$ and wherein one or more H atoms can be replaced by deuterium, CN, $CF_3$ or $NO_2$;
a branched or cyclic alkyl, alkenyl, alkynyl, alkoxy or thioalkoxy group having 3 to 40 C atoms, which can in each case be substituted with one or more radicals $R^5$, wherein one or more non-adjacent $CH_2$ groups can be replaced by $R^5C=CR^5$, $C\equiv C$, $Si(R^5)_2$, $Ge(R^5)_2$, $Sn(R^5)_2$, $C=O$, $C=S$, $C=Se$, $C=NR^5$, $P(=O)(R^5)$, SO, $SO_2$, $NR^5$, O, S or $CONR^5$ and wherein one or more H atoms can be replaced by deuterium, CN, $CF_3$ or $NO_2$;
an aromatic ring system having 6 to 60 aromatic ring atoms, which can in each case be substituted with one or more radicals $R^5$;
a heteroaromatic ring system having 5 to 60 aromatic ring atoms, which can in each case be substituted with one or more radicals $R^5$;
an aryloxy or heteroaryloxy group having 5 to 60 aromatic ring atoms, which can in each case be substituted with one or more radicals $R^5$; and
a diarylamino group, diheteroarylamino group or arylheteroarylamino group having 10 to 40 aromatic ring atoms, which can in each case be substituted with one or more radicals $R^5$;
$R^5$ is the same or different in each occurrence and is selected from the group consisting of:
H, deuterium, $N(R^6)_2$, OH, $Si(R^6)_3$, $B(OR^6)_2$, $OSO_2R^6$, $CF_3$, CN, F, Br, I;
a linear alkyl, alkoxy or thioalkoxy group having 1 to 40 C atoms, which can in each case be substituted with one or more radicals $R^6$, wherein one or more non-adjacent $CH_2$ groups can be replaced by $R^6C=CR^6$, $C\equiv C$, $Si(R^6)_2$, $Ge(R^6)_2$, $Sn(R^6)_2$, $C=O$, $C=S$, $C=Se$, $C=NR^6$, $P(=O)(R^6)$, SO, $SO_2$, $NR^6$, O, S or $CONR^6$ and wherein one or more H atoms can be replaced by deuterium, CN, $CF_3$ or $NO_2$;
a linear alkenyl or alkynyl group having 2 to 40 C atoms, which can in each case be substituted with one or more radicals $R^6$, wherein one or more non-adjacent $CH_2$ groups can be replaced by $R^6C=CR^6$, $C\equiv C$, $Si(R^6)_2$, $Ge(R^6)_2$, $Sn(R^6)_2$, $C=O$, $C=S$, $C=Se$, $C=NR^6$, $P(=O)(R^6)$, SO, $SO_2$, $NR^6$, O, S or $CONR^6$ and wherein one or more H atoms can be replaced by deuterium, CN, $CF_3$ or $NO_2$;

a branched or cyclic alkyl, alkenyl, alkynyl, alkoxy or thioalkoxy group having 3 to 40 C atoms, which can in each case be substituted with one or more radicals $R^6$, wherein one or more non-adjacent $CH_2$ groups can be replaced by $R^6C=CR^6$, $C\equiv C$, $Si(R^6)_2$, $Ge(R^6)_2$, $Sn(R^6)_2$, $C=O$, $C=S$, $C=Se$, $C=NR^6$, $P(=O)(R^6)$, SO, $SO_2$, $NR^6$, O, S or $CONR^6$ and wherein one or more H atoms can be replaced by deuterium, CN, $CF_3$ or $NO_2$;

an aromatic ring system having 6 to 60 aromatic ring atoms, which can in each case be substituted with one or more radicals $R^6$;

a heteroaromatic ring system having 5 to 60 aromatic ring atoms, which can in each case be substituted with one or more radicals $R^6$;

an aryloxy or heteroaryloxy group having 5 to 60 aromatic ring atoms, which can in each case be substituted with one or more radicals $R^6$; and a diarylamino group, diheteroarylamino group or arylheteroarylamino group having 10 to 40 aromatic ring atoms, which can in each case be substituted with one or more radicals $R^6$;

$R^6$ is the same or different in each occurrence and is selected from the group consisting of:

H, deuterium, OH, $CF_3$, CN, F;

a linear alkyl, alkoxy or thioalkoxy group having 1 to 5 C atoms, wherein one or more H atoms can be replaced by deuterium, CN, $CF_3$ or $NO_2$;

a linear alkenyl or alkynyl group having 2 to 5 C atoms, wherein one or more H atoms can be replaced by deuterium, CN, $CF_3$ or $NO_2$;

a branched or cyclic alkyl, alkenyl, alkynyl, alkoxy or thioalkoxy group having 3 to 5 C atoms, wherein one or more H atoms can be replaced by deuterium, CN, $CF_3$ or $NO_2$;

an aromatic ring system having 6 to 60 aromatic ring atoms;

a heteroaromatic ring system having 5 to 60 aromatic ring atoms;

an aryloxy or heteroaryloxy group having 5 to 60 aromatic ring atoms; and a diarylamino group, diheteroarylamino group or arylheteroarylamino group having 10 to 40 aromatic ring atoms;

wherein each of the radicals $R^a$, $R^3$, $R^4$ or $R^5$ can also form a mono- or polycyclic, aliphatic, aromatic and/or benzoannelated ring system with one or more further radicals $R^a$, $R^3$, $R^4$ or $R^5$;

wherein exactly one radical selected from the group consisting of W, X and Y is CN or $CF_3$ and exactly two radicals selected from the group consisting of T, V, W, X and Y are a point of attachment of the single bond between the first chemical unit and a second chemical unit.

2. The organic molecule according to claim 1, wherein $R^1$ is the same or different in each occurrence and is methyl or phenyl.

3. The organic molecule according to claim 1, wherein $R^2$ is H.

4. The organic molecule according to claim 1, wherein W is CN.

5. The organic molecule according to claim 1, wherein the second chemical unit is the same or different in each occurrence and has a structure of Formula IIa:

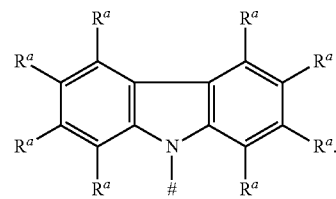

Formula IIa

6. The organic molecule according to claim 1, wherein, in each case, the second chemical unit has a structure of Formula IIb:

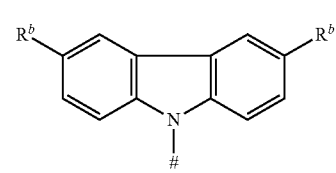

Formula IIb wherein $R^b$ is the same or different in each occurrence and is selected from the group consisting of:

$N(R^5)_2$, OH, $Si(R^5)_3$, $B(OR^5)_2$, $OSOR^5$, $CF_3$, CN, F, Br, I;

a linear alkyl, alkoxy or thioalkoxy group having 1 to 40 C atoms, wherein one or more non-adjacent $CH_2$ groups can be replaced by $R^5C=CR^5$, $C\equiv C$, $Si(R^5)_2$, $Ge(R^5)_2$, $Sn(R^5)_2$, $C=O$, $C=S$, $C=Se$, $C=NR^5$, $P(=O)(R^5)$, SO, $SO_2$, $NR^5$, O, S or $CONR^5$ and wherein one or more H atoms can be replaced by deuterium, CN, $CF_3$ or $NO_2$;

a linear alkenyl or alkynyl group having 2 to 40 C atoms, wherein one or more non-adjacent $CH_2$ groups can be replaced by $R^5C=CR^5$, $C\equiv C$, $Si(R^5)_2$, $Ge(R^5)_2$, $Sn(R^5)_2$, $C=O$, $C=S$, $C=Se$, $C=NR^5$, $P(=O)(R^5)$, SO, $SO_2$, $NR^5$, O, S or $CONR^5$ and wherein one or more H atoms can be replaced by deuterium, CN, $CF_3$ or $NO_2$;

a branched or cyclic alkyl, alkenyl, alkynyl, alkoxy or thioalkoxy group having 3 to 40 C atoms, which can in each case be substituted with one or more radicals $R^5$, wherein one or more non-adjacent $CH_2$ groups can be replaced by $R^5C=CR^5$, $C\equiv C$, $Si(R^5)_2$, $Ge(R^5)_2$, $Sn(R^5)_2$, $C=O$, $C=S$, $C=Se$, $C=NR^5$, $P(=O)(R^5)$, SO, $SO_2$, $NR^5$, O, S or $CONR^5$ and wherein one or more H atoms can be replaced by deuterium, CN, $CF_3$ or $NO_2$;

an aromatic ring system having 6 to 60 aromatic ring atoms, which can in each case be substituted with one or more radicals $R^5$;

a heteroaromatic ring system having 5 to 60 aromatic ring atoms, which can in each case be substituted with one or more radicals $R^5$;

an aryloxy or heteroaryloxy group having 5 to 60 aromatic ring atoms, which can in each case be substituted with one or more radicals $R^5$; and a diarylamino group, diheteroarylamino group or arylheteroarylamino group having 10 to 40 aromatic ring atoms, which can in each case be substituted with one or more radicals $R^5$.

7. The organic molecule according to claim 1, wherein, in each case, the second chemical unit has a structure of Formula IIc:

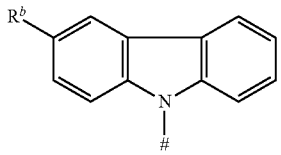

Formula IIc wherein
$R^b$ is the same or different in each occurrence and is selected from the group consisting of:
$N(R^5)_2$, OH, $Si(R^5)_3$, $B(OR^5)_2$, $OSOR^5$, $CF_3$, CN, F, Br, I;
a linear alkyl, alkoxy or thioalkoxy group having 1 to 40 C atoms, wherein one or more non-adjacent $CH_2$ groups can be replaced by $R^5C=CR^5$, C≡C, $Si(R^5)_2$, $Ge(R^5)_2$, $Sn(R^5)_2$, C=O, C=S, C=Se, $C=NR^5$, $P(=O)(R^5)$, SO, $SO_2$, $NR^5$, O, S or $CONR^5$ and wherein one or more H atoms can be replaced by deuterium, CN, $CF_3$ or $NO_2$;
a linear alkenyl or alkynyl group having 2 to 40 C atoms, wherein one or more non-adjacent $CH_2$ groups can be replaced by $R^5C=CR^5$, C≡C, $Si(R^5)_2$, $Ge(R^5)_2$, $Sn(R^5)_2$, C=O, C=S, C=Se, $C=NR^5$, $P(=O)(R^5)$, SO, $SO_2$, $NR^5$, O, S or $CONR^5$ and wherein one or more H atoms can be replaced by deuterium, CN, $CF_3$ or $NO_2$;
a branched or cyclic alkyl, alkenyl, alkynyl, alkoxy or thioalkoxy group having 3 to 40 C atoms, which can in each case be substituted with one or more radicals $R^5$, wherein one or more non-adjacent $CH_2$ groups can be replaced by $R^5C=CR^5$, C≡C, $Si(R^5)_2$, $Ge(R^5)_2$, $Sn(R^5)_2$, C=O, C=S, C=Se, $C=NR^5$, $P(=O)(R^5)$, SO, $SO_2$, $NR^5$, O, S or $CONR^5$ and wherein one or more H atoms can be replaced by deuterium, CN, $CF_3$ or $NO_2$;
an aromatic ring system having 6 to 60 aromatic ring atoms, which can in each case be substituted with one or more radicals $R^5$;
a heteroaromatic ring system having 5 to 60 aromatic ring atoms, which can in each case be substituted with one or more radicals $R^5$;
an aryloxy or heteroaryloxy group having 5 to 60 aromatic ring atoms, which can in each case be substituted with one or more radicals $R^5$; and
a diarylamino group, diheteroarylamino group or arylheteroarylamino group having 10 to 40 aromatic ring atoms, which can in each case be substituted with one or more radicals $R^5$.

8. The organic molecule according to claim 6, wherein $R^b$ is the same or different in each occurrence and is selected from the group consisting of Me, $^iPr$, $^tBu$, CN, $CF_3$,
Ph, which can in each case be substituted with one or more radicals selected independently of one another from Me, $^iPr$, $^tBu$, CN, $CF_3$ or Ph,
pyridinyl, which can in each case be substituted with one or more radicals selected independently of one another from Me, $^iPr$, $^tBu$, CN, $CF_3$ or Ph,
pyrimidinyl, which can in each case be substituted with one or more radicals selected independently of one another from Me, $^iPr$, $^tBu$, CN, $CF_3$ or Ph,
triazinyl, which can in each case be substituted with one or more radicals selected independently of one another from Me, $^iPr$, $^tBu$, CN, $CF_3$ or Ph,
carbazolyl which can in each case be substituted with one or more radicals selected independently of one another from Me, $^iPr$, $^tBu$, CN, $CF_3$ or Ph and $N(Ph)_2$.

9. A composition comprising:
(a) at least one organic molecule according to claim 1 as an emitter and/or host;
(b) one or more emitter and/or host materials different from the at least one organic molecule according to claim 1; and
(c) optionally one or more dyes and/or one or more solvents.

10. An optoelectronic device comprising the organic molecule according to claim 1.

11. The optoelectronic device according to claim 10, wherein the optoelectronic device is an organic light-emitting diode, a light-emitting electrochemical cell, an organic light-emitting sensor, an organic diode, an organic solar cell, an organic transistor, an organic field-effect transistor, an organic laser or a down-conversion element.

12. The optoelectronic device according to claim 10, wherein the organic molecule is one of a luminescent emitter, a host material, an electron transport material, a hole injection material or a hole blocking material in the optoelectronic device.

13. The optoelectronic device according to claim 10, comprising:
a substrate;
an anode;
a cathode, wherein the anode or the cathode is applied to the substrate; and
at least one light-emitting layer disposed between the anode and the cathode and which comprises the organic molecule.

14. An optoelectronic device comprising the organic molecule according to claim 2.

15. The optoelectronic device according to claim 14, comprising:
a substrate;
an anode;
a cathode, wherein the anode or the cathode is applied to the substrate; and
at least one light-emitting layer disposed between the anode and the cathode and which comprises the organic molecule.

16. An optoelectronic device comprising the composition according to claim 9.

17. The optoelectronic device according to claim 16, comprising:
a substrate;
an anode;
a cathode, wherein the anode or the cathode is applied to the substrate; and
at least one light-emitting layer disposed between the anode and the cathode and which comprises the composition.

18. The optoelectronic device according to claim 16, wherein the optoelectronic device is an organic light-emitting diode, a light-emitting electrochemical cell, an organic light-emitting sensor, an organic diode, an organic solar cell, an organic transistor, an organic field-effect transistor, an organic laser or a down-conversion element.

19. A process for producing an optoelectronic device, comprising processing of the organic molecule according to claim 1 by a vacuum evaporation method or from a solution.

20. A process for producing an optoelectronic device, comprising processing of the composition according to claim 9 by a vacuum evaporation method or from a solution.

* * * * *